US011572395B2

United States Patent
Gigout et al.

(10) Patent No.: US 11,572,395 B2
(45) Date of Patent: Feb. 7, 2023

(54) FUSION PROTEIN COMPRISING AN FGF-18 MOIETY

(71) Applicant: MERCK PATENT GMBH, Darmstadt (DE)

(72) Inventors: Anne Gigout, Griesheim (DE); Christian Brenneis, Kleinostheim (DE); Thomas Rysiok, Dudenhofen (DE); Stefan Zielonka, Darmstadt (DE)

(*) Notice: Subject to any disclaimer, the term of this patent is extended or adjusted under 35 U.S.C. 154(b) by 66 days.

(21) Appl. No.: 16/648,677

(22) PCT Filed: Sep. 20, 2018

(86) PCT No.: PCT/EP2018/075432
§ 371 (c)(1),
(2) Date: Mar. 19, 2020

(87) PCT Pub. No.: WO2019/057805
PCT Pub. Date: Mar. 28, 2019

(65) Prior Publication Data
US 2020/0299347 A1    Sep. 24, 2020

(30) Foreign Application Priority Data

Sep. 21, 2017  (EP) .................................... 17192467
Jul. 10, 2018  (EP) .................................... 18182696

(51) Int. Cl.
*A61K 38/18* (2006.01)
*C07K 14/50* (2006.01)
*A61P 19/02* (2006.01)
*C07K 16/28* (2006.01)
*C12N 15/63* (2006.01)
*A61K 39/00* (2006.01)

(52) U.S. Cl.
CPC ............ *C07K 14/50* (2013.01); *A61P 19/02* (2018.01); *C07K 16/2875* (2013.01); *C12N 15/63* (2013.01); *A61K 2039/505* (2013.01); *C07K 2317/55* (2013.01); *C07K 2317/565* (2013.01); *C07K 2317/569* (2013.01); *C07K 2317/622* (2013.01); *C07K 2319/30* (2013.01)

(58) Field of Classification Search
None
See application file for complete search history.

(56) References Cited

U.S. PATENT DOCUMENTS

| 8,207,115 B2* | 6/2012 | Gimona ............. A61K 38/1825 514/9.1 |
| 8,809,499 B2* | 8/2014 | Fan ...................... C07K 14/605 530/350 |
| 9,505,829 B2* | 11/2016 | Lacy .................. A61K 39/3955 |
| 2018/0236032 A1 | 8/2018 | Ladel et al. |

FOREIGN PATENT DOCUMENTS

| WO | WO 2015/114150 | 8/2015 |
| WO | WO 2017/025611 | 2/2017 |

OTHER PUBLICATIONS

Davis et al. Protein Engineering, Design & Selection 23(4): 195-202, 2010.*
Spierings et al. (PAIN 154: 1603-1612, 2013).*
Martel-Pelletier et al. (Bone 51: 297-311, 2012).*
Vinatier, C. et al. "Osteoarthritis: from pathogenic mechanisms and recent clinical developments to novel prospective therapeutic options" *Drug Discovery Today*, 2016, pp. 1932-1937, vol. 21, No. 12.
Written Opinion in International Application No. PCT/EP2018/075432, prepared by Authorized Officer Franz Chavanne, posted in PatentScope on Mar. 28, 2019, dated Nov. 16, 2018, pp. 1-8.

* cited by examiner

*Primary Examiner* — Christine J Saoud
(74) *Attorney, Agent, or Firm* — Saliwanchik, Lloyd & Eisenschenk

(57) ABSTRACT

The present invention relates to new fusion proteins comprising an FGF-18 moiety fused to an anti-NGF moiety. Said fusion protein can be used for the treatment of a cartilage disorder such as osteoarthritis or cartilage injury.

5 Claims, 10 Drawing Sheets
Specification includes a Sequence Listing.

FIG. 1A  FGF-18-scFv
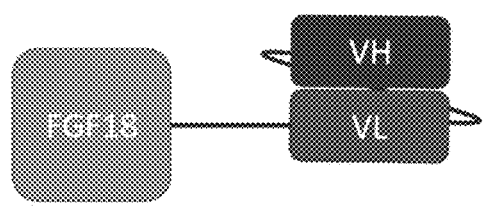
FIG. 1B  FGF-18 -SEEDbody
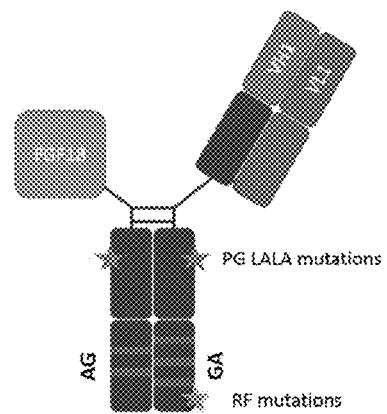
FIG. 1C  FGF-18 -SEEDbody
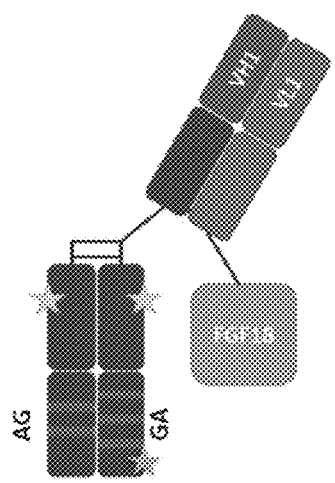
FIG. 1D  FGF-18 -SEEDbody
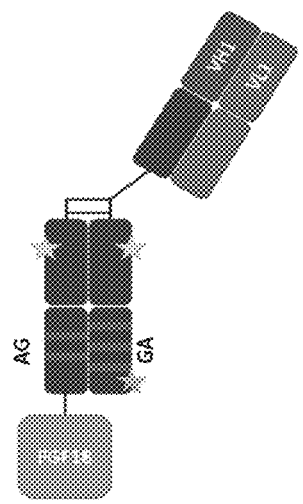
FIG. 1E  FGF-18-Fab
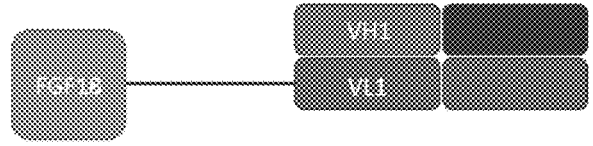
FIG. 1F  FGF-18-Fab
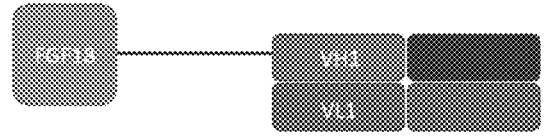

FIG. 1G    Fab- FGF-18
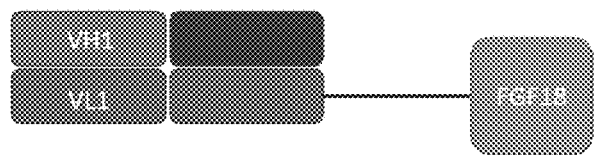
FIG. 1H    Fab- FGF-18
FIG. 1I    FGF-18-IgG
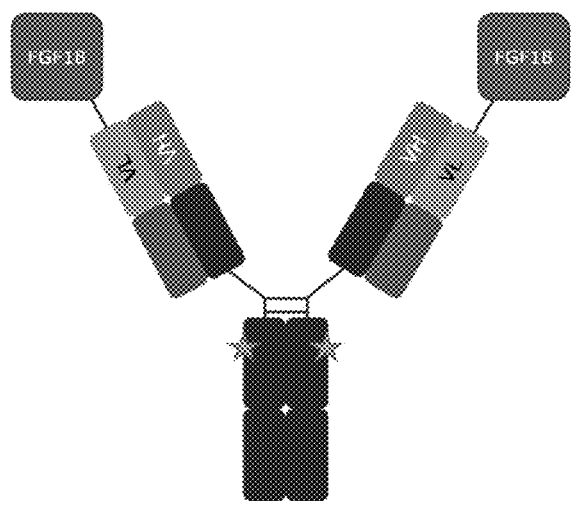
FIG. 1J    FGF-18-IgG
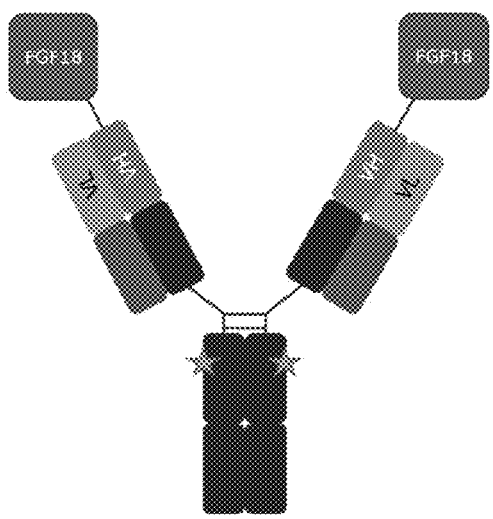
FIG. 1K    IgG- FGF-18
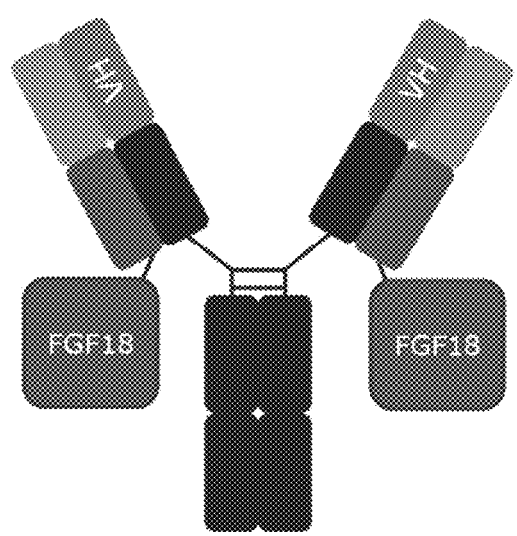
FIG. 1L    IgG- FGF-18
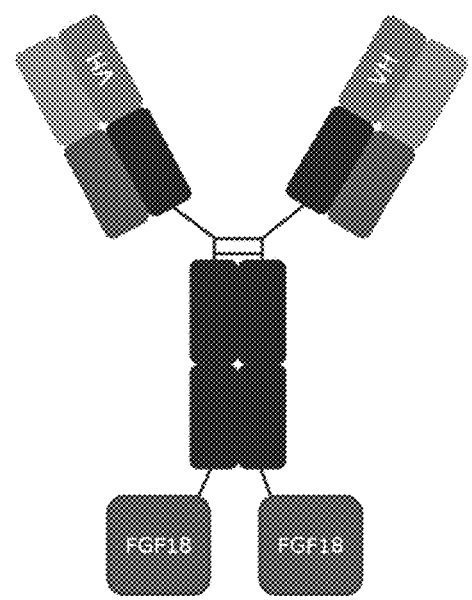

Catwalk test for pain behavior

FIG. 4A  Time course of gait disturbance:
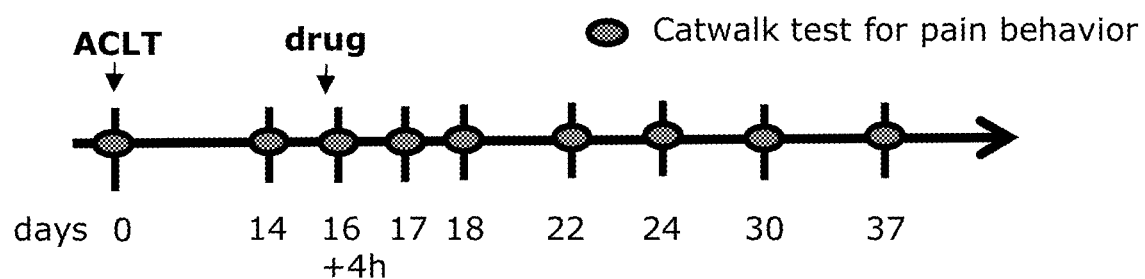

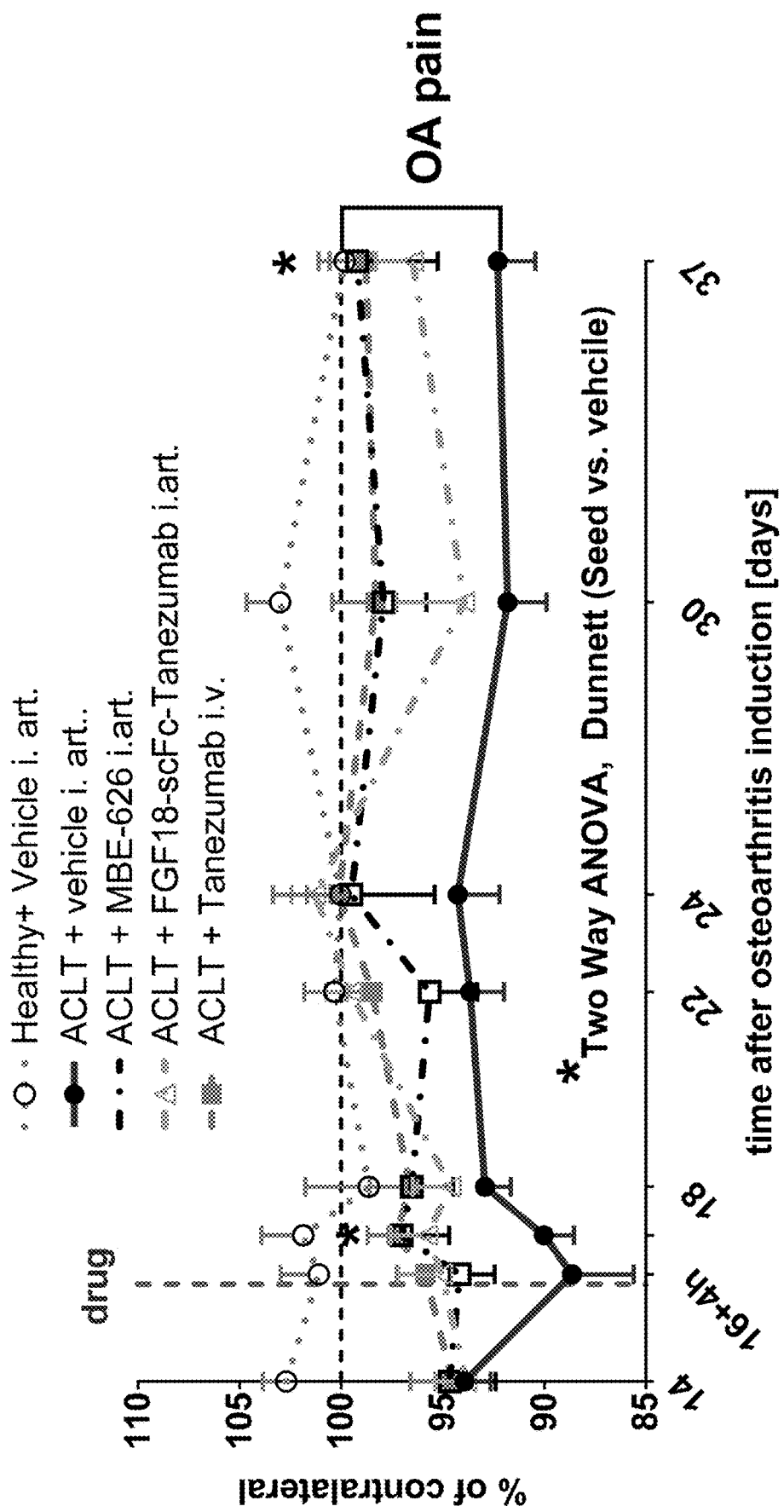
FIG. 4B   Gait disturbance over time

FIG. 4C    Gait disturbance during 3 weeks post injection:
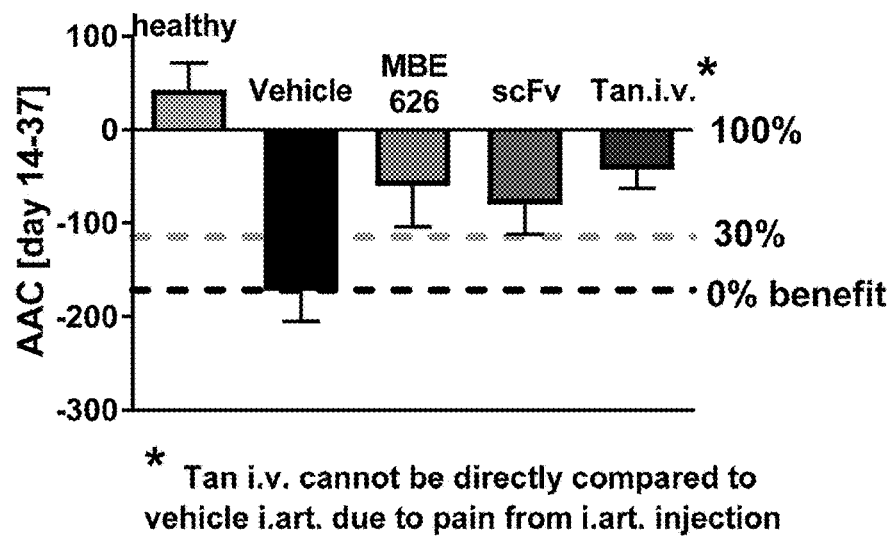
\* Tan i.v. cannot be directly compared to vehicle i.art. due to pain from i.art. injection
FIG. 5A    Time course of gait disturbance:
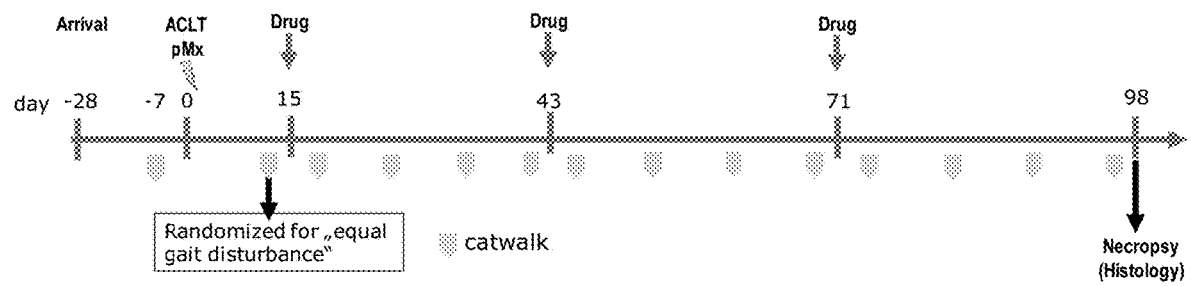

SEQUENCE LISTING

<160> NUMBER OF SEQ ID NOS: 140

<210> SEQ ID NO 1
<211> LENGTH: 207
<212> TYPE: PRT
<213> ORGANISM: Homo sapiens

<400> SEQUENCE: 1

```
Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205
```

<210> SEQ ID NO 2
<211> LENGTH: 169
<212> TYPE: PRT
<213> ORGANISM: artificial sequence
<220> FEATURE:
<223> OTHER INFORMATION: Amino acid sequence of a recombinant truncated FGF-18 (trFGF-18)

<400> SEQUENCE: 2

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys
                165

<210> SEQ ID NO 3
<211> LENGTH: 161
<212> TYPE: PRT
<213> ORGANISM: artificial sequence
<220> FEATURE:
<223> OTHER INFORMATION: Amino acid sequence of FGF18_delta8

<400> SEQUENCE: 3

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro

<210> SEQ ID NO 4
<211> LENGTH: 171
<212> TYPE: PRT
```

<213> ORGANISM: artificial sequence
<220> FEATURE:
<223> OTHER INFORMATION: Amino acid sequence of FGF18_TF

<400> SEQUENCE: 4

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Gly Gly Gly Gly Ser Gly Gly Gly Ser
                165                 170

<210> SEQ ID NO 5
<211> LENGTH: 169
<212> TYPE: PRT
<213> ORGANISM: artificial sequence
<220> FEATURE:
<223> OTHER INFORMATION: Amino acid sequence of FGF18_QNQS

<400> SEQUENCE: 5

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Gln
145                 150                 155                 160

Asn Phe Gln Ser Thr Thr Val Thr Lys
            165

<210> SEQ ID NO 6
<211> LENGTH: 169
<212> TYPE: PRT
<213> ORGANISM: artificial sequence
<220> FEATURE:
<223> OTHER INFORMATION: Amino acid sequence of FGF18_Y191P

<400> SEQUENCE: 6

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Pro Thr Thr Val Thr Lys
                165

<210> SEQ ID NO 7
<211> LENGTH: 169
<212> TYPE: PRT
<213> ORGANISM: artificial sequence
<220> FEATURE:
<223> OTHER INFORMATION: Amino acid sequence of FGF18_3Ala

<400> SEQUENCE: 7

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
            130                 135                 140

Val His Phe Met Lys Arg Tyr Pro Lys Gly Gln Pro Glu Leu Gln Ala
145                 150                 155                 160

Ala Phe Ala Tyr Thr Thr Val Thr Lys
                165

<210> SEQ ID NO 8
<211> LENGTH: 169
<212> TYPE: PRT
<213> ORGANISM: artificial sequence
<220> FEATURE:
<223> OTHER INFORMATION: Amino acid sequence of FGF18_VS

<400> SEQUENCE: 8

Glu Glu Asn Val Asp Phe Arg Ile His Val Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Val Ser Thr Thr Val Thr Lys
                165

<210> SEQ ID NO 9
<211> LENGTH: 447
<212> TYPE: PRT
<213> ORGANISM: artificial sequence
<220> FEATURE:
<223> OTHER INFORMATION: Amino acid sequence of the full heavy chain of
      tanezumab

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 451
<212> TYPE: PRT
<213> ORGANISM: artificial sequence
<220> FEATURE:
<223> OTHER INFORMATION: Amino acid sequence of the full heavy chain of
      tanezumab, with point mutations

<400> SEQUENCE: 10
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65              70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 11
<211> LENGTH: 214
<212> TYPE: PRT
<213> ORGANISM: artificial sequence
<220> FEATURE:
<223> OTHER INFORMATION: Amino acid sequence of the full light chain of
      tanezumab

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 446
<212> TYPE: PRT
<213> ORGANISM: artificial sequence
<220> FEATURE:
<223> OTHER INFORMATION: Amino acid sequence of the full heavy chain of
      fasinumab

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30
```

```
Ser Ile His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Thr Ser Leu Arg Ser Glu Asp Thr Ala Val Tyr Tyr Cys
                 85                  90                  95

Ser Thr Ile Phe Gly Val Val Thr Asn Phe Asp Asn Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Cys Ser Arg Ser Thr Ser Glu Ser Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Lys Thr Tyr Thr Cys Asn Val Asp His Lys Pro
         195                 200                 205

Ser Asn Thr Lys Val Asp Lys Arg Val Glu Ser Lys Tyr Gly Pro Pro
 210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser Gln Glu Asp Pro Glu Val
             260                 265                 270

Gln Phe Asn Trp Tyr Val Asp Gly Val Glu Val His Asn Ala Lys Thr
         275                 280                 285

Lys Pro Arg Glu Glu Gln Phe Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                 325                 330                 335

Lys Ala Lys Gly Gln Pro Arg Glu Pro Gln Val Tyr Thr Leu Pro Pro
         340                 345                 350

Ser Gln Glu Glu Met Thr Lys Asn Gln Val Ser Leu Thr Cys Leu Val
 355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                 405                 410                 415

Gln Glu Gly Asn Val Phe Ser Cys Ser Val Met His Glu Ala Leu His
             420                 425                 430

Asn His Tyr Thr Gln Lys Ser Leu Ser Leu Ser Leu Gly Lys
         435                 440                 445
```

```
<210> SEQ ID NO 13
<211> LENGTH: 214
<212> TYPE: PRT
<213> ORGANISM: artificial sequence
<220> FEATURE:
<223> OTHER INFORMATION: Amino acid sequence of the full light chain of
      fasinumab

<400> SEQUENCE: 13

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 449
<212> TYPE: PRT
<213> ORGANISM: artificial sequence
<220> FEATURE:
<223> OTHER INFORMATION: Amino acid sequence of heavy chain of
      fulranumab

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
```

```
            85                  90                  95
Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Asn Phe Gly Thr Gln Thr Tyr Thr Cys Asn Val
                    195                 200                 205

Asp His Lys Pro Ser Asn Thr Lys Val Asp Lys Thr Val Glu Arg Lys
            210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Gln Phe Asn Trp Tyr Val Asp Gly Val Glu Val His Asn
                    275                 280                 285

Ala Lys Thr Lys Pro Arg Glu Glu Gln Phe Asn Ser Thr Phe Arg Val
            290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                    325                 330                 335

Thr Ile Ser Lys Thr Lys Gly Gln Pro Arg Glu Pro Gln Val Tyr Thr
                    340                 345                 350

Leu Pro Pro Ser Arg Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys

<210> SEQ ID NO 15
<211> LENGTH: 214
<212> TYPE: PRT
<213> ORGANISM: artificial sequence
<220> FEATURE:
<223> OTHER INFORMATION: Amino acid sequence of light chain of
      fulranumab
```

```
<400> SEQUENCE: 15

Ala Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 16
<211> LENGTH: 224
<212> TYPE: PRT
<213> ORGANISM: artificial sequence
<220> FEATURE:
<223> OTHER INFORMATION: Amino acid sequence of the heavy chain Fab
      fragment of tanezumab

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser Ser Ala Ser Thr Lys Gly Pro Ser
            115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 17
<211> LENGTH: 214
<212> TYPE: PRT
<213> ORGANISM: artificial sequence
<220> FEATURE:
<223> OTHER INFORMATION: Amino acid sequence of the light chain Fab
      fragment of tanezumab

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 222
<212> TYPE: PRT
<213> ORGANISM: artificial sequence
<220> FEATURE:
<223> OTHER INFORMATION: Amino acid sequence of the heavy chain Fab
      fragment of fasinumab

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 19
<211> LENGTH: 214
<212> TYPE: PRT
<213> ORGANISM: artificial sequence
<220> FEATURE:
<223> OTHER INFORMATION: Amino acid sequence of the light chain Fab fragment of fasinumab

<400> SEQUENCE: 19

```
Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 20
<211> LENGTH: 226
<212> TYPE: PRT
<213> ORGANISM: artificial sequence
<220> FEATURE:
<223> OTHER INFORMATION: Amino acid sequence of the heavy chain Fab
      fragment of fulranumab

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Ser His Thr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

```
<210> SEQ ID NO 21
<211> LENGTH: 214
<212> TYPE: PRT
```

<213> ORGANISM: artificial sequence
<220> FEATURE:
<223> OTHER INFORMATION: Amino acid sequence of the light chain Fab
      fragment of fulranumab

<400> SEQUENCE: 21

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 243
<212> TYPE: PRT
<213> ORGANISM: artificial sequence
<220> FEATURE:
<223> OTHER INFORMATION: Amino acid sequence of scFv of tanezumab

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Gly Gly Gly Gly Ser
            100                 105                 110

```
Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
    130                 135                 140

Thr Val Ser Gly Phe Ser Leu Ile Gly Tyr Asp Leu Asn Trp Ile Arg
145                 150                 155                 160

Gln Pro Pro Gly Lys Gly Leu Glu Trp Ile Gly Ile Ile Trp Gly Asp
                165                 170                 175

Gly Thr Thr Asp Tyr Asn Ser Ala Val Lys Ser Arg Val Thr Ile Ser
                180                 185                 190

Lys Asp Thr Ser Lys Asn Gln Phe Ser Leu Lys Leu Ser Ser Val Thr
                195                 200                 205

Ala Ala Asp Thr Ala Val Tyr Tyr Cys Ala Arg Gly Gly Tyr Trp Tyr
            210                 215                 220

Ala Thr Ser Tyr Tyr Phe Asp Tyr Trp Gly Gln Gly Thr Leu Val Thr
225                 230                 235                 240

Val Ser Ser

<210> SEQ ID NO 23
<211> LENGTH: 241
<212> TYPE: PRT
<213> ORGANISM: artificial sequence
<220> FEATURE:
<223> OTHER INFORMATION: Amino acid sequence of scFv of fasinumab

<400> SEQUENCE: 23

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gln Val Gln Leu Val Gln
            115                 120                 125

Ser Gly Ala Glu Val Lys Lys Pro Gly Ala Ser Val Lys Val Ser Cys
    130                 135                 140

Lys Val Ser Gly Phe Thr Leu Thr Glu Leu Ser Ile His Trp Val Arg
145                 150                 155                 160

Gln Ala Pro Gly Lys Gly Leu Glu Trp Met Gly Gly Phe Asp Pro Glu
                165                 170                 175

Asp Gly Glu Thr Ile Tyr Ala Gln Lys Phe Gln Gly Arg Val Thr Met
                180                 185                 190

Thr Glu Asp Thr Ser Thr Asp Thr Ala Tyr Met Glu Leu Thr Ser Leu
            195                 200                 205

Arg Ser Glu Asp Thr Ala Val Tyr Tyr Cys Ser Thr Ile Phe Gly Val
            210                 215                 220
```

```
Val Thr Asn Phe Asp Asn Trp Gly Gln Gly Thr Leu Val Thr Val Ser
225                 230                 235                 240

Ser

<210> SEQ ID NO 24
<211> LENGTH: 245
<212> TYPE: PRT
<213> ORGANISM: artificial sequence
<220> FEATURE:
<223> OTHER INFORMATION: Amino acid sequence of scFv of fulranumab

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Leu Arg Ser Tyr Ser Met Asn Trp Val Arg
145                 150                 155                 160

Gln Ala Pro Gly Lys Gly Leu Glu Trp Val Ser Tyr Ile Ser Arg Ser
                165                 170                 175

Ser His Thr Ile Phe Tyr Ala Asp Ser Val Lys Gly Arg Phe Thr Ile
            180                 185                 190

Ser Arg Asp Asn Ala Lys Asn Ser Leu Tyr Leu Gln Met Asp Ser Leu
        195                 200                 205

Arg Asp Glu Asp Thr Ala Met Tyr Tyr Cys Ala Arg Val Tyr Ser Ser
    210                 215                 220

Gly Trp His Val Ser Asp Tyr Phe Asp Tyr Trp Gly Gln Gly Ile Leu
225                 230                 235                 240

Val Thr Val Ser Ser
                245

<210> SEQ ID NO 25
<211> LENGTH: 427
<212> TYPE: PRT
<213> ORGANISM: artificial sequence
<220> FEATURE:
<223> OTHER INFORMATION: Amino acid sequence of FGF-18-scFv-tanezumab,
      fusion via N-terminus of light domain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
```

```
<220> FEATURE:
<221> NAME/KEY: MISC_FEATURE
<222> LOCATION: (185)..(427)
<223> OTHER INFORMATION: scFv tanezumab as the anti-NGF inhibitor moiety

<400> SEQUENCE: 25
```

| | | | | | | | | | | | | | | |
|---|---|---|---|---|---|---|---|---|---|---|---|---|---|---|
| Glu | Glu | Asn | Val | Asp | Phe | Arg | Ile | His | Val | Glu | Asn | Gln | Thr | Arg | Ala |
| 1 | | | | 5 | | | | | 10 | | | | | 15 |
| Arg | Asp | Asp | Val | Ser | Arg | Lys | Gln | Leu | Arg | Leu | Tyr | Gln | Leu | Tyr | Ser |
| | | | 20 | | | | | 25 | | | | | 30 | | |
| Arg | Thr | Ser | Gly | Lys | His | Ile | Gln | Val | Leu | Gly | Arg | Arg | Ile | Ser | Ala |
| | | 35 | | | | | 40 | | | | | 45 | | | |
| Arg | Gly | Glu | Asp | Gly | Asp | Lys | Tyr | Ala | Gln | Leu | Leu | Val | Glu | Thr | Asp |
| 50 | | | | | 55 | | | | | 60 | | | | | |
| Thr | Phe | Gly | Ser | Gln | Val | Arg | Ile | Lys | Gly | Lys | Glu | Thr | Glu | Phe | Tyr |
| 65 | | | | | 70 | | | | | 75 | | | | | 80 |
| Leu | Cys | Met | Asn | Arg | Lys | Gly | Lys | Leu | Val | Gly | Lys | Pro | Asp | Gly | Thr |
| | | | | 85 | | | | | 90 | | | | | 95 | |
| Ser | Lys | Glu | Cys | Val | Phe | Ile | Glu | Lys | Val | Leu | Glu | Asn | Asn | Tyr | Thr |
| | | | 100 | | | | | 105 | | | | | 110 | | |
| Ala | Leu | Met | Ser | Ala | Lys | Tyr | Ser | Gly | Trp | Tyr | Val | Gly | Phe | Thr | Lys |
| | | 115 | | | | | 120 | | | | | 125 | | | |
| Lys | Gly | Arg | Pro | Arg | Lys | Gly | Pro | Lys | Thr | Arg | Glu | Asn | Gln | Gln | Asp |
| 130 | | | | | 135 | | | | | 140 | | | | | |
| Val | His | Phe | Met | Lys | Arg | Tyr | Pro | Lys | Gly | Gln | Pro | Glu | Leu | Gln | Lys |
| 145 | | | | | 150 | | | | | 155 | | | | | 160 |
| Pro | Phe | Lys | Tyr | Thr | Thr | Val | Thr | Lys | Gly | Gly | Gly | Ser | Gly | Gly |
| | | | | 165 | | | | | 170 | | | | | 175 |
| Gly | Gly | Ser | Gly | Gly | Gly | Gly | Ser | Asp | Ile | Gln | Met | Thr | Gln | Ser | Pro |
| | | | 180 | | | | | 185 | | | | | 190 | | |
| Ser | Ser | Leu | Ser | Ala | Ser | Val | Gly | Asp | Arg | Val | Thr | Ile | Thr | Cys | Arg |
| | | 195 | | | | | 200 | | | | | 205 | | | |
| Ala | Ser | Gln | Ser | Ile | Ser | Asn | Asn | Leu | Asn | Trp | Tyr | Gln | Gln | Lys | Pro |
| 210 | | | | | 215 | | | | | 220 | | | | | |
| Gly | Lys | Ala | Pro | Lys | Leu | Leu | Ile | Tyr | Tyr | Thr | Ser | Arg | Phe | His | Ser |
| 225 | | | | | 230 | | | | | 235 | | | | | 240 |
| Gly | Val | Pro | Ser | Arg | Phe | Ser | Gly | Ser | Gly | Ser | Gly | Thr | Asp | Phe | Thr |
| | | | | 245 | | | | | 250 | | | | | 255 | |
| Phe | Thr | Ile | Ser | Ser | Leu | Gln | Pro | Glu | Asp | Ile | Ala | Thr | Tyr | Tyr | Cys |
| | | | 260 | | | | | 265 | | | | | 270 | | |
| Gln | Gln | Glu | His | Thr | Leu | Pro | Tyr | Thr | Phe | Gly | Gln | Gly | Thr | Lys | Leu |
| | | | 275 | | | | | 280 | | | | | 285 | | |
| Glu | Ile | Lys | Gly | Gly | Gly | Gly | Ser | Gly | Gly | Gly | Gly | Ser | Gly | Gly | Gly |
| | 290 | | | | | 295 | | | | | 300 | | | | |
| Gly | Ser | Gln | Val | Gln | Leu | Gln | Glu | Ser | Gly | Pro | Gly | Leu | Val | Lys | Pro |
| 305 | | | | | 310 | | | | | 315 | | | | | 320 |
| Ser | Glu | Thr | Leu | Ser | Leu | Thr | Cys | Thr | Val | Ser | Gly | Phe | Ser | Leu | Ile |
| | | | | 325 | | | | | 330 | | | | | 335 | |
| Gly | Tyr | Asp | Leu | Asn | Trp | Ile | Arg | Gln | Pro | Pro | Gly | Lys | Gly | Leu | Glu |
| | | | 340 | | | | | 345 | | | | | 350 | | |
| Trp | Ile | Gly | Ile | Ile | Trp | Gly | Asp | Gly | Thr | Thr | Asp | Tyr | Asn | Ser | Ala |
| | | | 355 | | | | | 360 | | | | | 365 | | |
| Val | Lys | Ser | Arg | Val | Thr | Ile | Ser | Lys | Asp | Thr | Ser | Lys | Asn | Gln | Phe |
| 370 | | | | | 375 | | | | | 380 | | | | | |

```
Ser Leu Lys Leu Ser Ser Val Thr Ala Ala Asp Thr Ala Val Tyr Tyr
385                 390                 395                 400

Cys Ala Arg Gly Gly Tyr Trp Tyr Ala Thr Ser Tyr Tyr Phe Asp Tyr
                405                 410                 415

Trp Gly Gln Gly Thr Leu Val Thr Val Ser Ser
                420                 425

<210> SEQ ID NO 26
<211> LENGTH: 425
<212> TYPE: PRT
<213> ORGANISM: artificial sequence
<220> FEATURE:
<223> OTHER INFORMATION: Amino acid sequence of FGF-18-scFv-fasinumab,
      fusion via N-terminus of light domain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(425)
<223> OTHER INFORMATION: scFv fasinumab as the anti-NGF inhibitor moiety

<400> SEQUENCE: 26

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175

Gly Gly Ser Gly Gly Gly Gly Ser Asp Ile Gln Met Thr Gln Ser Pro
            180                 185                 190

Ser Ser Leu Ser Ala Ser Ala Gly Asp Arg Val Thr Ile Thr Cys Arg
        195                 200                 205

Ala Ser Gln Ala Ile Arg Asn Asp Leu Gly Trp Tyr Gln Gln Lys Pro
    210                 215                 220

Gly Lys Ala Pro Lys Arg Leu Ile Tyr Ala Ala Phe Asn Leu Gln Ser
225                 230                 235                 240

Gly Val Pro Ser Arg Phe Ser Gly Ser Gly Ser Gly Thr Glu Phe Thr
                245                 250                 255
```

-continued

```
Leu Thr Ile Ser Ser Leu Gln Pro Glu Asp Leu Ala Ser Tyr Tyr Cys
            260                 265                 270

Gln Gln Tyr Asn Arg Tyr Pro Trp Thr Phe Gly Gln Gly Thr Lys Val
        275                 280                 285

Glu Ile Lys Gly Gly Gly Gly Ser Gly Gly Gly Gly Ser Gly Gly Gly
    290                 295                 300

Gly Ser Gln Val Gln Leu Val Gln Ser Gly Ala Glu Val Lys Lys Pro
305                 310                 315                 320

Gly Ala Ser Val Lys Val Ser Cys Lys Val Ser Gly Phe Thr Leu Thr
                325                 330                 335

Glu Leu Ser Ile His Trp Val Arg Gln Ala Pro Gly Lys Gly Leu Glu
            340                 345                 350

Trp Met Gly Gly Phe Asp Pro Glu Asp Gly Glu Thr Ile Tyr Ala Gln
        355                 360                 365

Lys Phe Gln Gly Arg Val Thr Met Thr Glu Asp Thr Ser Thr Asp Thr
    370                 375                 380

Ala Tyr Met Glu Leu Thr Ser Leu Arg Ser Glu Asp Thr Ala Val Tyr
385                 390                 395                 400

Tyr Cys Ser Thr Ile Phe Gly Val Val Thr Asn Phe Asp Asn Trp Gly
                405                 410                 415

Gln Gly Thr Leu Val Thr Val Ser Ser
            420                 425

<210> SEQ ID NO 27
<211> LENGTH: 429
<212> TYPE: PRT
<213> ORGANISM: artificial sequence
<220> FEATURE:
<223> OTHER INFORMATION: Amino acid sequence of FGF-18-scFv-fulranumab,
      fusion via N-terminus of light domain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(429)
<223> OTHER INFORMATION: scFv fulranumab as the anti-NGF inhibitor
      moiety

<400> SEQUENCE: 27

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110
```

```
Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175

Gly Gly Ser Gly Gly Gly Ser Ala Ile Gln Leu Thr Gln Ser Pro
            180                 185                 190

Ser Ser Leu Ser Ala Ser Val Gly Asp Arg Val Thr Ile Thr Cys Arg
            195                 200                 205

Ala Ser Gln Gly Ile Ser Ser Ala Leu Ala Trp Tyr Gln Gln Lys Pro
            210                 215                 220

Gly Lys Ala Pro Lys Leu Leu Ile Tyr Asp Ala Ser Ser Leu Glu Ser
225                 230                 235                 240

Gly Val Pro Ser Arg Phe Ser Gly Ser Gly Ser Gly Thr Asp Phe Thr
                245                 250                 255

Leu Thr Ile Ser Ser Leu Gln Pro Glu Asp Phe Ala Thr Tyr Tyr Cys
            260                 265                 270

Gln Gln Phe Asn Ser Tyr Pro Leu Thr Phe Gly Gly Gly Thr Lys Val
            275                 280                 285

Glu Ile Lys Gly Gly Gly Gly Ser Gly Gly Gly Gly Ser Gly Gly
            290                 295                 300

Gly Ser Glu Val Gln Leu Val Glu Ser Gly Gly Gly Leu Val Gln Pro
305                 310                 315                 320

Gly Gly Ser Leu Arg Leu Ser Cys Ala Ala Ser Gly Phe Thr Leu Arg
                325                 330                 335

Ser Tyr Ser Met Asn Trp Val Arg Gln Ala Pro Gly Lys Gly Leu Glu
            340                 345                 350

Trp Val Ser Tyr Ile Ser Arg Ser Ser His Thr Ile Phe Tyr Ala Asp
            355                 360                 365

Ser Val Lys Gly Arg Phe Thr Ile Ser Arg Asp Asn Ala Lys Asn Ser
370                 375                 380

Leu Tyr Leu Gln Met Asp Ser Leu Arg Asp Glu Asp Thr Ala Met Tyr
385                 390                 395                 400

Tyr Cys Ala Arg Val Tyr Ser Ser Gly Trp His Val Ser Asp Tyr Phe
                405                 410                 415

Asp Tyr Trp Gly Gln Gly Ile Leu Val Thr Val Ser Ser
            420                 425
```

<210> SEQ ID NO 28
<211> LENGTH: 398
<212> TYPE: PRT
<213> ORGANISM: artificial sequence
<220> FEATURE:
<223> OTHER INFORMATION: Amino acid sequence of FGF-18-Fab of anti-NGF, fusion via N-terminus of the light chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)

<223> OTHER INFORMATION: Fab moiety

<400> SEQUENCE: 28

```
Glu Glu Asn Val Asp Phe Arg Ile His Val Glu Asn Gln Thr Arg Ala
1               5                   10                  15
Arg Asp Asp Val Ser Arg Lys Gln Leu Arg Leu Tyr Gln Leu Tyr Ser
                20                  25                  30
Arg Thr Ser Gly Lys His Ile Gln Val Leu Gly Arg Arg Ile Ser Ala
            35                  40                  45
Arg Gly Glu Asp Gly Asp Lys Tyr Ala Gln Leu Leu Val Glu Thr Asp
        50                  55                  60
Thr Phe Gly Ser Gln Val Arg Ile Lys Gly Lys Glu Thr Glu Phe Tyr
65                  70                  75                  80
Leu Cys Met Asn Arg Lys Gly Lys Leu Val Gly Lys Pro Asp Gly Thr
                85                  90                  95
Ser Lys Glu Cys Val Phe Ile Glu Lys Val Leu Glu Asn Asn Tyr Thr
            100                 105                 110
Ala Leu Met Ser Ala Lys Tyr Ser Gly Trp Tyr Val Gly Phe Thr Lys
        115                 120                 125
Lys Gly Arg Pro Arg Lys Gly Pro Lys Thr Arg Glu Asn Gln Gln Asp
130                 135                 140
Val His Phe Met Lys Arg Tyr Pro Lys Gly Gln Pro Glu Leu Gln Lys
145                 150                 155                 160
Pro Phe Lys Tyr Thr Thr Val Thr Lys Gly Gly Gly Ser Gly Gly Gly
                165                 170                 175
Gly Gly Ser Gly Gly Gly Gly Ser Asp Ile Gln Met Thr Gln Ser Pro
            180                 185                 190
Ser Ser Leu Ser Ala Ser Val Gly Asp Arg Val Thr Ile Thr Cys Arg
        195                 200                 205
Ala Ser Gln Ser Ile Ser Asn Asn Leu Asn Trp Tyr Gln Gln Lys Pro
    210                 215                 220
Gly Lys Ala Pro Lys Leu Leu Ile Tyr Tyr Thr Ser Arg Phe His Ser
225                 230                 235                 240
Gly Val Pro Ser Arg Phe Ser Gly Ser Gly Ser Gly Thr Asp Phe Thr
                245                 250                 255
Phe Thr Ile Ser Ser Leu Gln Pro Glu Asp Ile Ala Thr Tyr Tyr Cys
            260                 265                 270
Gln Gln Glu His Thr Leu Pro Tyr Thr Phe Gly Gln Gly Thr Lys Leu
        275                 280                 285
Glu Ile Lys Arg Thr Val Ala Ala Pro Ser Val Phe Ile Phe Pro Pro
    290                 295                 300
Ser Asp Glu Gln Leu Lys Ser Gly Thr Ala Ser Val Val Cys Leu Leu
305                 310                 315                 320
Asn Asn Phe Tyr Pro Arg Glu Ala Lys Val Gln Trp Lys Val Asp Asn
                325                 330                 335
Ala Leu Gln Ser Gly Asn Ser Gln Glu Ser Val Thr Glu Gln Asp Ser
            340                 345                 350
Lys Asp Ser Thr Tyr Ser Leu Ser Ser Thr Leu Thr Leu Ser Lys Ala
        355                 360                 365
Asp Tyr Glu Lys His Lys Val Tyr Ala Cys Glu Val Thr His Gln Gly
    370                 375                 380
Leu Ser Ser Pro Val Thr Lys Ser Phe Asn Arg Gly Glu Cys
385                 390                 395
```

```
<210> SEQ ID NO 29
<211> LENGTH: 400
<212> TYPE: PRT
<213> ORGANISM: artificial sequence
<220> FEATURE:
<223> OTHER INFORMATION: Amino acid sequence of FGF18TF-Fab of anti-NGF,
      fusion via N-terminus of the light chain
<220> FEATURE:
<221> NAME/KEY: MISC_FEATURE
<222> LOCATION: (1)..(161)
<223> OTHER INFORMATION: FGF-18 moiety
<220> FEATURE:
<221> NAME/KEY: MISC_FEATURE
<222> LOCATION: (162)..(186)
<223> OTHER INFORMATION: linker
<220> FEATURE:
<221> NAME/KEY: MISC_FEATURE
<222> LOCATION: (187)..(400)
<223> OTHER INFORMATION: Fab moiety

<400> SEQUENCE: 29
```

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Gly Gly Gly Ser Gly Gly Gly Ser Glu Pro Lys Ser Ser
                165                 170                 175

Asp Lys Thr His Thr Gly Gly Gly Ser Asp Ile Gln Met Thr Gln
            180                 185                 190

Ser Pro Ser Ser Leu Ser Ala Ser Val Gly Asp Arg Val Thr Ile Thr
            195                 200                 205

Cys Arg Ala Ser Gln Ser Ile Ser Asn Asn Leu Asn Trp Tyr Gln Gln
    210                 215                 220

Lys Pro Gly Lys Ala Pro Lys Leu Leu Ile Tyr Tyr Thr Ser Arg Phe
225                 230                 235                 240

His Ser Gly Val Pro Ser Arg Phe Ser Gly Ser Gly Ser Gly Thr Asp
                245                 250                 255

Phe Thr Phe Thr Ile Ser Ser Leu Gln Pro Glu Asp Ile Ala Thr Tyr
            260                 265                 270

Tyr Cys Gln Gln Glu His Thr Leu Pro Tyr Thr Phe Gly Gln Gly Thr
        275                 280                 285

Lys Leu Glu Ile Lys Arg Thr Val Ala Ala Pro Ser Val Phe Ile Phe
    290                 295                 300

```
Pro Pro Ser Asp Glu Gln Leu Lys Ser Gly Thr Ala Ser Val Val Cys
305                 310                 315                 320

Leu Leu Asn Asn Phe Tyr Pro Arg Glu Ala Lys Val Gln Trp Lys Val
                325                 330                 335

Asp Asn Ala Leu Gln Ser Gly Asn Ser Gln Glu Ser Val Thr Glu Gln
            340                 345                 350

Asp Ser Lys Asp Ser Thr Tyr Ser Leu Ser Ser Thr Leu Thr Leu Ser
        355                 360                 365

Lys Ala Asp Tyr Glu Lys His Lys Val Tyr Ala Cys Glu Val Thr His
    370                 375                 380

Gln Gly Leu Ser Ser Pro Val Thr Lys Ser Phe Asn Arg Gly Glu Cys
385                 390                 395                 400
```

<210> SEQ ID NO 30
<211> LENGTH: 398
<212> TYPE: PRT
<213> ORGANISM: artificial sequence
<220> FEATURE:
<223> OTHER INFORMATION: Amino acid sequence of FGF18QNQS Fab of
      anti-NGF, fusion via N-terminus of the light chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)
<223> OTHER INFORMATION: Fab moiety

<400> SEQUENCE: 30

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Gln
145                 150                 155                 160

Asn Phe Gln Ser Thr Thr Val Thr Lys Glu Pro Lys Ser Ser Asp Lys
                165                 170                 175

Thr His Thr Gly Gly Gly Gly Ser Asp Ile Gln Met Thr Gln Ser Pro
            180                 185                 190

Ser Ser Leu Ser Ala Ser Val Gly Asp Arg Val Thr Ile Thr Cys Arg
```

```
              195                 200                 205
Ala Ser Gln Ser Ile Ser Asn Asn Leu Asn Trp Tyr Gln Gln Lys Pro
        210                 215                 220

Gly Lys Ala Pro Lys Leu Leu Ile Tyr Tyr Thr Ser Arg Phe His Ser
225                 230                 235                 240

Gly Val Pro Ser Arg Phe Ser Gly Ser Gly Ser Gly Thr Asp Phe Thr
                245                 250                 255

Phe Thr Ile Ser Ser Leu Gln Pro Glu Asp Ile Ala Thr Tyr Tyr Cys
            260                 265                 270

Gln Gln Glu His Thr Leu Pro Tyr Thr Phe Gly Gln Gly Thr Lys Leu
        275                 280                 285

Glu Ile Lys Arg Thr Val Ala Ala Pro Ser Val Phe Ile Phe Pro Pro
290                 295                 300

Ser Asp Glu Gln Leu Lys Ser Gly Thr Ala Ser Val Val Cys Leu Leu
305                 310                 315                 320

Asn Asn Phe Tyr Pro Arg Glu Ala Lys Val Gln Trp Lys Val Asp Asn
                325                 330                 335

Ala Leu Gln Ser Gly Asn Ser Gln Glu Ser Val Thr Glu Gln Asp Ser
            340                 345                 350

Lys Asp Ser Thr Tyr Ser Leu Ser Ser Thr Leu Thr Leu Ser Lys Ala
        355                 360                 365

Asp Tyr Glu Lys His Lys Val Tyr Ala Cys Glu Val Thr His Gln Gly
370                 375                 380

Leu Ser Ser Pro Val Thr Lys Ser Phe Asn Arg Gly Glu Cys
385                 390                 395

<210> SEQ ID NO 31
<211> LENGTH: 398
<212> TYPE: PRT
<213> ORGANISM: artificial sequence
<220> FEATURE:
<223> OTHER INFORMATION: Amino acid sequence of FGF18Y191P Fab of
      anti-NGF, fusion via N-terminus of the light chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)
<223> OTHER INFORMATION: Fab moiety

<400> SEQUENCE: 31

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95
```

-continued

```
Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
        130                 135                 140

Val His Phe Met Lys Arg Tyr Pro Lys Gly Gln Pro Glu Leu Gln Lys
145                 150                 155                 160

Pro Phe Lys Pro Thr Thr Val Thr Lys Glu Pro Lys Ser Ser Asp Lys
                165                 170                 175

Thr His Thr Gly Gly Gly Gly Ser Asp Ile Gln Met Thr Gln Ser Pro
            180                 185                 190

Ser Ser Leu Ser Ala Ser Val Gly Asp Arg Val Thr Ile Thr Cys Arg
        195                 200                 205

Ala Ser Gln Ser Ile Ser Asn Asn Leu Asn Trp Tyr Gln Gln Lys Pro
    210                 215                 220

Gly Lys Ala Pro Lys Leu Leu Ile Tyr Tyr Thr Ser Arg Phe His Ser
225                 230                 235                 240

Gly Val Pro Ser Arg Phe Ser Gly Ser Gly Ser Gly Thr Asp Phe Thr
                245                 250                 255

Phe Thr Ile Ser Ser Leu Gln Pro Glu Asp Ile Ala Thr Tyr Tyr Cys
            260                 265                 270

Gln Gln Glu His Thr Leu Pro Tyr Thr Phe Gly Gln Gly Thr Lys Leu
        275                 280                 285

Glu Ile Lys Arg Thr Val Ala Ala Pro Ser Val Phe Ile Phe Pro Pro
    290                 295                 300

Ser Asp Glu Gln Leu Lys Ser Gly Thr Ala Ser Val Val Cys Leu Leu
305                 310                 315                 320

Asn Asn Phe Tyr Pro Arg Glu Ala Lys Val Gln Trp Lys Val Asp Asn
                325                 330                 335

Ala Leu Gln Ser Gly Asn Ser Gln Glu Ser Val Thr Glu Gln Asp Ser
            340                 345                 350

Lys Asp Ser Thr Tyr Ser Leu Ser Ser Thr Leu Thr Leu Ser Lys Ala
        355                 360                 365

Asp Tyr Glu Lys His Lys Val Tyr Ala Cys Glu Val Thr His Gln Gly
    370                 375                 380

Leu Ser Ser Pro Val Thr Lys Ser Phe Asn Arg Gly Glu Cys
385                 390                 395

<210> SEQ ID NO 32
<211> LENGTH: 398
<212> TYPE: PRT
<213> ORGANISM: artificial sequence
<220> FEATURE:
<223> OTHER INFORMATION: Amino acid sequence of FGF18_3Ala Fab of
      anti-NGF, fusion via N-terminus of the light chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)
<223> OTHER INFORMATION: Fab moiety

<400> SEQUENCE: 32
```

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Ala
145                 150                 155                 160

Ala Phe Ala Tyr Thr Thr Val Thr Lys Glu Pro Lys Ser Ser Asp Lys
                165                 170                 175

Thr His Thr Gly Gly Gly Ser Asp Ile Gln Met Thr Gln Ser Pro
            180                 185                 190

Ser Ser Leu Ser Ala Ser Val Gly Asp Arg Val Thr Ile Thr Cys Arg
        195                 200                 205

Ala Ser Gln Ser Ile Ser Asn Asn Leu Asn Trp Tyr Gln Gln Lys Pro
210                 215                 220

Gly Lys Ala Pro Lys Leu Leu Ile Tyr Tyr Thr Ser Arg Phe His Ser
225                 230                 235                 240

Gly Val Pro Ser Arg Phe Ser Gly Ser Gly Ser Gly Thr Asp Phe Thr
                245                 250                 255

Phe Thr Ile Ser Ser Leu Gln Pro Glu Asp Ile Ala Thr Tyr Tyr Cys
            260                 265                 270

Gln Gln Glu His Thr Leu Pro Tyr Thr Phe Gly Gln Gly Thr Lys Leu
        275                 280                 285

Glu Ile Lys Arg Thr Val Ala Ala Pro Ser Val Phe Ile Phe Pro Pro
290                 295                 300

Ser Asp Glu Gln Leu Lys Ser Gly Thr Ala Ser Val Val Cys Leu Leu
305                 310                 315                 320

Asn Asn Phe Tyr Pro Arg Glu Ala Lys Val Gln Trp Lys Val Asp Asn
                325                 330                 335

Ala Leu Gln Ser Gly Asn Ser Gln Glu Ser Val Thr Glu Gln Asp Ser
            340                 345                 350

Lys Asp Ser Thr Tyr Ser Leu Ser Ser Thr Leu Thr Leu Ser Lys Ala
        355                 360                 365

Asp Tyr Glu Lys His Lys Val Tyr Ala Cys Glu Val Thr His Gln Gly
370                 375                 380

Leu Ser Ser Pro Val Thr Lys Ser Phe Asn Arg Gly Glu Cys
385                 390                 395

<210> SEQ ID NO 33
<211> LENGTH: 398

```
<212> TYPE: PRT
<213> ORGANISM: artificial sequence
<220> FEATURE:
<223> OTHER INFORMATION: Amino acid sequence of FGF18VS Fab of anti-NGF,
      fusion via N-terminus of the light chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)
<223> OTHER INFORMATION: Fab moiety

<400> SEQUENCE: 33

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Val Ser Thr Thr Val Thr Lys Glu Pro Lys Ser Ser Asp Lys
                165                 170                 175

Thr His Thr Gly Gly Gly Gly Ser Asp Ile Gln Met Thr Gln Ser Pro
            180                 185                 190

Ser Ser Leu Ser Ala Ser Val Gly Asp Arg Val Thr Ile Thr Cys Arg
        195                 200                 205

Ala Ser Gln Ser Ile Ser Asn Asn Leu Asn Trp Tyr Gln Gln Lys Pro
    210                 215                 220

Gly Lys Ala Pro Lys Leu Leu Ile Tyr Tyr Thr Ser Arg Phe His Ser
225                 230                 235                 240

Gly Val Pro Ser Arg Phe Ser Gly Ser Gly Ser Gly Thr Asp Phe Thr
                245                 250                 255

Phe Thr Ile Ser Ser Leu Gln Pro Glu Asp Ile Ala Thr Tyr Tyr Cys
            260                 265                 270

Gln Gln Glu His Thr Leu Pro Tyr Thr Phe Gly Gln Gly Thr Lys Leu
        275                 280                 285

Glu Ile Lys Arg Thr Val Ala Ala Pro Ser Val Phe Ile Phe Pro Pro
    290                 295                 300

Ser Asp Glu Gln Leu Lys Ser Gly Thr Ala Ser Val Val Cys Leu Leu
305                 310                 315                 320
```

```
Asn Asn Phe Tyr Pro Arg Glu Ala Lys Val Gln Trp Lys Val Asp Asn
            325                 330                 335

Ala Leu Gln Ser Gly Asn Ser Gln Glu Ser Val Thr Glu Gln Asp Ser
        340                 345                 350

Lys Asp Ser Thr Tyr Ser Leu Ser Ser Thr Leu Thr Leu Ser Lys Ala
        355                 360                 365

Asp Tyr Glu Lys His Lys Val Tyr Ala Cys Glu Val Thr His Gln Gly
    370                 375                 380

Leu Ser Ser Pro Val Thr Lys Ser Phe Asn Arg Gly Glu Cys
385                 390                 395

<210> SEQ ID NO 34
<211> LENGTH: 403
<212> TYPE: PRT
<213> ORGANISM: artificial sequence
<220> FEATURE:
<223> OTHER INFORMATION: Amino acid sequence of FGF18-Fab of anti-NGF,
      fusion via N-terminus of the heavy chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(403)
<223> OTHER INFORMATION: Fab moiety

<400> SEQUENCE: 34

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175

Gly Gly Ser Gln Val Gln Leu Gln Glu Ser Gly Pro Gly Leu Val Lys
            180                 185                 190

Pro Ser Glu Thr Leu Ser Leu Thr Cys Thr Val Ser Gly Phe Ser Leu
        195                 200                 205

Ile Gly Tyr Asp Leu Asn Trp Ile Arg Gln Pro Pro Gly Lys Gly Leu
```

```
                    210                 215                 220
Glu Trp Ile Gly Ile Ile Trp Gly Asp Gly Thr Thr Asp Tyr Asn Ser
225                 230                 235                 240

Ala Val Lys Ser Arg Val Thr Ile Ser Lys Asp Thr Ser Lys Asn Gln
                245                 250                 255

Phe Ser Leu Lys Leu Ser Ser Val Thr Ala Ala Asp Thr Ala Val Tyr
                260                 265                 270

Tyr Cys Ala Arg Gly Gly Tyr Trp Tyr Ala Thr Ser Tyr Tyr Phe Asp
            275                 280                 285

Tyr Trp Gly Gln Gly Thr Leu Val Thr Val Ser Ser Ala Ser Thr Lys
        290                 295                 300

Gly Pro Ser Val Phe Pro Leu Ala Pro Ser Ser Lys Ser Thr Ser Gly
305                 310                 315                 320

Gly Thr Ala Ala Leu Gly Cys Leu Val Lys Asp Tyr Phe Pro Glu Pro
                325                 330                 335

Val Thr Val Ser Trp Asn Ser Gly Ala Leu Thr Ser Gly Val His Thr
                340                 345                 350

Phe Pro Ala Val Leu Gln Ser Ser Gly Leu Tyr Ser Leu Ser Ser Val
            355                 360                 365

Val Thr Val Pro Ser Ser Ser Leu Gly Thr Gln Thr Tyr Ile Cys Asn
        370                 375                 380

Val Asn His Lys Pro Ser Asn Thr Lys Val Asp Lys Lys Val Glu Pro
385                 390                 395                 400

Lys Ser Cys
```

<210> SEQ ID NO 35
<211> LENGTH: 410
<212> TYPE: PRT
<213> ORGANISM: artificial sequence
<220> FEATURE:
<223> OTHER INFORMATION: Amino acid sequence of FGF18TF-Fab of anti-NGF,
      fusion via N-terminus of the heavy chain
<220> FEATURE:
<221> NAME/KEY: MISC_FEATURE
<222> LOCATION: (1)..(161)
<223> OTHER INFORMATION: FGF-18 moiety
<220> FEATURE:
<221> NAME/KEY: MISC_FEATURE
<222> LOCATION: (162)..(186)
<223> OTHER INFORMATION: linker
<220> FEATURE:
<221> NAME/KEY: MISC_FEATURE
<222> LOCATION: (187)..(410)
<223> OTHER INFORMATION: Fab moiety

<400> SEQUENCE: 35

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
```

```
                100                 105                 110
Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Gly Gly Gly Ser Gly Gly Gly Ser Glu Pro Lys Ser Ser
                165                 170                 175

Asp Lys Thr His Thr Gly Gly Gly Ser Gln Val Gln Leu Gln Glu
                180                 185                 190

Ser Gly Pro Gly Leu Val Lys Pro Ser Glu Thr Leu Ser Leu Thr Cys
            195                 200                 205

Thr Val Ser Gly Phe Ser Leu Ile Gly Tyr Asp Leu Asn Trp Ile Arg
            210                 215                 220

Gln Pro Pro Gly Lys Gly Leu Glu Trp Ile Gly Ile Trp Gly Asp
225                 230                 235                 240

Gly Thr Thr Asp Tyr Asn Ser Ala Val Lys Ser Arg Val Thr Ile Ser
                245                 250                 255

Lys Asp Thr Ser Lys Asn Gln Phe Ser Leu Lys Leu Ser Ser Val Thr
                260                 265                 270

Ala Ala Asp Thr Ala Val Tyr Tyr Cys Ala Arg Gly Gly Tyr Trp Tyr
            275                 280                 285

Ala Thr Ser Tyr Tyr Phe Asp Tyr Trp Gly Gln Gly Thr Leu Val Thr
            290                 295                 300

Val Ser Ser Ala Ser Thr Lys Gly Pro Ser Val Phe Pro Leu Ala Pro
305                 310                 315                 320

Ser Ser Lys Ser Thr Ser Gly Gly Thr Ala Ala Leu Gly Cys Leu Val
                325                 330                 335

Lys Asp Tyr Phe Pro Glu Pro Val Thr Val Ser Trp Asn Ser Gly Ala
            340                 345                 350

Leu Thr Ser Gly Val His Thr Phe Pro Ala Val Leu Gln Ser Ser Gly
            355                 360                 365

Leu Tyr Ser Leu Ser Ser Val Val Thr Val Pro Ser Ser Ser Leu Gly
            370                 375                 380

Thr Gln Thr Tyr Ile Cys Asn Val Asn His Lys Pro Ser Asn Thr Lys
385                 390                 395                 400

Val Asp Lys Lys Val Glu Pro Lys Ser Cys
                405                 410

<210> SEQ ID NO 36
<211> LENGTH: 408
<212> TYPE: PRT
<213> ORGANISM: artificial sequence
<220> FEATURE:
<223> OTHER INFORMATION: Amino acid sequence of FGF18QNQS Fab of
      anti-NGF, fusion via N-terminus of the heavy chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(408)
<223> OTHER INFORMATION: Fab moiety
```

<400> SEQUENCE: 36

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Gln
145                 150                 155                 160

Asn Phe Gln Ser Thr Thr Val Thr Lys Glu Pro Lys Ser Ser Asp Lys
                165                 170                 175

Thr His Thr Gly Gly Gly Ser Gln Val Gln Leu Gln Glu Ser Gly
            180                 185                 190

Pro Gly Leu Val Lys Pro Ser Glu Thr Leu Ser Leu Thr Cys Thr Val
    195                 200                 205

Ser Gly Phe Ser Leu Ile Gly Tyr Asp Leu Asn Trp Ile Arg Gln Pro
210                 215                 220

Pro Gly Lys Gly Leu Glu Trp Ile Gly Ile Ile Trp Gly Asp Gly Thr
225                 230                 235                 240

Thr Asp Tyr Asn Ser Ala Val Lys Ser Arg Val Thr Ile Ser Lys Asp
                245                 250                 255

Thr Ser Lys Asn Gln Phe Ser Leu Lys Leu Ser Ser Val Thr Ala Ala
            260                 265                 270

Asp Thr Ala Val Tyr Tyr Cys Ala Arg Gly Gly Tyr Trp Tyr Ala Thr
        275                 280                 285

Ser Tyr Tyr Phe Asp Tyr Trp Gly Gln Gly Thr Leu Val Thr Val Ser
    290                 295                 300

Ser Ala Ser Thr Lys Gly Pro Ser Val Phe Pro Leu Ala Pro Ser Ser
305                 310                 315                 320

Lys Ser Thr Ser Gly Gly Thr Ala Ala Leu Gly Cys Leu Val Lys Asp
                325                 330                 335

Tyr Phe Pro Glu Pro Val Thr Val Ser Trp Asn Ser Gly Ala Leu Thr
            340                 345                 350

Ser Gly Val His Thr Phe Pro Ala Val Leu Gln Ser Ser Gly Leu Tyr
        355                 360                 365

Ser Leu Ser Ser Val Val Thr Val Pro Ser Ser Ser Leu Gly Thr Gln
    370                 375                 380

Thr Tyr Ile Cys Asn Val Asn His Lys Pro Ser Asn Thr Lys Val Asp
385                 390                 395                 400

Lys Lys Val Glu Pro Lys Ser Cys

-continued

```
                405

<210> SEQ ID NO 37
<211> LENGTH: 408
<212> TYPE: PRT
<213> ORGANISM: artificial sequence
<220> FEATURE:
<223> OTHER INFORMATION: Amino acid sequence of FGF18Y191P Fab of
      anti-NGF, fusion via N-terminus of the heavy chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(408)
<223> OTHER INFORMATION: Fab moiety

<400> SEQUENCE: 37

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Pro Thr Thr Val Thr Lys Glu Pro Lys Ser Ser Asp Lys
                165                 170                 175

Thr His Thr Gly Gly Gly Ser Gln Val Gln Leu Gln Glu Ser Gly
            180                 185                 190

Pro Gly Leu Val Lys Pro Ser Glu Thr Leu Ser Leu Thr Cys Thr Val
        195                 200                 205

Ser Gly Phe Ser Leu Ile Gly Tyr Asp Leu Asn Trp Ile Arg Gln Pro
    210                 215                 220

Pro Gly Lys Gly Leu Glu Trp Ile Gly Ile Ile Trp Gly Asp Gly Thr
225                 230                 235                 240

Thr Asp Tyr Asn Ser Ala Val Lys Ser Arg Val Thr Ile Ser Lys Asp
                245                 250                 255

Thr Ser Lys Asn Gln Phe Ser Leu Lys Leu Ser Ser Val Thr Ala Ala
            260                 265                 270

Asp Thr Ala Val Tyr Tyr Cys Ala Arg Gly Gly Tyr Trp Tyr Ala Thr
        275                 280                 285
```

-continued

```
Ser Tyr Tyr Phe Asp Tyr Trp Gly Gln Gly Thr Leu Val Thr Val Ser
290                 295                 300

Ser Ala Ser Thr Lys Gly Pro Ser Val Phe Pro Leu Ala Pro Ser Ser
305                 310                 315                 320

Lys Ser Thr Ser Gly Gly Thr Ala Ala Leu Gly Cys Leu Val Lys Asp
                325                 330                 335

Tyr Phe Pro Glu Pro Val Thr Val Ser Trp Asn Ser Gly Ala Leu Thr
            340                 345                 350

Ser Gly Val His Thr Phe Pro Ala Val Leu Gln Ser Ser Gly Leu Tyr
        355                 360                 365

Ser Leu Ser Ser Val Val Thr Val Pro Ser Ser Leu Gly Thr Gln
370                 375                 380

Thr Tyr Ile Cys Asn Val Asn His Lys Pro Ser Asn Thr Lys Val Asp
385                 390                 395                 400

Lys Lys Val Glu Pro Lys Ser Cys
                405

<210> SEQ ID NO 38
<211> LENGTH: 408
<212> TYPE: PRT
<213> ORGANISM: artificial sequence
<220> FEATURE:
<223> OTHER INFORMATION: Amino acid sequence of FGF18_3Ala Fab of
      anti-NGF, fusion via N-terminus of the heavy chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(408)
<223> OTHER INFORMATION: Fab moiety

<400> SEQUENCE: 38

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Ala
145                 150                 155                 160

Ala Phe Ala Tyr Thr Thr Val Thr Lys Glu Pro Lys Ser Ser Asp Lys
                165                 170                 175
```

```
Thr His Thr Gly Gly Gly Ser Gln Val Gln Leu Gln Glu Ser Gly
            180                 185                 190

Pro Gly Leu Val Lys Pro Ser Glu Thr Leu Ser Leu Thr Cys Thr Val
        195                 200                 205

Ser Gly Phe Ser Leu Ile Gly Tyr Asp Leu Asn Trp Ile Arg Gln Pro
    210                 215                 220

Pro Gly Lys Gly Leu Glu Trp Ile Gly Ile Ile Trp Gly Asp Gly Thr
225                 230                 235                 240

Thr Asp Tyr Asn Ser Ala Val Lys Ser Arg Val Thr Ile Ser Lys Asp
                245                 250                 255

Thr Ser Lys Asn Gln Phe Ser Leu Lys Leu Ser Ser Val Thr Ala Ala
            260                 265                 270

Asp Thr Ala Val Tyr Tyr Cys Ala Arg Gly Gly Tyr Trp Tyr Ala Thr
        275                 280                 285

Ser Tyr Tyr Phe Asp Tyr Trp Gly Gln Gly Thr Leu Val Thr Val Ser
    290                 295                 300

Ser Ala Ser Thr Lys Gly Pro Ser Val Phe Pro Leu Ala Pro Ser Ser
305                 310                 315                 320

Lys Ser Thr Ser Gly Gly Thr Ala Ala Leu Gly Cys Leu Val Lys Asp
                325                 330                 335

Tyr Phe Pro Glu Pro Val Thr Val Ser Trp Asn Ser Gly Ala Leu Thr
            340                 345                 350

Ser Gly Val His Thr Phe Pro Ala Val Leu Gln Ser Ser Gly Leu Tyr
        355                 360                 365

Ser Leu Ser Ser Val Val Thr Val Pro Ser Ser Ser Leu Gly Thr Gln
    370                 375                 380

Thr Tyr Ile Cys Asn Val Asn His Lys Pro Ser Asn Thr Lys Val Asp
385                 390                 395                 400

Lys Lys Val Glu Pro Lys Ser Cys
                405

<210> SEQ ID NO 39
<211> LENGTH: 408
<212> TYPE: PRT
<213> ORGANISM: artificial sequence
<220> FEATURE:
<223> OTHER INFORMATION: Amino acid sequence of FGF18VS Fab of anti-NGF,
      fusion via N-terminus of the heavy chain
<220> FEATURE:
<221> NAME/KEY: MISC_FEATURE
<222> LOCATION: (1)..(169)
<223> OTHER INFORMATION: FGF-18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(408)
<223> OTHER INFORMATION: Fab moiety

<400> SEQUENCE: 39

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
```

```
                    50                  55                  60
Thr Phe Gly Ser Gln Val Arg Ile Lys Gly Lys Glu Thr Glu Phe Tyr
 65                  70                  75                  80

Leu Cys Met Asn Arg Lys Gly Lys Leu Val Gly Lys Pro Asp Gly Thr
                     85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
                115                 120                 125

Lys Gly Arg Pro Arg Lys Gly Pro Lys Thr Arg Glu Asn Gln Gln Asp
            130                 135                 140

Val His Phe Met Lys Arg Tyr Pro Lys Gly Gln Pro Glu Leu Gln Lys
145                 150                 155                 160

Pro Phe Val Ser Thr Thr Val Thr Lys Glu Pro Lys Ser Ser Asp Lys
                165                 170                 175

Thr His Thr Gly Gly Gly Gly Ser Gln Val Gln Leu Gln Glu Ser Gly
                180                 185                 190

Pro Gly Leu Val Lys Pro Ser Glu Thr Leu Ser Leu Thr Cys Thr Val
                195                 200                 205

Ser Gly Phe Ser Leu Ile Gly Tyr Asp Leu Asn Trp Ile Arg Gln Pro
        210                 215                 220

Pro Gly Lys Gly Leu Glu Trp Ile Gly Ile Ile Trp Gly Asp Gly Thr
225                 230                 235                 240

Thr Asp Tyr Asn Ser Ala Val Lys Ser Arg Val Thr Ile Ser Lys Asp
                245                 250                 255

Thr Ser Lys Asn Gln Phe Ser Leu Lys Leu Ser Ser Val Thr Ala Ala
                260                 265                 270

Asp Thr Ala Val Tyr Tyr Cys Ala Arg Gly Gly Tyr Trp Tyr Ala Thr
            275                 280                 285

Ser Tyr Tyr Phe Asp Tyr Trp Gly Gln Gly Thr Leu Val Thr Val Ser
        290                 295                 300

Ser Ala Ser Thr Lys Gly Pro Ser Val Phe Pro Leu Ala Pro Ser Ser
305                 310                 315                 320

Lys Ser Thr Ser Gly Gly Thr Ala Ala Leu Gly Cys Leu Val Lys Asp
                325                 330                 335

Tyr Phe Pro Glu Pro Val Thr Val Ser Trp Asn Ser Gly Ala Leu Thr
                340                 345                 350

Ser Gly Val His Thr Phe Pro Ala Val Leu Gln Ser Ser Gly Leu Tyr
            355                 360                 365

Ser Leu Ser Ser Val Val Thr Val Pro Ser Ser Ser Leu Gly Thr Gln
        370                 375                 380

Thr Tyr Ile Cys Asn Val Asn His Lys Pro Ser Asn Thr Lys Val Asp
385                 390                 395                 400

Lys Lys Val Glu Pro Lys Ser Cys
                405

<210> SEQ ID NO 40
<211> LENGTH: 395
<212> TYPE: PRT
<213> ORGANISM: artificial sequence
<220> FEATURE:
<223> OTHER INFORMATION: Amino acid sequence of Fab of anti-NGF-
      FGF18_delta8, fusion via C-terminus of the light chain
<220> FEATURE:
<221> NAME/KEY: MISC_FEATURE
<222> LOCATION: (1)..(214)
```

<223> OTHER INFORMATION: Fab moiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(395)
<223> OTHER INFORMATION: FGF-18 moiety

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Pro Lys Ser Ser
    210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

Lys Tyr Ala Gln Leu Leu Val Glu Thr Asp Thr Phe Gly Ser Gln Val
    290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys

```
            355                 360                 365
Gly Pro Lys Thr Arg Glu Asn Gln Gln Asp Val His Phe Met Lys Arg
        370                 375                 380

Tyr Pro Lys Gly Gln Pro Glu Leu Gln Lys Pro
385                 390                 395

<210> SEQ ID NO 41
<211> LENGTH: 403
<212> TYPE: PRT
<213> ORGANISM: artificial sequence
<220> FEATURE:
<223> OTHER INFORMATION: Amino acid sequence of Fab of anti-NGF-
      FGF18QNQS, fusion via C-terminus of the light chain
<220> FEATURE:
<221> NAME/KEY: MISC_FEATURE
<222> LOCATION: (1)..(214)
<223> OTHER INFORMATION: Fab moiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF-18 moiety

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
    210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255
```

```
Lys Gln Leu Arg Leu Tyr Gln Leu Tyr Ser Arg Thr Ser Gly Lys His
                260                 265                 270

Ile Gln Val Leu Gly Arg Arg Ile Ser Ala Arg Gly Glu Asp Gly Asp
            275                 280                 285

Lys Tyr Ala Gln Leu Leu Val Glu Thr Asp Thr Phe Gly Ser Gln Val
        290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
370                 375                 380

Tyr Pro Lys Gly Gln Pro Glu Leu Gln Gln Asn Phe Gln Ser Thr Thr
385                 390                 395                 400

Val Thr Lys

<210> SEQ ID NO 42
<211> LENGTH: 403
<212> TYPE: PRT
<213> ORGANISM: artificial sequence
<220> FEATURE:
<223> OTHER INFORMATION: Amino acid sequence of Fab of anti-NGF-
      FGF18Y191P, fusion via C-terminus of the light chain
<220> FEATURE:
<221> NAME/KEY: MISC_FEATURE
<222> LOCATION: (1)..(214)
<223> OTHER INFORMATION: Fabmoiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF-18 moiety

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
    210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
                260                 265                 270

Ile Gln Val Leu Gly Arg Arg Ile Ser Ala Arg Gly Glu Asp Gly Asp
            275                 280                 285

Lys Tyr Ala Gln Leu Leu Val Glu Thr Asp Thr Phe Gly Ser Gln Val
290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
    370                 375                 380

Tyr Pro Lys Gly Gln Pro Glu Leu Gln Lys Pro Phe Lys Pro Thr Thr
385                 390                 395                 400

Val Thr Lys

<210> SEQ ID NO 43
<211> LENGTH: 403
<212> TYPE: PRT
<213> ORGANISM: artificial sequence
<220> FEATURE:
<223> OTHER INFORMATION: Amino acid sequence of Fab of anti-NGF-
      FGF18_3Ala, fusion via C-terminus of the light chain
<220> FEATURE:
<221> NAME/KEY: MISC_FEATURE
<222> LOCATION: (1)..(214)
<223> OTHER INFORMATION: Fab moiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF-18 moiety

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30
```

```
Leu Asn Trp Tyr Gln Gln Lys Pro Gly Lys Ala Pro Lys Leu Leu Ile
         35                  40                  45

Tyr Tyr Thr Ser Arg Phe His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Glu His Thr Leu Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
    210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

Lys Tyr Ala Gln Leu Leu Val Glu Thr Asp Thr Phe Gly Ser Gln Val
290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
370                 375                 380

Tyr Pro Lys Gly Gln Pro Glu Leu Gln Ala Ala Phe Ala Tyr Thr Thr
385                 390                 395                 400

Val Thr Lys

<210> SEQ ID NO 44
<211> LENGTH: 403
<212> TYPE: PRT
<213> ORGANISM: artificial sequence
<220> FEATURE:
<223> OTHER INFORMATION: Amino acid sequence of Fab of anti-NGF-FGF18VS,
      fusion via C-terminus of the light chain
```

-continued

```
<220> FEATURE:
<221> NAME/KEY: MISC_FEATURE
<222> LOCATION: (1)..(214)
<223> OTHER INFORMATION: Fab moiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF-18 moiety

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

Lys Tyr Ala Gln Leu Leu Val Glu Thr Asp Thr Phe Gly Ser Gln Val
290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
```

```
                340                 345                 350
Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
        370                 375                 380

Tyr Pro Lys Gly Gln Pro Glu Leu Gln Lys Pro Phe Val Ser Thr Thr
385                 390                 395                 400

Val Thr Lys

<210> SEQ ID NO 45
<211> LENGTH: 405
<212> TYPE: PRT
<213> ORGANISM: artificial sequence
<220> FEATURE:
<223> OTHER INFORMATION: Amino acid sequence of Fab of anti-NGF-
      FGF18TF, fusion via C-terminus of the heavy chain
<220> FEATURE:
<221> NAME/KEY: MISC_FEATURE
<222> LOCATION: (1)..(224)
<223> OTHER INFORMATION: Fab moiety
<220> FEATURE:
<221> NAME/KEY: MISC_FEATURE
<222> LOCATION: (225)..(244)
<223> OTHER INFORMATION: linker
<220> FEATURE:
<221> NAME/KEY: MISC_FEATURE
<222> LOCATION: (245)..(405)
<223> OTHER INFORMATION: FGF-18 moiety

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Gly Gly Gly Gly Ser Glu Pro Lys Ser Ser Asp Lys Thr His Thr Gly
```

-continued

```
                225                 230                 235                 240
        Gly Gly Gly Ser Glu Glu Asn Val Asp Phe Arg Ile His Val Glu Asn
                        245                 250                 255

Gln Thr Arg Ala Arg Asp Val Ser Arg Lys Gln Leu Arg Leu Tyr
                        260                 265                 270

Gln Leu Tyr Ser Arg Thr Ser Gly Lys His Ile Gln Val Leu Gly Arg
                        275                 280                 285

Arg Ile Ser Ala Arg Gly Glu Asp Gly Asp Lys Tyr Ala Gln Leu Leu
                        290                 295                 300

Val Glu Thr Asp Thr Phe Gly Ser Gln Val Arg Ile Lys Gly Lys Glu
        305                 310                 315                 320

Thr Glu Phe Tyr Leu Cys Met Asn Arg Lys Gly Lys Leu Val Gly Lys
                        325                 330                 335

Pro Asp Gly Thr Ser Lys Glu Cys Val Phe Ile Glu Lys Val Leu Glu
                        340                 345                 350

Asn Asn Tyr Thr Ala Leu Met Ser Ala Lys Tyr Ser Gly Trp Tyr Val
                        355                 360                 365

Gly Phe Thr Lys Lys Gly Arg Pro Arg Lys Gly Pro Lys Thr Arg Glu
                        370                 375                 380

Asn Gln Gln Asp Val His Phe Met Lys Arg Tyr Pro Lys Gly Gln Pro
        385                 390                 395                 400

Glu Leu Gln Lys Pro
                        405

<210> SEQ ID NO 46
<211> LENGTH: 413
<212> TYPE: PRT
<213> ORGANISM: artificial sequence
<220> FEATURE:
<223> OTHER INFORMATION: Amino acid sequence of Fab of anti-NGF-
      FGF18QNQS, fusion via C-terminus of the heavy chain
<220> FEATURE:
<221> NAME/KEY: MISC_FEATURE
<222> LOCATION: (1)..(224)
<223> OTHER INFORMATION: Fab moiety
<220> FEATURE:
<221> NAME/KEY: MISC_FEATURE
<222> LOCATION: (225)..(244)
<223> OTHER INFORMATION: linker
<220> FEATURE:
<221> NAME/KEY: MISC_FEATURE
<222> LOCATION: (245)..(413)
<223> OTHER INFORMATION: FGF-18 moiety

<400> SEQUENCE: 46

Gln Val Gln Leu Gln Glu Ser Gly Pro Gly Leu Val Lys Pro Ser Glu
        1               5                   10                  15

Thr Leu Ser Leu Thr Cys Thr Val Ser Gly Phe Ser Leu Ile Gly Tyr
                        20                  25                  30

Asp Leu Asn Trp Ile Arg Gln Pro Pro Gly Lys Gly Leu Glu Trp Ile
                        35                  40                  45

Gly Ile Ile Trp Gly Asp Gly Thr Thr Asp Tyr Asn Ser Ala Val Lys
                        50                  55                  60

Ser Arg Val Thr Ile Ser Lys Asp Thr Ser Lys Asn Gln Phe Ser Leu
        65                  70                  75                  80

Lys Leu Ser Ser Val Thr Ala Ala Asp Thr Ala Val Tyr Tyr Cys Ala
                        85                  90                  95

Arg Gly Gly Tyr Trp Tyr Ala Thr Ser Tyr Tyr Phe Asp Tyr Trp Gly
                        100                 105                 110
```

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Gly Ser Glu Pro Lys Ser Ser Asp Lys Thr His Thr Gly
225                 230                 235                 240

Gly Gly Gly Ser Glu Glu Asn Val Asp Phe Arg Ile His Val Glu Asn
                245                 250                 255

Gln Thr Arg Ala Arg Asp Asp Val Ser Arg Lys Gln Leu Arg Leu Tyr
            260                 265                 270

Gln Leu Tyr Ser Arg Thr Ser Gly Lys His Ile Gln Val Leu Gly Arg
        275                 280                 285

Arg Ile Ser Ala Arg Gly Glu Asp Gly Asp Lys Tyr Ala Gln Leu Leu
    290                 295                 300

Val Glu Thr Asp Thr Phe Gly Ser Gln Val Arg Ile Lys Gly Lys Glu
305                 310                 315                 320

Thr Glu Phe Tyr Leu Cys Met Asn Arg Lys Gly Lys Leu Val Gly Lys
                325                 330                 335

Pro Asp Gly Thr Ser Lys Glu Cys Val Phe Ile Glu Lys Val Leu Glu
            340                 345                 350

Asn Asn Tyr Thr Ala Leu Met Ser Ala Lys Tyr Ser Gly Trp Tyr Val
        355                 360                 365

Gly Phe Thr Lys Lys Gly Arg Pro Arg Lys Gly Pro Lys Thr Arg Glu
    370                 375                 380

Asn Gln Gln Asp Val His Phe Met Lys Arg Tyr Pro Lys Gly Gln Pro
385                 390                 395                 400

Glu Leu Gln Gln Asn Phe Gln Ser Thr Thr Val Thr Lys
                405                 410

<210> SEQ ID NO 47
<211> LENGTH: 413
<212> TYPE: PRT
<213> ORGANISM: artificial sequence
<220> FEATURE:
<223> OTHER INFORMATION: Amino acid sequence of Fab of anti-NGF-
      FGF18Y191P, fusion via C-terminus of the heavy chain
<220> FEATURE:
<221> NAME/KEY: MISC_FEATURE
<222> LOCATION: (1)..(224)
<223> OTHER INFORMATION: Fab moiety
<220> FEATURE:
<221> NAME/KEY: MISC_FEATURE
<222> LOCATION: (225)..(244)
<223> OTHER INFORMATION: linker
<220> FEATURE:
<221> NAME/KEY: MISC_FEATURE
<222> LOCATION: (245)..(413)
<223> OTHER INFORMATION: FGF-18 moiety

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Gly Gly Gly Gly Ser Glu Pro Lys Ser Ser Asp Lys Thr His Thr Gly
225                 230                 235                 240

Gly Gly Gly Ser Glu Glu Asn Val Asp Phe Arg Ile His Val Glu Asn
                245                 250                 255

Gln Thr Arg Ala Arg Asp Asp Val Ser Arg Lys Gln Leu Arg Leu Tyr
            260                 265                 270

Gln Leu Tyr Ser Arg Thr Ser Gly Lys His Ile Gln Val Leu Gly Arg
            275                 280                 285

Arg Ile Ser Ala Arg Gly Glu Asp Gly Asp Lys Tyr Ala Gln Leu Leu
            290                 295                 300

Val Glu Thr Asp Thr Phe Gly Ser Gln Val Arg Ile Lys Gly Lys Glu
305                 310                 315                 320

Thr Glu Phe Tyr Leu Cys Met Asn Arg Lys Gly Lys Leu Val Gly Lys
                325                 330                 335

Pro Asp Gly Thr Ser Lys Glu Cys Val Phe Ile Glu Lys Val Leu Glu
            340                 345                 350

Asn Asn Tyr Thr Ala Leu Met Ser Ala Lys Tyr Ser Gly Trp Tyr Val
            355                 360                 365

Gly Phe Thr Lys Lys Gly Arg Pro Arg Lys Gly Pro Lys Thr Arg Glu
        370                 375                 380

Asn Gln Gln Asp Val His Phe Met Lys Arg Tyr Pro Lys Gly Gln Pro
385                 390                 395                 400

Glu Leu Gln Lys Pro Phe Lys Pro Thr Thr Val Thr Lys
            405                 410

```
<210> SEQ ID NO 48
<211> LENGTH: 413
<212> TYPE: PRT
<213> ORGANISM: artificial sequence
<220> FEATURE:
<223> OTHER INFORMATION: Amino acid sequence of Fab of anti-NGF-
      FGF18_3Ala, fusion via C-terminus of the heavy chain
<220> FEATURE:
<221> NAME/KEY: MISC_FEATURE
<222> LOCATION: (1)..(224)
<223> OTHER INFORMATION: Fab moiety
<220> FEATURE:
<221> NAME/KEY: MISC_FEATURE
<222> LOCATION: (225)..(244)
<223> OTHER INFORMATION: linker
<220> FEATURE:
<221> NAME/KEY: MISC_FEATURE
<222> LOCATION: (245)..(413)
<223> OTHER INFORMATION: FGF-18 moiety

<400> SEQUENCE: 48
```

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Gly Ser Glu Pro Lys Ser Ser Asp Lys Thr His Thr Gly
225                 230                 235                 240

Gly Gly Gly Ser Glu Glu Asn Val Asp Phe Arg Ile His Val Glu Asn
                245                 250                 255

Gln Thr Arg Ala Arg Asp Asp Val Ser Arg Lys Gln Leu Arg Leu Tyr
            260                 265                 270

Gln Leu Tyr Ser Arg Thr Ser Gly Lys His Ile Gln Val Leu Gly Arg
        275                 280                 285

Arg Ile Ser Ala Arg Gly Glu Asp Gly Asp Lys Tyr Ala Gln Leu Leu
    290                 295                 300

```
Val Glu Thr Asp Thr Phe Gly Ser Gln Val Arg Ile Lys Gly Lys Glu
305                 310                 315                 320

Thr Glu Phe Tyr Leu Cys Met Asn Arg Lys Gly Lys Leu Val Gly Lys
                325                 330                 335

Pro Asp Gly Thr Ser Lys Glu Cys Val Phe Ile Glu Lys Val Leu Glu
            340                 345                 350

Asn Asn Tyr Thr Ala Leu Met Ser Ala Lys Tyr Ser Gly Trp Tyr Val
        355                 360                 365

Gly Phe Thr Lys Lys Gly Arg Pro Arg Lys Gly Pro Lys Thr Arg Glu
    370                 375                 380

Asn Gln Gln Asp Val His Phe Met Lys Arg Tyr Pro Lys Gly Gln Pro
385                 390                 395                 400

Glu Leu Gln Ala Ala Phe Ala Tyr Thr Thr Val Thr Lys
                405                 410
```

<210> SEQ ID NO 49
<211> LENGTH: 413
<212> TYPE: PRT
<213> ORGANISM: artificial sequence
<220> FEATURE:
<223> OTHER INFORMATION: Amino acid sequence of Fab of anti-NGF-FGF18VS, fusion via C-terminus of the heavy chain
<220> FEATURE:
<221> NAME/KEY: MISC_FEATURE
<222> LOCATION: (1)..(224)
<223> OTHER INFORMATION: Fab moiety
<220> FEATURE:
<221> NAME/KEY: MISC_FEATURE
<222> LOCATION: (225)..(244)
<223> OTHER INFORMATION: linker
<220> FEATURE:
<221> NAME/KEY: MISC_FEATURE
<222> LOCATION: (245)..(413)
<223> OTHER INFORMATION: FGF-18 moiety

<400> SEQUENCE: 49

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

-continued

```
                180                 185                 190
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Gly Gly Gly Gly Ser Glu Pro Lys Ser Ser Asp Lys Thr His Thr Gly
225                 230                 235                 240

Gly Gly Gly Ser Glu Glu Asn Val Asp Phe Arg Ile His Val Glu Asn
            245                 250                 255

Gln Thr Arg Ala Arg Asp Asp Val Ser Arg Lys Gln Leu Arg Leu Tyr
        260                 265                 270

Gln Leu Tyr Ser Arg Thr Ser Gly Lys His Ile Gln Val Leu Gly Arg
    275                 280                 285

Arg Ile Ser Ala Arg Gly Glu Asp Gly Asp Lys Tyr Ala Gln Leu Leu
        290                 295                 300

Val Glu Thr Asp Thr Phe Gly Ser Gln Val Arg Ile Lys Gly Lys Glu
305                 310                 315                 320

Thr Glu Phe Tyr Leu Cys Met Asn Arg Lys Gly Lys Leu Val Gly Lys
            325                 330                 335

Pro Asp Gly Thr Ser Lys Glu Cys Val Phe Ile Glu Lys Val Leu Glu
        340                 345                 350

Asn Asn Tyr Thr Ala Leu Met Ser Ala Lys Tyr Ser Gly Trp Tyr Val
    355                 360                 365

Gly Phe Thr Lys Lys Gly Arg Pro Arg Lys Gly Pro Lys Thr Arg Glu
        370                 375                 380

Asn Gln Gln Asp Val His Phe Met Lys Arg Tyr Pro Lys Gly Gln Pro
385                 390                 395                 400

Glu Leu Gln Lys Pro Phe Val Ser Thr Thr Val Thr Lys
            405                 410
```

<210> SEQ ID NO 50
<211> LENGTH: 393
<212> TYPE: PRT
<213> ORGANISM: artificial sequence
<220> FEATURE:
<223> OTHER INFORMATION: Amino acid sequence of FGF-18-Fab of anti-NGF,
    fusion via N-terminus of light chain of fasinumab
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(393)
<223> OTHER INFORMATION: Fab moiety

<400> SEQUENCE: 50

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60
```

```
Thr Phe Gly Ser Gln Val Arg Ile Lys Gly Lys Glu Thr Glu Phe Tyr
 65                  70                  75                  80

Leu Cys Met Asn Arg Lys Gly Lys Leu Val Gly Lys Pro Asp Gly Thr
             85                  90                  95

Ser Lys Glu Cys Val Phe Ile Glu Lys Val Leu Glu Asn Asn Tyr Thr
        100                 105                 110

Ala Leu Met Ser Ala Lys Tyr Ser Gly Trp Tyr Val Gly Phe Thr Lys
    115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly Gly
                165                 170                 175

Gly Gly Ser Asp Ile Gln Met Thr Gln Ser Pro Ser Ser Leu Ser Ala
            180                 185                 190

Ser Ala Gly Asp Arg Val Thr Ile Thr Cys Arg Ala Ser Gln Ala Ile
        195                 200                 205

Arg Asn Asp Leu Gly Trp Tyr Gln Gln Lys Pro Gly Lys Ala Pro Lys
210                 215                 220

Arg Leu Ile Tyr Ala Ala Phe Asn Leu Gln Ser Gly Val Pro Ser Arg
225                 230                 235                 240

Phe Ser Gly Ser Gly Ser Gly Thr Glu Phe Thr Leu Thr Ile Ser Ser
                245                 250                 255

Leu Gln Pro Glu Asp Leu Ala Ser Tyr Tyr Cys Gln Gln Tyr Asn Arg
            260                 265                 270

Tyr Pro Trp Thr Phe Gly Gln Gly Thr Lys Val Glu Ile Lys Arg Thr
        275                 280                 285

Val Ala Ala Pro Ser Val Phe Ile Phe Pro Pro Ser Asp Glu Gln Leu
    290                 295                 300

Lys Ser Gly Thr Ala Ser Val Val Cys Leu Leu Asn Asn Phe Tyr Pro
305                 310                 315                 320

Arg Glu Ala Lys Val Gln Trp Lys Val Asp Asn Ala Leu Gln Ser Gly
                325                 330                 335

Asn Ser Gln Glu Ser Val Thr Glu Gln Asp Ser Lys Asp Ser Thr Tyr
            340                 345                 350

Ser Leu Ser Ser Thr Leu Thr Leu Ser Lys Ala Asp Tyr Glu Lys His
        355                 360                 365

Lys Val Tyr Ala Cys Glu Val Thr His Gln Gly Leu Ser Ser Pro Val
370                 375                 380

Thr Lys Ser Phe Asn Arg Gly Glu Cys
385                 390

<210> SEQ ID NO 51
<211> LENGTH: 401
<212> TYPE: PRT
<213> ORGANISM: artificial sequence
<220> FEATURE:
<223> OTHER INFORMATION: Amino acid sequence of FGF-18-Fab of anti-NGF,
      fusion via N-terminus of heavy chain of fasinumab
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
```

```
<220> FEATURE:
<221> NAME/KEY: MISC_FEATURE
<222> LOCATION: (180)..(401)
<223> OTHER INFORMATION: Fab moiety

<400> SEQUENCE: 51
```

| | | | | | | | | | | | | | | | |
|---|---|---|---|---|---|---|---|---|---|---|---|---|---|---|---|
| Glu | Glu | Asn | Val | Asp | Phe | Arg | Ile | His | Val | Glu | Asn | Gln | Thr | Arg | Ala |
| 1 | | | | 5 | | | | | 10 | | | | | 15 | |
| Arg | Asp | Asp | Val | Ser | Arg | Lys | Gln | Leu | Arg | Leu | Tyr | Gln | Leu | Tyr | Ser |
| | | | 20 | | | | | 25 | | | | | 30 | | |
| Arg | Thr | Ser | Gly | Lys | His | Ile | Gln | Val | Leu | Gly | Arg | Arg | Ile | Ser | Ala |
| | | 35 | | | | | 40 | | | | | 45 | | | |
| Arg | Gly | Glu | Asp | Gly | Asp | Lys | Tyr | Ala | Gln | Leu | Leu | Val | Glu | Thr | Asp |
| | 50 | | | | | 55 | | | | | 60 | | | | |
| Thr | Phe | Gly | Ser | Gln | Val | Arg | Ile | Lys | Gly | Lys | Glu | Thr | Glu | Phe | Tyr |
| 65 | | | | | 70 | | | | | 75 | | | | | 80 |
| Leu | Cys | Met | Asn | Arg | Lys | Gly | Lys | Leu | Val | Gly | Lys | Pro | Asp | Gly | Thr |
| | | | | 85 | | | | | 90 | | | | | 95 | |
| Ser | Lys | Glu | Cys | Val | Phe | Ile | Glu | Lys | Val | Leu | Glu | Asn | Asn | Tyr | Thr |
| | | | 100 | | | | | 105 | | | | | 110 | | |
| Ala | Leu | Met | Ser | Ala | Lys | Tyr | Ser | Gly | Trp | Tyr | Val | Gly | Phe | Thr | Lys |
| | | | 115 | | | | | 120 | | | | | 125 | | |
| Lys | Gly | Arg | Pro | Arg | Lys | Gly | Pro | Lys | Thr | Arg | Glu | Asn | Gln | Gln | Asp |
| 130 | | | | | 135 | | | | | 140 | | | | | |
| Val | His | Phe | Met | Lys | Arg | Tyr | Pro | Lys | Gly | Gln | Pro | Glu | Leu | Gln | Lys |
| 145 | | | | | 150 | | | | | 155 | | | | | 160 |
| Pro | Phe | Lys | Tyr | Thr | Thr | Val | Thr | Lys | Gly | Gly | Gly | Ser | Gly | Gly |
| | | | | 165 | | | | | 170 | | | | | 175 | |
| Gly | Gly | Ser | Gln | Val | Gln | Leu | Val | Gln | Ser | Gly | Ala | Glu | Val | Lys | Lys |
| | | | 180 | | | | | 185 | | | | | 190 | | |
| Pro | Gly | Ala | Ser | Val | Lys | Val | Ser | Cys | Lys | Val | Ser | Gly | Phe | Thr | Leu |
| | | | 195 | | | | | 200 | | | | | 205 | | |
| Thr | Glu | Leu | Ser | Ile | His | Trp | Val | Arg | Gln | Ala | Pro | Gly | Lys | Gly | Leu |
| | 210 | | | | | 215 | | | | | 220 | | | | |
| Glu | Trp | Met | Gly | Gly | Phe | Asp | Pro | Glu | Asp | Gly | Glu | Thr | Ile | Tyr | Ala |
| 225 | | | | | 230 | | | | | 235 | | | | | 240 |
| Gln | Lys | Phe | Gln | Gly | Arg | Val | Thr | Met | Thr | Glu | Asp | Thr | Ser | Thr | Asp |
| | | | | 245 | | | | | 250 | | | | | 255 | |
| Thr | Ala | Tyr | Met | Glu | Leu | Thr | Ser | Leu | Arg | Ser | Glu | Asp | Thr | Ala | Val |
| | | | 260 | | | | | 265 | | | | | 270 | | |
| Tyr | Tyr | Cys | Ser | Thr | Ile | Phe | Gly | Val | Val | Thr | Asn | Phe | Asp | Asn | Trp |
| | | 275 | | | | | 280 | | | | | 285 | | | |
| Gly | Gln | Gly | Thr | Leu | Val | Thr | Val | Ser | Ser | Ala | Ser | Thr | Lys | Gly | Pro |
| | 290 | | | | | 295 | | | | | 300 | | | | |
| Ser | Val | Phe | Pro | Leu | Ala | Pro | Ser | Ser | Lys | Ser | Thr | Ser | Gly | Gly | Thr |
| 305 | | | | | 310 | | | | | 315 | | | | | 320 |
| Ala | Ala | Leu | Gly | Cys | Leu | Val | Lys | Asp | Tyr | Phe | Pro | Glu | Pro | Val | Thr |
| | | | | 325 | | | | | 330 | | | | | 335 | |
| Val | Ser | Trp | Asn | Ser | Gly | Ala | Leu | Thr | Ser | Gly | Val | His | Thr | Phe | Pro |
| | | | 340 | | | | | 345 | | | | | 350 | | |
| Ala | Val | Leu | Gln | Ser | Ser | Gly | Leu | Tyr | Ser | Leu | Ser | Ser | Val | Val | Thr |
| | | | 355 | | | | | 360 | | | | | 365 | | |
| Val | Pro | Ser | Ser | Ser | Leu | Gly | Thr | Gln | Thr | Tyr | Ile | Cys | Asn | Val | Asn |
| | 370 | | | | | 375 | | | | | 380 | | | | |

His Lys Pro Ser Asn Thr Lys Val Asp Lys Lys Val Glu Pro Lys Ser
385                 390                 395                 400

Cys

<210> SEQ ID NO 52
<211> LENGTH: 393
<212> TYPE: PRT
<213> ORGANISM: artificial sequence
<220> FEATURE:
<223> OTHER INFORMATION: Amino acid sequence of FGF-18-Fab of anti-NGF,
      fusion via N-terminus of light chain of fulranumab
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(393)
<223> OTHER INFORMATION: Fab moiety

<400> SEQUENCE: 52

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175

Gly Gly Ser Ala Ile Gln Leu Thr Gln Ser Pro Ser Ser Leu Ser Ala
            180                 185                 190

Ser Val Gly Asp Arg Val Thr Ile Thr Cys Arg Ala Ser Gln Gly Ile
        195                 200                 205

Ser Ser Ala Leu Ala Trp Tyr Gln Gln Lys Pro Gly Lys Ala Pro Lys
    210                 215                 220

Leu Leu Ile Tyr Asp Ala Ser Ser Leu Glu Ser Gly Val Pro Ser Arg
225                 230                 235                 240

Phe Ser Gly Ser Gly Ser Gly Thr Asp Phe Thr Leu Thr Ile Ser Ser
                245                 250                 255

Leu Gln Pro Glu Asp Phe Ala Thr Tyr Tyr Cys Gln Gln Phe Asn Ser
            260                 265                 270

```
Tyr Pro Leu Thr Phe Gly Gly Thr Lys Val Glu Ile Lys Arg Thr
            275                 280                 285

Val Ala Ala Pro Ser Val Phe Ile Phe Pro Pro Ser Asp Glu Gln Leu
    290                 295                 300

Lys Ser Gly Thr Ala Ser Val Val Cys Leu Leu Asn Asn Phe Tyr Pro
305                 310                 315                 320

Arg Glu Ala Lys Val Gln Trp Lys Val Asp Asn Ala Leu Gln Ser Gly
                325                 330                 335

Asn Ser Gln Glu Ser Val Thr Glu Gln Asp Ser Lys Asp Ser Thr Tyr
            340                 345                 350

Ser Leu Ser Ser Thr Leu Thr Leu Ser Lys Ala Asp Tyr Glu Lys His
        355                 360                 365

Lys Val Tyr Ala Cys Glu Val Thr His Gln Gly Leu Ser Ser Pro Val
    370                 375                 380

Thr Lys Ser Phe Asn Arg Gly Glu Cys
385                 390

<210> SEQ ID NO 53
<211> LENGTH: 405
<212> TYPE: PRT
<213> ORGANISM: artificial sequence
<220> FEATURE:
<223> OTHER INFORMATION: Amino acid sequence of FGF-18-Fab of anti-NGF,
      fusion via N-terminus of heavy chain of fulranumab
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(405)
<223> OTHER INFORMATION: Fab moiety

<400> SEQUENCE: 53

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175
```

```
Gly Gly Ser Glu Val Gln Leu Val Glu Ser Gly Gly Leu Val Gln
            180                 185                 190

Pro Gly Gly Ser Leu Arg Leu Ser Cys Ala Ala Ser Gly Phe Thr Leu
            195                 200                 205

Arg Ser Tyr Ser Met Asn Trp Val Arg Gln Ala Pro Gly Lys Gly Leu
        210                 215                 220

Glu Trp Val Ser Tyr Ile Ser Arg Ser Ser His Thr Ile Phe Tyr Ala
225                 230                 235                 240

Asp Ser Val Lys Gly Arg Phe Thr Ile Ser Arg Asp Asn Ala Lys Asn
                245                 250                 255

Ser Leu Tyr Leu Gln Met Asp Ser Leu Arg Asp Glu Asp Thr Ala Met
            260                 265                 270

Tyr Tyr Cys Ala Arg Val Tyr Ser Ser Gly Trp His Val Ser Asp Tyr
            275                 280                 285

Phe Asp Tyr Trp Gly Gln Gly Ile Leu Val Thr Val Ser Ser Ala Ser
        290                 295                 300

Thr Lys Gly Pro Ser Val Phe Pro Leu Ala Pro Ser Ser Lys Ser Thr
305                 310                 315                 320

Ser Gly Gly Thr Ala Ala Leu Gly Cys Leu Val Lys Asp Tyr Phe Pro
                325                 330                 335

Glu Pro Val Thr Val Ser Trp Asn Ser Gly Ala Leu Thr Ser Gly Val
            340                 345                 350

His Thr Phe Pro Ala Val Leu Gln Ser Ser Gly Leu Tyr Ser Leu Ser
            355                 360                 365

Ser Val Val Thr Val Pro Ser Ser Leu Gly Thr Gln Thr Tyr Ile
        370                 375                 380

Cys Asn Val Asn His Lys Pro Ser Asn Thr Lys Val Asp Lys Lys Val
385                 390                 395                 400

Glu Pro Lys Ser Cys
                405

<210> SEQ ID NO 54
<211> LENGTH: 414
<212> TYPE: PRT
<213> ORGANISM: artificial sequence
<220> FEATURE:
<223> OTHER INFORMATION: Amino acid sequence of FGF18-SEED, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(515)
<223> OTHER INFORMATION: AG chain moiety

<400> SEQUENCE: 54

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60
```

Thr Phe Gly Ser Gln Val Arg Ile Lys Gly Lys Thr Glu Phe Tyr
65                  70                  75                  80

Leu Cys Met Asn Arg Lys Gly Lys Leu Val Gly Lys Pro Asp Gly Thr
            85                  90                  95

Ser Lys Glu Cys Val Phe Ile Glu Lys Val Leu Glu Asn Asn Tyr Thr
        100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Ser Gly Gly Ser Gly
                165                 170                 175

Ser Gly Ser Glu Pro Lys Ser Ser Asp Lys Thr His Thr Cys Pro Pro
            180                 185                 190

Cys Pro Ala Pro Glu Ala Ala Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Phe Arg Pro Glu Val His Leu Leu Pro Pro Ser Arg Glu
305                 310                 315                 320

Glu Met Thr Lys Asn Gln Val Ser Leu Thr Cys Leu Ala Arg Gly Phe
                325                 330                 335

Tyr Pro Lys Asp Ile Ala Val Glu Trp Glu Ser Asn Gly Gln Pro Glu
            340                 345                 350

Asn Asn Tyr Lys Thr Thr Pro Ser Arg Gln Glu Pro Ser Gln Gly Thr
        355                 360                 365

Thr Thr Phe Ala Val Thr Ser Lys Leu Thr Val Asp Lys Ser Arg Trp
    370                 375                 380

Gln Gln Gly Asn Val Phe Ser Cys Ser Val Met His Glu Ala Leu His
385                 390                 395                 400

Asn His Tyr Thr Gln Lys Thr Ile Ser Leu Ser Pro Gly Lys
                405                 410

<210> SEQ ID NO 55
<211> LENGTH: 409
<212> TYPE: PRT
<213> ORGANISM: artificial sequence
<220> FEATURE:
<223> OTHER INFORMATION: Amino acid sequence of FGF18-SEED, AG chain
<220> FEATURE:
<221> NAME/KEY: MISC_FEATURE
<222> LOCATION: (1)..(169)
<223> OTHER INFORMATION: FGF18 moiety
<220> FEATURE:

<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(409)
<223> OTHER INFORMATION: AG chain moiety

<400> SEQUENCE: 55

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Gly Ser Gly Gly
                165                 170                 175

Gly Gly Ser Asp Lys Thr His Thr Cys Pro Pro Cys Pro Ala Pro Glu
            180                 185                 190

Ala Ala Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Phe Arg
    290                 295                 300

Pro Glu Val His Leu Leu Pro Pro Ser Arg Glu Glu Met Thr Lys Asn
305                 310                 315                 320

Gln Val Ser Leu Thr Cys Leu Ala Arg Gly Phe Tyr Pro Lys Asp Ile
                325                 330                 335

Ala Val Glu Trp Glu Ser Asn Gly Gln Pro Glu Asn Asn Tyr Lys Thr
            340                 345                 350

Thr Pro Ser Arg Gln Glu Pro Ser Gln Gly Thr Thr Thr Phe Ala Val
        355                 360                 365
```

```
Thr Ser Lys Leu Thr Val Asp Lys Ser Arg Trp Gln Gln Gly Asn Val
        370             375             380
Phe Ser Cys Ser Val Met His Glu Ala Leu His Asn His Tyr Thr Gln
385             390             395             400
Lys Thr Ile Ser Leu Ser Pro Gly Lys
                405

<210> SEQ ID NO 56
<211> LENGTH: 454
<212> TYPE: PRT
<213> ORGANISM: artificial sequence
<220> FEATURE:
<223> OTHER INFORMATION: Amino acid sequence of an anti-NGF GA chain

<400> SEQUENCE: 56

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Ile Gly Tyr
            20                  25                  30
Asp Leu Asn Trp Ile Arg Gln Pro Pro Gly Lys Gly Leu Glu Trp Ile
        35                  40                  45
Gly Ile Ile Trp Gly Asp Gly Thr Thr Asp Tyr Asn Ser Ala Val Lys
    50                  55                  60
Ser Arg Val Thr Ile Ser Lys Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Gly Tyr Trp Tyr Ala Thr Ser Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Glu Glu Leu Ala Leu Asn Glu Leu Val
            355                 360                 365
Thr Leu Thr Cys Leu Val Lys Gly Phe Tyr Pro Ser Asp Ile Ala Val
        370                 375                 380
Glu Trp Leu Gln Gly Ser Gln Glu Leu Pro Arg Glu Lys Tyr Leu Thr
385                 390                 395                 400
Trp Ala Pro Val Leu Asp Ser Asp Gly Ser Phe Phe Leu Tyr Ser Ile
                405                 410                 415
Leu Arg Val Ala Ala Glu Asp Trp Lys Lys Gly Asp Thr Phe Ser Cys
                420                 425                 430
Ser Val Met His Glu Ala Leu His Asn Arg Phe Thr Gln Lys Ser Leu
                435                 440                 445
Asp Arg Ser Pro Gly Lys
    450

<210> SEQ ID NO 57
<211> LENGTH: 409
<212> TYPE: PRT
<213> ORGANISM: artificial sequence
<220> FEATURE:
<223> OTHER INFORMATION: Amino acid sequence of FGF18-SEED, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(409)
<223> OTHER INFORMATION: AG chain moiety

<400> SEQUENCE: 57

Glu Glu Asn Val Asp Phe Arg Ile His Val Glu Asn Gln Thr Arg Ala
1               5                   10                  15
Arg Asp Asp Val Ser Arg Lys Gln Leu Arg Leu Tyr Gln Leu Tyr Ser
            20                  25                  30
Arg Thr Ser Gly Lys His Ile Gln Val Leu Gly Arg Arg Ile Ser Ala
        35                  40                  45
Arg Gly Glu Asp Gly Asp Lys Tyr Ala Gln Leu Leu Val Glu Thr Asp
    50                  55                  60
Thr Phe Gly Ser Gln Val Arg Ile Lys Gly Lys Glu Thr Glu Phe Tyr
65                  70                  75                  80
Leu Cys Met Asn Arg Lys Gly Lys Leu Val Gly Lys Pro Asp Gly Thr
                85                  90                  95
Ser Lys Glu Cys Val Phe Ile Glu Lys Val Leu Glu Asn Asn Tyr Thr
            100                 105                 110
Ala Leu Met Ser Ala Lys Tyr Ser Gly Trp Tyr Val Gly Phe Thr Lys
        115                 120                 125
Lys Gly Arg Pro Arg Lys Gly Pro Lys Thr Arg Glu Asn Gln Gln Asp
    130                 135                 140
Val His Phe Met Lys Arg Tyr Pro Lys Gly Gln Pro Glu Leu Gln Lys
145                 150                 155                 160
```

Pro Phe Lys Tyr Thr Thr Val Thr Lys Gly Gly Gly Ser Gly Gly
                165                 170                 175

Gly Gly Ser Asp Lys Thr His Thr Cys Pro Pro Cys Pro Ala Pro Glu
            180                 185                 190

Ala Ala Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Phe Arg
    290                 295                 300

Pro Glu Val His Leu Leu Pro Pro Ser Arg Glu Glu Met Thr Lys Asn
305                 310                 315                 320

Gln Val Ser Leu Thr Cys Leu Ala Arg Gly Phe Tyr Pro Lys Asp Ile
                325                 330                 335

Ala Val Glu Trp Glu Ser Asn Gly Gln Pro Glu Asn Asn Tyr Lys Thr
            340                 345                 350

Thr Pro Ser Arg Gln Glu Pro Ser Gln Gly Thr Thr Thr Phe Ala Val
        355                 360                 365

Thr Ser Lys Leu Thr Val Asp Lys Ser Arg Trp Gln Gln Gly Asn Val
    370                 375                 380

Phe Ser Cys Ser Val Met His Glu Ala Leu His Asn His Tyr Thr Gln
385                 390                 395                 400

Lys Thr Ile Ser Leu Ser Pro Gly Lys
                405

<210> SEQ ID NO 58
<211> LENGTH: 452
<212> TYPE: PRT
<213> ORGANISM: artificial sequence
<220> FEATURE:
<223> OTHER INFORMATION: Amino acid sequence of an anti-NGF GA chain

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Pro Ser Glu Glu Leu Ala Leu Asn Glu Leu Val Thr Leu
        355                 360                 365

Thr Cys Leu Val Lys Gly Phe Tyr Pro Ser Asp Ile Ala Val Glu Trp
370                 375                 380

Leu Gln Gly Ser Gln Glu Leu Pro Arg Glu Lys Tyr Leu Thr Trp Ala
385                 390                 395                 400

Pro Val Leu Asp Ser Asp Gly Ser Phe Phe Leu Tyr Ser Ile Leu Arg
                405                 410                 415

Val Ala Ala Glu Asp Trp Lys Lys Gly Asp Thr Phe Ser Cys Ser Val
            420                 425                 430

Met His Glu Ala Leu His Asn Arg Phe Thr Gln Lys Ser Leu Asp Arg
        435                 440                 445

Ser Pro Gly Lys
        450

<210> SEQ ID NO 59
<211> LENGTH: 409
<212> TYPE: PRT
<213> ORGANISM: artificial sequence
<220> FEATURE:
<223> OTHER INFORMATION: Amino acid sequence of an FGF18-SEED, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
```

```
<222> LOCATION: (170)..(179)
<223> OTHER INFORMATION: linker
<220> FEATURE:
<221> NAME/KEY: MISC_FEATURE
<222> LOCATION: (180)..(409)
<223> OTHER INFORMATION: AG chain moiety

<400> SEQUENCE: 59
```

| | | | | | | | | | | | | | | |
|---|---|---|---|---|---|---|---|---|---|---|---|---|---|---|
| Glu | Glu | Asn | Val | Asp | Phe | Arg | Ile | His | Val | Glu | Asn | Gln | Thr | Arg | Ala |
| 1 | | | | 5 | | | | | 10 | | | | | 15 | |
| Arg | Asp | Asp | Val | Ser | Arg | Lys | Gln | Leu | Arg | Leu | Tyr | Gln | Leu | Tyr | Ser |
| | | | 20 | | | | | 25 | | | | | 30 | | |
| Arg | Thr | Ser | Gly | Lys | His | Ile | Gln | Val | Leu | Gly | Arg | Arg | Ile | Ser | Ala |
| | | 35 | | | | | 40 | | | | | 45 | | | |
| Arg | Gly | Glu | Asp | Gly | Asp | Lys | Tyr | Ala | Gln | Leu | Leu | Val | Glu | Thr | Asp |
| | 50 | | | | | 55 | | | | | 60 | | | | |
| Thr | Phe | Gly | Ser | Gln | Val | Arg | Ile | Lys | Gly | Lys | Glu | Thr | Glu | Phe | Tyr |
| 65 | | | | | 70 | | | | | 75 | | | | | 80 |
| Leu | Cys | Met | Asn | Arg | Lys | Gly | Lys | Leu | Val | Gly | Lys | Pro | Asp | Gly | Thr |
| | | | | 85 | | | | | 90 | | | | | 95 | |
| Ser | Lys | Glu | Cys | Val | Phe | Ile | Glu | Lys | Val | Leu | Glu | Asn | Asn | Tyr | Thr |
| | | | 100 | | | | | 105 | | | | | 110 | | |
| Ala | Leu | Met | Ser | Ala | Lys | Tyr | Ser | Gly | Trp | Tyr | Val | Gly | Phe | Thr | Lys |
| | | 115 | | | | | 120 | | | | | 125 | | | |
| Lys | Gly | Arg | Pro | Arg | Lys | Gly | Pro | Lys | Thr | Arg | Glu | Asn | Gln | Gln | Asp |
| | 130 | | | | | 135 | | | | | 140 | | | | |
| Val | His | Phe | Met | Lys | Arg | Tyr | Pro | Lys | Gly | Gln | Pro | Glu | Leu | Gln | Lys |
| 145 | | | | | 150 | | | | | 155 | | | | | 160 |
| Pro | Phe | Lys | Tyr | Thr | Thr | Val | Thr | Lys | Gly | Gly | Gly | Ser | Gly | Gly |
| | | | | 165 | | | | | 170 | | | | | 175 |
| Gly | Gly | Ser | Asp | Lys | Thr | His | Thr | Cys | Pro | Pro | Cys | Pro | Ala | Pro | Glu |
| | | | 180 | | | | | 185 | | | | | 190 | | |
| Ala | Ala | Gly | Gly | Pro | Ser | Val | Phe | Leu | Phe | Pro | Pro | Lys | Pro | Lys | Asp |
| | | 195 | | | | | 200 | | | | | 205 | | | |
| Thr | Leu | Met | Ile | Ser | Arg | Thr | Pro | Glu | Val | Thr | Cys | Val | Val | Val | Asp |
| 210 | | | | | 215 | | | | | 220 | | | | | |
| Val | Ser | His | Glu | Asp | Pro | Glu | Val | Lys | Phe | Asn | Trp | Tyr | Val | Asp | Gly |
| 225 | | | | | 230 | | | | | 235 | | | | | 240 |
| Val | Glu | Val | His | Asn | Ala | Lys | Thr | Lys | Pro | Arg | Glu | Glu | Gln | Tyr | Asn |
| | | | | 245 | | | | | 250 | | | | | 255 | |
| Ser | Thr | Tyr | Arg | Val | Val | Ser | Val | Leu | Thr | Val | Leu | His | Gln | Asp | Trp |
| | | | 260 | | | | | 265 | | | | | 270 | | |
| Leu | Asn | Gly | Lys | Glu | Tyr | Lys | Cys | Lys | Val | Ser | Asn | Lys | Ala | Leu | Pro |
| | | 275 | | | | | 280 | | | | | 285 | | | |
| Ala | Pro | Ile | Glu | Lys | Thr | Ile | Ser | Lys | Ala | Lys | Gly | Gln | Pro | Phe | Arg |
| | 290 | | | | | 295 | | | | | 300 | | | | |
| Pro | Glu | Val | His | Leu | Leu | Pro | Pro | Ser | Arg | Glu | Glu | Met | Thr | Lys | Asn |
| 305 | | | | | 310 | | | | | 315 | | | | | 320 |
| Gln | Val | Ser | Leu | Thr | Cys | Leu | Ala | Arg | Gly | Phe | Tyr | Pro | Lys | Asp | Ile |
| | | | | 325 | | | | | 330 | | | | | 335 | |
| Ala | Val | Glu | Trp | Glu | Ser | Asn | Gly | Gln | Pro | Glu | Asn | Asn | Tyr | Lys | Thr |
| | | | 340 | | | | | 345 | | | | | 350 | | |
| Thr | Pro | Ser | Arg | Gln | Glu | Pro | Ser | Gln | Gly | Thr | Thr | Thr | Phe | Ala | Val |
| | | 355 | | | | | 360 | | | | | 365 | | | |
| Thr | Ser | Lys | Leu | Thr | Val | Asp | Lys | Ser | Arg | Trp | Gln | Gln | Gly | Asn | Val |

```
                    370                 375                 380
Phe Ser Cys Ser Val Met His Glu Ala Leu His Asn His Tyr Thr Gln
385                 390                 395                 400

Lys Thr Ile Ser Leu Ser Pro Gly Lys
                405

<210> SEQ ID NO 60
<211> LENGTH: 456
<212> TYPE: PRT
<213> ORGANISM: artificial sequence
<220> FEATURE:
<223> OTHER INFORMATION: Amino acid sequence of an anti-NGF GA chain

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
                20                  25                  30

Ser Met Asn Trp Val Arg Gln Ala Pro Gly Lys Gly Leu Glu Trp Val
            35                  40                  45

Ser Tyr Ile Ser Arg Ser Ser His Thr Ile Phe Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Met Tyr Tyr Cys
                85                  90                  95

Ala Arg Val Tyr Ser Ser Gly Trp His Val Ser Asp Tyr Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                      325                 330                 335
Pro Ile Glu Lys Thr Ile Ser Lys Ala Lys Gly Gln Pro Arg Glu Pro
            340                 345                 350

Gln Val Tyr Thr Leu Pro Pro Ser Glu Glu Leu Ala Leu Asn Glu
        355                 360                 365

Leu Val Thr Leu Thr Cys Leu Val Lys Gly Phe Tyr Pro Ser Asp Ile
        370                 375                 380

Ala Val Glu Trp Leu Gln Gly Ser Gln Glu Leu Pro Arg Glu Lys Tyr
385                 390                 395                 400

Leu Thr Trp Ala Pro Val Leu Asp Ser Asp Gly Ser Phe Phe Leu Tyr
                405                 410                 415

Ser Ile Leu Arg Val Ala Ala Glu Asp Trp Lys Lys Gly Asp Thr Phe
                420                 425                 430

Ser Cys Ser Val Met His Glu Ala Leu His Asn Arg Phe Thr Gln Lys
                435                 440                 445

Ser Leu Asp Arg Ser Pro Gly Lys
        450                 455

<210> SEQ ID NO 61
<211> LENGTH: 398
<212> TYPE: PRT
<213> ORGANISM: artificial sequence
<220> FEATURE:
<223> OTHER INFORMATION: Amino acid sequence of FGF18_3Ala_IgG-light
      chain, fusion via the N-terminus of the sequence
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(398)
<223> OTHER INFORMATION: light chain moiety

<400> SEQUENCE: 61

Glu Glu Asn Val Asp Phe Arg Ile His Val Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Ala
145                 150                 155                 160
```

-continued

```
Ala Phe Ala Tyr Thr Thr Val Thr Lys Glu Pro Lys Ser Ser Asp Lys
                165                 170                 175

Thr His Thr Gly Gly Gly Gly Ser Asp Ile Gln Met Thr Gln Ser Pro
            180                 185                 190

Ser Ser Leu Ser Ala Ser Val Gly Asp Arg Val Thr Ile Thr Cys Arg
        195                 200                 205

Ala Ser Gln Ser Ile Ser Asn Asn Leu Asn Trp Tyr Gln Gln Lys Pro
    210                 215                 220

Gly Lys Ala Pro Lys Leu Leu Ile Tyr Tyr Thr Ser Arg Phe His Ser
225                 230                 235                 240

Gly Val Pro Ser Arg Phe Ser Gly Ser Gly Ser Gly Thr Asp Phe Thr
                245                 250                 255

Phe Thr Ile Ser Ser Leu Gln Pro Glu Asp Ile Ala Thr Tyr Tyr Cys
            260                 265                 270

Gln Gln Glu His Thr Leu Pro Tyr Thr Phe Gly Gln Gly Thr Lys Leu
        275                 280                 285

Glu Ile Lys Arg Thr Val Ala Ala Pro Ser Val Phe Ile Phe Pro Pro
    290                 295                 300

Ser Asp Glu Gln Leu Lys Ser Gly Thr Ala Ser Val Val Cys Leu Leu
305                 310                 315                 320

Asn Asn Phe Tyr Pro Arg Glu Ala Lys Val Gln Trp Lys Val Asp Asn
                325                 330                 335

Ala Leu Gln Ser Gly Asn Ser Gln Glu Ser Val Thr Glu Gln Asp Ser
            340                 345                 350

Lys Asp Ser Thr Tyr Ser Leu Ser Ser Thr Leu Thr Leu Ser Lys Ala
        355                 360                 365

Asp Tyr Glu Lys His Lys Val Tyr Ala Cys Glu Val Thr His Gln Gly
    370                 375                 380

Leu Ser Ser Pro Val Thr Lys Ser Phe Asn Arg Gly Glu Cys
385                 390                 395
```

```
<210> SEQ ID NO 62
<211> LENGTH: 635
<212> TYPE: PRT
<213> ORGANISM: artificial sequence
<220> FEATURE:
<223> OTHER INFORMATION: Amino acid sequence of FGF18_3Ala_IgG-heavy
      chain, fusion via the N-terminus of the sequence
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(635)
<223> OTHER INFORMATION: AG chain moiety

<400> SEQUENCE: 62

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60
```

```
Thr Phe Gly Ser Gln Val Arg Ile Lys Gly Lys Glu Thr Glu Phe Tyr
 65                  70                  75                  80

Leu Cys Met Asn Arg Lys Gly Lys Leu Val Gly Lys Pro Asp Gly Thr
                 85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Ala
145                 150                 155                 160

Ala Phe Ala Tyr Thr Thr Val Thr Lys Glu Pro Lys Ser Ser Asp Lys
                165                 170                 175

Thr His Thr Gly Gly Gly Gly Ser Gln Val Gln Leu Gln Glu Ser Gly
                180                 185                 190

Pro Gly Leu Val Lys Pro Ser Glu Thr Leu Ser Leu Thr Cys Thr Val
            195                 200                 205

Ser Gly Phe Ser Leu Ile Gly Tyr Asp Leu Asn Trp Ile Arg Gln Pro
210                 215                 220

Pro Gly Lys Gly Leu Glu Trp Ile Gly Ile Ile Trp Gly Asp Gly Thr
225                 230                 235                 240

Thr Asp Tyr Asn Ser Ala Val Lys Ser Arg Val Thr Ile Ser Lys Asp
                245                 250                 255

Thr Ser Lys Asn Gln Phe Ser Leu Lys Leu Ser Ser Val Thr Ala Ala
                260                 265                 270

Asp Thr Ala Val Tyr Tyr Cys Ala Arg Gly Gly Tyr Trp Tyr Ala Thr
            275                 280                 285

Ser Tyr Tyr Phe Asp Tyr Trp Gly Gln Gly Thr Leu Val Thr Val Ser
290                 295                 300

Ser Ala Ser Thr Lys Gly Pro Ser Val Phe Pro Leu Ala Pro Ser Ser
305                 310                 315                 320

Lys Ser Thr Ser Gly Gly Thr Ala Ala Leu Gly Cys Leu Val Lys Asp
                325                 330                 335

Tyr Phe Pro Glu Pro Val Thr Val Ser Trp Asn Ser Gly Ala Leu Thr
                340                 345                 350

Ser Gly Val His Thr Phe Pro Ala Val Leu Gln Ser Ser Gly Leu Tyr
            355                 360                 365

Ser Leu Ser Ser Val Val Thr Val Pro Ser Ser Ser Leu Gly Thr Gln
370                 375                 380

Thr Tyr Ile Cys Asn Val Asn His Lys Pro Ser Asn Thr Lys Val Asp
385                 390                 395                 400

Lys Lys Val Glu Pro Lys Ser Cys Asp Lys Thr His Thr Cys Pro Pro
                405                 410                 415

Cys Pro Ala Pro Glu Ala Ala Gly Gly Pro Ser Val Phe Leu Phe Pro
                420                 425                 430

Pro Lys Pro Lys Asp Thr Leu Met Ile Ser Arg Thr Pro Glu Val Thr
            435                 440                 445

Cys Val Val Val Asp Val Ser His Glu Asp Pro Glu Val Lys Phe Asn
450                 455                 460

Trp Tyr Val Asp Gly Val Glu Val His Asn Ala Lys Thr Lys Pro Arg
465                 470                 475                 480
```

-continued

```
Glu Glu Gln Tyr Asn Ser Thr Tyr Arg Val Val Ser Val Leu Thr Val
                485                 490                 495

Leu His Gln Asp Trp Leu Asn Gly Lys Glu Tyr Lys Cys Lys Val Ser
        500                 505                 510

Asn Lys Ala Leu Gly Ala Pro Ile Glu Lys Thr Ile Ser Lys Ala Lys
        515                 520                 525

Gly Gln Pro Arg Glu Pro Gln Val Tyr Thr Leu Pro Pro Ser Arg Asp
    530                 535                 540

Glu Leu Thr Lys Asn Gln Val Ser Leu Thr Cys Leu Val Lys Gly Phe
545                 550                 555                 560

Tyr Pro Ser Asp Ile Ala Val Glu Trp Glu Ser Asn Gly Gln Pro Glu
                565                 570                 575

Asn Asn Tyr Lys Thr Thr Pro Pro Val Leu Asp Ser Asp Gly Ser Phe
            580                 585                 590

Phe Leu Tyr Ser Lys Leu Thr Val Asp Lys Ser Arg Trp Gln Gln Gly
        595                 600                 605

Asn Val Phe Ser Cys Ser Val Met His Glu Ala Leu His Asn His Tyr
    610                 615                 620

Thr Gln Lys Ser Leu Ser Leu Ser Pro Gly Lys
625                 630                 635

<210> SEQ ID NO 63
<211> LENGTH: 403
<212> TYPE: PRT
<213> ORGANISM: artificial sequence
<220> FEATURE:
<223> OTHER INFORMATION: Amino acid sequence of IgG-light chain -
      FGF18_3Ala, fusion via the C-terminus of the sequence
<220> FEATURE:
<221> NAME/KEY: MISC_FEATURE
<222> LOCATION: (1)..(214)
<223> OTHER INFORMATION: light chain moiety
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF18 moiety

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
                20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
            245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

Lys Tyr Ala Gln Leu Leu Val Glu Thr Asp Thr Phe Gly Ser Gln Val
290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
    370                 375                 380

Tyr Pro Lys Gly Gln Pro Glu Leu Gln Ala Ala Phe Ala Tyr Thr Thr
385                 390                 395                 400

Val Thr Lys

<210> SEQ ID NO 64
<211> LENGTH: 640
<212> TYPE: PRT
<213> ORGANISM: artificial sequence
<220> FEATURE:
<223> OTHER INFORMATION: Amino acid sequence of IgG-heavy chain -
      FGF18_3Ala, fusion via the C-terminus of the sequence
<220> FEATURE:
<221> NAME/KEY: MISC_FEATURE
<222> LOCATION: (1)..(451)
<223> OTHER INFORMATION: heavy chain moiety
<220> FEATURE:
<221> NAME/KEY: MISC_FEATURE
<222> LOCATION: (452)..(471)
<223> OTHER INFORMATION: linker
<220> FEATURE:
<221> NAME/KEY: MISC_FEATURE
<222> LOCATION: (472)..(640)
<223> OTHER INFORMATION: FGF18 moiety

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30
```

```
Asp Leu Asn Trp Ile Arg Gln Pro Pro Gly Lys Gly Leu Glu Trp Ile
         35                  40                  45

Gly Ile Ile Trp Gly Asp Gly Thr Thr Asp Tyr Asn Ser Ala Val Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Trp Tyr Ala Thr Ser Tyr Tyr Phe Asp Tyr Trp Gly
                100                 105                 110

Gln Gly Thr Leu Val Thr Val Ser Ser Ala Ser Thr Lys Gly Pro Ser
             115                 120                 125

Val Phe Pro Leu Ala Pro Ser Ser Lys Ser Thr Ser Gly Gly Thr Ala
         130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Gln Thr Tyr Ile Cys Asn Val Asn His
         195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                 325                 330                 335

Glu Lys Thr Ile Ser Lys Ala Lys Gly Gln Pro Arg Glu Pro Gln Val
             340                 345                 350

Tyr Thr Leu Pro Pro Ser Arg Asp Glu Leu Thr Lys Asn Gln Val Ser
         355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445
```

```
Pro Gly Lys Gly Gly Gly Ser Glu Pro Lys Ser Asp Lys Thr
    450             455             460
His Thr Gly Gly Gly Ser Glu Glu Asn Val Asp Phe Arg Ile His
465             470             475             480
Val Glu Asn Gln Thr Arg Ala Arg Asp Asp Val Ser Arg Lys Gln Leu
            485             490             495
Arg Leu Tyr Gln Leu Tyr Ser Arg Thr Ser Gly Lys His Ile Gln Val
        500             505             510
Leu Gly Arg Arg Ile Ser Ala Arg Gly Glu Asp Gly Asp Lys Tyr Ala
        515             520             525
Gln Leu Leu Val Glu Thr Asp Thr Phe Gly Ser Gln Val Arg Ile Lys
    530             535             540
Gly Lys Glu Thr Glu Phe Tyr Leu Cys Met Asn Arg Lys Gly Lys Leu
545             550             555             560
Val Gly Lys Pro Asp Gly Thr Ser Lys Glu Cys Val Phe Ile Glu Lys
            565             570             575
Val Leu Glu Asn Asn Tyr Thr Ala Leu Met Ser Ala Lys Tyr Ser Gly
        580             585             590
Trp Tyr Val Gly Phe Thr Lys Lys Gly Arg Pro Arg Lys Gly Pro Lys
        595             600             605
Thr Arg Glu Asn Gln Gln Asp Val His Phe Met Lys Arg Tyr Pro Lys
    610             615             620
Gly Gln Pro Glu Leu Gln Ala Ala Phe Ala Tyr Thr Thr Val Thr Lys
625             630             635             640

<210> SEQ ID NO 65
<211> LENGTH: 454
<212> TYPE: PRT
<213> ORGANISM: artificial sequence
<220> FEATURE:
<223> OTHER INFORMATION: Amino acid sequence of an anti-NGF GA chain
      with point mutations

<400> SEQUENCE: 65

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Ile Gly Tyr
            20                  25                  30
Asp Leu Asn Trp Ile Arg Gln Pro Pro Gly Lys Gly Leu Glu Trp Ile
        35                  40                  45
Gly Ile Ile Trp Gly Asp Gly Thr Thr Asp Tyr Asn Ser Ala Val Lys
    50                  55                  60
Ser Arg Val Thr Ile Ser Lys Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Gly Tyr Trp Tyr Ala Thr Ser Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Pro Ser Glu Glu Leu Ala Leu Asn Glu Leu Val
            355                 360                 365

Thr Leu Thr Cys Leu Val Lys Gly Phe Tyr Pro Ser Asp Ile Ala Val
            370                 375                 380

Glu Trp Leu Gln Gly Ser Gln Glu Leu Pro Arg Glu Lys Tyr Leu Thr
385                 390                 395                 400

Trp Ala Pro Val Leu Asp Ser Asp Gly Ser Phe Phe Leu Tyr Ser Ile
                405                 410                 415

Leu Arg Val Ala Ala Glu Asp Trp Lys Lys Gly Asp Thr Phe Ser Cys
            420                 425                 430

Ser Val Met His Glu Ala Leu His Asn Arg Phe Thr Gln Lys Ser Leu
            435                 440                 445

Asp Arg Ser Pro Gly Lys
        450

<210> SEQ ID NO 66
<211> LENGTH: 406
<212> TYPE: PRT
<213> ORGANISM: artificial sequence
<220> FEATURE:
<223> OTHER INFORMATION: Amino acid sequence of FGF18TF_SEED, AG chain
<220> FEATURE:
<221> NAME/KEY: MISC_FEATURE
<222> LOCATION: (1)..(162)
<223> OTHER INFORMATION: FGF18 moiety
<220> FEATURE:
<221> NAME/KEY: MISC_FEATURE
<222> LOCATION: (163)..(176)
<223> OTHER INFORMATION: linker
<220> FEATURE:
<221> NAME/KEY: MISC_FEATURE
<222> LOCATION: (177)..(406)
<223> OTHER INFORMATION: AG chain moiety

<400> SEQUENCE: 66

Glu Glu Asn Val Asp Phe Arg Ile His Val Glu Asn Gln Thr Arg Ala
1               5                   10                  15
```

```
Arg Asp Asp Val Ser Arg Lys Gln Leu Arg Leu Tyr Gln Leu Tyr Ser
            20                  25                  30
Arg Thr Ser Gly Lys His Ile Gln Val Leu Gly Arg Arg Ile Ser Ala
        35                  40                  45
Arg Gly Glu Asp Gly Asp Lys Tyr Ala Gln Leu Leu Val Glu Thr Asp
    50                  55                  60
Thr Phe Gly Ser Gln Val Arg Ile Lys Gly Lys Glu Thr Glu Phe Tyr
65                  70                  75                  80
Leu Cys Met Asn Arg Lys Gly Lys Leu Val Gly Lys Pro Asp Gly Thr
                85                  90                  95
Ser Lys Glu Cys Val Phe Ile Glu Lys Val Leu Glu Asn Asn Tyr Thr
            100                 105                 110
Ala Leu Met Ser Ala Lys Tyr Ser Gly Trp Tyr Val Gly Phe Thr Lys
        115                 120                 125
Lys Gly Arg Pro Arg Lys Gly Pro Lys Thr Arg Glu Asn Gln Gln Asp
    130                 135                 140
Val His Phe Met Lys Arg Tyr Pro Lys Gly Gln Pro Glu Leu Gln Lys
145                 150                 155                 160
Pro Gly Gly Gly Ser Gly Gly Gly Ser Glu Pro Lys Ser Ser
                165                 170                 175
Asp Lys Thr His Thr Cys Pro Pro Cys Pro Ala Pro Glu Ala Ala Gly
            180                 185                 190
Gly Pro Ser Val Phe Leu Phe Pro Pro Lys Pro Lys Asp Thr Leu Met
        195                 200                 205
Ile Ser Arg Thr Pro Glu Val Thr Cys Val Val Val Asp Val Ser His
    210                 215                 220
Glu Asp Pro Glu Val Lys Phe Asn Trp Tyr Val Asp Gly Val Glu Val
225                 230                 235                 240
His Asn Ala Lys Thr Lys Pro Arg Glu Glu Gln Tyr Asn Ser Thr Tyr
                245                 250                 255
Arg Val Val Ser Val Leu Thr Val Leu His Gln Asp Trp Leu Asn Gly
            260                 265                 270
Lys Glu Tyr Lys Cys Lys Val Ser Asn Lys Ala Leu Gly Ala Pro Ile
        275                 280                 285
Glu Lys Thr Ile Ser Lys Ala Lys Gly Gln Pro Phe Arg Pro Glu Val
    290                 295                 300
His Leu Leu Pro Pro Ser Arg Glu Glu Met Thr Lys Asn Gln Val Ser
305                 310                 315                 320
Leu Thr Cys Leu Ala Arg Gly Phe Tyr Pro Lys Asp Ile Ala Val Glu
                325                 330                 335
Trp Glu Ser Asn Gly Gln Pro Glu Asn Asn Tyr Lys Thr Thr Pro Ser
            340                 345                 350
Arg Gln Glu Pro Ser Gln Gly Thr Thr Thr Phe Ala Val Thr Ser Lys
        355                 360                 365
Leu Thr Val Asp Lys Ser Arg Trp Gln Gln Gly Asn Val Phe Ser Cys
    370                 375                 380
Ser Val Met His Glu Ala Leu His Asn His Tyr Thr Gln Lys Thr Ile
385                 390                 395                 400
Ser Leu Ser Pro Gly Lys
                405

<210> SEQ ID NO 67
<211> LENGTH: 404
```

```
<212> TYPE: PRT
<213> ORGANISM: artificial sequence
<220> FEATURE:
<223> OTHER INFORMATION: Amino acid sequence of FGF18QNQS_SEED, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (176)..(404)
<223> OTHER INFORMATION: AG chain moiety

<400> SEQUENCE: 67
```

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Gln
145                 150                 155                 160

Asn Phe Gln Ser Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
            195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Phe Arg Pro Glu Val His Leu
        290                 295                 300

Leu Pro Pro Ser Arg Glu Glu Met Thr Lys Asn Gln Val Ser Leu Thr
305                 310                 315                 320

```
Cys Leu Ala Arg Gly Phe Tyr Pro Lys Asp Ile Ala Val Glu Trp Glu
                325                 330                 335

Ser Asn Gly Gln Pro Glu Asn Asn Tyr Lys Thr Thr Pro Ser Arg Gln
            340                 345                 350

Glu Pro Ser Gln Gly Thr Thr Thr Phe Ala Val Thr Ser Lys Leu Thr
        355                 360                 365

Val Asp Lys Ser Arg Trp Gln Gln Gly Asn Val Phe Ser Cys Ser Val
370                 375                 380

Met His Glu Ala Leu His Asn His Tyr Thr Gln Lys Thr Ile Ser Leu
385                 390                 395                 400

Ser Pro Gly Lys

<210> SEQ ID NO 68
<211> LENGTH: 404
<212> TYPE: PRT
<213> ORGANISM: artificial sequence
<220> FEATURE:
<223> OTHER INFORMATION: Amino acid sequence of FGF18Y191P_SEED, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: AG chain moiety

<400> SEQUENCE: 68

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Phe Lys Pro Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
        195                 200                 205
```

```
Arg Thr Pro Glu Val Thr Cys Val Val Asp Val Ser His Glu Asp
    210                 215                 220
Pro Glu Val Lys Phe Asn Trp Tyr Val Asp Gly Val Glu Val His Asn
225                 230                 235                 240
Ala Lys Thr Lys Pro Arg Glu Glu Gln Tyr Asn Ser Thr Tyr Arg Val
                245                 250                 255
Val Ser Val Leu Thr Val Leu His Gln Asp Trp Leu Asn Gly Lys Glu
            260                 265                 270
Tyr Lys Cys Lys Val Ser Asn Lys Ala Leu Gly Ala Pro Ile Glu Lys
        275                 280                 285
Thr Ile Ser Lys Ala Lys Gly Gln Pro Phe Arg Pro Glu Val His Leu
    290                 295                 300
Leu Pro Pro Ser Arg Glu Glu Met Thr Lys Asn Gln Val Ser Leu Thr
305                 310                 315                 320
Cys Leu Ala Arg Gly Phe Tyr Pro Lys Asp Ile Ala Val Glu Trp Glu
                325                 330                 335
Ser Asn Gly Gln Pro Glu Asn Asn Tyr Lys Thr Thr Pro Ser Arg Gln
            340                 345                 350
Glu Pro Ser Gln Gly Thr Thr Thr Phe Ala Val Thr Ser Lys Leu Thr
        355                 360                 365
Val Asp Lys Ser Arg Trp Gln Gln Gly Asn Val Phe Ser Cys Ser Val
    370                 375                 380
Met His Glu Ala Leu His Asn His Tyr Thr Gln Lys Thr Ile Ser Leu
385                 390                 395                 400
Ser Pro Gly Lys

<210> SEQ ID NO 69
<211> LENGTH: 404
<212> TYPE: PRT
<213> ORGANISM: artificial sequence
<220> FEATURE:
<223> OTHER INFORMATION: Amino acid sequence of FGF18_3Ala_SEED, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: AG chain moiety

<400> SEQUENCE: 69

Glu Glu Asn Val Asp Phe Arg Ile His Val Glu Asn Gln Thr Arg Ala
1               5                   10                  15
Arg Asp Asp Val Ser Arg Lys Gln Leu Arg Leu Tyr Gln Leu Tyr Ser
                20                  25                  30
Arg Thr Ser Gly Lys His Ile Gln Val Leu Gly Arg Arg Ile Ser Ala
            35                  40                  45
Arg Gly Glu Asp Gly Asp Lys Tyr Ala Gln Leu Leu Val Glu Thr Asp
        50                  55                  60
Thr Phe Gly Ser Gln Val Arg Ile Lys Gly Lys Glu Thr Glu Phe Tyr
65                  70                  75                  80
Leu Cys Met Asn Arg Lys Gly Lys Leu Val Gly Lys Pro Asp Gly Thr
                85                  90                  95
```

-continued

```
Ser Lys Glu Cys Val Phe Ile Glu Lys Val Leu Glu Asn Asn Tyr Thr
            100                 105                 110
Ala Leu Met Ser Ala Lys Tyr Ser Gly Trp Tyr Val Gly Phe Thr Lys
        115                 120                 125
Lys Gly Arg Pro Arg Lys Gly Pro Lys Thr Arg Glu Asn Gln Gln Asp
    130                 135                 140
Val His Phe Met Lys Arg Tyr Pro Lys Gly Gln Pro Glu Leu Gln Ala
145                 150                 155                 160
Ala Phe Ala Tyr Thr Thr Val Thr Lys Glu Pro Lys Ser Ser Asp Lys
                165                 170                 175
Thr His Thr Cys Pro Pro Cys Pro Ala Pro Glu Ala Ala Gly Gly Pro
            180                 185                 190
Ser Val Phe Leu Phe Pro Pro Lys Pro Lys Asp Thr Leu Met Ile Ser
        195                 200                 205
Arg Thr Pro Glu Val Thr Cys Val Val Val Asp Val Ser His Glu Asp
    210                 215                 220
Pro Glu Val Lys Phe Asn Trp Tyr Val Asp Gly Val Glu Val His Asn
225                 230                 235                 240
Ala Lys Thr Lys Pro Arg Glu Glu Gln Tyr Asn Ser Thr Tyr Arg Val
                245                 250                 255
Val Ser Val Leu Thr Val Leu His Gln Asp Trp Leu Asn Gly Lys Glu
            260                 265                 270
Tyr Lys Cys Lys Val Ser Asn Lys Ala Leu Gly Ala Pro Ile Glu Lys
        275                 280                 285
Thr Ile Ser Lys Ala Lys Gly Gln Pro Phe Arg Pro Glu Val His Leu
    290                 295                 300
Leu Pro Pro Ser Arg Glu Glu Met Thr Lys Asn Gln Val Ser Leu Thr
305                 310                 315                 320
Cys Leu Ala Arg Gly Phe Tyr Pro Lys Asp Ile Ala Val Glu Trp Glu
                325                 330                 335
Ser Asn Gly Gln Pro Glu Asn Asn Tyr Lys Thr Thr Pro Ser Arg Gln
            340                 345                 350
Glu Pro Ser Gln Gly Thr Thr Thr Phe Ala Val Thr Ser Lys Leu Thr
        355                 360                 365
Val Asp Lys Ser Arg Trp Gln Gln Gly Asn Val Phe Ser Cys Ser Val
    370                 375                 380
Met His Glu Ala Leu His Asn His Tyr Thr Gln Lys Thr Ile Ser Leu
385                 390                 395                 400
Ser Pro Gly Lys

<210> SEQ ID NO 70
<211> LENGTH: 404
<212> TYPE: PRT
<213> ORGANISM: artificial sequence
<220> FEATURE:
<223> OTHER INFORMATION: Amino acid sequence of FGF18VS_SEED, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: AG chain moiety
```

```
<400> SEQUENCE: 70

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Val Ser Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Phe Arg Pro Glu Val His Leu
    290                 295                 300

Leu Pro Pro Ser Arg Glu Glu Met Thr Lys Asn Gln Val Ser Leu Thr
305                 310                 315                 320

Cys Leu Ala Arg Gly Phe Tyr Pro Lys Asp Ile Ala Val Glu Trp Glu
                325                 330                 335

Ser Asn Gly Gln Pro Glu Asn Asn Tyr Lys Thr Thr Pro Ser Arg Gln
            340                 345                 350

Glu Pro Ser Gln Gly Thr Thr Thr Phe Ala Val Thr Ser Lys Leu Thr
        355                 360                 365

Val Asp Lys Ser Arg Trp Gln Gln Gly Asn Val Phe Ser Cys Ser Val
    370                 375                 380

Met His Glu Ala Leu His Asn His Tyr Thr Gln Lys Thr Ile Ser Leu
385                 390                 395                 400

Ser Pro Gly Lys
```

<210> SEQ ID NO 71
<211> LENGTH: 454
<212> TYPE: PRT
<213> ORGANISM: artificial sequence
<220> FEATURE:
<223> OTHER INFORMATION: Amino acid sequence of an anti-NGF AG chain

<400> SEQUENCE: 71

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Phe Arg Pro Glu Val
            340                 345                 350

His Leu Leu Pro Pro Ser Arg Glu Glu Met Thr Lys Asn Gln Val Ser
        355                 360                 365
```

```
Leu Thr Cys Leu Ala Arg Gly Phe Tyr Pro Lys Asp Ile Ala Val Glu
    370                 375                 380

Trp Glu Ser Asn Gly Gln Pro Glu Asn Asn Tyr Lys Thr Thr Pro Ser
385                 390                 395                 400

Arg Gln Glu Pro Ser Gln Gly Thr Thr Thr Phe Ala Val Thr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Thr Ile
            435                 440                 445

Ser Leu Ser Pro Gly Lys
    450
```

<210> SEQ ID NO 72
<211> LENGTH: 406
<212> TYPE: PRT
<213> ORGANISM: artificial sequence
<220> FEATURE:
<223> OTHER INFORMATION: Amino acid sequence of SEED_FGF18TF, GA chain
<220> FEATURE:
<221> NAME/KEY: MISC_FEATURE
<222> LOCATION: (1)..(161)
<223> OTHER INFORMATION: FGF18 moiety
<220> FEATURE:
<221> NAME/KEY: MISC_FEATURE
<222> LOCATION: (162)..(176)
<223> OTHER INFORMATION: linker
<220> FEATURE:
<221> NAME/KEY: MISC_FEATURE
<222> LOCATION: (177)..(406)
<223> OTHER INFORMATION: GA chain moiety

<400> SEQUENCE: 72

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
145                 150                 155                 160

Pro Gly Gly Gly Gly Ser Gly Gly Gly Ser Glu Pro Lys Ser Ser
                165                 170                 175

Asp Lys Thr His Thr Cys Pro Pro Cys Pro Ala Pro Glu Ala Ala Gly
            180                 185                 190

Gly Pro Ser Val Phe Leu Phe Pro Pro Lys Pro Lys Asp Thr Leu Met
        195                 200                 205
```

```
Ile Ser Arg Thr Pro Glu Val Thr Cys Val Val Asp Val Ser His
210                 215                 220

Glu Asp Pro Glu Val Lys Phe Asn Trp Tyr Val Asp Gly Val Glu Val
225                 230                 235                 240

His Asn Ala Lys Thr Lys Pro Arg Glu Gln Tyr Asn Ser Thr Tyr
            245                 250                 255

Arg Val Val Ser Val Leu Thr Val Leu His Gln Asp Trp Leu Asn Gly
        260                 265                 270

Lys Glu Tyr Lys Cys Lys Val Ser Asn Lys Ala Leu Gly Ala Pro Ile
            275                 280                 285

Glu Lys Thr Ile Ser Lys Ala Lys Gly Gln Pro Arg Glu Pro Gln Val
290                 295                 300

Tyr Thr Leu Pro Pro Ser Glu Glu Leu Ala Leu Asn Glu Leu Val
305                 310                 315                 320

Thr Leu Thr Cys Leu Val Lys Gly Phe Tyr Pro Ser Asp Ile Ala Val
            325                 330                 335

Glu Trp Leu Gln Gly Ser Gln Glu Leu Pro Arg Glu Lys Tyr Leu Thr
            340                 345                 350

Trp Ala Pro Val Leu Asp Ser Asp Gly Ser Phe Phe Leu Tyr Ser Ile
            355                 360                 365

Leu Arg Val Ala Ala Glu Asp Trp Lys Lys Gly Asp Thr Phe Ser Cys
370                 375                 380

Ser Val Met His Glu Ala Leu His Asn Arg Phe Thr Gln Lys Ser Leu
385                 390                 395                 400

Asp Arg Ser Pro Gly Lys
                405

<210> SEQ ID NO 73
<211> LENGTH: 404
<212> TYPE: PRT
<213> ORGANISM: artificial sequence
<220> FEATURE:
<223> OTHER INFORMATION: Amino acid sequence of SEED_FGF18QNQS, GA chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: GA chain moiety

<400> SEQUENCE: 73

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95
```

```
Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Gln
145                 150                 155                 160

Asn Phe Gln Ser Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Pro Ser Glu Glu Leu Ala Leu Asn Glu Leu Val Thr Leu
305                 310                 315                 320

Thr Cys Leu Val Lys Gly Phe Tyr Pro Ser Asp Ile Ala Val Glu Trp
                325                 330                 335

Leu Gln Gly Ser Gln Glu Leu Pro Arg Glu Lys Tyr Leu Thr Trp Ala
            340                 345                 350

Pro Val Leu Asp Ser Asp Gly Ser Phe Phe Leu Tyr Ser Ile Leu Arg
        355                 360                 365

Val Ala Ala Glu Asp Trp Lys Lys Gly Asp Thr Phe Ser Cys Ser Val
    370                 375                 380

Met His Glu Ala Leu His Asn Arg Phe Thr Gln Lys Ser Leu Asp Arg
385                 390                 395                 400

Ser Pro Gly Lys

<210> SEQ ID NO 74
<211> LENGTH: 404
<212> TYPE: PRT
<213> ORGANISM: artificial sequence
<220> FEATURE:
<223> OTHER INFORMATION: Amino acid sequence of SEED_FGF18Y191P, GA
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: GA chain moiety
```

<400> SEQUENCE: 74

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Pro Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Pro Ser Glu Glu Leu Ala Leu Asn Glu Leu Val Thr Leu
305                 310                 315                 320

Thr Cys Leu Val Lys Gly Phe Tyr Pro Ser Asp Ile Ala Val Glu Trp
                325                 330                 335

Leu Gln Gly Ser Gln Glu Leu Pro Arg Glu Lys Tyr Leu Thr Trp Ala
            340                 345                 350

Pro Val Leu Asp Ser Asp Gly Ser Phe Phe Leu Tyr Ser Ile Leu Arg
        355                 360                 365

Val Ala Ala Glu Asp Trp Lys Lys Gly Asp Thr Phe Ser Cys Ser Val
    370                 375                 380

Met His Glu Ala Leu His Asn Arg Phe Thr Gln Lys Ser Leu Asp Arg
385                 390                 395                 400

Ser Pro Gly Lys
```

```
<210> SEQ ID NO 75
<211> LENGTH: 404
<212> TYPE: PRT
<213> ORGANISM: artificial sequence
<220> FEATURE:
<223> OTHER INFORMATION: Amino acid sequence of SEED_FGF18_3Ala, GA
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: GA chain moiety

<400> SEQUENCE: 75

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Ala
145                 150                 155                 160

Ala Phe Ala Tyr Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Arg Glu Pro Gln Val Tyr Thr
```

```
                290             295             300
Leu Pro Pro Ser Glu Glu Leu Ala Leu Asn Glu Leu Val Thr Leu
305                 310             315                 320

Thr Cys Leu Val Lys Gly Phe Tyr Pro Ser Asp Ile Ala Val Glu Trp
                325             330             335

Leu Gln Gly Ser Gln Glu Leu Pro Arg Glu Lys Tyr Leu Thr Trp Ala
                340             345             350

Pro Val Leu Asp Ser Asp Gly Ser Phe Phe Leu Tyr Ser Ile Leu Arg
                355             360             365

Val Ala Ala Glu Asp Trp Lys Lys Gly Asp Thr Phe Ser Cys Ser Val
        370             375             380

Met His Glu Ala Leu His Asn Arg Phe Thr Gln Lys Ser Leu Asp Arg
385             390             395                 400

Ser Pro Gly Lys

<210> SEQ ID NO 76
<211> LENGTH: 404
<212> TYPE: PRT
<213> ORGANISM: artificial sequence
<220> FEATURE:
<223> OTHER INFORMATION: Amino acid sequence of SEED_FGF18VS, GA chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: GA chain moiety

<400> SEQUENCE: 76

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Val Ser Thr Thr Val Thr Lys Glu Pro Lys Ser Ser Asp Lys
                165                 170                 175

Thr His Thr Cys Pro Pro Cys Pro Ala Pro Glu Ala Ala Gly Gly Pro
            180                 185                 190
```

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
        210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
        245                 250                 255

Val Ser Val Leu Thr Val Leu His Gln Asp Trp Leu Asn Gly Lys Glu
        260                 265                 270

Tyr Lys Cys Lys Val Ser Asn Lys Ala Leu Gly Ala Pro Ile Glu Lys
        275                 280                 285

Thr Ile Ser Lys Ala Lys Gly Gln Pro Arg Glu Pro Gln Val Tyr Thr
        290                 295                 300

Leu Pro Pro Pro Ser Glu Glu Leu Ala Leu Asn Glu Leu Val Thr Leu
305                 310                 315                 320

Thr Cys Leu Val Lys Gly Phe Tyr Pro Ser Asp Ile Ala Val Glu Trp
                325                 330                 335

Leu Gln Gly Ser Gln Glu Leu Pro Arg Glu Lys Tyr Leu Thr Trp Ala
        340                 345                 350

Pro Val Leu Asp Ser Asp Gly Ser Phe Phe Leu Tyr Ser Ile Leu Arg
        355                 360                 365

Val Ala Ala Glu Asp Trp Lys Lys Gly Asp Thr Phe Ser Cys Ser Val
        370                 375                 380

Met His Glu Ala Leu His Asn Arg Phe Thr Gln Lys Ser Leu Asp Arg
385                 390                 395                 400

Ser Pro Gly Lys

<210> SEQ ID NO 77
<211> LENGTH: 409
<212> TYPE: PRT
<213> ORGANISM: artificial sequence
<220> FEATURE:
<223> OTHER INFORMATION: Amino acid sequence of FGF18_SEED _GS, AG chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(179)
<223> OTHER INFORMATION: linker
<220> FEATURE:
<221> NAME/KEY: MISC_FEATURE
<222> LOCATION: (180)..(409)
<223> OTHER INFORMATION: AG chain moiety

<400> SEQUENCE: 77

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

```
Leu Cys Met Asn Arg Lys Gly Lys Leu Val Gly Lys Pro Asp Gly Thr
            85                  90                  95
Ser Lys Glu Cys Val Phe Ile Glu Lys Val Leu Glu Asn Asn Tyr Thr
        100                 105                 110
Ala Leu Met Ser Ala Lys Tyr Ser Gly Trp Tyr Val Gly Phe Thr Lys
    115                 120                 125
Lys Gly Arg Pro Arg Lys Gly Pro Lys Thr Arg Glu Asn Gln Gln Asp
130                 135                 140
Val His Phe Met Lys Arg Tyr Pro Lys Gly Gln Pro Glu Leu Gln Lys
145                 150                 155                 160
Pro Phe Lys Tyr Thr Thr Val Thr Lys Gly Gly Ser Gly Gly Ser Gly
                165                 170                 175
Ser Gly Ser Asp Lys Thr His Thr Cys Pro Pro Cys Pro Ala Pro Glu
            180                 185                 190
Ala Ala Gly Gly Pro Ser Val Phe Leu Phe Pro Pro Lys Pro Lys Asp
        195                 200                 205
Thr Leu Met Ile Ser Arg Thr Pro Glu Val Thr Cys Val Val Val Asp
    210                 215                 220
Val Ser His Glu Asp Pro Glu Val Lys Phe Asn Trp Tyr Val Asp Gly
225                 230                 235                 240
Val Glu Val His Asn Ala Lys Thr Lys Pro Arg Glu Glu Gln Tyr Asn
                245                 250                 255
Ser Thr Tyr Arg Val Val Ser Val Leu Thr Val Leu His Gln Asp Trp
            260                 265                 270
Leu Asn Gly Lys Glu Tyr Lys Cys Lys Val Ser Asn Lys Ala Leu Pro
        275                 280                 285
Ala Pro Ile Glu Lys Thr Ile Ser Lys Ala Lys Gly Gln Pro Phe Arg
    290                 295                 300
Pro Glu Val His Leu Leu Pro Pro Ser Arg Glu Glu Met Thr Lys Asn
305                 310                 315                 320
Gln Val Ser Leu Thr Cys Leu Ala Arg Gly Phe Tyr Pro Lys Asp Ile
                325                 330                 335
Ala Val Glu Trp Glu Ser Asn Gly Gln Pro Glu Asn Asn Tyr Lys Thr
            340                 345                 350
Thr Pro Ser Arg Gln Glu Pro Ser Gln Gly Thr Thr Thr Phe Ala Val
        355                 360                 365
Thr Ser Lys Leu Thr Val Asp Lys Ser Arg Trp Gln Gln Gly Asn Val
    370                 375                 380
Phe Ser Cys Ser Val Met His Glu Ala Leu His Asn His Tyr Thr Gln
385                 390                 395                 400
Lys Thr Ile Ser Leu Ser Pro Gly Lys
                405

<210> SEQ ID NO 78
<211> LENGTH: 407
<212> TYPE: PRT
<213> ORGANISM: artificial sequence
<220> FEATURE:
<223> OTHER INFORMATION: Amino acid sequence of FGF18_SEED _CH2, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(177)
<223> OTHER INFORMATION: linker
```

```
<220> FEATURE:
<221> NAME/KEY: MISC_FEATURE
<222> LOCATION: (178)..(407)
<223> OTHER INFORMATION: AG chain moiety

<400> SEQUENCE: 78
```

| | | | | | | | | | | | | | | |
|---|---|---|---|---|---|---|---|---|---|---|---|---|---|---|
| Glu | Glu | Asn | Val | Asp | Phe | Arg | Ile | His | Val | Glu | Asn | Gln | Thr | Arg | Ala |
| 1 | | | | 5 | | | | | 10 | | | | | 15 | |
| Arg | Asp | Asp | Val | Ser | Arg | Lys | Gln | Leu | Arg | Leu | Tyr | Gln | Leu | Tyr | Ser |
| | | | 20 | | | | | 25 | | | | | 30 | | |
| Arg | Thr | Ser | Gly | Lys | His | Ile | Gln | Val | Leu | Gly | Arg | Arg | Ile | Ser | Ala |
| | | | 35 | | | | | 40 | | | | | 45 | | |
| Arg | Gly | Glu | Asp | Gly | Asp | Lys | Tyr | Ala | Gln | Leu | Leu | Val | Glu | Thr | Asp |
| | 50 | | | | | 55 | | | | | 60 | | | | |
| Thr | Phe | Gly | Ser | Gln | Val | Arg | Ile | Lys | Gly | Lys | Glu | Thr | Glu | Phe | Tyr |
| 65 | | | | | 70 | | | | | 75 | | | | | 80 |
| Leu | Cys | Met | Asn | Arg | Lys | Gly | Lys | Leu | Val | Gly | Lys | Pro | Asp | Gly | Thr |
| | | | | 85 | | | | | 90 | | | | | 95 | |
| Ser | Lys | Glu | Cys | Val | Phe | Ile | Glu | Lys | Val | Leu | Glu | Asn | Asn | Tyr | Thr |
| | | | 100 | | | | | 105 | | | | | 110 | | |
| Ala | Leu | Met | Ser | Ala | Lys | Tyr | Ser | Gly | Trp | Tyr | Val | Gly | Phe | Thr | Lys |
| | | | 115 | | | | | 120 | | | | | 125 | | |
| Lys | Gly | Arg | Pro | Arg | Lys | Gly | Pro | Lys | Thr | Arg | Glu | Asn | Gln | Gln | Asp |
| | 130 | | | | | 135 | | | | | 140 | | | | |
| Val | His | Phe | Met | Lys | Arg | Tyr | Pro | Lys | Gly | Gln | Pro | Glu | Leu | Gln | Lys |
| 145 | | | | | 150 | | | | | 155 | | | | | 160 |
| Pro | Phe | Lys | Tyr | Thr | Thr | Val | Thr | Lys | Pro | Ala | Pro | Glu | Ala | Ala | Gly |
| | | | | 165 | | | | | 170 | | | | | 175 | |
| Gly | Asp | Lys | Thr | His | Thr | Cys | Pro | Pro | Cys | Pro | Ala | Pro | Glu | Ala | Ala |
| | | | 180 | | | | | 185 | | | | | 190 | | |
| Gly | Gly | Pro | Ser | Val | Phe | Leu | Phe | Pro | Pro | Lys | Pro | Lys | Asp | Thr | Leu |
| | | | 195 | | | | | 200 | | | | | 205 | | |
| Met | Ile | Ser | Arg | Thr | Pro | Glu | Val | Thr | Cys | Val | Val | Val | Asp | Val | Ser |
| | 210 | | | | | 215 | | | | | 220 | | | | |
| His | Glu | Asp | Pro | Glu | Val | Lys | Phe | Asn | Trp | Tyr | Val | Asp | Gly | Val | Glu |
| 225 | | | | | 230 | | | | | 235 | | | | | 240 |
| Val | His | Asn | Ala | Lys | Thr | Lys | Pro | Arg | Glu | Glu | Gln | Tyr | Asn | Ser | Thr |
| | | | | 245 | | | | | 250 | | | | | 255 | |
| Tyr | Arg | Val | Val | Ser | Val | Leu | Thr | Val | Leu | His | Gln | Asp | Trp | Leu | Asn |
| | | | 260 | | | | | 265 | | | | | 270 | | |
| Gly | Lys | Glu | Tyr | Lys | Cys | Lys | Val | Ser | Asn | Lys | Ala | Leu | Pro | Ala | Pro |
| | | | 275 | | | | | 280 | | | | | 285 | | |
| Ile | Glu | Lys | Thr | Ile | Ser | Lys | Ala | Lys | Gly | Gln | Pro | Phe | Arg | Pro | Glu |
| | | | 290 | | | | | 295 | | | | | 300 | | |
| Val | His | Leu | Leu | Pro | Pro | Ser | Arg | Glu | Glu | Met | Thr | Lys | Asn | Gln | Val |
| 305 | | | | | 310 | | | | | 315 | | | | | 320 |
| Ser | Leu | Thr | Cys | Leu | Ala | Arg | Gly | Phe | Tyr | Pro | Lys | Asp | Ile | Ala | Val |
| | | | | 325 | | | | | 330 | | | | | 335 | |
| Glu | Trp | Glu | Ser | Asn | Gly | Gln | Pro | Glu | Asn | Asn | Tyr | Lys | Thr | Thr | Pro |
| | | | | 340 | | | | | 345 | | | | | 350 | |
| Ser | Arg | Gln | Glu | Pro | Ser | Gln | Gly | Thr | Thr | Thr | Phe | Ala | Val | Thr | Ser |
| | | | | 355 | | | | | 360 | | | | | 365 | |
| Lys | Leu | Thr | Val | Asp | Lys | Ser | Arg | Trp | Gln | Gln | Gly | Asn | Val | Phe | Ser |
| | | | 370 | | | | | 375 | | | | | 380 | | |

Cys Ser Val Met His Glu Ala Leu His Asn His Tyr Thr Gln Lys Thr
385                 390                 395                 400

Ile Ser Leu Ser Pro Gly Lys
                405

<210> SEQ ID NO 79
<211> LENGTH: 408
<212> TYPE: PRT
<213> ORGANISM: artificial sequence
<220> FEATURE:
<223> OTHER INFORMATION: Amino acid sequence of FGF18_SEED_ YOL, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(178)
<223> OTHER INFORMATION: linker
<220> FEATURE:
<221> NAME/KEY: MISC_FEATURE
<222> LOCATION: (179)..(408)
<223> OTHER INFORMATION: AG chain moiety

<400> SEQUENCE: 79

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Glu Glu Gly Glu Phe Ser Glu
                165                 170                 175

Ala Arg Asp Lys Thr His Thr Cys Pro Pro Cys Pro Ala Pro Glu Ala
                180                 185                 190

Ala Gly Gly Pro Ser Val Phe Leu Phe Pro Pro Lys Pro Lys Asp Thr
            195                 200                 205

Leu Met Ile Ser Arg Thr Pro Glu Val Thr Cys Val Val Val Asp Val
        210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

```
Asn Gly Lys Glu Tyr Lys Cys Lys Val Ser Asn Lys Ala Leu Pro Ala
            275                 280                 285

Pro Ile Glu Lys Thr Ile Ser Lys Ala Lys Gly Gln Pro Phe Arg Pro
        290                 295                 300

Glu Val His Leu Leu Pro Pro Ser Arg Glu Glu Met Thr Lys Asn Gln
305                 310                 315                 320

Val Ser Leu Thr Cys Leu Ala Arg Gly Phe Tyr Pro Lys Asp Ile Ala
            325                 330                 335

Val Glu Trp Glu Ser Asn Gly Gln Pro Glu Asn Asn Tyr Lys Thr Thr
        340                 345                 350

Pro Ser Arg Gln Glu Pro Ser Gln Gly Thr Thr Thr Phe Ala Val Thr
    355                 360                 365

Ser Lys Leu Thr Val Asp Lys Ser Arg Trp Gln Gln Gly Asn Val Phe
            370                 375                 380

Ser Cys Ser Val Met His Glu Ala Leu His Asn His Tyr Thr Gln Lys
385                 390                 395                 400

Thr Ile Ser Leu Ser Pro Gly Lys
            405
```

<210> SEQ ID NO 80
<211> LENGTH: 404
<212> TYPE: PRT
<213> ORGANISM: artificial sequence
<220> FEATURE:
<223> OTHER INFORMATION: Amino acid sequence of FGF18_SEED_ Hinge, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(174)
<223> OTHER INFORMATION: linker
<220> FEATURE:
<221> NAME/KEY: MISC_FEATURE
<222> LOCATION: (175)..(404)
<223> OTHER INFORMATION: AG chain moiety

<400> SEQUENCE: 80

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
            85                  90                  95

Ser Lys Glu Cys Val Phe Ile Glu Lys Val Leu Glu Asn Asn Tyr Thr
        100                 105                 110

Ala Leu Met Ser Ala Lys Tyr Ser Gly Trp Tyr Val Gly Phe Thr Lys
    115                 120                 125

Lys Gly Arg Pro Arg Lys Gly Pro Lys Thr Arg Glu Asn Gln Gln Asp
130                 135                 140

Val His Phe Met Lys Arg Tyr Pro Lys Gly Gln Pro Glu Leu Gln Lys
```

```
                145                 150                 155                 160
Pro Phe Lys Tyr Thr Thr Val Thr Lys Glu Pro Lys Ser Ser Asp Lys
                    165                 170                 175

Thr His Thr Cys Pro Cys Pro Ala Pro Glu Ala Ala Gly Gly Pro
                    180                 185                 190

Ser Val Phe Leu Phe Pro Pro Lys Pro Lys Asp Thr Leu Met Ile Ser
                    195                 200                 205

Arg Thr Pro Glu Val Thr Cys Val Val Val Asp Val Ser His Glu Asp
                    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                    245                 250                 255

Val Ser Val Leu Thr Val Leu His Gln Asp Trp Leu Asn Gly Lys Glu
                    260                 265                 270

Tyr Lys Cys Lys Val Ser Asn Lys Ala Leu Pro Ala Pro Ile Glu Lys
                    275                 280                 285

Thr Ile Ser Lys Ala Lys Gly Gln Pro Phe Arg Pro Glu Val His Leu
                    290                 295                 300

Leu Pro Pro Ser Arg Glu Glu Met Thr Lys Asn Gln Val Ser Leu Thr
305                 310                 315                 320

Cys Leu Ala Arg Gly Phe Tyr Pro Lys Asp Ile Ala Val Glu Trp Glu
                    325                 330                 335

Ser Asn Gly Gln Pro Glu Asn Asn Tyr Lys Thr Thr Pro Ser Arg Gln
                    340                 345                 350

Glu Pro Ser Gln Gly Thr Thr Thr Phe Ala Val Thr Ser Lys Leu Thr
                    355                 360                 365

Val Asp Lys Ser Arg Trp Gln Gln Gly Asn Val Phe Ser Cys Ser Val
                    370                 375                 380

Met His Glu Ala Leu His Asn His Tyr Thr Gln Lys Thr Ile Ser Leu
385                 390                 395                 400

Ser Pro Gly Lys

<210> SEQ ID NO 81
<211> LENGTH: 399
<212> TYPE: PRT
<213> ORGANISM: artificial sequence
<220> FEATURE:
<223> OTHER INFORMATION: Amino acid sequence of FGF18_SEED_ shin, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(399)
<223> OTHER INFORMATION: AG chain moiety

<400> SEQUENCE: 81

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
                35                  40                  45

Arg Gly Glu Asp Gly Asp Lys Tyr Ala Gln Leu Leu Val Glu Thr Asp
                50                  55                  60
```

```
Thr Phe Gly Ser Gln Val Arg Ile Lys Gly Lys Thr Glu Phe Tyr
 65                  70                  75                  80

Leu Cys Met Asn Arg Lys Gly Lys Leu Val Gly Lys Pro Asp Gly Thr
                 85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Asp Lys Thr His Thr Cys Pro
                165                 170                 175

Pro Cys Pro Ala Pro Glu Ala Ala Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Phe Arg Pro Glu Val His Leu Leu Pro Pro Ser Arg
    290                 295                 300

Glu Glu Met Thr Lys Asn Gln Val Ser Leu Thr Cys Leu Ala Arg Gly
305                 310                 315                 320

Phe Tyr Pro Lys Asp Ile Ala Val Glu Trp Glu Ser Asn Gly Gln Pro
                325                 330                 335

Glu Asn Asn Tyr Lys Thr Thr Pro Ser Arg Gln Glu Pro Ser Gln Gly
            340                 345                 350

Thr Thr Thr Phe Ala Val Thr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Thr Ile Ser Leu Ser Pro Gly Lys
385                 390                 395

<210> SEQ ID NO 82
<211> LENGTH: 402
<212> TYPE: PRT
<213> ORGANISM: artificial sequence
<220> FEATURE:
<223> OTHER INFORMATION: Amino acid sequence of FGF18_SEED_ 3Ala, AG
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(172)
```

```
<223> OTHER INFORMATION: linker
<220> FEATURE:
<221> NAME/KEY: MISC_FEATURE
<222> LOCATION: (173)..(402)
<223> OTHER INFORMATION: AG chain moiety

<400> SEQUENCE: 82
```

| | | | | | | | | | | | | | | | |
|---|---|---|---|---|---|---|---|---|---|---|---|---|---|---|---|
| Glu | Glu | Asn | Val | Asp | Phe | Arg | Ile | His | Val | Glu | Asn | Gln | Thr | Arg | Ala |
| 1 | | | | 5 | | | | | 10 | | | | | 15 | |
| Arg | Asp | Asp | Val | Ser | Arg | Lys | Gln | Leu | Arg | Leu | Tyr | Gln | Leu | Tyr | Ser |
| | | | 20 | | | | | 25 | | | | | 30 | | |
| Arg | Thr | Ser | Gly | Lys | His | Ile | Gln | Val | Leu | Gly | Arg | Arg | Ile | Ser | Ala |
| | | | 35 | | | | | 40 | | | | | 45 | | |
| Arg | Gly | Glu | Asp | Gly | Asp | Lys | Tyr | Ala | Gln | Leu | Leu | Val | Glu | Thr | Asp |
| | 50 | | | | | 55 | | | | | 60 | | | | |
| Thr | Phe | Gly | Ser | Gln | Val | Arg | Ile | Lys | Gly | Lys | Glu | Thr | Glu | Phe | Tyr |
| 65 | | | | | 70 | | | | | 75 | | | | | 80 |
| Leu | Cys | Met | Asn | Arg | Lys | Gly | Lys | Leu | Val | Gly | Lys | Pro | Asp | Gly | Thr |
| | | | | 85 | | | | | 90 | | | | | 95 | |
| Ser | Lys | Glu | Cys | Val | Phe | Ile | Glu | Lys | Val | Leu | Glu | Asn | Asn | Tyr | Thr |
| | | | 100 | | | | | 105 | | | | | 110 | | |
| Ala | Leu | Met | Ser | Ala | Lys | Tyr | Ser | Gly | Trp | Tyr | Val | Gly | Phe | Thr | Lys |
| | | | 115 | | | | | 120 | | | | | 125 | | |
| Lys | Gly | Arg | Pro | Arg | Lys | Gly | Pro | Lys | Thr | Arg | Glu | Asn | Gln | Gln | Asp |
| | 130 | | | | | 135 | | | | | 140 | | | | |
| Val | His | Phe | Met | Lys | Arg | Tyr | Pro | Lys | Gly | Gln | Pro | Glu | Leu | Gln | Lys |
| 145 | | | | | 150 | | | | | 155 | | | | | 160 |
| Pro | Phe | Lys | Tyr | Thr | Thr | Val | Thr | Lys | Ala | Ala | Ala | Asp | Lys | Thr | His |
| | | | | 165 | | | | | 170 | | | | | 175 | |
| Thr | Cys | Pro | Pro | Cys | Pro | Ala | Pro | Glu | Ala | Ala | Gly | Gly | Pro | Ser | Val |
| | | | 180 | | | | | 185 | | | | | 190 | | |
| Phe | Leu | Phe | Pro | Pro | Lys | Pro | Lys | Asp | Thr | Leu | Met | Ile | Ser | Arg | Thr |
| | | | 195 | | | | | 200 | | | | | 205 | | |
| Pro | Glu | Val | Thr | Cys | Val | Val | Val | Asp | Val | Ser | His | Glu | Asp | Pro | Glu |
| | 210 | | | | | 215 | | | | | 220 | | | | |
| Val | Lys | Phe | Asn | Trp | Tyr | Val | Asp | Gly | Val | Glu | Val | His | Asn | Ala | Lys |
| 225 | | | | | 230 | | | | | 235 | | | | | 240 |
| Thr | Lys | Pro | Arg | Glu | Glu | Gln | Tyr | Asn | Ser | Thr | Tyr | Arg | Val | Val | Ser |
| | | | | 245 | | | | | 250 | | | | | 255 | |
| Val | Leu | Thr | Val | Leu | His | Gln | Asp | Trp | Leu | Asn | Gly | Lys | Glu | Tyr | Lys |
| | | | 260 | | | | | 265 | | | | | 270 | | |
| Cys | Lys | Val | Ser | Asn | Lys | Ala | Leu | Pro | Ala | Pro | Ile | Glu | Lys | Thr | Ile |
| | | | 275 | | | | | 280 | | | | | 285 | | |
| Ser | Lys | Ala | Lys | Gly | Gln | Pro | Phe | Arg | Pro | Glu | Val | His | Leu | Leu | Pro |
| | 290 | | | | | 295 | | | | | 300 | | | | |
| Pro | Ser | Arg | Glu | Glu | Met | Thr | Lys | Asn | Gln | Val | Ser | Leu | Thr | Cys | Leu |
| 305 | | | | | 310 | | | | | 315 | | | | | 320 |
| Ala | Arg | Gly | Phe | Tyr | Pro | Lys | Asp | Ile | Ala | Val | Glu | Trp | Glu | Ser | Asn |
| | | | | 325 | | | | | 330 | | | | | 335 | |
| Gly | Gln | Pro | Glu | Asn | Asn | Tyr | Lys | Thr | Thr | Pro | Ser | Arg | Gln | Glu | Pro |
| | | | 340 | | | | | 345 | | | | | 350 | | |
| Ser | Gln | Gly | Thr | Thr | Thr | Phe | Ala | Val | Thr | Ser | Lys | Leu | Thr | Val | Asp |
| | | | 355 | | | | | 360 | | | | | 365 | | |
| Lys | Ser | Arg | Trp | Gln | Gln | Gly | Asn | Val | Phe | Ser | Cys | Ser | Val | Met | His |
| | 370 | | | | | 375 | | | | | 380 | | | | |

Glu Ala Leu His Asn His Tyr Thr Gln Lys Thr Ile Ser Leu Ser Pro
385                 390                 395                 400

Gly Lys

<210> SEQ ID NO 83
<211> LENGTH: 188
<212> TYPE: PRT
<213> ORGANISM: artificial sequence
<220> FEATURE:
<223> OTHER INFORMATION: Amino acid sequence of FGF18CFGF8
<220> FEATURE:
<221> NAME/KEY: MISC_FEATURE
<222> LOCATION: (1)..(155)
<223> OTHER INFORMATION: FGF18 moiety
<220> FEATURE:
<221> NAME/KEY: MISC_FEATURE
<222> LOCATION: (156)..(188)
<223> OTHER INFORMATION: FGF8 moiety

<400> SEQUENCE: 83

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln His Thr Thr Glu Gln
145                 150                 155                 160

Ser Leu Arg Phe Glu Phe Leu Asn Tyr Pro Pro Phe Thr Arg Ser Leu
                165                 170                 175

Arg Gly Ser Gln Arg Thr Trp Ala Pro Glu Pro Arg
            180                 185

<210> SEQ ID NO 84
<211> LENGTH: 173
<212> TYPE: PRT
<213> ORGANISM: artificial sequence
<220> FEATURE:
<223> OTHER INFORMATION: Amino acid sequence of FGF18CFGF8T
<220> FEATURE:
<221> NAME/KEY: MISC_FEATURE
<222> LOCATION: (1)..(155)
<223> OTHER INFORMATION: FGF18 moiety
<220> FEATURE:
<221> NAME/KEY: MISC_FEATURE
<222> LOCATION: (156)..(173)
<223> OTHER INFORMATION: FGF8T moiety

<400> SEQUENCE: 84

Glu Glu Asn Val Asp Phe Arg Ile His Val Glu Asn Gln Thr Arg Ala

```
1               5                   10                  15
Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
                35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                      70                  75                  80

Leu Cys Met Asn Arg Lys Gly Lys Leu Val Gly Lys Pro Asp Gly Thr
                    85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
                115                 120                 125

Lys Gly Arg Pro Arg Lys Gly Pro Lys Thr Arg Glu Asn Gln Gln Asp
            130                 135                 140

Val His Phe Met Lys Arg Tyr Pro Lys Gly Gln His Thr Thr Glu Gln
145                 150                 155                 160

Ser Leu Arg Phe Glu Phe Leu Asn Tyr Pro Pro Phe Thr
                    165                 170
```

<210> SEQ ID NO 85
<211> LENGTH: 177
<212> TYPE: PRT
<213> ORGANISM: artificial sequence
<220> FEATURE:
<223> OTHER INFORMATION: Amino acid sequence of FGF18
<220> FEATURE:
<221> NAME/KEY: MISC_FEATURE
<222> LOCATION: (1)..(155)
<223> OTHER INFORMATION: FGF18 moiety
<220> FEATURE:
<221> NAME/KEY: MISC_FEATURE
<222> LOCATION: (156)..(177)
<223> OTHER INFORMATION: FGF17T chain moiety

<400> SEQUENCE: 85

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
                35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                      70                  75                  80

Leu Cys Met Asn Arg Lys Gly Lys Leu Val Gly Lys Pro Asp Gly Thr
                    85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
                115                 120                 125

Lys Gly Arg Pro Arg Lys Gly Pro Lys Thr Arg Glu Asn Gln Gln Asp
            130                 135                 140

Val His Phe Met Lys Arg Tyr Pro Lys Gly Gln Leu Pro Phe Pro Asn
145                 150                 155                 160
```

His Ala Glu Lys Gln Lys Gln Phe Glu Phe Val Gly Ser Ala Pro Thr
                165                 170                 175
Arg

<210> SEQ ID NO 86
<211> LENGTH: 168
<212> TYPE: PRT
<213> ORGANISM: artificial sequence
<220> FEATURE:
<223> OTHER INFORMATION: Amino acid sequence of FGF18CFGF9
<220> FEATURE:
<221> NAME/KEY: MISC_FEATURE
<222> LOCATION: (1)..(147)
<223> OTHER INFORMATION: FGF18 moiety
<220> FEATURE:
<221> NAME/KEY: MISC_FEATURE
<222> LOCATION: (148)..(169)
<223> OTHER INFORMATION: FGF9 moiety

<400> SEQUENCE: 86

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
                100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
        130                 135                 140

Val His Phe Leu Pro Arg Pro Val Asp Pro Asp Lys Val Pro Glu Leu
145                 150                 155                 160

Tyr Lys Asp Ile Leu Ser Gln Ser
                165

<210> SEQ ID NO 87
<211> LENGTH: 169
<212> TYPE: PRT
<213> ORGANISM: artificial sequence
<220> FEATURE:
<223> OTHER INFORMATION: Amino acid sequence of FGF18Y191F

<400> SEQUENCE: 87

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

```
Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
        130                 135                 140

Val His Phe Met Lys Arg Tyr Pro Lys Gly Gln Pro Glu Leu Gln Lys
145                 150                 155                 160

Pro Phe Lys Phe Thr Thr Val Thr Lys
                165

<210> SEQ ID NO 88
<211> LENGTH: 651
<212> TYPE: PRT
<213> ORGANISM: artificial sequence
<220> FEATURE:
<223> OTHER INFORMATION: Amino acid sequence of IgG-heavy chain - wild
      type FGF18, fusion via the C-terminus of the sequence
<220> FEATURE:
<221> NAME/KEY: MISC_FEATURE
<222> LOCATION: (1)..(451)
<223> OTHER INFORMATION: heavy chain moiety
<220> FEATURE:
<221> NAME/KEY: MISC_FEATURE
<222> LOCATION: (452)..(471)
<223> OTHER INFORMATION: linker
<220> FEATURE:
<221> NAME/KEY: MISC_FEATURE
<222> LOCATION: (472)..(651)
<223> OTHER INFORMATION: FGF18 moiety

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Glu Pro Lys Ser Ser Asp Lys Thr
    450                 455                 460

His Thr Gly Gly Gly Gly Ser Glu Glu Asn Val Asp Phe Arg Ile His
465                 470                 475                 480

Val Glu Asn Gln Thr Arg Ala Arg Asp Asp Val Ser Arg Lys Gln Leu
                485                 490                 495

Arg Leu Tyr Gln Leu Tyr Ser Arg Thr Ser Gly Lys His Ile Gln Val
            500                 505                 510

Leu Gly Arg Arg Ile Ser Ala Arg Gly Glu Asp Gly Asp Lys Tyr Ala
        515                 520                 525

Gln Leu Leu Val Glu Thr Asp Thr Phe Gly Ser Gln Val Arg Ile Lys
    530                 535                 540

Gly Lys Glu Thr Glu Phe Tyr Leu Cys Met Asn Arg Lys Gly Lys Leu
545                 550                 555                 560

Val Gly Lys Pro Asp Gly Thr Ser Lys Glu Cys Val Phe Ile Glu Lys
                565                 570                 575

Val Leu Glu Asn Asn Tyr Thr Ala Leu Met Ser Ala Lys Tyr Ser Gly
            580                 585                 590

Trp Tyr Val Gly Phe Thr Lys Lys Gly Arg Pro Arg Lys Gly Pro Lys
        595                 600                 605
```

```
Thr Arg Glu Asn Gln Gln Asp Val His Phe Met Lys Arg Tyr Pro Lys
            610                 615                 620

Gly Gln Pro Glu Leu Gln Lys Pro Phe Lys Tyr Thr Thr Val Thr Lys
625                 630                 635                 640

Arg Ser Arg Arg Ile Arg Pro Thr His Pro Ala
                645                 650

<210> SEQ ID NO 89
<211> LENGTH: 640
<212> TYPE: PRT
<213> ORGANISM: artificial sequence
<220> FEATURE:
<223> OTHER INFORMATION: Amino acid sequence of IgG-heavy chain -
      sprifermin, fusion via the C-terminus of the sequence
<220> FEATURE:
<221> NAME/KEY: MISC_FEATURE
<222> LOCATION: (1)..(451)
<223> OTHER INFORMATION: heavy chain moiety
<220> FEATURE:
<221> NAME/KEY: MISC_FEATURE
<222> LOCATION: (452)..(471)
<223> OTHER INFORMATION: linker
<220> FEATURE:
<221> NAME/KEY: MISC_FEATURE
<222> LOCATION: (472)..(640)
<223> OTHER INFORMATION: FGF18 moiety

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255
```

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                 325                 330                 335

Glu Lys Thr Ile Ser Lys Ala Lys Gly Gln Pro Arg Glu Pro Gln Val
             340                 345                 350

Tyr Thr Leu Pro Pro Ser Arg Asp Glu Leu Thr Lys Asn Gln Val Ser
         355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445

Pro Gly Lys Gly Gly Gly Ser Glu Pro Lys Ser Ser Asp Lys Thr
450                 455                 460

His Thr Gly Gly Gly Gly Ser Glu Glu Asn Val Asp Phe Arg Ile His
465                 470                 475                 480

Val Glu Asn Gln Thr Arg Ala Arg Asp Asp Val Ser Arg Lys Gln Leu
                 485                 490                 495

Arg Leu Tyr Gln Leu Tyr Ser Arg Thr Ser Gly Lys His Ile Gln Val
             500                 505                 510

Leu Gly Arg Arg Ile Ser Ala Arg Gly Glu Asp Gly Asp Lys Tyr Ala
         515                 520                 525

Gln Leu Leu Val Glu Thr Asp Thr Phe Gly Ser Gln Val Arg Ile Lys
530                 535                 540

Gly Lys Glu Thr Glu Phe Tyr Leu Cys Met Asn Arg Lys Gly Lys Leu
545                 550                 555                 560

Val Gly Lys Pro Asp Gly Thr Ser Lys Glu Cys Val Phe Ile Glu Lys
                 565                 570                 575

Val Leu Glu Asn Asn Tyr Thr Ala Leu Met Ser Ala Lys Tyr Ser Gly
             580                 585                 590

Trp Tyr Val Gly Phe Thr Lys Lys Gly Arg Pro Arg Lys Gly Pro Lys
         595                 600                 605

Thr Arg Glu Asn Gln Gln Asp Val His Phe Met Lys Arg Tyr Pro Lys
610                 615                 620

Gly Gln Pro Glu Leu Gln Lys Pro Phe Lys Tyr Thr Thr Val Thr Lys
625                 630                 635                 640

<210> SEQ ID NO 90
<211> LENGTH: 414
<212> TYPE: PRT
<213> ORGANISM: artificial sequence
<220> FEATURE:

<223> OTHER INFORMATION: Amino acid sequence of SEED_sprifermin, GA
      chain
<220> FEATURE:
<221> NAME/KEY: MISC_FEATURE
<222> LOCATION: (1)..(169)
<223> OTHER INFORMATION: FGF18 moiety
<220> FEATURE:
<221> NAME/KEY: MISC_FEATURE
<222> LOCATION: (170)..(184)
<223> OTHER INFORMATION: linker
<220> FEATURE:
<221> NAME/KEY: MISC_FEATURE
<222> LOCATION: (185)..(414)
<223> OTHER INFORMATION: GA chain moiety

<400> SEQUENCE: 90

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Gly Gly Ser Gly Gly Ser Gly
                165                 170                 175

Ser Gly Ser Glu Pro Lys Ser Ser Asp Lys Thr His Thr Cys Pro Pro
            180                 185                 190

Cys Pro Ala Pro Glu Ala Ala Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Gly Ala Pro Ile Glu Lys Thr Ile Ser Lys Ala Lys
    290                 295                 300

Gly Gln Pro Arg Glu Pro Gln Val Tyr Thr Leu Pro Pro Ser Glu
305                 310                 315                 320

Glu Leu Ala Leu Asn Glu Leu Val Thr Leu Thr Cys Leu Val Lys Gly
                325                 330                 335

```
Phe Tyr Pro Ser Asp Ile Ala Val Glu Trp Leu Gln Gly Ser Gln Glu
            340                 345                 350

Leu Pro Arg Glu Lys Tyr Leu Thr Trp Ala Pro Val Leu Asp Ser Asp
            355                 360                 365

Gly Ser Phe Phe Leu Tyr Ser Ile Leu Arg Val Ala Ala Glu Asp Trp
            370                 375                 380

Lys Lys Gly Asp Thr Phe Ser Cys Ser Val Met His Glu Ala Leu His
385                 390                 395                 400

Asn Arg Phe Thr Gln Lys Ser Leu Asp Arg Ser Pro Gly Lys
            405                 410

<210> SEQ ID NO 91
<211> LENGTH: 415
<212> TYPE: PRT
<213> ORGANISM: artificial sequence
<220> FEATURE:
<223> OTHER INFORMATION: Amino acid sequence of SEED_wild-typeFGF18, GA
      chain
<220> FEATURE:
<221> NAME/KEY: MISC_FEATURE
<222> LOCATION: (1)..(180)
<223> OTHER INFORMATION: FGF18 moiety
<220> FEATURE:
<221> NAME/KEY: MISC_FEATURE
<222> LOCATION: (181)..(185)
<223> OTHER INFORMATION: linker
<220> FEATURE:
<221> NAME/KEY: MISC_FEATURE
<222> LOCATION: (186)..(415)
<223> OTHER INFORMATION: GA chain moiety

<400> SEQUENCE: 91

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
            50                  55                  60

Thr Phe Gly Ser Gln Val Arg Ile Lys Gly Lys Glu Thr Glu Phe Tyr
65              70                  75                  80

Leu Cys Met Asn Arg Lys Gly Lys Leu Val Gly Lys Pro Asp Gly Thr
            85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
            130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
            165                 170                 175

Thr His Pro Ala Glu Pro Lys Ser Ser Asp Lys Thr His Thr Cys Pro
            180                 185                 190

Pro Cys Pro Ala Pro Glu Ala Ala Gly Gly Pro Ser Val Phe Leu Phe
            195                 200                 205

Pro Pro Lys Pro Lys Asp Thr Leu Met Ile Ser Arg Thr Pro Glu Val
```

```
                  210                 215                 220
Thr Cys Val Val Val Asp Val Ser His Glu Asp Pro Glu Val Lys Phe
225                 230                 235                 240

Asn Trp Tyr Val Asp Gly Val Glu Val His Asn Ala Lys Thr Lys Pro
                    245                 250                 255

Arg Glu Glu Gln Tyr Asn Ser Thr Tyr Arg Val Val Ser Val Leu Thr
                260                 265                 270

Val Leu His Gln Asp Trp Leu Asn Gly Lys Glu Tyr Lys Cys Lys Val
            275                 280                 285

Ser Asn Lys Ala Leu Gly Ala Pro Ile Glu Lys Thr Ile Ser Lys Ala
        290                 295                 300

Lys Gly Gln Pro Phe Arg Pro Glu Val His Leu Leu Pro Pro Ser Arg
305                 310                 315                 320

Glu Glu Met Thr Lys Asn Gln Val Ser Leu Thr Cys Leu Ala Arg Gly
                325                 330                 335

Phe Tyr Pro Lys Asp Ile Ala Val Glu Trp Glu Ser Asn Gly Gln Pro
            340                 345                 350

Glu Asn Asn Tyr Lys Thr Thr Pro Ser Arg Gln Glu Pro Ser Gln Gly
        355                 360                 365

Thr Thr Thr Phe Ala Val Thr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Thr Ile Ser Leu Ser Pro Gly Lys
                405                 410                 415

<210> SEQ ID NO 92
<211> LENGTH: 423
<212> TYPE: PRT
<213> ORGANISM: artificial sequence
<220> FEATURE:
<223> OTHER INFORMATION: Amino acid sequence of SEED_ FGF18CFGF8, AG
      chain
<220> FEATURE:
<221> NAME/KEY: MISC_FEATURE
<222> LOCATION: (1)..(188)
<223> OTHER INFORMATION: FGF18 moiety
<220> FEATURE:
<221> NAME/KEY: MISC_FEATURE
<222> LOCATION: (189)..(193)
<223> OTHER INFORMATION: linker
<220> FEATURE:
<221> NAME/KEY: MISC_FEATURE
<222> LOCATION: (194)..(423)
<223> OTHER INFORMATION: AG chain moiety

<400> SEQUENCE: 92

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95
```

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln His Thr Thr Glu Gln
145                 150                 155                 160

Ser Leu Arg Phe Glu Phe Leu Asn Tyr Pro Pro Phe Thr Arg Ser Leu
                165                 170                 175

Arg Gly Ser Gln Arg Thr Trp Ala Pro Glu Pro Arg Glu Pro Lys Ser
            180                 185                 190

Ser Asp Lys Thr His Thr Cys Pro Pro Cys Pro Ala Pro Glu Ala Ala
        195                 200                 205

Gly Gly Pro Ser Val Phe Leu Phe Pro Pro Lys Pro Lys Asp Thr Leu
    210                 215                 220

Met Ile Ser Arg Thr Pro Glu Val Thr Cys Val Val Val Asp Val Ser
225                 230                 235                 240

His Glu Asp Pro Glu Val Lys Phe Asn Trp Tyr Val Asp Gly Val Glu
                245                 250                 255

Val His Asn Ala Lys Thr Lys Pro Arg Glu Glu Gln Tyr Asn Ser Thr
            260                 265                 270

Tyr Arg Val Val Ser Val Leu Thr Val Leu His Gln Asp Trp Leu Asn
        275                 280                 285

Gly Lys Glu Tyr Lys Cys Lys Val Ser Asn Lys Ala Leu Gly Ala Pro
    290                 295                 300

Ile Glu Lys Thr Ile Ser Lys Ala Lys Gly Gln Pro Phe Arg Pro Glu
305                 310                 315                 320

Val His Leu Leu Pro Pro Ser Arg Glu Glu Met Thr Lys Asn Gln Val
                325                 330                 335

Ser Leu Thr Cys Leu Ala Arg Gly Phe Tyr Pro Lys Asp Ile Ala Val
            340                 345                 350

Glu Trp Glu Ser Asn Gly Gln Pro Glu Asn Asn Tyr Lys Thr Thr Pro
        355                 360                 365

Ser Arg Gln Glu Pro Ser Gln Gly Thr Thr Thr Phe Ala Val Thr Ser
    370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Thr
                405                 410                 415

Ile Ser Leu Ser Pro Gly Lys
            420

<210> SEQ ID NO 93
<211> LENGTH: 408
<212> TYPE: PRT
<213> ORGANISM: artificial sequence
<220> FEATURE:
<223> OTHER INFORMATION: Amino acid sequence of SEED_ FGF18CFGF8T, AG
      chain
<220> FEATURE:
<221> NAME/KEY: MISC_FEATURE
<222> LOCATION: (1)..(173)
<223> OTHER INFORMATION: FGF18 moiety
<220> FEATURE:
<221> NAME/KEY: MISC_FEATURE
<222> LOCATION: (174)..(178)
<223> OTHER INFORMATION: linker

```
<220> FEATURE:
<221> NAME/KEY: MISC_FEATURE
<222> LOCATION: (179)..(408)
<223> OTHER INFORMATION: AG chain moiety

<400> SEQUENCE: 93

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln His Thr Thr Glu Gln
145                 150                 155                 160

Ser Leu Arg Phe Glu Phe Leu Asn Tyr Pro Pro Phe Thr Glu Pro Lys
                165                 170                 175

Ser Ser Asp Lys Thr His Thr Cys Pro Pro Cys Pro Ala Pro Glu Ala
            180                 185                 190

Ala Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Gly Ala
        275                 280                 285

Pro Ile Glu Lys Thr Ile Ser Lys Ala Lys Gly Gln Pro Phe Arg Pro
    290                 295                 300

Glu Val His Leu Leu Pro Pro Ser Arg Glu Glu Met Thr Lys Asn Gln
305                 310                 315                 320

Val Ser Leu Thr Cys Leu Ala Arg Gly Phe Tyr Pro Lys Asp Ile Ala
                325                 330                 335

Val Glu Trp Glu Ser Asn Gly Gln Pro Glu Asn Asn Tyr Lys Thr Thr
            340                 345                 350

Pro Ser Arg Gln Glu Pro Ser Gln Gly Thr Thr Thr Phe Ala Val Thr
        355                 360                 365

Ser Lys Leu Thr Val Asp Lys Ser Arg Trp Gln Gln Gly Asn Val Phe
    370                 375                 380
```

```
Ser Cys Ser Val Met His Glu Ala Leu His Asn His Tyr Thr Gln Lys
385                 390                 395                 400

Thr Ile Ser Leu Ser Pro Gly Lys
                405
```

<210> SEQ ID NO 94
<211> LENGTH: 412
<212> TYPE: PRT
<213> ORGANISM: artificial sequence
<220> FEATURE:
<223> OTHER INFORMATION: Amino acid sequence of SEED_ FGF18CFGF17, AG
      chain
<220> FEATURE:
<221> NAME/KEY: MISC_FEATURE
<222> LOCATION: (1)..(177)
<223> OTHER INFORMATION: FGF18 moiety
<220> FEATURE:
<221> NAME/KEY: MISC_FEATURE
<222> LOCATION: (178)..(182)
<223> OTHER INFORMATION: linker
<220> FEATURE:
<221> NAME/KEY: MISC_FEATURE
<222> LOCATION: (183)..(412)
<223> OTHER INFORMATION: AG chain moiety

<400> SEQUENCE: 94

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Leu Pro Phe Pro Asn
145                 150                 155                 160

His Ala Glu Lys Gln Lys Gln Phe Glu Phe Val Gly Ser Ala Pro Thr
                165                 170                 175

Arg Glu Pro Lys Ser Ser Asp Lys Thr His Thr Cys Pro Pro Cys Pro
            180                 185                 190

Ala Pro Glu Ala Ala Gly Gly Pro Ser Val Phe Leu Phe Pro Pro Lys
        195                 200                 205

Pro Lys Asp Thr Leu Met Ile Ser Arg Thr Pro Glu Val Thr Cys Val
    210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
            260                 265                 270
```

```
Gln Asp Trp Leu Asn Gly Lys Glu Tyr Lys Cys Lys Val Ser Asn Lys
        275                 280                 285
Ala Leu Gly Ala Pro Ile Glu Lys Thr Ile Ser Lys Ala Lys Gly Gln
        290                 295                 300
Pro Phe Arg Pro Glu Val His Leu Leu Pro Pro Ser Arg Glu Glu Met
305                 310                 315                 320
Thr Lys Asn Gln Val Ser Leu Thr Cys Leu Ala Arg Gly Phe Tyr Pro
                325                 330                 335
Lys Asp Ile Ala Val Glu Trp Glu Ser Asn Gly Gln Pro Glu Asn Asn
            340                 345                 350
Tyr Lys Thr Thr Pro Ser Arg Gln Glu Pro Ser Gln Gly Thr Thr Thr
                355                 360                 365
Phe Ala Val Thr Ser Lys Leu Thr Val Asp Lys Ser Arg Trp Gln Gln
        370                 375                 380
Gly Asn Val Phe Ser Cys Ser Val Met His Glu Ala Leu His Asn His
385                 390                 395                 400
Tyr Thr Gln Lys Thr Ile Ser Leu Ser Pro Gly Lys
                405                 410

<210> SEQ ID NO 95
<211> LENGTH: 403
<212> TYPE: PRT
<213> ORGANISM: artificial sequence
<220> FEATURE:
<223> OTHER INFORMATION: Amino acid sequence of SEED_ FGF18CFGF9, AG
      chain
<220> FEATURE:
<221> NAME/KEY: MISC_FEATURE
<222> LOCATION: (1)..(168)
<223> OTHER INFORMATION: FGF18 moiety
<220> FEATURE:
<221> NAME/KEY: MISC_FEATURE
<222> LOCATION: (169)..(173)
<223> OTHER INFORMATION: linker
<220> FEATURE:
<221> NAME/KEY: MISC_FEATURE
<222> LOCATION: (174)..(403)
<223> OTHER INFORMATION: AG chain moiety

<400> SEQUENCE: 95

Glu Glu Asn Val Asp Phe Arg Ile His Val Glu Asn Gln Thr Arg Ala
1               5                   10                  15
Arg Asp Asp Val Ser Arg Lys Gln Leu Arg Leu Tyr Gln Leu Tyr Ser
                20                  25                  30
Arg Thr Ser Gly Lys His Ile Gln Val Leu Gly Arg Arg Ile Ser Ala
            35                  40                  45
Arg Gly Glu Asp Gly Asp Lys Tyr Ala Gln Leu Leu Val Glu Thr Asp
        50                  55                  60
Thr Phe Gly Ser Gln Val Arg Ile Lys Gly Lys Glu Thr Glu Phe Tyr
65                  70                  75                  80
Leu Cys Met Asn Arg Lys Gly Lys Leu Val Gly Lys Pro Asp Gly Thr
                85                  90                  95
Ser Lys Glu Cys Val Phe Ile Glu Lys Val Leu Glu Asn Asn Tyr Thr
            100                 105                 110
Ala Leu Met Ser Ala Lys Tyr Ser Gly Trp Tyr Val Gly Phe Thr Lys
        115                 120                 125
Lys Gly Arg Pro Arg Lys Gly Pro Lys Thr Arg Glu Asn Gln Gln Asp
    130                 135                 140
Val His Phe Leu Pro Arg Pro Val Asp Pro Asp Lys Val Pro Glu Leu
```

```
                145                 150                 155                 160
Tyr Lys Asp Ile Leu Ser Gln Ser Glu Pro Lys Ser Ser Asp Lys Thr
                    165                 170                 175

His Thr Cys Pro Pro Cys Pro Ala Pro Glu Ala Ala Gly Gly Pro Ser
                    180                 185                 190

Val Phe Leu Phe Pro Pro Lys Pro Lys Asp Thr Leu Met Ile Ser Arg
                    195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                    245                 250                 255

Ser Val Leu Thr Val Leu His Gln Asp Trp Leu Asn Gly Lys Glu Tyr
                    260                 265                 270

Lys Cys Lys Val Ser Asn Lys Ala Leu Gly Ala Pro Ile Glu Lys Thr
                    275                 280                 285

Ile Ser Lys Ala Lys Gly Gln Pro Phe Arg Pro Glu Val His Leu Leu
                    290                 295                 300

Pro Pro Ser Arg Glu Glu Met Thr Lys Asn Gln Val Ser Leu Thr Cys
305                 310                 315                 320

Leu Ala Arg Gly Phe Tyr Pro Lys Asp Ile Ala Val Glu Trp Glu Ser
                    325                 330                 335

Asn Gly Gln Pro Glu Asn Asn Tyr Lys Thr Thr Pro Ser Arg Gln Glu
                    340                 345                 350

Pro Ser Gln Gly Thr Thr Thr Phe Ala Val Thr Ser Lys Leu Thr Val
                    355                 360                 365

Asp Lys Ser Arg Trp Gln Gln Gly Asn Val Phe Ser Cys Ser Val Met
                    370                 375                 380

His Glu Ala Leu His Asn His Tyr Thr Gln Lys Thr Ile Ser Leu Ser
385                 390                 395                 400

Pro Gly Lys

<210> SEQ ID NO 96
<211> LENGTH: 454
<212> TYPE: PRT
<213> ORGANISM: artificial sequence
<220> FEATURE:
<223> OTHER INFORMATION: Amino acid sequence of a mutated AG chain

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                    20                  25                  30

Asp Leu Asn Trp Ile Arg Gln Pro Pro Gly Lys Gly Leu Glu Trp Ile
                    35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                    85                  90                  95

Arg Gly Gly Tyr Trp Tyr Ala Thr Ser Tyr Tyr Phe Asp Tyr Trp Gly
                    100                 105                 110
```

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Pro Ser Glu Glu Leu Ala Leu Asn Glu Leu Val
        355                 360                 365

Thr Leu Thr Cys Leu Val Lys Gly Phe Tyr Pro Ser Asp Ile Ala Val
        370                 375                 380

Glu Trp Leu Gln Gly Ser Gln Glu Leu Pro Arg Glu Lys Tyr Leu Thr
385                 390                 395                 400

Trp Ala Pro Val Leu Asp Ser Asp Gly Ser Phe Phe Leu Tyr Ser Ile
                405                 410                 415

Leu Arg Val Ala Ala Glu Asp Trp Lys Lys Gly Asp Thr Phe Ser Cys
            420                 425                 430

Ser Val Met His Glu Ala Leu His Asn Arg Phe Thr Gln Lys Ser Leu
        435                 440                 445

Asp Arg Ser Pro Gly Lys
    450

<210> SEQ ID NO 97
<211> LENGTH: 414
<212> TYPE: PRT
<213> ORGANISM: artificial sequence
<220> FEATURE:
<223> OTHER INFORMATION: Amino acid sequence of SEED_ sprifermin, GA
      chain
<220> FEATURE:
<221> NAME/KEY: MISC_FEATURE
<222> LOCATION: (1)..(235)
<223> OTHER INFORMATION: GA chain moiety
<220> FEATURE:
<221> NAME/KEY: MISC_FEATURE
<222> LOCATION: (236)..(245)
<223> OTHER INFORMATION: linker
<220> FEATURE:
<221> NAME/KEY: MISC_FEATURE
<222> LOCATION: (246)..(414)
<223> OTHER INFORMATION: FGF18 moiety

<400> SEQUENCE: 97

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
        195                 200                 205

Asp Thr Phe Ser Cys Ser Val Met His Glu Ala Leu His Asn Arg Phe
    210                 215                 220

Thr Gln Lys Ser Leu Asp Arg Ser Pro Gly Lys Glu Pro Lys Ser Ser
225                 230                 235                 240

Asp Lys Thr His Thr Glu Glu Asn Val Asp Phe Arg Ile His Val Glu
                245                 250                 255

Asn Gln Thr Arg Ala Arg Asp Asp Val Ser Arg Lys Gln Leu Arg Leu
            260                 265                 270

Tyr Gln Leu Tyr Ser Arg Thr Ser Gly Lys His Ile Gln Val Leu Gly
        275                 280                 285

Arg Arg Ile Ser Ala Arg Gly Glu Asp Gly Asp Lys Tyr Ala Gln Leu
    290                 295                 300

Leu Val Glu Thr Asp Thr Phe Gly Ser Gln Val Arg Ile Lys Gly Lys
305                 310                 315                 320

Glu Thr Glu Phe Tyr Leu Cys Met Asn Arg Lys Gly Lys Leu Val Gly
                325                 330                 335

Lys Pro Asp Gly Thr Ser Lys Glu Cys Val Phe Ile Glu Lys Val Leu
            340                 345                 350

Glu Asn Asn Tyr Thr Ala Leu Met Ser Ala Lys Tyr Ser Gly Trp Tyr
        355                 360                 365
```

-continued

Val Gly Phe Thr Lys Lys Gly Arg Pro Arg Lys Gly Pro Lys Thr Arg
    370                 375                 380

Glu Asn Gln Gln Asp Val His Phe Met Lys Arg Tyr Pro Lys Gly Gln
385                 390                 395                 400

Pro Glu Leu Gln Lys Pro Phe Lys Tyr Thr Thr Val Thr Lys
                405                 410

<210> SEQ ID NO 98
<211> LENGTH: 424
<212> TYPE: PRT
<213> ORGANISM: artificial sequence
<220> FEATURE:
<223> OTHER INFORMATION: Amino acid sequence of SEED_ sprifermin, GA
      chain
<220> FEATURE:
<221> NAME/KEY: MISC_FEATURE
<222> LOCATION: (1)..(235)
<223> OTHER INFORMATION: GA chain moiety
<220> FEATURE:
<221> NAME/KEY: MISC_FEATURE
<222> LOCATION: (236)..(255)
<223> OTHER INFORMATION: linker
<220> FEATURE:
<221> NAME/KEY: MISC_FEATURE
<222> LOCATION: (256)..(424)
<223> OTHER INFORMATION: FGF18 moiety

<400> SEQUENCE: 98

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
        195                 200                 205

Asp Thr Phe Ser Cys Ser Val Met His Glu Ala Leu His Asn Arg Phe
    210                 215                 220

Thr Gln Lys Ser Leu Asp Arg Ser Pro Gly Lys Gly Gly Gly Gly Ser
225                 230                 235                 240

Glu Pro Lys Ser Ser Asp Lys Thr His Thr Gly Gly Gly Gly Ser Glu

```
                    245                 250                 255
Glu Asn Val Asp Phe Arg Ile His Val Glu Asn Gln Thr Arg Ala Arg
            260                 265                 270

Asp Asp Val Ser Arg Lys Gln Leu Arg Leu Tyr Gln Leu Tyr Ser Arg
        275                 280                 285

Thr Ser Gly Lys His Ile Gln Val Leu Gly Arg Arg Ile Ser Ala Arg
    290                 295                 300

Gly Glu Asp Gly Asp Lys Tyr Ala Gln Leu Leu Val Glu Thr Asp Thr
305                 310                 315                 320

Phe Gly Ser Gln Val Arg Ile Lys Gly Lys Glu Thr Glu Phe Tyr Leu
                325                 330                 335

Cys Met Asn Arg Lys Gly Lys Leu Val Gly Lys Pro Asp Gly Thr Ser
            340                 345                 350

Lys Glu Cys Val Phe Ile Glu Lys Val Leu Glu Asn Asn Tyr Thr Ala
        355                 360                 365

Leu Met Ser Ala Lys Tyr Ser Gly Trp Tyr Val Gly Phe Thr Lys Lys
    370                 375                 380

Gly Arg Pro Arg Lys Gly Pro Lys Thr Arg Glu Asn Gln Gln Asp Val
385                 390                 395                 400

His Phe Met Lys Arg Tyr Pro Lys Gly Gln Pro Glu Leu Gln Lys Pro
                405                 410                 415

Phe Lys Tyr Thr Thr Val Thr Lys
            420

<210> SEQ ID NO 99
<211> LENGTH: 419
<212> TYPE: PRT
<213> ORGANISM: artificial sequence
<220> FEATURE:
<223> OTHER INFORMATION: Amino acid sequence of SEED_ sprifermin, GA
      chain
<220> FEATURE:
<221> NAME/KEY: MISC_FEATURE
<222> LOCATION: (1)..(235)
<223> OTHER INFORMATION: GA chain moiety
<220> FEATURE:
<221> NAME/KEY: MISC_FEATURE
<222> LOCATION: (236)..(250)
<223> OTHER INFORMATION: linker
<220> FEATURE:
<221> NAME/KEY: MISC_FEATURE
<222> LOCATION: (251)..(419)
<223> OTHER INFORMATION: FGF18 moiety

<400> SEQUENCE: 99

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

Leu Gly Ala Pro Ile Glu Lys Thr Ile Ser Lys Ala Lys Gly Gln Pro
            115                 120                 125

Arg Glu Pro Gln Val Tyr Thr Leu Pro Pro Ser Glu Glu Leu Ala
130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
            195                 200                 205

Asp Thr Phe Ser Cys Ser Val Met His Glu Ala Leu His Asn Arg Phe
            210                 215                 220

Thr Gln Lys Ser Leu Asp Arg Ser Pro Gly Lys Gly Gly Gly Gly Ser
225                 230                 235                 240

Gly Gly Gly Gly Ser Gly Gly Gly Ser Glu Glu Asn Val Asp Phe
                245                 250                 255

Arg Ile His Val Glu Asn Gln Thr Arg Ala Arg Asp Asp Val Ser Arg
            260                 265                 270

Lys Gln Leu Arg Leu Tyr Gln Leu Tyr Ser Arg Thr Ser Gly Lys His
275                 280                 285

Ile Gln Val Leu Gly Arg Arg Ile Ser Ala Arg Gly Glu Asp Gly Asp
            290                 295                 300

Lys Tyr Ala Gln Leu Leu Val Glu Thr Asp Thr Phe Gly Ser Gln Val
305                 310                 315                 320

Arg Ile Lys Gly Lys Glu Thr Glu Phe Tyr Leu Cys Met Asn Arg Lys
                325                 330                 335

Gly Lys Leu Val Gly Lys Pro Asp Gly Thr Ser Lys Glu Cys Val Phe
            340                 345                 350

Ile Glu Lys Val Leu Glu Asn Asn Tyr Thr Ala Leu Met Ser Ala Lys
            355                 360                 365

Tyr Ser Gly Trp Tyr Val Gly Phe Thr Lys Lys Gly Arg Pro Arg Lys
370                 375                 380

Gly Pro Lys Thr Arg Glu Asn Gln Gln Asp Val His Phe Met Lys Arg
385                 390                 395                 400

Tyr Pro Lys Gly Gln Pro Glu Leu Gln Lys Pro Phe Lys Tyr Thr Thr
                405                 410                 415

Val Thr Lys

<210> SEQ ID NO 100
<211> LENGTH: 435
<212> TYPE: PRT
<213> ORGANISM: artificial sequence
<220> FEATURE:
<223> OTHER INFORMATION: Amino acid sequence of SEED_ wildtype FGF18, GA
      chain
<220> FEATURE:
<221> NAME/KEY: MISC_FEATURE
<222> LOCATION: (1)..(235)
<223> OTHER INFORMATION: GA chain moiety
<220> FEATURE:
<221> NAME/KEY: MISC_FEATURE
<222> LOCATION: (236)..(255)
<223> OTHER INFORMATION: linker
<220> FEATURE:
<221> NAME/KEY: MISC_FEATURE
<222> LOCATION: (256)..(435)
<223> OTHER INFORMATION: FGF18 moiety

<400> SEQUENCE: 100

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
        195                 200                 205

Asp Thr Phe Ser Cys Ser Val Met His Glu Ala Leu His Asn Arg Phe
    210                 215                 220

Thr Gln Lys Ser Leu Asp Arg Ser Pro Gly Lys Gly Gly Gly Gly Ser
225                 230                 235                 240

Glu Pro Lys Ser Ser Asp Lys Thr His Thr Gly Gly Gly Gly Ser Glu
                245                 250                 255

Glu Asn Val Asp Phe Arg Ile His Val Glu Asn Gln Thr Arg Ala Arg
            260                 265                 270

Asp Asp Val Ser Arg Lys Gln Leu Arg Leu Tyr Gln Leu Tyr Ser Arg
        275                 280                 285

Thr Ser Gly Lys His Ile Gln Val Leu Gly Arg Arg Ile Ser Ala Arg
    290                 295                 300

Gly Glu Asp Gly Asp Lys Tyr Ala Gln Leu Leu Val Glu Thr Asp Thr
305                 310                 315                 320

Phe Gly Ser Gln Val Arg Ile Lys Gly Lys Glu Thr Glu Phe Tyr Leu
                325                 330                 335

Cys Met Asn Arg Lys Gly Lys Leu Val Gly Lys Pro Asp Gly Thr Ser
            340                 345                 350

Lys Glu Cys Val Phe Ile Glu Lys Val Leu Glu Asn Asn Tyr Thr Ala
        355                 360                 365

Leu Met Ser Ala Lys Tyr Ser Gly Trp Tyr Val Gly Phe Thr Lys Lys
    370                 375                 380

Gly Arg Pro Arg Lys Gly Pro Lys Thr Arg Glu Asn Gln Gln Asp Val
385                 390                 395                 400

His Phe Met Lys Arg Tyr Pro Lys Gly Gln Pro Glu Leu Gln Lys Pro
```

```
                      405                 410                 415
Phe Lys Tyr Thr Thr Val Thr Lys Arg Ser Arg Arg Ile Arg Pro Thr
                420                 425                 430

His Pro Ala
        435

<210> SEQ ID NO 101
<211> LENGTH: 424
<212> TYPE: PRT
<213> ORGANISM: artificial sequence
<220> FEATURE:
<223> OTHER INFORMATION: Amino acid sequence of SEED_ sprifermin, AG
      chain
<220> FEATURE:
<221> NAME/KEY: MISC_FEATURE
<222> LOCATION: (1)..(235)
<223> OTHER INFORMATION: AG chain moiety
<220> FEATURE:
<221> NAME/KEY: MISC_FEATURE
<222> LOCATION: (236)..(255)
<223> OTHER INFORMATION: linker
<220> FEATURE:
<221> NAME/KEY: MISC_FEATURE
<222> LOCATION: (256)..(424)
<223> OTHER INFORMATION: FGF18 moiety

<400> SEQUENCE: 101

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Phe Arg Pro Glu Val His Leu Leu Pro Pro Ser Arg Glu Glu Met Thr
130                 135                 140

Lys Asn Gln Val Ser Leu Thr Cys Leu Ala Arg Gly Phe Tyr Pro Lys
145                 150                 155                 160

Asp Ile Ala Val Glu Trp Glu Ser Asn Gly Gln Pro Glu Asn Asn Tyr
                165                 170                 175

Lys Thr Thr Pro Ser Arg Gln Glu Pro Ser Gln Gly Thr Thr Thr Phe
            180                 185                 190

Ala Val Thr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Thr Ile Ser Leu Ser Pro Gly Lys Gly Gly Gly Gly Ser
225                 230                 235                 240

Glu Pro Lys Ser Ser Asp Lys Thr His Thr Gly Gly Gly Gly Ser Glu
                245                 250                 255
```

```
Glu Asn Val Asp Phe Arg Ile His Val Asn Gln Thr Arg Ala Arg
            260                 265                 270

Asp Asp Val Ser Arg Lys Gln Leu Arg Leu Tyr Gln Leu Tyr Ser Arg
        275                 280                 285

Thr Ser Gly Lys His Ile Gln Val Leu Gly Arg Arg Ile Ser Ala Arg
    290                 295                 300

Gly Glu Asp Gly Asp Lys Tyr Ala Gln Leu Leu Val Glu Thr Asp Thr
305                 310                 315                 320

Phe Gly Ser Gln Val Arg Ile Lys Gly Lys Thr Glu Phe Tyr Leu
                325                 330                 335

Cys Met Asn Arg Lys Gly Lys Leu Val Gly Lys Pro Asp Gly Thr Ser
            340                 345                 350

Lys Glu Cys Val Phe Ile Glu Lys Val Leu Glu Asn Asn Tyr Thr Ala
            355                 360                 365

Leu Met Ser Ala Lys Tyr Ser Gly Trp Tyr Val Gly Phe Thr Lys Lys
        370                 375                 380

Gly Arg Pro Arg Lys Gly Pro Lys Thr Arg Glu Asn Gln Gln Asp Val
385                 390                 395                 400

His Phe Met Lys Arg Tyr Pro Lys Gly Gln Pro Glu Leu Gln Lys Pro
                405                 410                 415

Phe Lys Tyr Thr Thr Val Thr Lys
                420

<210> SEQ ID NO 102
<211> LENGTH: 235
<212> TYPE: PRT
<213> ORGANISM: artificial sequence
<220> FEATURE:
<223> OTHER INFORMATION: Amino acid sequence of the CH2-CH3 domains of a
      GA chain

<400> SEQUENCE: 102

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190
```

```
Phe Leu Tyr Ser Ile Leu Arg Val Ala Ala Glu Asp Trp Lys Lys Gly
            195                 200                 205

Asp Thr Phe Ser Cys Ser Val Met His Glu Ala Leu His Asn Arg Phe
    210                 215                 220

Thr Gln Lys Ser Leu Asp Arg Ser Pro Gly Lys
225                 230                 235

<210> SEQ ID NO 103
<211> LENGTH: 643
<212> TYPE: PRT
<213> ORGANISM: artificial sequence
<220> FEATURE:
<223> OTHER INFORMATION: Amino acid sequence of SEED_ sprifermin, AG
      chain
<220> FEATURE:
<221> NAME/KEY: MISC_FEATURE
<222> LOCATION: (1)..(454)
<223> OTHER INFORMATION: AG chain moiety
<220> FEATURE:
<221> NAME/KEY: MISC_FEATURE
<222> LOCATION: (455)..(474)
<223> OTHER INFORMATION: linker
<220> FEATURE:
<221> NAME/KEY: MISC_FEATURE
<222> LOCATION: (475)..(643)
<223> OTHER INFORMATION: FGF18 moiety

<400> SEQUENCE: 103

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
```

245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Phe Arg Pro Glu Val
            340                 345                 350
His Leu Leu Pro Pro Ser Arg Glu Glu Met Thr Lys Asn Gln Val Ser
        355                 360                 365
Leu Thr Cys Leu Ala Arg Gly Phe Tyr Pro Lys Asp Ile Ala Val Glu
    370                 375                 380
Trp Glu Ser Asn Gly Gln Pro Glu Asn Asn Tyr Lys Thr Thr Pro Ser
385                 390                 395                 400
Arg Gln Glu Pro Ser Gln Gly Thr Thr Thr Phe Ala Val Thr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Thr Ile
        435                 440                 445
Ser Leu Ser Pro Gly Lys Gly Gly Gly Ser Glu Pro Lys Ser Ser
    450                 455                 460
Asp Lys Thr His Thr Gly Gly Gly Ser Glu Glu Asn Val Asp Phe
465                 470                 475                 480
Arg Ile His Val Glu Asn Gln Thr Arg Ala Arg Asp Asp Val Ser Arg
                485                 490                 495
Lys Gln Leu Arg Leu Tyr Gln Leu Tyr Ser Arg Thr Ser Gly Lys His
            500                 505                 510
Ile Gln Val Leu Gly Arg Arg Ile Ser Ala Arg Gly Glu Asp Gly Asp
        515                 520                 525
Lys Tyr Ala Gln Leu Leu Val Glu Thr Asp Thr Phe Gly Ser Gln Val
    530                 535                 540
Arg Ile Lys Gly Lys Glu Thr Glu Phe Tyr Leu Cys Met Asn Arg Lys
545                 550                 555                 560
Gly Lys Leu Val Gly Lys Pro Asp Gly Thr Ser Lys Glu Cys Val Phe
                565                 570                 575
Ile Glu Lys Val Leu Glu Asn Asn Tyr Thr Ala Leu Met Ser Ala Lys
            580                 585                 590
Tyr Ser Gly Trp Tyr Val Gly Phe Thr Lys Lys Gly Arg Pro Arg Lys
        595                 600                 605
Gly Pro Lys Thr Arg Glu Asn Gln Gln Asp Val His Phe Met Lys Arg
    610                 615                 620
Tyr Pro Lys Gly Gln Pro Glu Leu Gln Lys Pro Phe Lys Tyr Thr Thr
625                 630                 635                 640
Val Thr Lys

<210> SEQ ID NO 104
<211> LENGTH: 643

```
<212> TYPE: PRT
<213> ORGANISM: artificial sequence
<220> FEATURE:
<223> OTHER INFORMATION: Amino acid sequence of SEED_ FGF18Y191P, AG
      chain
<220> FEATURE:
<221> NAME/KEY: MISC_FEATURE
<222> LOCATION: (1)..(454)
<223> OTHER INFORMATION: AG chain moiety
<220> FEATURE:
<221> NAME/KEY: MISC_FEATURE
<222> LOCATION: (455)..(474)
<223> OTHER INFORMATION: linker
<220> FEATURE:
<221> NAME/KEY: MISC_FEATURE
<222> LOCATION: (475)..(643)
<223> OTHER INFORMATION: FGF18 moiety

<400> SEQUENCE: 104
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
            Lys Glu Tyr Lys Cys Lys Val Ser Asn Lys Ala Leu Gly Ala Pro Ile
                            325                 330                 335

Glu Lys Thr Ile Ser Lys Ala Lys Gly Gln Pro Phe Arg Pro Glu Val
                        340                 345                 350

His Leu Leu Pro Pro Ser Arg Glu Glu Met Thr Lys Asn Gln Val Ser
                    355                 360                 365

Leu Thr Cys Leu Ala Arg Gly Phe Tyr Pro Lys Asp Ile Ala Val Glu
                370                 375                 380

Trp Glu Ser Asn Gly Gln Pro Glu Asn Asn Tyr Lys Thr Thr Pro Ser
            385                 390                 395                 400

Arg Gln Glu Pro Ser Gln Gly Thr Thr Thr Phe Ala Val Thr Ser Lys
                            405                 410                 415

Leu Thr Val Asp Lys Ser Arg Trp Gln Gln Gly Asn Val Phe Ser Cys
                        420                 425                 430

Ser Val Met His Glu Ala Leu His Asn His Tyr Thr Gln Lys Thr Ile
                    435                 440                 445

Ser Leu Ser Pro Gly Lys Gly Gly Gly Ser Glu Pro Lys Ser Ser
                450                 455                 460

Asp Lys Thr His Thr Gly Gly Gly Gly Ser Glu Glu Asn Val Asp Phe
            465                 470                 475                 480

Arg Ile His Val Glu Asn Gln Thr Arg Ala Arg Asp Asp Val Ser Arg
                            485                 490                 495

Lys Gln Leu Arg Leu Tyr Gln Leu Tyr Ser Arg Thr Ser Gly Lys His
                        500                 505                 510

Ile Gln Val Leu Gly Arg Arg Ile Ser Ala Arg Gly Glu Asp Gly Asp
                    515                 520                 525

Lys Tyr Ala Gln Leu Leu Val Glu Thr Asp Thr Phe Gly Ser Gln Val
                530                 535                 540

Arg Ile Lys Gly Lys Glu Thr Glu Phe Tyr Leu Cys Met Asn Arg Lys
            545                 550                 555                 560

Gly Lys Leu Val Gly Lys Pro Asp Gly Thr Ser Lys Glu Cys Val Phe
                            565                 570                 575

Ile Glu Lys Val Leu Glu Asn Asn Tyr Thr Ala Leu Met Ser Ala Lys
                        580                 585                 590

Tyr Ser Gly Trp Tyr Val Gly Phe Thr Lys Lys Gly Arg Pro Arg Lys
                    595                 600                 605

Gly Pro Lys Thr Arg Glu Asn Gln Gln Asp Val His Phe Met Lys Arg
                610                 615                 620

Tyr Pro Lys Gly Gln Pro Glu Leu Gln Lys Pro Phe Lys Pro Thr Thr
            625                 630                 635                 640

Val Thr Lys

<210> SEQ ID NO 105
<211> LENGTH: 643
<212> TYPE: PRT
<213> ORGANISM: artificial sequence
<220> FEATURE:
<223> OTHER INFORMATION: Amino acid sequence of SEED_ FGF18Y191F, AG
      chain
<220> FEATURE:
<221> NAME/KEY: MISC_FEATURE
<222> LOCATION: (1)..(454)
<223> OTHER INFORMATION: AG chain moiety
<220> FEATURE:
<221> NAME/KEY: MISC_FEATURE
<222> LOCATION: (455)..(474)
<223> OTHER INFORMATION: linker
```

```
<220> FEATURE:
<221> NAME/KEY: MISC_FEATURE
<222> LOCATION: (475)..(643)
<223> OTHER INFORMATION: FGF18 moiety

<400> SEQUENCE: 105
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 |

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Phe Arg Pro Glu Val
            340                 345                 350

His Leu Leu Pro Pro Ser Arg Glu Glu Met Thr Lys Asn Gln Val Ser
        355                 360                 365

Leu Thr Cys Leu Ala Arg Gly Phe Tyr Pro Lys Asp Ile Ala Val Glu
370                 375                 380

Trp Glu Ser Asn Gly Gln Pro Glu Asn Asn Tyr Lys Thr Thr Pro Ser
385                 390                 395                 400

Arg Gln Glu Pro Ser Gln Gly Thr Thr Thr Phe Ala Val Thr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Thr Ile
            435                 440                 445

Ser Leu Ser Pro Gly Lys Gly Gly Gly Ser Glu Pro Lys Ser Ser
            450                 455                 460

Asp Lys Thr His Thr Gly Gly Gly Ser Glu Glu Asn Val Asp Phe
465                 470                 475                 480

Arg Ile His Val Glu Asn Gln Thr Arg Ala Arg Asp Asp Val Ser Arg
            485                 490                 495

Lys Gln Leu Arg Leu Tyr Gln Leu Tyr Ser Arg Thr Ser Gly Lys His
            500                 505                 510

Ile Gln Val Leu Gly Arg Arg Ile Ser Ala Arg Gly Glu Asp Gly Asp
            515                 520                 525

Lys Tyr Ala Gln Leu Leu Val Glu Thr Asp Thr Phe Gly Ser Gln Val
530                 535                 540

Arg Ile Lys Gly Lys Glu Thr Glu Phe Tyr Leu Cys Met Asn Arg Lys
545                 550                 555                 560

Gly Lys Leu Val Gly Lys Pro Asp Gly Thr Ser Lys Glu Cys Val Phe
            565                 570                 575

Ile Glu Lys Val Leu Glu Asn Asn Tyr Thr Ala Leu Met Ser Ala Lys
            580                 585                 590

Tyr Ser Gly Trp Tyr Val Gly Phe Thr Lys Lys Gly Arg Pro Arg Lys
            595                 600                 605

Gly Pro Lys Thr Arg Glu Asn Gln Gln Asp Val His Phe Met Lys Arg
610                 615                 620

Tyr Pro Lys Gly Gln Pro Glu Leu Gln Lys Pro Phe Lys Phe Thr Thr
625                 630                 635                 640

Val Thr Lys

<210> SEQ ID NO 106
<211> LENGTH: 643
<212> TYPE: PRT
<213> ORGANISM: artificial sequence
<220> FEATURE:
<223> OTHER INFORMATION: Amino acid sequence of SEED_ FGF18VS, AG
<220> FEATURE:
<221> NAME/KEY: MISC_FEATURE
<222> LOCATION: (1)..(454)
<223> OTHER INFORMATION: AG chain moiety
<220> FEATURE:
<221> NAME/KEY: MISC_FEATURE
<222> LOCATION: (455)..(474)
<223> OTHER INFORMATION: linker
<220> FEATURE:
<221> NAME/KEY: MISC_FEATURE
<222> LOCATION: (475)..(643)
<223> OTHER INFORMATION: FGF18 moiety

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile

```
                35                  40                  45
Gly Ile Ile Trp Gly Asp Gly Thr Thr Asp Tyr Asn Ser Ala Val Lys
 50                  55                  60
Ser Arg Val Thr Ile Ser Lys Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Gly Gly Tyr Trp Tyr Ala Thr Ser Tyr Tyr Phe Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Phe Arg Pro Glu Val
                340                 345                 350
His Leu Leu Pro Pro Ser Arg Glu Glu Met Thr Lys Asn Gln Val Ser
                355                 360                 365
Leu Thr Cys Leu Ala Arg Gly Phe Tyr Pro Lys Asp Ile Ala Val Glu
                370                 375                 380
Trp Glu Ser Asn Gly Gln Pro Glu Asn Asn Tyr Lys Thr Thr Pro Ser
385                 390                 395                 400
Arg Gln Glu Pro Ser Gln Gly Thr Thr Thr Phe Ala Val Thr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Thr Ile
                435                 440                 445
Ser Leu Ser Pro Gly Lys Gly Gly Gly Gly Ser Glu Pro Lys Ser Ser
                450                 455                 460
```

```
Asp Lys Thr His Thr Gly Gly Gly Ser Glu Glu Asn Val Asp Phe
465                 470                 475                 480

Arg Ile His Val Glu Asn Gln Thr Arg Ala Arg Asp Asp Val Ser Arg
            485                 490                 495

Lys Gln Leu Arg Leu Tyr Gln Leu Tyr Ser Arg Thr Ser Gly Lys His
        500                 505                 510

Ile Gln Val Leu Gly Arg Arg Ile Ser Ala Arg Gly Glu Asp Gly Asp
            515                 520                 525

Lys Tyr Ala Gln Leu Leu Val Glu Thr Asp Thr Phe Gly Ser Gln Val
    530                 535                 540

Arg Ile Lys Gly Lys Glu Thr Glu Phe Tyr Leu Cys Met Asn Arg Lys
545                 550                 555                 560

Gly Lys Leu Val Gly Lys Pro Asp Gly Thr Ser Lys Glu Cys Val Phe
                565                 570                 575

Ile Glu Lys Val Leu Glu Asn Asn Tyr Thr Ala Leu Met Ser Ala Lys
            580                 585                 590

Tyr Ser Gly Trp Tyr Val Gly Phe Thr Lys Lys Gly Arg Pro Arg Lys
        595                 600                 605

Gly Pro Lys Thr Arg Glu Asn Gln Gln Asp Val His Phe Met Lys Arg
610                 615                 620

Tyr Pro Lys Gly Gln Pro Glu Leu Gln Lys Pro Phe Val Ser Thr Thr
625                 630                 635                 640

Val Thr Lys

<210> SEQ ID NO 107
<211> LENGTH: 235
<212> TYPE: PRT
<213> ORGANISM: artificial sequence
<220> FEATURE:
<223> OTHER INFORMATION: Amino acid sequence of the CH2-CH3 domains of
      an AG chain

<400> SEQUENCE: 107

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Phe Arg Pro Glu Val His Leu Leu Pro Pro Ser Arg Glu Glu Met Thr
    130                 135                 140

Lys Asn Gln Val Ser Leu Thr Cys Leu Ala Arg Gly Phe Tyr Pro Lys
145                 150                 155                 160

Asp Ile Ala Val Glu Trp Glu Ser Asn Gly Gln Pro Glu Asn Asn Tyr
                165                 170                 175
```

-continued

```
Lys Thr Thr Pro Ser Arg Gln Glu Pro Ser Gln Gly Thr Thr Thr Phe
                180                 185                 190
Ala Val Thr Ser Lys Leu Thr Val Asp Lys Ser Arg Trp Gln Gln Gly
            195                 200                 205
Asn Val Phe Ser Cys Ser Val Met His Glu Ala Leu His Asn His Tyr
210                 215                 220
Thr Gln Lys Thr Ile Ser Leu Ser Pro Gly Lys
225                 230                 235

<210> SEQ ID NO 108
<211> LENGTH: 643
<212> TYPE: PRT
<213> ORGANISM: artificial sequence
<220> FEATURE:
<223> OTHER INFORMATION: Amino acid sequence of SEED_ FGF18VS, GA chain
<220> FEATURE:
<221> NAME/KEY: MISC_FEATURE
<222> LOCATION: (1)..(454)
<223> OTHER INFORMATION: GA chain moiety
<220> FEATURE:
<221> NAME/KEY: MISC_FEATURE
<222> LOCATION: (455)..(474)
<223> OTHER INFORMATION: linker
<220> FEATURE:
<221> NAME/KEY: MISC_FEATURE
<222> LOCATION: (475)..(643)
<223> OTHER INFORMATION: FGF18 moiety

<400> SEQUENCE: 108

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Ile Gly Tyr
                20                  25                  30
Asp Leu Asn Trp Ile Arg Gln Pro Pro Gly Lys Gly Leu Glu Trp Ile
            35                  40                  45
Gly Ile Ile Trp Gly Asp Gly Thr Thr Asp Tyr Asn Ser Ala Val Lys
        50                  55                  60
Ser Arg Val Thr Ile Ser Lys Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Gly Tyr Trp Tyr Ala Thr Ser Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Ala Ala Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Glu Glu Leu Ala Leu Asn Glu Leu Val
                355                 360                 365

Thr Leu Thr Cys Leu Val Lys Gly Phe Tyr Pro Ser Asp Ile Ala Val
            370                 375                 380

Glu Trp Leu Gln Gly Ser Gln Glu Leu Pro Arg Glu Lys Tyr Leu Thr
385                 390                 395                 400

Trp Ala Pro Val Leu Asp Ser Asp Gly Ser Phe Phe Leu Tyr Ser Ile
                405                 410                 415

Leu Arg Val Ala Ala Glu Asp Trp Lys Lys Gly Asp Thr Phe Ser Cys
                420                 425                 430

Ser Val Met His Glu Ala Leu His Asn Arg Phe Thr Gln Lys Ser Leu
            435                 440                 445

Asp Arg Ser Pro Gly Lys Gly Gly Gly Ser Glu Pro Lys Ser Ser
450                 455                 460

Asp Lys Thr His Thr Gly Gly Gly Ser Glu Glu Asn Val Asp Phe
465                 470                 475                 480

Arg Ile His Val Glu Asn Gln Thr Arg Ala Arg Asp Asp Val Ser Arg
                485                 490                 495

Lys Gln Leu Arg Leu Tyr Gln Leu Tyr Ser Arg Thr Ser Gly Lys His
                500                 505                 510

Ile Gln Val Leu Gly Arg Arg Ile Ser Ala Arg Gly Glu Asp Gly Asp
                515                 520                 525

Lys Tyr Ala Gln Leu Leu Val Glu Thr Asp Thr Phe Gly Ser Gln Val
                530                 535                 540

Arg Ile Lys Gly Lys Glu Thr Glu Phe Tyr Leu Cys Met Asn Arg Lys
545                 550                 555                 560

Gly Lys Leu Val Gly Lys Pro Asp Gly Thr Ser Lys Glu Cys Val Phe
                565                 570                 575

Ile Glu Lys Val Leu Glu Asn Asn Tyr Thr Ala Leu Met Ser Ala Lys
                580                 585                 590

Tyr Ser Gly Trp Tyr Val Gly Phe Thr Lys Lys Gly Arg Pro Arg Lys
                595                 600                 605

Gly Pro Lys Thr Arg Glu Asn Gln Gln Asp Val His Phe Met Lys Arg
                610                 615                 620

Tyr Pro Lys Gly Gln Pro Glu Leu Gln Lys Pro Phe Lys Tyr Thr Thr
625                 630                 635                 640

Val Thr Lys
```

<210> SEQ ID NO 109
<211> LENGTH: 1362
<212> TYPE: DNA
<213> ORGANISM: artificial sequence
<220> FEATURE:
<223> OTHER INFORMATION: synthetic

<400> SEQUENCE: 109

| | | | | | |
|---|---|---|---|---|---|
| caggtccagc | tgcaagaatc | tggccctggc | ctggtcaagc | cttccgagac | actgtctctg | 60 |
| acctgcaccg | tgtctggctt | ctccctgatc | ggctacgacc | tgaactggat | cagacagcct | 120 |
| cctggcaaag | gcctggaatg | gatcggaatc | atctggggcg | acggcaccac | cgactacaac | 180 |
| tctgccgtga | agtccagagt | gaccatctcc | aaggacacct | ccaagaacca | gttcagcctg | 240 |
| aagctgtcct | ccgtgaccgc | tgctgatacc | gccgtgtact | actgtgccag | aggcggctat | 300 |
| tggtacgcca | cctcctacta | cttcgactac | tggggccagg | gcaccctggt | cacagtttct | 360 |
| tccgcttcca | ccaagggacc | cagcgtgttc | cctctggctc | cttccagcaa | gtctacctct | 420 |
| ggcggaacag | ctgctctggg | ctgtctggtc | aaggactact | ccctgagcc | tgtgaccgtg | 480 |
| tcctggaact | ctggcgctct | gacatctggc | gtgcacacct | tccagctgt | gctgcagtcc | 540 |
| tccggcctgt | actctctgtc | ctctgtcgtg | accgtgcctt | ccagctctct | gggaacccag | 600 |
| acctacatct | gcaatgtgaa | ccacaagcct | agcaacacca | aggtggacaa | gaaggtggaa | 660 |
| cccaagtcct | gcgacaagac | ccacacctgt | cctccatgtc | ctgctccaga | agctgctggc | 720 |
| ggcccttccg | tgtttctgtt | ccctccaaag | cctaaggaca | ccctgatgat | ctctcggacc | 780 |
| cctgaagtga | cctgcgtggt | ggtggatgtg | tctcacgagg | acccagaagt | gaagttcaat | 840 |
| tggtacgtgg | acggcgtgga | agtgcacaac | gccaagacca | agcctagaga | ggaacagtac | 900 |
| aactccacct | acagagtggt | gtccgtgctg | accgtgctgc | accaggattg | gctgaacggc | 960 |
| aaagagtaca | agtgcaaggt | gtccaacaag | gccctgggcg | ctcccatcga | aaagaccatc | 1020 |
| agcaaggcta | agggccagcc | tttccggcct | gaagtgcatc | tgctgcctcc | aagcagagaa | 1080 |
| gagatgacca | agaatcaggt | gtccctgacc | tgtctggcca | ggggcttcta | ccctaaggat | 1140 |
| atcgccgtgg | aatgggagtc | caacggccag | cctgagaaca | actacaagac | aaccccctagc | 1200 |
| cggcaagagc | cctctcaggg | caccacaacc | tttgccgtga | cctccaagct | gacagtggac | 1260 |
| aagtccagat | ggcagcaggg | caacgtgttc | tcctgctccg | tgatgcacga | ggccctgcac | 1320 |
| aaccactaca | cccagaaaac | catttctctg | agccccggca | ag | | 1362 |

<210> SEQ ID NO 110
<211> LENGTH: 1242
<212> TYPE: DNA
<213> ORGANISM: artificial sequence
<220> FEATURE:
<223> OTHER INFORMATION: synthetic

<400> SEQUENCE: 110

| | | | | | |
|---|---|---|---|---|---|
| gaggaaaacg | tggactttag | aatccacgtc | gagaaccaga | ccagagccag | ggacgacgtg | 60 |
| tccagaaagc | agctgagact | gtaccagctg | taccccggga | cctccggcaa | gcacattcag | 120 |
| gtgctgggca | gaagaatctc | cgccagaggc | gaggacggcg | ataagtatgc | acagctgctg | 180 |
| gtggaaaccc | acaccttcgg | aagccaagtg | cggatcaagg | gcaaagagac | agagttctac | 240 |
| ctgtgcatga | accggaaggg | caagctcgtg | ggcaagcctg | acggcacctc | taagaatgc | 300 |
| gtgttcatcg | agaaggtgct | cgagaacaac | tacaccgctc | tgatgtccgc | caagtactcc | 360 |
| ggatggtacg | tgggcttcac | caagaagggc | agacccagaa | agggccccaa | gaccagagaa | 420 |

| | |
|---|---|
| aaccagcagg acgtgcactt tatgaagcgc taccccaagg gccagcctga gctgcagaag | 480 |
| cccttttaagt acaccaccgt gaccaaaggc ggctccggcg aagtggatc tggatctgaa | 540 |
| cctaagtcct ccgacaagac ccacacctgt cctccatgtc ctgctccaga agctgctggc | 600 |
| ggcccttccg tgtttctgtt ccctccaaag cctaaggaca ccctgatgat ctctcggacc | 660 |
| cctgaagtga cctgcgtggt ggtggatgtg tctcacgagg acccagaagt gaagttcaat | 720 |
| tggtacgtcg acggcgtgga agtgcacaac gccaagacca gcctagaga ggaacagtac | 780 |
| aactccacct acagagtggt gtccgtgctg accgtgctgc accaggattg gctgaacggc | 840 |
| aaagagtaca agtgcaaggt gtccaacaag gccctgggcg ctcccatcga aaagaccatc | 900 |
| tctaaggcca agggacagcc ccgggaacct caggtttaca cactgcctcc accttccgag | 960 |
| gaactggccc tgaatgagct ggtcaccctg acctgtctgg tcaagggctt ttaccctcc | 1020 |
| gatatcgccg tggaatggct gcagggatct caagagctgc cagagagaa gtacctgacc | 1080 |
| tgggctcctg tgctggactc cgacggctct ttcttcctgt actccatcct gagagtggcc | 1140 |
| gccgaggatt ggaagaaggg cgataccttc tcctgctccg tgatgcacga ggccctgcac | 1200 |
| aacagattca cacagaagtc cctggacaga tcccctggca ag | 1242 |

<210> SEQ ID NO 111
<211> LENGTH: 642
<212> TYPE: DNA
<213> ORGANISM: artificial sequence
<220> FEATURE:
<223> OTHER INFORMATION: synthetic

<400> SEQUENCE: 111

| | |
|---|---|
| gacatccaga tgacacagag ccctagcagc ctgtctgcca gcgtgggaga cagagtgacc | 60 |
| atcacctgta gagccagcca gagcatctcc aacaacctga actggtatca gcagaagccc | 120 |
| ggcaaggccc ctaagctgct gatctactac accagcagat ccacagcgg cgtgccctct | 180 |
| agattttctg gcagcggctc tggcaccgac ttcaccttca ccataagcag cctgcagcct | 240 |
| gaggatatcg ccacctacta ctgccagcaa gagcacaccc tgccttacac ctttggccag | 300 |
| ggcaccaagc tggaaatcaa gcggacagtg gccgctccta gcgtgttcat cttttccacct | 360 |
| agcgacgagc agctgaagtc cggcacagcc tctgttgtgt gcctgctgaa caacttctac | 420 |
| cccagagaag ccaaggtgca gtggaaggtg gacaacgccc tgcagagcgg caatagccaa | 480 |
| gagagcgtga ccgagcagga cagcaaggac tctacctact ctctgagcag caccctgaca | 540 |
| ctgagcaagg ccgactacga gaagcacaaa gtgtacgcct gcgaagtgac ccaccagggc | 600 |
| ctttctagcc ctgtgaccaa gagcttcaac cggggcgagt gc | 642 |

<210> SEQ ID NO 112
<211> LENGTH: 1362
<212> TYPE: DNA
<213> ORGANISM: artificial sequence
<220> FEATURE:
<223> OTHER INFORMATION: synthetic

<400> SEQUENCE: 112

| | |
|---|---|
| caggtccagc tgcaagaatc tggccctggc ctggtcaagc cttccgagac actgtctctg | 60 |
| acctgcaccg tgtctggctt ctccctgatc ggctacgacc tgaactggat cagacagcct | 120 |
| cctggcaaag gcctggaatg gatcggaatc atctggggcg acggcaccac cgactacaac | 180 |
| tctgccgtga agtccagagt gaccatctcc aaggacacct ccaagaacca gttcagcctg | 240 |
| aagctgtcct ccgtgaccgc tgctgatacc gccgtgtact actgtgccag aggcggctat | 300 |

```
tggtacgcca cctcctacta cttcgactac tggggccagg gcaccctggt cacagtttct      360
tccgcttcca ccaagggacc cagcgtgttc cctctggctc cttccagcaa gtctacctct      420
ggcggaacag ctgctctggg ctgtctggtc aaggactact ccctgagcc tgtgaccgtg       480 tcctggaact ctggcgctct gacatctggc gtgcacacct ttccagctgt gctgcagtcc      540
tccggcctgt actctctgtc ctctgtcgtg accgtgcctt ccagctctct gggaacccag      600
acctacatct gcaatgtgaa ccacaagcct agcaacacca aggtggacaa gaaggtggaa      660
cccaagtcct gcgacaagac ccacacctgt cctccatgtc ctgctccaga agctgctggc      720
ggcccttccg tgtttctgtt ccctccaaag cctaaggaca ccctgatgat ctctcggacc      780
cctgaagtga cctgcgtggt ggtggatgtg tctcacgagg acccagaagt gaagttcaat      840
tggtacgtgg acggcgtgga agtgcacaac gccaagacca gcctagaga ggaacagtac       900 aactccacct acagagtggt gtccgtgctg accgtgctgc accaggattg gctgaacggc      960
aaagagtaca gtgcaaggt gtccaacaag gccctgggcg ctcccatcga aaagaccatc      1020
agcaaggcta agggccagcc tttccggcct gaagtgcatc tgctgcctcc aagcagagaa      1080
gagatgacca agaatcaggt gtccctgacc tgtctggcca ggggcttcta ccctaaggat      1140
atcgccgtgg aatgggagtc caacggccag cctgagaaca actacaagac aaccccctagc     1200 cggcaagagc cctctcaggg caccacaacc tttgccgtga cctccaagct gacagtggac      1260
aagtccagat ggcagcaggg caacgtgttc tcctgctccg tgatgcacga ggccctgcac      1320
aaccactaca cccagaaaac catttctctg agcccggca ag                          1362
```

<210> SEQ ID NO 113
<211> LENGTH: 1242
<212> TYPE: DNA
<213> ORGANISM: artificial sequence
<220> FEATURE:
<223> OTHER INFORMATION: synthetic

<400> SEQUENCE: 113

```
gagcctaagt cctccgataa gacccacacc tgtcctccat gtcctgctcc agaagctgct       60 ggcggcccctt ccgtgtttct gttccctcca agcctaagg acaccctgat gatctctcgg      120
acccctgaag tgacctgcgt ggtggtggat gtgtctcacg aggacccaga agtgaagttc      180
aattggtacg tggacggcgt ggaagtgcac aacgccaaga ccaagcctag agaggaacag      240
tacaactcca cctacagagt ggtgtccgtg ctgaccgtgc tgcaccagga ttggctgaac      300
ggcaaagagt acaagtgcaa ggtgtccaac aaggccctgg gcgctcccat cgaaaagacc      360
atctctaagg ccaagggcca gcctcgggaa ccccaggttt acacattgcc tccaccttcc      420
gaggaactgg ccctgaatga gctggtcacc ctgacctgtc tggtcaaggg cttctacccc      480
tccgatatcg ccgtggaatg gctgcaggga agccaagagc tgcccagaga agtacctg       540 acctgggctc ctgtgctgga ctccgacggc tctttcttcc tgtactccat cctgagagtg      600
gccgccgagg attggaagaa gggcgacacc ttcagctgct ccgtgatgca cgaggccctg      660
cacaacagat tcacacagaa gtccctggac agatccctg gcaaagagcc caagtccagc      720
gacaagacac ataccgagga aaacgtggac ttccgcatcc acgtcgagaa ccagaccaga      780
gccagagatg acgtgtcccg gaagcagctg agactgtacc agctgtactc tagaacctcc      840
ggcaagcaca tccaggtgct gggcagaaga atctccgcca gaggcgagga cggcgataag      900
tatgcacagc tgctggtgga aaccgacacc tttggctccc aagtgcggat caagggcaaa      960
```

| | |
|---|---:|
| gagacagagt tctacctgtg catgaaccgg aagggcaagc tcgtgggcaa gcctgacggc | 1020 |
| acctctaaag aatgcgtgtt catcgagaag gtgctcgaga acaactacac cgctctgatg | 1080 |
| tccgccaagt actccggatg gtacgtcggc ttcaccaaga agggcagacc cagaaagggc | 1140 |
| cccaagacca gagaaaacca gcaggacgtg cactttatga agcgctaccc caagggacag | 1200 |
| cccgagctgc agaagccttt caagtacacc accgtgacca ag | 1242 |

<210> SEQ ID NO 114
<211> LENGTH: 1305
<212> TYPE: DNA
<213> ORGANISM: artificial sequence
<220> FEATURE:
<223> OTHER INFORMATION: synthetic

<400> SEQUENCE: 114

| | |
|---|---:|
| gagcctaagt cctccgataa gacccacacc tgtcctccat gtcctgctcc agaagctgct | 60 |
| ggcggccctt ccgtgtttct gttccctcca aagcctaagg acaccctgat gatctctcgg | 120 |
| acccctgaag tgacctgcgt ggtggtggat gtgtctcacg aggacccaga agtgaagttc | 180 |
| aattggtacg tggacggcgt ggaagtgcac aacgccaaga ccaagcctag agaggaacag | 240 |
| tacaactcca cctacagagt ggtgtccgtg ctgaccgtgc tgcaccagga ttggctgaac | 300 |
| ggcaaagagt acaagtgcaa ggtgtccaac aaggccctgg cgctcccat cgaaaagacc | 360 |
| atctctaagg ccaagggcca gcctcgggaa ccccaggttt acacattgcc tccaccttcc | 420 |
| gaggaactgg ccctgaatga gctggtcacc ctgacctgtc tggtcaaggg cttctacccc | 480 |
| tccgatatcg ccgtggaatg gctgcaggga agccaagagc tgcccagaga agtacctg | 540 |
| acctgggctc ctgtgctgga ctccgacggc tcttctcttcc tgtactccat cctgagagtg | 600 |
| gccgccgagt gggaagaa gggcgacacc ttcagctgct ccgtgatgca cgaggccctg | 660 |
| cacaacagat tcacacagaa gtccctggac agatcccctg gcaaaggtgg cggaggatct | 720 |
| gagcccaagt ctagcgacaa gacccataca ggcggaggcg gctctgagga aaacgtggac | 780 |
| tttagaatcc acgtcgagaa ccagaccaga gccagggacg acgtgtccag aaagcagctg | 840 |
| agactgtacc agctgtactc ccggacctcc ggcaagcaca ttcaggtgct gggcagaaga | 900 |
| atctccgcca gaggcgagga cggcgataag tatgcacagc tgctggtgga aaccgacacc | 960 |
| tttggctccc aagtgcggat caagggcaaa gagacagagt tctacctgtg catgaaccgg | 1020 |
| aagggcaagc tcgtgggcaa gcctgacggc acctctaaag aatgcgtgtt catcgagaag | 1080 |
| gtgctcgaga caactacac cgctctgatg tccgccaagt actccggatg gtacgtcggc | 1140 |
| ttcaccaaga agggcagacc cagaaagggc cccaagacca gagaaaacca gcaggacgtg | 1200 |
| cactttatga agcgctaccc caagggacag cccgagctgc agaagccttt caagtacacc | 1260 |
| accgtgacca agcggtcccg gcggatcaga cctacacacc ctgct | 1305 |

<210> SEQ ID NO 115
<211> LENGTH: 705
<212> TYPE: DNA
<213> ORGANISM: artificial sequence
<220> FEATURE:
<223> OTHER INFORMATION: synthetic

<400> SEQUENCE: 115

| | |
|---|---:|
| gagcctaagt cctccgataa gacccacacc tgtcctccat gtcctgctcc agaagctgct | 60 |
| ggcggccctt ccgtgtttct gttccctcca aagcctaagg acaccctgat gatctctcgg | 120 |
| acccctgaag tgacctgcgt ggtggtggat gtgtctcacg aggacccaga agtgaagttc | 180 |

| | |
|---|---|
| aattggtacg tggacggcgt ggaagtgcac aacgccaaga ccaagcctag agaggaacag | 240 |
| tacaactcca cctacagagt ggtgtccgtg ctgaccgtgc tgcaccagga ttggctgaac | 300 |
| ggcaaagagt acaagtgcaa ggtgtccaac aaggccctgg gcgctcccat cgaaaagacc | 360 |
| atctctaagg ccaagggcca gcctcgggaa ccccaggttt acacattgcc tccaccttcc | 420 |
| gaggaactgg ccctgaatga gctggtcacc ctgacctgtc tggtcaaggg cttctacccc | 480 |
| tccgatatcg ccgtggaatg gctgcaggga agccaagagc tgcccagaga agtacctg | 540 |
| acctgggctc ctgtgctgga ctccgacggc tctttcttcc tgtactccat cctgagagtg | 600 |
| gccgccgagg attggaagaa gggcgacacc ttcagctgct ccgtgatgca cgaggccctg | 660 |
| cacaacagat tcacacagaa gtccctggac agatcccctg gcaag | 705 |

<210> SEQ ID NO 116
<211> LENGTH: 1209
<212> TYPE: DNA
<213> ORGANISM: artificial sequence
<220> FEATURE:
<223> OTHER INFORMATION: synthetic

<400> SEQUENCE: 116

| | |
|---|---|
| gacatccaga tgacccagtc tccatcctct ctgtccgcct ctgtgggcga cagagtgacc | 60 |
| atcacctgtc gggcctctca gtccatctcc aacaacctga ctggtatca gcagaagccc | 120 |
| ggcaaggccc ctaagctgct gatctactac accagccggt tccactctgg cgtgccctct | 180 |
| agattttccg gctctggctc tggcaccgac tttaccttta caatctccag cctgcagcct | 240 |
| gaggatatcg ccacctacta ctgccagcaa gagcacaccc tgccttacac cttggccag | 300 |
| ggcaccaagc tggaaatcaa gcggacagtg gccgctcctt ccgtgttcat cttcccacct | 360 |
| tccgacgagc agctgaagtc cggcacagct tctgtcgtgt gcctgctgaa caacttctac | 420 |
| cctcgggaag ccaaggtgca gtggaaggtg acaatgccc tgcagtccgg caactcccaa | 480 |
| gagtctgtga ccgagcagga ctccaaggac agcacctaca gcctgagcag cacctgaca | 540 |
| ctgtccaagg ccgactacga gaagcacaag gtgtacgcct gcgaagtgac ccatcagggc | 600 |
| ctgtctagcc ctgtgaccaa gtctttcaac agaggcgagt gtggcggcgg aggctctgaa | 660 |
| cctaagtcct ctgataagac ccacactggc ggaggcggct ccgaggaaaa cgtggacttt | 720 |
| agaatccacg tcgagaacca gaccagggcc agagatgacg tgtcccggaa acagctgaga | 780 |
| ctgtaccagc tgtactcccg gacctccggc aagcacattc aggtgctggg cagaagaatc | 840 |
| tccgctagag gcgaggacgg cgataagtac gctcagctcc tggtggaaac cgacaccttc | 900 |
| ggatctcaag tgcggatcaa gggcaaagag acagagttct acctgtgcat gaatcggaag | 960 |
| ggcaagctcg tgggcaagcc tgacggcacc tctaaagaat gcgtgttcat tgagaaggtg | 1020 |
| ctcgagaaca actacaccgc tctgatgtcc gccaagtact ccggatggta cgtgggcttc | 1080 |
| accaagaagg gcagacccag aaagggcccc aagaccagaa aaaccagca ggacgtgcac | 1140 |
| tttatgaagc gctaccccaa gggccagcca gagctgcaga agcctttcaa gtacaccacc | 1200 |
| gtgacaaag | 1209 |

<210> SEQ ID NO 117
<211> LENGTH: 672
<212> TYPE: DNA
<213> ORGANISM: artificial sequence
<220> FEATURE:
<223> OTHER INFORMATION: synthetic

```
<400> SEQUENCE: 117
caggtgcagc tgcaggagtc tggacctgga ctggtgaagc ctagcgagac actgtccctg    60
acctgcacag tgtctggctt tagcctgatc ggctacgacc tgaactggat caggcagccc   120
cctggcaagg gactggagtg gatcggcatc atctggggcg acggcaccac agattataac   180
tctgccgtga agagcagggt gaccatctcc aaggacacat ctaagaatca gttctccctg   240
aagctgagcc tcgtgaccgc cgctgataca gccgtgtact attgcgctag ggcggctac    300 tggtatgcta ccagctacta tttcgactac tggggccagg gcaccctggt gacagtgtct   360
agcgccagca aagggccc ctccgtgttt cctctggctc catcctctaa gagcacctcc     420
ggcggcacag ccgctctggg ctgtctggtg aaggattatt cccagagcc cgtgaccgtg    480 tcctggaact ctggcgccct gacctccgga gtgcacacat tccccgctgt gctgcagagc   540
tccggcctgt actctctgtc tagcgtggtg accgtgcctt cctctagcct gggcacccag   600
acatatatct gcaacgtgaa tcacaagcct tctaatacaa aggtggataa gaaggtggag   660
ccaaagagct gt                                                       672

<210> SEQ ID NO 118
<211> LENGTH: 20
<212> TYPE: PRT
<213> ORGANISM: artificial sequence
<220> FEATURE:
<223> OTHER INFORMATION: linker

<400> SEQUENCE: 118

Gly Gly Gly Gly Ser Glu Pro Lys Ser Ser Asp Lys Thr His Thr Gly
1               5                   10                  15

Gly Gly Gly Ser
            20

<210> SEQ ID NO 119
<211> LENGTH: 15
<212> TYPE: PRT
<213> ORGANISM: artificial sequence
<220> FEATURE:
<223> OTHER INFORMATION: linker

<400> SEQUENCE: 119

Gly Gly Gly Gly Ser Gly Gly Gly Gly Ser Gly Gly Gly Gly Ser
1               5                   10                  15

<210> SEQ ID NO 120
<211> LENGTH: 10
<212> TYPE: PRT
<213> ORGANISM: artificial sequence
<220> FEATURE:
<223> OTHER INFORMATION: linker

<400> SEQUENCE: 120

Glu Pro Lys Ser Ser Asp Lys Thr His Thr
1               5                   10

<210> SEQ ID NO 121
<211> LENGTH: 215
<212> TYPE: PRT
<213> ORGANISM: artificial sequence
<220> FEATURE:
<223> OTHER INFORMATION: Amino acid sequence of human FGF8 precursor

<400> SEQUENCE: 121

Met Gly Ser Pro Arg Ser Ala Leu Ser Cys Leu Leu Leu His Leu Leu
```

```
              1               5              10              15
            Val Leu Cys Leu Gln Ala Gln Val Thr Val Gln Ser Ser Pro Asn Phe
                             20              25              30

Thr Gln His Val Arg Glu Gln Ser Leu Val Thr Asp Gln Leu Ser Arg
                             35              40              45

Arg Leu Ile Arg Thr Tyr Gln Leu Tyr Ser Arg Thr Ser Gly Lys His
                             50              55              60

Val Gln Val Leu Ala Asn Lys Arg Ile Asn Ala Met Ala Glu Asp Gly
             65              70              75              80

Asp Pro Phe Ala Lys Leu Ile Val Glu Thr Asp Thr Phe Gly Ser Arg
                             85              90              95

Val Arg Val Arg Gly Ala Glu Thr Gly Leu Tyr Ile Cys Met Asn Lys
                            100             105             110

Lys Gly Lys Leu Ile Ala Lys Ser Asn Gly Lys Gly Lys Asp Cys Val
                            115             120             125

Phe Thr Glu Ile Val Leu Glu Asn Asn Tyr Thr Ala Leu Gln Asn Ala
            130             135             140

Lys Tyr Glu Gly Trp Tyr Met Ala Phe Thr Arg Lys Gly Arg Pro Arg
            145             150             155             160

Lys Gly Ser Lys Thr Arg Gln His Gln Arg Glu Val His Phe Met Lys
                            165             170             175

Arg Leu Pro Arg Gly His His Thr Thr Glu Gln Ser Leu Arg Phe Glu
                            180             185             190

Phe Leu Asn Tyr Pro Pro Phe Thr Arg Ser Leu Arg Gly Ser Gln Arg
                            195             200             205

Thr Trp Ala Pro Glu Pro Arg
                            210             215

<210> SEQ ID NO 122
<211> LENGTH: 208
<212> TYPE: PRT
<213> ORGANISM: artificial sequence
<220> FEATURE:
<223> OTHER INFORMATION: Amino acid sequence of human FGF9 precursor

<400> SEQUENCE: 122

Met Ala Pro Leu Gly Glu Val Gly Asn Tyr Phe Gly Val Gln Asp Ala
1               5                  10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
                35                  40                  45

Pro Ala Val Thr Asp Leu Asp His Leu Lys Gly Ile Leu Arg Arg Arg
                50                  55                  60

Gln Leu Tyr Cys Arg Thr Gly Phe His Leu Glu Ile Phe Pro Asn Gly
65              70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
                130                 135                 140

Tyr Asn Thr Tyr Ser Ser Asn Leu Tyr Lys His Val Asp Thr Gly Arg
```

```
                145                 150                 155                 160
Arg Tyr Tyr Val Ala Leu Asn Lys Asp Gly Thr Pro Arg Glu Gly Thr
                    165                 170                 175

Arg Thr Lys Arg His Gln Lys Phe Thr His Phe Leu Pro Arg Pro Val
                    180                 185                 190

Asp Pro Asp Lys Val Pro Glu Leu Tyr Lys Asp Ile Leu Ser Gln Ser
                    195                 200                 205

<210> SEQ ID NO 123
<211> LENGTH: 205
<212> TYPE: PRT
<213> ORGANISM: artificial sequence
<220> FEATURE:
<223> OTHER INFORMATION: Amino acid sequence of human FGF17

<400> SEQUENCE: 123

Met Gly Ala Ala Arg Leu Leu Pro Asn Leu Thr Leu Cys Leu Gln Leu
1               5                   10                  15

Leu Ile Leu Cys Cys Gln Thr Gln Tyr Val Arg Asp Gln Gly Ala Met
                20                  25                  30

Thr Asp Gln Leu Ser Arg Arg Gln Ile Arg Glu Tyr Gln Leu Tyr Ser
                35                  40                  45

Arg Thr Ser Gly Lys His Val Gln Val Thr Gly Arg Arg Ile Ser Ala
                50                  55                  60

Thr Ala Glu Asp Gly Asn Lys Phe Ala Lys Leu Ile Val Glu Thr Asp
65                  70                  75                  80

Thr Phe Gly Ser Arg Val Arg Ile Lys Gly Ala Glu Ser Glu Lys Tyr
                85                  90                  95

Ile Cys Met Asn Lys Arg Gly Lys Leu Ile Gly Lys Pro Ser Gly Lys
                100                 105                 110

Ser Lys Asp Cys Val Phe Thr Glu Ile Val Leu Glu Asn Asn Tyr Thr
                115                 120                 125

Ala Phe Gln Asn Ala Arg His Glu Gly Trp Phe Met Ala Phe Thr Arg
                130                 135                 140

Gln Gly Arg Pro Arg Gln Ala Ser Arg Ser Arg Gln Asn Gln Arg Glu
145                 150                 155                 160

Ala His Phe Ile Lys Arg Leu Tyr Gln Gly Gln Leu Pro Phe Pro Asn
                165                 170                 175

His Ala Glu Lys Gln Lys Gln Phe Glu Phe Val Gly Ser Ala Pro Thr
                180                 185                 190

Arg Arg Thr Lys Arg Thr Arg Arg Pro Gln Pro Leu Thr
                195                 200                 205

<210> SEQ ID NO 124
<211> LENGTH: 403
<212> TYPE: PRT
<213> ORGANISM: artificial sequence
<220> FEATURE:
<223> OTHER INFORMATION: Amino acid sequence of a light chain with
      sprifermin in C-term
<220> FEATURE:
<221> NAME/KEY: MISC_FEATURE
<222> LOCATION: (1)..(214)
<223> OTHER INFORMATION: light chain
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
```

<223> OTHER INFORMATION: sprifermin moiety

<400> SEQUENCE: 124

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

Lys Tyr Ala Gln Leu Leu Val Glu Thr Asp Thr Phe Gly Ser Gln Val
290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
        355                 360                 365

Gly Pro Lys Thr Arg Glu Asn Gln Gln Asp Val His Phe Met Lys Arg
370                 375                 380

Tyr Pro Lys Gly Gln Pro Glu Leu Gln Lys Pro Phe Lys Tyr Thr Thr
385                 390                 395                 400
```

Val Thr Lys

```
<210> SEQ ID NO 125
<211> LENGTH: 414
<212> TYPE: PRT
<213> ORGANISM: artificial sequence
<220> FEATURE:
<223> OTHER INFORMATION: Amino acid sequence of a light chain with
      wildtype FGF18 term
<220> FEATURE:
<221> NAME/KEY: MISC_FEATURE
<222> LOCATION: (1)..(214)
<223> OTHER INFORMATION: light chain
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(414)
<223> OTHER INFORMATION: FGF18 moiety
```

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
210                 215                 220

Asp Lys Thr His Thr Gly Gly Gly Ser Glu Asn Val Asp Phe
225                 230                 235                 240

Arg Ile His Val Glu Asn Gln Thr Arg Ala Arg Asp Asp Val Ser Arg
                245                 250                 255

Lys Gln Leu Arg Leu Tyr Gln Leu Tyr Ser Arg Thr Ser Gly Lys His
            260                 265                 270

Ile Gln Val Leu Gly Arg Arg Ile Ser Ala Arg Gly Glu Asp Gly Asp
        275                 280                 285

```
Lys Tyr Ala Gln Leu Leu Val Glu Thr Asp Thr Phe Gly Ser Gln Val
            290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
                340                 345                 350

Tyr Ser Gly Trp Tyr Val Gly Phe Thr Lys Lys Gly Arg Pro Arg Lys
                355                 360                 365

Gly Pro Lys Thr Arg Glu Asn Gln Gln Asp Val His Phe Met Lys Arg
370                 375                 380

Tyr Pro Lys Gly Gln Pro Glu Leu Gln Lys Pro Phe Lys Tyr Thr Thr
385                 390                 395                 400

Val Thr Lys Arg Ser Arg Arg Ile Arg Pro Thr His Pro Ala
                405                 410
```

<210> SEQ ID NO 126
<211> LENGTH: 403
<212> TYPE: PRT
<213> ORGANISM: artificial sequence
<220> FEATURE:
<223> OTHER INFORMATION: Amino acid sequence of light chain with FGF18
      in C-term
<220> FEATURE:
<221> NAME/KEY: MISC_FEATURE
<222> LOCATION: (1)..(214)
<223> OTHER INFORMATION: light chain
<220> FEATURE:
<221> NAME/KEY: MISC_FEATURE
<222> LOCATION: (215)..(234)
<223> OTHER INFORMATION: linker
<220> FEATURE:
<221> NAME/KEY: MISC_FEATURE
<222> LOCATION: (235)..(403)
<223> OTHER INFORMATION: FGF18 moiety

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
                20                  25                  30

Leu Asn Trp Tyr Gln Gln Lys Pro Gly Lys Ala Pro Lys Leu Leu Ile
            35                  40                  45

Tyr Tyr Thr Ser Arg Phe His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Pro Lys Ser Ser
210                 215                 220

Asp Lys Thr His Thr Gly Gly Gly Ser Glu Glu Asn Val Asp Phe
225                 230                 235                 240

Arg Ile His Val Glu Asn Gln Thr Arg Ala Arg Asp Val Ser Arg
                245                 250                 255

Lys Gln Leu Arg Leu Tyr Gln Leu Tyr Ser Arg Thr Ser Gly Lys His
                260                 265                 270

Ile Gln Val Leu Gly Arg Arg Ile Ser Ala Arg Gly Glu Asp Gly Asp
                275                 280                 285

Lys Tyr Ala Gln Leu Leu Val Glu Thr Asp Thr Phe Gly Ser Gln Val
            290                 295                 300

Arg Ile Lys Gly Lys Glu Thr Glu Phe Tyr Leu Cys Met Asn Arg Lys
305                 310                 315                 320

Gly Lys Leu Val Gly Lys Pro Asp Gly Thr Ser Lys Glu Cys Val Phe
                325                 330                 335

Ile Glu Lys Val Leu Glu Asn Asn Tyr Thr Ala Leu Met Ser Ala Lys
            340                 345                 350

Tyr Ser Gly Trp Tyr Val Gly Phe Thr Lys Lys Gly Arg Pro Arg Lys
            355                 360                 365

Gly Pro Lys Thr Arg Glu Asn Gln Gln Asp Val His Phe Met Lys Arg
370                 375                 380

Tyr Pro Lys Gly Gln Pro Glu Leu Gln Lys Pro Phe Lys Tyr Thr Thr
385                 390                 395                 400

Val Thr Lys

<210> SEQ ID NO 127
<211> LENGTH: 15
<212> TYPE: PRT
<213> ORGANISM: artificial sequence
<220> FEATURE:
<223> OTHER INFORMATION: linker

<400> SEQUENCE: 127

Gly Gly Ser Gly Gly Ser Gly Ser Gly Ser Glu Pro Lys Ser Ser
1               5                   10                  15

<210> SEQ ID NO 128
<211> LENGTH: 10
<212> TYPE: PRT
<213> ORGANISM: artificial sequence
<220> FEATURE:
<223> OTHER INFORMATION: linker

<400> SEQUENCE: 128

Gly Gly Gly Gly Ser Gly Gly Gly Gly Ser
1               5                   10

<210> SEQ ID NO 129
<211> LENGTH: 5
<212> TYPE: PRT
<213> ORGANISM: artificial sequence
<220> FEATURE:
<223> OTHER INFORMATION: linker
```

<400> SEQUENCE: 129

Glu Pro Lys Ser Ser
1               5

<210> SEQ ID NO 130
<211> LENGTH: 25
<212> TYPE: PRT
<213> ORGANISM: artificial sequence
<220> FEATURE:
<223> OTHER INFORMATION: linker

<400> SEQUENCE: 130

Gly Gly Gly Gly Ser Gly Gly Gly Ser Glu Pro Lys Ser Ser Asp
1               5                   10                  15

Lys Thr His Thr Gly Gly Gly Gly Ser
            20                  25

<210> SEQ ID NO 131
<211> LENGTH: 10
<212> TYPE: PRT
<213> ORGANISM: artificial sequence
<220> FEATURE:
<223> OTHER INFORMATION: linker

<400> SEQUENCE: 131

Glu Pro Lys Ser Ser Asp Lys Thr His Thr
1               5                   10

<210> SEQ ID NO 132
<211> LENGTH: 1209
<212> TYPE: DNA
<213> ORGANISM: artificial sequence
<220> FEATURE:
<223> OTHER INFORMATION: synthetic

<400> SEQUENCE: 132

| | | | | |
|---|---|---|---|---|
| gacatccaga | tgacccagtc | tccatcctct | ctgtccgcct | ctgtgggcga | cagagtgacc |    60 |
| atcacctgtc | gggcctctca | gtccatctcc | aacaacctga | actggtatca | gcagaagccc |   120 |
| ggcaaggccc | ctaagctgct | gatctactac | accagccggt | tccactctgg | cgtgccctct |   180 |
| agatttccg | gctctggctc | tggcaccgac | tttacctta | caatctccag | cctgcagcct |   240 |
| gaggatatcg | ccacctacta | ctgccagcaa | gagcacaccc | tgccttacac | ctttggccag |   300 |
| ggcaccaagc | tggaaatcaa | gcggacagtg | gccgctcctt | ccgtgttcat | cttcccacct |   360 |
| tccgacgagc | agctgaagtc | cggcacagct | tctgtcgtgt | gcctgctgaa | caacttctac |   420 |
| cctcgggaag | ccaaggtgca | gtggaaggtg | gacaatgccc | tgcagtccgg | caactcccaa |   480 |
| gagtctgtga | ccgagcagga | ctccaaggac | agcacctaca | gcctgagcag | caccctgaca |   540 |
| ctgtccaagg | ccgactacga | gaagcacaag | gtgtacgcct | gcgaagtgac | ccatcagggc |   600 |
| ctgtctagcc | ctgtgaccaa | gtctttcaac | agaggcgagt | gtggcggcgg | aggctctgaa |   660 |
| cctaagtcct | ctgataagac | ccacactggc | ggaggcggct | ccgaggaaaa | cgtggacttt |   720 |
| agaatccacg | tcgagaacca | gaccagggcc | agatgacg | tgtcccggaa | acagctgaga |   780 |
| ctgtaccagc | tgtactcccg | gacctccggc | aagcacattc | aggtgctggg | cagaagaatc |   840 |
| tccgctagag | gcgaggacgg | cgataagtac | gctcagctcc | tggtggaaac | cgacaccttc |   900 |
| ggatctcaag | tgcggatcaa | gggcaaagag | acagagttct | acctgtgcat | gaatcggaag |   960 |
| ggcaagctcg | tggcaagcc | tgacggcacc | tctaaagaat | gcgtgttcat | tgagaaggtg |  1020 |
| ctcgagaaca | actacaccgc | tctgatgtcc | gccaagtact | ccggatggta | cgtgggcttc |  1080 |

```
accaagaagg gcagacccag aaagggcccc aagaccagag aaaaccagca ggacgtgcac    1140
tttatgaagc gctaccccaa gggccagcca gagctgcaga agccttttaa gcctaccacc    1200
gtgacaaag                                                            1209
```

<210> SEQ ID NO 133
<211> LENGTH: 20
<212> TYPE: DNA
<213> ORGANISM: artificial sequence
<220> FEATURE:
<223> OTHER INFORMATION: Forward primer

<400> SEQUENCE: 133

```
aaaggatctc ctggtgaagc                                                  20
```

<210> SEQ ID NO 134
<211> LENGTH: 20
<212> TYPE: DNA
<213> ORGANISM: artificial sequence
<220> FEATURE:
<223> OTHER INFORMATION: Reverse primer

<400> SEQUENCE: 134

```
cctgagtgga agagtggaga                                                  20
```

<210> SEQ ID NO 135
<211> LENGTH: 13
<212> TYPE: PRT
<213> ORGANISM: Artificial sequence
<220> FEATURE:
<223> OTHER INFORMATION: Amino acid sequence of an anti-NGF variant
      CDR-H1

<400> SEQUENCE: 135

```
Thr Val Ser Gly Phe Ser Leu Ile Gly Tyr Asp Leu Asn
1               5                   10
```

<210> SEQ ID NO 136
<211> LENGTH: 16
<212> TYPE: PRT
<213> ORGANISM: Artificial sequence
<220> FEATURE:
<223> OTHER INFORMATION: Amino acid sequence of an anti-NGF variant
      CDR-H2
<220> FEATURE:
<221> NAME/KEY: misc_feature
<222> LOCATION: (5)..(5)
<223> OTHER INFORMATION: Xaa can be any one of D or E
<220> FEATURE:
<221> NAME/KEY: misc_feature
<222> LOCATION: (11)..(11)
<223> OTHER INFORMATION: Xaa can be any one of N or H
<220> FEATURE:
<221> NAME/KEY: misc_feature
<222> LOCATION: (12)..(12)
<223> OTHER INFORMATION: Xaa can be any one of S, P, H, or Q
<220> FEATURE:
<221> NAME/KEY: misc_feature
<222> LOCATION: (13)..(13)
<223> OTHER INFORMATION: Xaa can be any one of A or S
<220> FEATURE:
<221> NAME/KEY: misc_feature
<222> LOCATION: (14)..(14)
<223> OTHER INFORMATION: Xaa can be any one of V or L

<400> SEQUENCE: 136

```
Ile Ile Trp Gly Xaa Gly Thr Thr Asp Tyr Xaa Xaa Xaa Xaa Lys Ser
1               5                   10                  15
```

```
<210> SEQ ID NO 137
<211> LENGTH: 15
<212> TYPE: PRT
<213> ORGANISM: Artificial sequence
<220> FEATURE:
<223> OTHER INFORMATION: Amino acid sequence of a anti-NGF variant
      CDR-H3

<400> SEQUENCE: 137

Ala Arg Gly Gly Tyr Trp Tyr Ala Thr Ser Tyr Tyr Phe Asp Tyr
1               5                   10                  15

<210> SEQ ID NO 138
<211> LENGTH: 11
<212> TYPE: PRT
<213> ORGANISM: Artificial sequence
<220> FEATURE:
<223> OTHER INFORMATION: Amino acid sequence of an anti-NGF variant
      CDR-L1
<220> FEATURE:
<221> NAME/KEY: misc_feature
<222> LOCATION: (8)..(8)
<223> OTHER INFORMATION: Xaa can be any one of N or Q
<220> FEATURE:
<221> NAME/KEY: misc_feature
<222> LOCATION: (9)..(9)
<223> OTHER INFORMATION: Xaa can be any one of N or H

<400> SEQUENCE: 138

Arg Ala Ser Gln Ser Ile Ser Xaa Xaa Leu Asn
1               5                   10

<210> SEQ ID NO 139
<211> LENGTH: 8
<212> TYPE: PRT
<213> ORGANISM: Artificial sequence
<220> FEATURE:
<223> OTHER INFORMATION: Amino acid sequence of an anti-NGF variant
      CDR-L2

<400> SEQUENCE: 139

Tyr Tyr Thr Ser Arg Phe His Ser
1               5

<210> SEQ ID NO 140
<211> LENGTH: 9
<212> TYPE: PRT
<213> ORGANISM: Artificial sequence
<220> FEATURE:
<223> OTHER INFORMATION: Amino acid sequence of an anti-NGF variant
      CDR-L3

<400> SEQUENCE: 140

Gln Gln Glu His Thr Leu Pro Tyr Thr
1               5
```

FUSION PROTEIN COMPRISING AN FGF-18 MOIETY

CROSS-REFERENCE TO RELATED APPLICATION

This application is the U.S. national stage application of International Patent Application No. PCT/EP2018/075432, filed Sep. 20, 2018.

REFERENCE TO SEQUENCE LISTING

The Sequence Listing for this application is labeled "Seq-List.txt" which was created on Feb. 26, 2020 and is 419,215 bytes. The entire content of the sequence listing is incorporated herein by reference in its entirety.

FIELD OF INVENTION

The present invention relates to new fusion proteins comprising an FGF-18 moiety fused to an anti-NGF moiety. Said fusion proteins can be used for the treatment of a cartilage disorder such as osteoarthritis or cartilage injury.

BACKGROUND OF THE INVENTION

Cartilage is composed of chondrocytes (cells derived from mesenchymal cells) which are dispersed in the matrix (a firm, gel-like ground substance). The cartilaginous matrix is produced by these cells and comprises mainly Type II collagen fibres (except fibrocartilage which also contains type I collagen fibres), proteoglycans, and elastin fibres. Cartilage is found among other places in the joints, the rib cage, and the ear, the nose, in the throat, in the trachea and in the intervertebral disks. There are three main types of cartilage: hyaline, elastic and fibrocartilage, providing different functional properties according to their histological morphology. Articular cartilage, for instance, is a hyaline cartilage, having viscoelastic properties, covering the articular surfaces of bones. The main purpose of articular cartilage is to provide smooth surfaces in order to ensure nearly frictionless movement of articulating bones.

Cartilage disorders broadly refer to diseases characterized by degeneration/disintegration of cartilage and abnormalities in the connective tissues which are manifested by inflammation, pain, stiffness and limitation of motion of the affected body parts. These disorders can be due to a pathology or can be the result of trauma or injury. Mature cartilage has very limited ability to self-repair, notably because mature chondrocytes have little potential for proliferation because of the limited supply with nutrients due to the absence of blood vessels in cartilage. Replacement of damaged cartilage, in particular articular cartilage, caused either by injury or disease is a major challenge for physicians, and available surgical treatment procedures are considered unpredictable and effective for only a limited time in younger patients without osteoarthritic changes. Therefore, most patients either do not seek treatment or are counselled to postpone treatment for as long as possible. When treatment is required, the standard procedure is age dependent and varies between total or partly joint replacement, transplantation of pieces of cartilage or chondrocytes or marrow stimulating technique (such as microfracture). Microfracture is a cheap and common procedure that involves penetration of the subchondral bone to stimulate cartilage deposition by bone marrow derived stem cells. However, it has been shown that this technique does not repair sufficiently the chondral defect and the new cartilage formed is mainly fibrocartilage, resulting in a short-lived repair tissue. Indeed, fibrocartilage does not have the same biomechanical properties as hyaline articular cartilage and lacks often proper lateral integration into the surrounding cartilage. For this reason, the newly synthesized fibrocartilage may breakdown more easily (expected time frame: 5-10 years).

For patients with osteoarthritis (OA) all these cartilage repair techniques fail. The remaining non-surgical treatment consists notably of physical therapy, lifestyle modification (e.g. body weight reduction), supportive devices, oral drugs (e.g. non-steroidal anti-inflammatory drugs) and injection of drugs (e.g. hyaluronic acid and corticoids), and food supplementation. All these treatments are unable to stop OA disease progression. If the pain therapy also fails, surgery, such as joint replacement or high tibial osteotomy for the knee joint, are the remaining options for the patients. Tibial or femoral osteotomies (cutting the bone to rebalance joint wear) may reduce symptoms, help to maintain an active lifestyle, and delay the need for total joint replacement. Total joint replacement can provide relief for the symptom of advanced osteoarthritis, but generally requires a significant change in a patient's lifestyle and/or activity level.

Current available drug treatments are mainly directed to pain relief. At this time, there is no commercially available treatment that restores the cartilage damages (see Lotz, 2010).

Anti-NGF compounds is a category of molecules being described in the context of pain linked to OA. Currently, tanezumab, fasinumab or yet fulranumab are being developed for treating pain in OA patients, and are all currently in phases II/III clinical trials for arthritis and/or chronic pain, based on promising results in phases I to III clinical trials (Sanga et al., 2013; Tiseo et al., 2014; Brown et al. 2012).

Fibroblast Growth factor 18 (FGF-18) is a member of the Fibroblast Growth Factor (FGF) family of proteins. It has been shown that FGF-18 is a proliferative agent for chondrocytes and osteoblasts (Ellsworth et al., 2002; Shimoaka et al., 2002). FGF-18 has been proposed for the treatment of cartilage disorder such as osteoarthritis and cartilage injury either alone (WO2008023063) or in combination with hyaluronic acid (WO2004032849). FGF-18 is currently investigated in clinical trials for the treatment of OA.

Although FGF18 provides good results in articular cartilage repair, there is a need of further molecules able to decrease pain/improve function, while maintaining the efficacy for the treatment of cartilage disorder. Indeed, pain is not only very often associated with cartilage disorders but represents the leading symptom for clinical detection of these disorders.

SUMMARY OF THE INVENTION

It is an object of the present invention to provide new fusion proteins comprising an FGF-18 moiety fused to an anti-NGF moiety (i.e. an inhibitor of NGF). The fusion proteins can be used in the treatment of a cartilage disorder. Said cartilage disorder is for instance osteoarthritis or cartilage injury.

The present invention further provides the preferred amino acid sequence of said fusion proteins.

Also encompassed are the polynucleotide sequences encoding the fusion proteins of the present invention, vectors and cell lines comprising said polynucleotide sequences.

Also described is a method for producing the fusion proteins according to the present invention.

Another embodiment of the present invention is a pharmaceutical composition comprising the fusion proteins according to the present invention with at least one excipient.

In a further embodiment, the fusion proteins according to the present invention are for use in the treatment of a cartilage disorder, such as osteoarthritis or cartilage injury.

Definitions

The term "FGF-18 moiety", "FGF18 moiety", "FGF-18" or "FGF18", as used herein, is intended to be a protein maintaining at least one biological activity of the human FGF-18 protein (i.e. Fibroblast Growth Factor 18). FGF-18 may be native, in its mature form, a recombinant form or a truncated form thereof. Biological activities of the human FGF-18 protein include notably the increase in chondrocyte or osteoblast proliferation (see WO9816644) or in cartilage formation (see WO2008023063). Native, or wild-type, human FGF-18 is a protein mostly produced during skeletal development and is involved in bone and cartilage formation (See Haque et al., 2007). Human FGF-18 was first designated zFGF-5 and is fully described in WO9816644. SEQ ID NO:1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207(Ala) of SEQ ID NO: 1 (180 amino acids). FGF-18 moieties according to the invention includes also active fragments of FGF-18 such as, but not limited to, truncated version comprising or consisting of residues 28(Glu) to 196(Lys) of SEQ ID NO: 1 (said truncated form is reproduced as SEQ ID NO:2), or mutants of FGF-18 (for instance mutants having at least 80% sequence identity with SEQ ID NO:1 or with the mature form of SEQ ID NO:2). Should the FGF-18 moiety be an active fragment of FGF-18 (or a truncated form of FGF-18), said FGF-18 fragment (or said truncated form of FGF-18) preferably comprises at least 150 amino acid residues. It has already been shown that an FGF-18 moiety comprising SEQ ID NO:2 displays similar activities as the mature human FGF-18, e.g. it increases chondrocyte proliferation and cartilage deposition leading to repair and reconstruction for a variety of cartilaginous tissues (see WO2008023063).

The term "FGF-8 moiety", "FGF8 moiety", "FGF-8" or "FGF8", as used herein, is intended to be a protein maintaining at least one biological activity of the human FGF-8 protein (i.e. Fibroblast Growth Factor 8). FGF-8 may be native, in its mature form, a recombinant form, a truncated form or a mutant form thereof. The native form is represented in SEQ ID NO:121.

The term "FGF-9 moiety", "FGF9 moiety", "FGF-9" or "FGF9", as used herein, is intended to be a protein maintaining at least one biological activity of the human FGF-9 protein (i.e. Fibroblast Growth Factor 9). FGF-9 may be native, in its mature form, a recombinant form, a truncated form or a mutant form thereof. The native form is represented in SEQ ID NO:122. FGF9 was shown to attenuate cartilage degradation in a DMM mice model, to reduce MMP13 expression and promote type II collagen expression in OA cartilage (Zhou et al., 2016).

The term "FGF-17 moiety", "FGF17 moiety", "FGF-17" or "FGF17", as used herein, is intended to be a protein maintaining at least one biological activity of the human FGF-17 protein (i.e. Fibroblast Growth Factor 17). FGF-17 may be native, in its mature form, a recombinant form, a truncated form or a mutant form thereof. The native form is represented in SEQ ID NO:123.

The term "inhibitor of NGF" or "anti-NGF moiety" as used herein refers to a compound that is able to bind to NGF (i.e. Nerve Growth Factor) and to inhibit the activity of said NGF, either partly or completely. The preferred "inhibitors of NGF" according to this invention are anti-NGF antibodies, or active fragments or active variants thereof, as well as nanobodies. Such a compound is for instance, but not limited to, tanezumab (See SEQ ID NOs: 9-11) or active fragments or active variants thereof, fasinumab (See SEQ ID NOs: 12-13) or active fragments or active variants thereof, fulranumab (See SEQ ID NOs: 14-15) or active fragments or active variants thereof. ANA-02, ABT-110, ALD-906 or MEDI-578 are other examples of known NGF receptor inhibitors.

The term "antibody", and its plural form "antibodies", as used herein includes, inter alia, polyclonal antibodies, affinity-purified polyclonal antibodies, monoclonal antibodies, and antigen-binding fragments, such as F(ab')2, Fab fragments, single chain variable region fragments (scFvs or shark VNAR), and single-domain antibodies (such as camelid VHH). It refers both to one-armed (monovalent; one pair of immunoglobulin chains) or two-armed (bivalent; two pairs of immunoglobulin chains) antibody. This term also includes the variants called knobs-into-holes based antibodies (Ridgway et al, 1996) and SEEDbodies (Davis et al. 2010 or U.S. Pat. No. 8,871,912). Genetically engineered intact antibodies or active fragments, such as chimeric antibodies, scFv and Fab fragments, as well as synthetic antigen-binding peptides and polypeptides, are also included. The basic structural unit of an antibody is a tetramer and consists of two identical pairs of immunoglobulin chains, each pair having one light and one heavy chain. A light chain has two parts: the variable domain (VL) and the constant domain (CL), which in the context of a light chain can be called constant region as well. A heavy chain has two parts as well: the variable domain (VH) and the constant region (CH). In each pair, the light and heavy chain variable domains are together responsible for binding to an antigen, and the constant regions are responsible for the antibody effector functions. Full-length immunoglobulin "light chains" (usually about 25 kDa) are encoded by a variable domain gene at the N-terminus (usually about 110 amino acids) and a kappa or lambda constant domain ($C_K$ and $C_\lambda$, respectively) gene at the C-terminus. Full-length immunoglobulin "heavy chains" (usually about 50 kDa), are similarly encoded by a variable domain gene (usually about 116 amino acids) and one of the other constant region genes (usually about 330 amino acids) mentioned hereinafter. There are five types of mammalian heavy chain denoted by the Greek letters: [alpha], [delta], [epsilon], [gamma], and [mu]. The type of heavy chain defines the antibody's isotype as IgA, IgD, IgE, IgG and IgM, respectively. The constant region is identical in all antibodies of the same isotype, but differs in antibodies of different isotypes. Heavy chains [gamma], [alpha] and [delta] have a constant region composed of three Ig constant domains (CH1, CH2, and CH3), and a hinge region for added flexibility; heavy chains [mu] and [epsilon] have a constant region composed of four Ig constant domains (CH1, CH2, CH3, and CH4) and a hinge region.

A light or heavy chain variable domain consists of a "framework" region interrupted by three hypervariable regions. which are responsible for antigen binding. The hypervariable region comprises amino acid residues from a "complementarity determining region" or "CDR (Kabat et al. 1991) and/or those residues from a "hypervariable loop"

(Chothia and Lesk 1987). "Framework region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen. Said antibodies (or immunoglobulins) can be chimeric, humanized, and fully human. They are most of the time recombinant (i.e. recombinant antibodies).

The term "recombinant antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

As used herein, the term "fragment" refers to an active fragment of an intact or a full-length chain antibody (here an anti-NGF antibody), usually the binding or variable region. Said portions, or fragments, should maintain at least one activity of the intact chain/antibody, i.e. they are "functional portions" or "functional fragments" or "active fragments". Should they maintain at least one activity, they preferably maintain the target binding property. Examples of antibody portions (or antibody fragments) include, but are not limited to, single-chain Fv, Fab, single-chain antibodies, Fv or scFv, VHH or vNAR. These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

The term "fragment" also refers to a "Fab fragment», comprising one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains.

The term "SEEDbody" (SEED for Strand-Exchange Engineered Domain; plural form: SEEDbodies) refers to a particular type of antibody comprising derivative of human IgG and IgA CH3 domains, creating complementary human SEED CH3 heterodimers that are composed of alternating segments of human IgG and IgA CH3 sequences (the resulting heterodimers are called AG part and GA part as shown in FIGS. 1A-1L). They are asymmetric fusion proteins. SEEDbodies and the SEED technology are described in Davis et al. 2010 or U.S. Pat. No. 8,871,912 which are incorporated herein in their entirety. They can be monovalent or bivalent.

The term "knobs-into-holes" based antibodies relates to a heavy chain heterodimerization technology as developed by Carter and co-workers in 1996 (Ridgway et al., 1996). In this approach, the designated 'knob' variant of the CH3 domain contains a replacement of a small amino acid by a larger one (T366Y). In contrast, the opposite CH3 domain, designed for heterodimerization and referred to as 'hole' variant contains a Y407T mutations i.e. a replacement of a large residue with a smaller one.

The term "treatment" within the context of this invention refers to any beneficial effect on progression of disease, including attenuation, reduction and decrease or diminishing of the pathological development after onset of disease.

The term "pharmaceutically acceptable" is meant to encompass any carrier, which does not interfere with the effectiveness of the biological activity of the active ingredient and that is not toxic to the host to which it is administered. For example, for intraarticular administration, the active protein(s) may be formulated in a unit dosage form for injection in vehicles such as, but not limited to, saline, dextrose solution, serum albumin and Ringer's solution.

The term "cartilage disorder", as used herein, encompasses disorders resulting from damages due to injury, such as traumatic injury, chondropathy or arthritis. Examples of cartilage disorders that may be treated by the administration of the fusion proteins described herein include but are not restricted to arthritis, such as osteoarthritis, and cartilage injury. Degenerative diseases/disorders of the cartilage or of the joint, such as chondrocalcinosis, polychondritis, relapsing polychondritis, ankylosing spondylitis or costochondritis are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of cartilage layer) and grade 4: the cartilage tear exposes the underlying (subchondral) bone. (see ICRS publication at Worldwide Website:cartilage.org/_files/content-management/ICRS_evaluation.pdf, page 13).

The term "arthritis" as used herein encompasses disorders such as osteoarthritis, rheumatoid arthritis, juvenile rheumatoid arthritis, infectious arthritis, psoriatic arthritis, Still's disease (onset of juvenile rheumatoid arthritis) or osteochondritis dissecan. It preferably includes diseases or disorders in which ones the cartilage is damaged.

The term "Osteoarthritis" is used to intend the most common form of arthritis. The term "osteoarthritis" encompasses both primary osteoarthritis and secondary osteoarthritis (see for instance The Merck Manual, $17^{th}$ edition, page 449). Osteoarthritis may be caused by the breakdown of cartilage. Bits of cartilage may break off and cause pain and swelling in the joint between bones. Over time, the cartilage may wear away entirely, and the bones will rub together. Osteoarthritis can affect any joint but usually concerns hands, shoulders and weight-bearing joints such as hips, knees, feet, and spine. In a preferred example, the osteoarthritis may be knee osteoarthritis or hip osteoarthritis. This wording encompasses notably the forms of osteoarthritis which are classified as stage 1 to stage 4 or grade 1 to grade 6 according to the OARSI classification system. The skilled person is fully aware of osteoarthritis classifications that are used in the art, in particular said OARSI assessment system (also named OOCHAS; see for instance Custers et al., 2007). Osteoarthritis is one of the preferred cartilage disorders that can be treated by administering the fusion proteins according to the present invention.

The term "cartilage injury" as used herein is a cartilage disorder or cartilage damage resulting notably from a trauma. Cartilage injuries can occur notably after traumatic mechanical destruction, notably further to an accident or surgery (for instance microfracture surgery). This term "cartilage injury" also includes chondral or osteochondral fracture and damage to meniscus. Also considered within this definition is sport-related injury or sport-related wear of tissues of the joint. The term also includes microdamage or blunt trauma, a chondral fracture, an osteochondral fracture or damage to meniscus.

The term "subject", or "patient" is intended to include (but not limited to) mammals such as humans, dogs, cows, horses, sheep, goats, cats, mice, rabbits, or rats. More preferably, the subject (or the patient) is a human.

DETAILED DESCRIPTION OF THE INVENTION

It has surprisingly been found by the inventors that the fusion proteins according to the present invention (i.e. having both an FGF-18 moiety and an anti-NGF moiety) maintain the activities of both FGF-18 on cartilage and NGF inhibitor on pain. Indeed, it was found, in vitro, that in overall 1) the effects of an FGF-18 moiety are preserved by the fusion to an inhibitor of NGF and 2) that an FGF-18 moiety does not affect the neutralization effect of the anti-NGF moiety. This finding was not expected because of the high molecular weight of each moiety of the fusion protein and because it is well known that fusion proteins may not exhibit the expected activities due to different refolding for instance. Also surprising, said activities are maintained, even at low dosage for each compound. In a disease setting, the advantage of the present invention will be to decrease pain/improve function, while maintaining the efficacy of FGF-18 moiety on cartilage structure.

In a first embodiment, the present invention provides new fusion proteins comprising FGF-18 moiety fused to an anti-NGF moiety (i.e. an inhibitor of NGF, preferably an anti-NGF antibody or fragment thereof). Optionally the fusion protein comprises a linker between the two moieties.

The FGF-18 moiety according to the invention as a whole can be the native form of FGF-18 as shown in SEQ ID NO:1 or its mature form (corresponding to the amino acid residue 28 to residue 207 of SEQ ID NO:1). Alternatively, it can be a truncated form, preferably comprising at least 150 amino acid residues, such as the truncated form shown in SEQ ID NO:2 (SEQ ID NO: 2 is a mature form of a truncated FGF-18 without any leader sequence). Said truncated form when expressed with an additional methionine residue in its N-terminal moiety is known as sprifermin. Other truncated forms, preferably comprising at least 150 amino acid residues, can also be used such as a form comprising or consisting of amino acid 1(Glu) to 167(Thr) of SEQ ID NO: 2, a form comprising or consisting of amino acid 1(Glu) to 161 (Pro) of SEQ ID NO: 2 (as represented in SEQ ID NO:3) or such as any forms having deletions of one to fifteen amino acid residues in the N-term and/or C-term moiety compared to SEQ ID NO: 2 and/or having some mutations (e.g. to diminish protease activity). Such truncated and/or mutated forms can be used as long as they keep the full biological activities of a native FGF-18 or of sprifermin. Examples of such other truncated and/or mutated forms are for instance the amino acid sequences selected from the group consisting of (but not limited to) SEQ ID NOs: 4 to 8 or 87 or a polypeptide comprising at least 150 consecutive amino acid residues of any one of SEQ ID NOs: 1 to 8 or 87. In another alternative, the FGF18 moiety can be an active variant having at least 80% of sequence identity with amino acid residue 28 to residue 207 of SEQ ID NO: 1 or with SEQ ID NO:2. Preferably said FGF18 variant has at least 85%, at least 90%, at least 91%, at least 92%, at least 93%, at least 94%, at least 95%, at least 96%, at least 97%, at least 98% or at least 99% of sequence identity with amino acid residue 28 to residue 207 of SEQ ID NO: 1 or with SEQ ID NO:2. Said (active) variants may be the result of punctual mutation(s) or of a fusion of an FGF18 moiety with a partial sequence coming from another FGF moiety, such as from an FGF8, FGF9 or FGF19 moiety. Examples of such variants are shown in SEQ ID NOs: 83-86.

The anti-NGF moiety of the present invention has to bind and neutralize NGF. Preferably, said anti-NGF moiety is based on an anti-NGF antibody, and is preferably an active fragment or an active variant thereof. The anti-NGF antibody that can be used according to the present invention is for instance tanezumab, fasinumab or fulranumab, but not limited to these antibodies. Preferably these anti-NGF moieties are either active fragments of anti-NGF antibodies, such as scFv, Fab active fragments, VHH or vNAR or are active variants of said anti-NGF antibodies, such as SEED-bodies or knobs-into-holes based antibodies. As examples, the (active) fragments of anti-NGF antibodies can be selected from the group consisting of amino acid sequences: SEQ ID NO: 22 (scFv of tanezumab), SEQ ID NO: 23 (scFv of fasinumab), SEQ ID NO: 24 (scFv of fulranumab), SEQ ID NO: 16 (VH-Fab of tanezumab), SEQ ID NO: 18 (VH-Fab of fasinumab), SEQ ID NO: 20 (VH-Fab of fulranumab), SEQ ID NO: 17 (VL-Fab of tanezumab), SEQ ID NO: 19 (VL-Fab of fasinumab) and SEQ ID NO: 21 (VL-Fab of fulranumab).

Alternatively, the anti-NGF antibodies according to the invention, or portions thereof, that binds to NGF, comprise a heavy chain variable domain comprising HCDR1, H-CDR2 and H-CDR3, and a light chain variable domain comprising L-CDR1, L-CDR2 and L-CDR3, wherein, 1) H-CDR1 comprises or consists of an amino acid sequence consisting of SEQ ID NO: 135, 2) H-CDR2 comprises or consists of an amino acid sequence consisting of SEQ ID NO: 136, 3) H-CDR3 comprises or consists of an amino acid sequence consisting of SEQ ID NO: 137, 4) L-CDR1 comprises or consists of an amino acid sequence consisting of SEQ ID NO: 138, 5) L-CDR2 comprises or consists of an amino acid sequence consisting of SEQ ID NO: 139 and 6) L-CDR3 comprises or consists of an amino acid sequence consisting of SEQ ID NO: 140.

The FGF-18 moiety of the present invention can be linked, directly or via a linker, via its N-terminus or its C-terminus to the anti-NGF moiety (see FIGS. 1A-1L).

Example of linkers that can be used indifferently in any of the constructs are represented in SEQ ID NOs: 118-120 or 127-131. The skilled person would understand that in any of the sequence identifier numbers for fusion proteins according to the present invention, he can change the linker by any other one of his choice.

When the fusion protein according to the invention is an FGF-18 moiety fused to an scFv moiety, this linkage can be done via the free VH-end or the free VL-end of the anti-NGF scFv moiety. Examples of such fusion proteins for instance comprise 1) an amino acid sequence selected from the group comprising or consisting of any one of SEQ ID NOs: 1 to 8 as FGF-18 moiety, and 2) an amino acid sequence selected from the group comprising or consisting of any one of SEQ ID NOs: 22 to 24 as the anti-NGF moiety, and optionally 3) a linker between the FGF-18 moiety and the anti-NGF moiety. Examples of specific fusion proteins are for instance selected form the group consisting of (but not limited to) amino acid sequences: SEQ ID NOs: 25-27.

When the construct (or the fusion protein) according to the invention is based on a Fab as the anti-NGF moiety, it will comprise both a VH-Fab domain and a VL-Fab domain, the FGF-18 being fused to any one of the VH-Fab domain and/or the VL-Fab domain, via the C-terminus and/or the N-terminus of said Fab moiety. Examples of such fusion proteins for instance comprise 1) an amino acid sequence selected from the group comprising or consisting of any one of SEQ ID NOs: 1 to 8 or 83-87 as FGF-18 moiety, and 2) an amino acid sequence selected from the group comprising or consisting of any one of SEQ ID NOs: 16 to 21 as the anti-NGF moiety, and optionally 3) a linker, which can be selected amongst the group comprising or consisting of any one of SEQ ID NOs: 118-120 or 127-131, between the FGF-18 moiety and the anti-NGF moiety. Examples of specific fusion proteins are for instance selected form the group consisting of (but not limited to) amino acid sequences: SEQ ID NOs: 28 to 53. Should the FGF-18 moiety be linked to a VH-Fab, the fusion protein will also comprise a regular VL-Fab. Examples of such molecule are for instance, but not limited to, a combination of SEQ ID NO: 37 and SEQ ID NO: 17, SEQ ID NO: 40 and SEQ ID NO: 17 or SEQ ID NO: 46 and SEQ ID NO: 17. Should the FGF-18 moiety be linked to a VL-Fab, the fusion protein will also comprise a regular VH-Fab. As Fab molecule comprises both a VH-Fab domain and a VL-Fab domain, said molecule can comprise i) the VH-Fab domain comprises an amino acid sequence selected from the group comprising or consisting of any one of SEQ ID NOs: 1 to 8 or 83-87 fused to an amino acid sequence selected from the group comprising or consisting of any one of SEQ ID NOs: 16, 18 or 20, optionally with a linker between the two amino acid sequence moieties; and the VL-Fab domain comprises to an amino acid sequence selected from the group comprising or consisting of any one of SEQ ID NOs: 17, 19 or 21, ii) the VL-Fab domain comprises an amino acid sequence selected from the group comprising or consisting of any one of SEQ ID NOs: 1 to 8 or 83-87 fused to an amino acid sequence selected from the group comprising or consisting of any one of SEQ ID NOs: 17, 19 or 21, optionally with a linker between the two amino acid sequence moieties; and the VH-Fab domain comprises to an amino acid sequence selected from the group comprising or consisting of any one of SEQ ID NOs: 16, 18 or 21, iii) the VH-Fab domain comprises an amino acid sequence selected from the group comprising or consisting of any one of SEQ ID NOs: 34 to 39, 45 to 49, 51 or 53; and the VL-Fab domain comprises to an amino acid sequence selected from the group comprising or consisting of any one of SEQ ID NOs: 17, 19 or 21 or iv) the VL-Fab domain comprises an amino acid sequence selected from the group comprising or consisting of any one of SEQ ID NOs: 28 to 33, 40 to 44, 50 or 52; and the VH-Fab domain comprises to an amino acid sequence selected from the group comprising or consisting of any one of SEQ ID NOs: 16, 18 or 21. Examples of such molecule are for instance, but not limited to, a combination of 1) SEQ ID NO: 28 and SEQ ID NO: 16, 2) SEQ ID NO: 31 and SEQ ID NO: 16, 3) SEQ ID NO: 40 and SEQ ID NO: 16, 4) SEQ ID NO: 41 and SEQ ID NO: 16 or 4) SEQ ID NO: 42 and SEQ ID NO: 16 (HOF3).

Alternatively, when the fusion protein according to the invention is an FGF-18 moiety fused to a SEEDbody form of an anti-NGF antibody, a monovalent form of the SEED-body will preferably be used (i.e. they will usually not form a homodimer comprising two full heavy chains and two light chains). A SEEDbody (as a monomer) consists of one full light chain comprising both variable and constant domains (such as the ones disclosed as SEQ ID NO:11, 13 or 15), one full heavy chain comprising both variable and constant domains (such as the ones disclosed as SEQ ID NOs: 56, 58, 60, 65, 71 or 96) as well as one partial heavy chain comprising only constant domains CH2 and CH3 of a SEEDbody (such as the ones disclosed as amino acid residues 185 to 414 of SEQ ID NO: 54, amino acid residues 180 to 409 of SEQ ID NO: 55, amino acid residues 180 to 409 of 57 or yet amino acid residues 180 to 409 of SEQ ID NO: 59, SEQ ID NO: 102 or SEQ ID NO: 107). The partial heavy chain is asymmetric to its counterpart on the full heavy chain (e.g. should the full heavy chain be a GA form, the partial heavy chain will be an AG form and vice versa). The FGF-18 moiety will be linked to the SEEDbody via the partial heavy chain (see FIG. 1B or 1D)), its full heavy chain or the light chain (see FIG. 1C), either in C-terminus or in N-terminus. Non-limiting examples of such FGF-18 moiety fused to an AG form are for instance selected form the group consisting of amino acid sequences SEQ ID NOs: 54, 55, 57, 59, 62, 66-70, 77-82, 91-95, 101 or 103-106. Non-limiting examples of such FGF-18 moiety fused to a GA form are for instance selected form the group consisting of amino acid sequences SEQ ID NOs: 72-76, 90, 97-100 or 108. Non-limiting examples of such FGF-18-SEEDbodies are for instance selected form the group consisting of amino acid sequences (each SEEDbody is formed by three sequences, here respectively FGF-18-partial heavy chain; full heavy chain and light chain): 1) SEQ ID NOs: 54, 56 and 11 (MBE626), 2) SEQ ID NOs: 55, 56 and 11, 3) SEQ ID NOs: 57, 58 and 13, 4) SEQ ID NOs: 59, 60 and 15, 5) SEQ ID NOs: 90, 71 and 11 (HO124), 6) SEQ ID NOs: 97, 96 and 11 (HO110), or 7) SEQ ID NOs: 100, 96 and 11 (HO113). Examples of FGF-18 moiety fused to the light chain are for instance selected form the group consisting of amino acid sequences: 40-44 or 124-126. Non-limiting examples of such FGF-18-SEEDbodies are for instance selected form the group consisting of amino acid sequences (each SEEDbody is formed by three sequences, here respectively full heavy chain; partial heavy chain and FGF-18-light chain): 1) SEQ ID NOs: 71, 102 and 126 (HO114), 2) SEQ ID NOs: 96, 102 and any one of 40-44 or 124-126, 3) 56, 107 and 40 or 124, 4) 58, 107 and 40 or 124 or 5) 60, 107 and 40 or 124.

In another alternatively, when the fusion protein according to the invention is an FGF-18 moiety fused to an active IgG variant form of an anti-NGF antibody, FGF-18 moiety will be linked to the active IgG variant via its heavy chain or its light chain, either in C-terminus or in N-terminus. Examples of such FGF-18-IgG fusions are for instance selected form the group consisting of amino acid sequences (each fusion protein is formed by two sequences, i.e. one heavy chain and one light chain): 1) SEQ ID NOs: 9 or 10 and 61, 2) SEQ ID NOs: 62 and 11, 3) SEQ ID NOs: 63 and 9 or 10, 4) SEQ ID NOs: 64 and 11, 5) SEQ ID NOs: 88 or 89 and 11, 6) SEQ ID NOs: 9 or 10 and 124 or 7) 5) SEQ ID NOs: 9 or 10 and 125.

The fusion proteins according to the present invention as a whole can be expressed with a molecule leader in the N-term. Additionally, amino acid sequences having at least 80% or more, at least 85% or more, at least 90% or more, at least 95% or more, or at least 99% or more sequence identity to the heavy chain variable region sequences or to full or partial heavy chain amino acid sequences disclosed herein are also provided. Similarly, amino acid sequences having at least 85% or more, at least 90% or more, at least 95% or more, or at least 99% or more sequence identity to the light chain variable region sequences disclosed herein are also provided.

Another embodiment of the present invention is an isolated nucleic acid molecule, or a polynucleotide, encoding any of the fusion proteins herein described, or a complementary strand or degenerated sequence thereof. In this regard, the terms "nucleic acid molecule", or interchangeably "polynucleotide" encompass all different types of nucleic acids, including without limitation deoxyribonucleic acids (e.g., DNA, cDNA, gDNA, synthetic DNA, etc.), ribonucleic acids (e.g., RNA) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

In a particular embodiment, when the fusion protein according to the invention is an FGF-18 moiety linked to an active scFv fragment of an active anti-NGF moiety, said fusion protein is encoded as a single molecule, i.e. the nucleotide sequence comprises the nucleotides needed to encode the two moieties as a whole.

Alternatively, when the fusion protein according to the invention is an FGF-18 moiety linked to a Fab moiety or an active IgG variant, one polynucleotide encodes the heavy chain of any one of the fusion proteins of the invention, another polynucleotide encodes the light chain of any one of the fusion proteins of the invention. Depending on the way the FGF-18 moiety is linked to the Fab, its encoding sequence will be attached to the encoding sequence of either the heavy chain or the light chain, in its N-term or in its C-terminus. Alternatively, when the fusion protein according to the invention is an FGF-18 moiety linked to a SEEDbody, one polynucleotide encodes the full heavy chain of any one of the fusion proteins of the invention, another polynucleotide encodes the partial heavy chain fused to the FGF-18 moiety of any one of the fusion proteins of the invention, and another one encodes the light chain of any one of the fusion proteins of the invention. The polynucleotide sequences encoding said proteins are usually preceded by a leader sequence. Non-limiting examples of the polynucleotide sequences that can be used according to the inventions are for instance those of SEQ ID NOs: 109-117 and 132.

Due to the degeneracy of the genetic code, it is to be understood that the polynucleotides encoding the fusion proteins according to the present invention can be optimized. Therefore, polynucleotide sequences having at least 90% or more, at least 95% or more, or at least 99% or more sequence identity to the polynucleotide sequences encoding the heavy chain variable region sequences disclosed herein, such as the preferred polynucleotide sequences listed above, are also provided. Similarly, polynucleotide sequences having at least 90% or more, at least 95% or more, or at least 99% or more sequence identity to the polynucleotide sequences encoding the light chain variable region sequences disclosed herein, such as the preferred polynucleotide sequences listed above, are also provided.

A further embodiment of this invention is a vector comprising a DNA encoding any of the fusion proteins described herein. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise the entire or part of the coding sequences for both the heavy and light chain, or either of the light and heavy chain coding sequences, or any portions thereof. Should the vector comprise coding sequences for both heavy and light chains (such as in the case of a Fab fusion protein or SEEDbody fusion protein), these coding sequences may each be operably linked to a promoter. The promoter may be the same or different for the heavy and light chain coding sequences. The heavy and light chain coding sequences may also be operably linked to one single promoter, in this case the coding sequences for the heavy and light chains may preferably be separated by an internal ribosomal entry site (IRES) or via viral 2A peptides. Suitable promoters for eukaryotic gene expression are, for example, promoters derived from viral genes such as the murine or human cytomegalovirus (CMV), the mouse bi-directional CMV promoter, the rous sarcoma virus (RSV) promoter or the human elongation factor-1 alpha (EF-1α) promoter, which are well known to the person skilled in the art. The vector may comprise regulatory elements, such as a promoter, terminator, enhancer, selection marker, origin of replication, insulator etc. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

A further embodiment of the present invention is a recombinant host cell, wherein said cell comprises one or more nucleic acid molecule(s)/polynucleotide(s) or one or more vector(s) as defined above. The host cell may be a prokaryotic or eukaryotic cell. Examples of prokaryotic cells include bacteria, such as E. coli. Examples of eukaryotic cells are yeast cells, plant cells, mammalian cells and insect cells including any primary cell culture or established cell line (e.g., 3T3, Vero, HEK293, TN5, etc.). Suitable host cells for the expression of glycosylated proteins are derived from multicellular organisms. Examples of preferred useful mammalian host cell lines include CHO (e.g. CHO—S, ExpiCHO™, CHO-k1 or CHO-LF), HEK293 (e.g. 293, 293-6E or Expi293™) NS0, SP2/0 and COS cells. The fusion proteins of the present invention may be produced by any technique known in the art, such as by recombinant technologies, chemical synthesis, cloning, ligations, or combinations thereof. Many books and reviews provide teachings on how to clone and produce recombinant proteins using vectors and prokaryotic or eukaryotic host cells. Should it be necessary to obtain a fusion protein having a lower glycosylation level or an aglycosylated fusion protein, a yeast expression system or engineered/glycoengineered CHO cell lines can be advantageously used. Similarly, should it be necessary to obtain a fusion protein having a lower fucosylation level or an afucosylated fusion protein, an engineered/glycoengineered yeast expression system or engineered/glycoengineered CHO cell lines can be advantageously used.

Another embodiment of this invention is therefore a method of producing a fusion protein of the present invention, the method comprising culturing a recombinant host cell of the invention under conditions allowing expression of the nucleic acid molecule(s) encoding any of the fusion proteins described herein or portions thereof, and recovering/isolating the fusion protein(s) produced. The fusion protein(s) as produced may be glycosylated or not, may be fucosylated or not or may contain other post-translational modifications depending on the host cell type used. The method of producing a fusion protein of the present invention may further comprise the steps of purifying the fusion proteins, and/or formulating said fusion proteins, into a pharmaceutical composition.

Other methods for preparing the polynucleotides (including DNA and RNA) encoding the fusion proteins described herein are well known in the art. Total RNA can be prepared using guanidinium isothiocyanate extraction followed by isolation by centrifugation in a CsCl gradient (Chirgwin et al. 1979). Poly(A)+ RNA is prepared from total RNA using the method of Aviv and Leder (Aviv and Leder 1972). Complementary DNA (cDNA) is prepared from poly(A)+ RNA using known methods. Alternatively, genomic DNA can be isolated. Polynucleotides encoding the fusion proteins are then identified and isolated by, for example, hybridization or PCR.

In the context of the invention as a whole, the fusion proteins are part of pharmaceutical formulations. The fusion proteins of the invention may be formulated as pharmaceutical composition, i.e. together with at least one pharmaceutically acceptable carrier, excipient(s) or the like. The definition of "pharmaceutically acceptable" is meant to encompass any carrier, excipient or the like, which does not interfere with effectiveness of the biological activity of the active ingredient and that is not toxic to the patient to which it is administered. The at least one excipient is for instance selected from the group consisting of a buffer, a surfactant, a salt, an antioxidant, a isotonicity agent, a bulking agent, a stabilizer or any combination thereof. For example, for parenteral administration, the fusion protein(s) may be formulated in a unit dosage form for injection in vehicles such as saline, dextrose solution, serum albumin and Ringer's solution or any kind of known buffers. Formulations for intraarticular application will comply with most of the requirements that also apply to other injection formulations, i.e., they need to be sterile and compatible with the physiological conditions at the application site (e.g., knee joint, synovial fluid). The excipients used for intraarticular injection may also be present in other injection formulations, e.g., for intravenous or subcutaneous application. Such formulations of fusion proteins, including at least one further pharmaceutically acceptable carrier, excipients or the like, are also useful in the context of the present invention.

In the context of the invention as a whole, the fusion proteins are used for treating cartilage disorders, such as osteoarthritis or cartilage injury. In particular they can be used for treating articular cartilage defects in synovial joints that are, for instance, due to superficial fibrillation (early osteoarthritis), cartilage degeneration due to osteoarthritis, and chondral or osteochondral defects due to injury or disease. The fusion proteins may also be used for treating joint disease caused by osteochondritis dissecans and degenerative joint diseases. In the field of reconstructive and plastic surgery, the fusion proteins will be useful for autogenous or allogenic cartilage expansion and transfer for reconstruction of extensive tissue defects. The fusion proteins according to the invention can be used to repair cartilage damage in conjunction with lavage of the joint, stimulation of bone marrow, abrasion arthroplasty, subchondral drilling, or microfracture of the subchondral bone.

In a preferred embodiment, the cartilage disorder to be treated according to the invention is osteoarthritis, such as knee osteoarthritis or hip osteoarthritis. The osteoarthritis to be treated can be, for example, and not limited to, primary osteoarthritis or secondary osteoarthritis, as well as osteoarthritis which is classified as stage 1 to stage 4 or grade 1 to grade 6 according to the OARSI classification system.

In another preferred embodiment, the cartilage disorder to be treated according to the invention is cartilage injury with or without surgical interventions as microfractures. Additionally, after the growth of cartilage due to the administration of the fusion proteins according to the invention, a surgical treatment may be necessary to suitably contour the newly formed cartilage surface.

In a preferred embodiment, the treatment comprises peri-synovial administration, intra-synovial administration, peri-articular administration or intra-articular administration of the fusion proteins according to the invention. Said fusion proteins can be applied by direct injection into the synovial fluid of the joint or directly into the defect, either alone or complexed with a suitable carrier for extended release of protein (e.g. sustained-release formulations) or restricted local release. The intraarticular administration is done in a joint selected from joint of the hip, knee, elbow, wrist, ankle, spine, feet, finger, toe, hand, shoulder, ribs, shoulder blades, thighs, shins, heels and along the bony points of the spine. In yet another preferred embodiment the intraarticular administration is done in the joint of the hip or the knee.

DESCRIPTION OF THE FIGURES

FIGS. 1A-1L: FIG. 1A) Structure of an FGF-18 moiety linked to a scFv moiety via the free VL part of said ScFv moiety. FIG. 1B) Structure of an FGF-18 moiety linked to a SEEDbody moiety via the N-term of the partial heavy chain of said SEEDbody, herein a AG part. FIG. 1C) Structure of an FGF-18 moiety linked to a SEEDbody moiety via the C-term of the light chain of said SEEDbody. FIG. 1D) Structure of an FGF-18 moiety linked to a SEEDbody moiety via the C-term of the partial heavy chain of said SEEDbody, herein a AG part. FIG. 1E) Structure of an FGF-18 moiety linked to a Fab moiety via the N-terminus of the light chain fusion FIG. 1F) Structure of an FGF-18 moiety linked to a Fab moiety via the N-terminus heavy chain fusion. FIG. 1G) Structure of an FGF-18 moiety linked to a Fab moiety via the C-terminus light chain fusion. FIG. 1H) Structure of an FGF-18 moiety linked to a Fab moiety via the C-terminus heavy chain fusion, FIG. 1I) Structure of an FGF-18 moiety linked to an IgG-moiety via the N-terminus light chain fusion FIG. 1J) Structure of an FGF-18 moiety linked to an IgG-moiety via the N-terminus heavy chain fusion. FIG. 1K) Structure of an FGF-18 moiety linked to an IgG-moiety via the C-terminus light chain fusion. FIG. 1L) Structure of an FGF-18 moiety linked to an IgG-moiety via the C-terminus heavy chain fusion.

FIG. 2A) Cell proliferation and type I collagen expression in porcine chondrocytes in monolayer cultured seven days with rhFGF18, the construct FGF18 scFv Tanezumab or MBE626. FIG. 2B) cell morphology (actin staining) of porcine chondrocytes in monolayer cultured five days with rhFGF18, the construct FGF18 scFv Tanezumab or MBE626 at 50.04 nM.

FIG. 3A) Design of the in vivo study to analyse gait disturbance in the MIA rat model. Intraarticular injections were made at day 1 after induction of osteoarthritis pain by 3 mg/joint MIA. Tanezumab was injected i.v. at the same time. Gait disturbance has been analysed by catwalk analysis. FIG. 3B) Dose dependent symptomatic benefit by FGF18-scFv-tanezumab during MIA induced osteoarthritis pain. Shown is the time course of the average of the % of contralateral hind paw print ±SEM of 7-8 rats/group ±SEM.

FIGS. 4A-4C: FIG. 4A) Design of the in vivo study to analyze gait disturbance in the ACLT tMx rat model of chronic osteoarthritis. (FIG. 4B) Gait disturbance over time. 100% gait quality corresponds to equal weight bearing at both hind paws. (FIG. 4C) Gait disturbance during 3 weeks after injection expressed as area above the curve (AAC; 100%=baseline). Shown is the average±SEM of 9-10 animals. Significance has been determined by a two-way ANOVA with a Dunnett post hoc test.

FIGS. 5A-5B: FIG. 5A) Intervention scheme for chronic study with MBE626 on structural and symptomatic benefit. FIG. 5B) Treatment effects of MBE626 on gait performance over time during chronic osteoarthritis. Shown is the % of contralateral for the parameter print length. 100% would indicate equal weight bearing. A decreased value indicated reduced weight bearing on the affected hindlimb which is due to knee pain. Data represents the mean±SEM of n=10-18 animal/group.

Figure 2A:
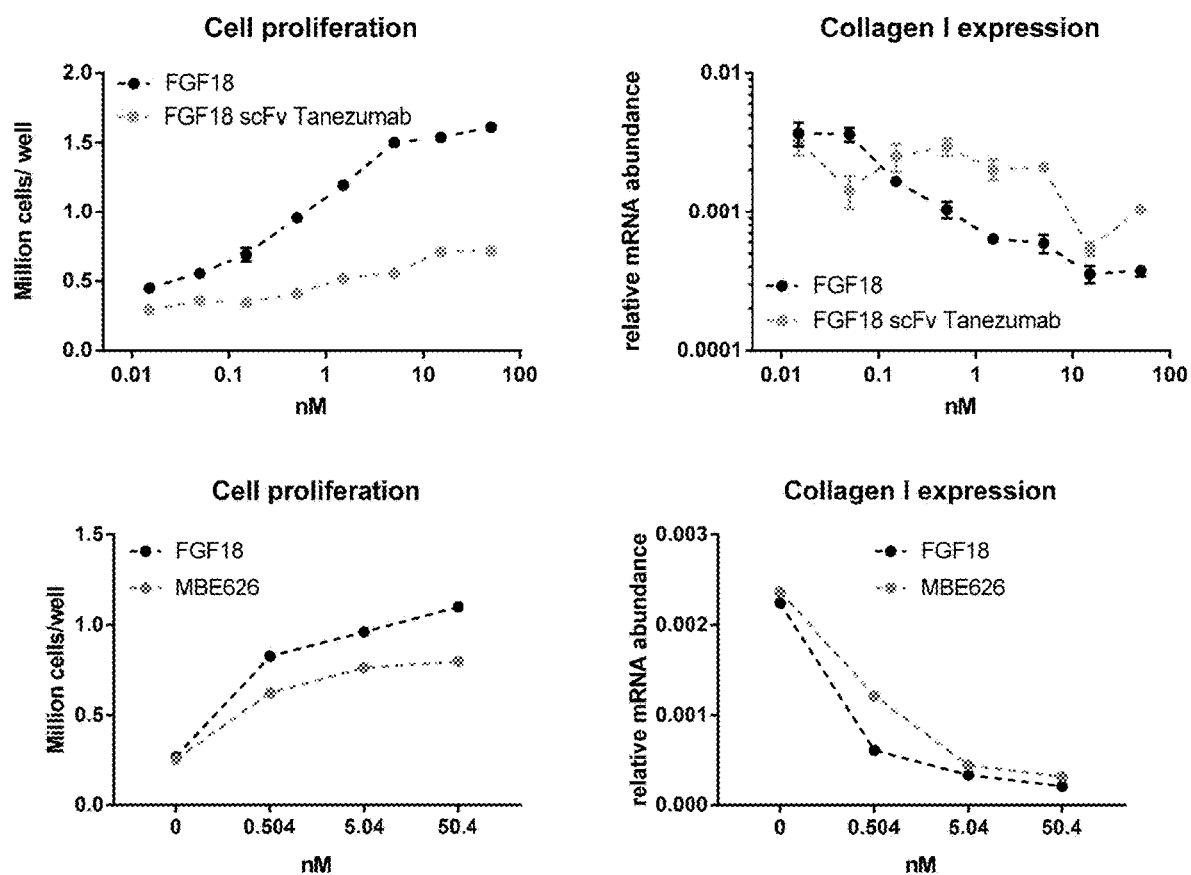
FIGS. 2A-2B.

```
List and description of the amino acid sequences
SEQ ID NO: 1: Amino acid sequence of the native human FGF-18
MYSAPSACTCLCLHFLLLCFQVQVLVAEENVDFRIHVENQTRARDDVSRKQLRLYQLYSRTSGKHIQVLG

RRISARGEDGDKYAQLLVETDTFGSQVRIKGKETEFYLCMNRKGKLVGKPDGTSKECVFIEKVLENNYTA

LMSAKYSGWYVGFTKKGRPRKGPKTRENQQDVHFMKRYPKGQPELQKPFKYTTVTKRSRRIRPTHPA

SEQ ID NO: 2: Amino acid sequence of a recombinant truncated
FGF-18 (trFGF-18)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTK

SEQ ID NO: 3: Amino acid sequence of FGF18_delta8
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKP

SEQ ID NO: 4: Amino acid sequence of FGF18_TF
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPGGGGSGGGGS

SEQ ID NO: 5: Amino acid sequence of FGF18_QNQS
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQQNFQSTTVTK

SEQ ID NO: 6: Amino acid sequence of FGF18_Y191P
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKPTTVTK
```

SEQ ID NO: 7: Amino acid sequence of FGF18_3Ala
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTK

SEQ ID NO: 8: Amino acid sequence of FGF18_VS
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFVSTTVTK

SEQ ID NO: 9: Amino acid sequence of the full heavy chain of tanezumab
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPCSRSTS

ESTAALGCLVKDYFPEPVTVSWNSGALTSGVHTFPAVLQSSGLYSLSSVVTVPSSNFGTQTYTCNVDHK

PSNTKVDKTVERKCCVECPPCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGLPSSIEKTISKTKGQPREPQ

VYTLPPSREEMTKNQVSLTCLVKGFYPSDIAVEWESNGQPENNYKTTPPMLDSDGSFFLYSKLTVDKSR

WQQGNVFSCSVMHEALHNHYTQKSLSLSPGK

SEQ ID NO: 10: Amino acid sequence of the full heavy chain
of tanezumab, with point mutations
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALGAPIEKTISKAKGQPRE

PQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

SEQ ID NO: 11: Amino acid sequence of the full light chain of tanezumab
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVGLLNNFYPR

EAKVQWKVDNALQSGNSQESVTEQDSKDSTYSLSSTLTLSKADYEKHKVYACEVTHQGLSSPVTKSFNR

GEC

SEQ ID NO: 12: Amino acid sequence of the full heavy chain of fasinumab
QVQLVQSGAEVKKPGASVKVSCKVSGFTLTELSIHWVRQAPGKGLEWMGGFDPEDGETIYAQKFQGRV

TMTEDTSTDTAYMELTSLRSEDTAVYYCSTIFGVVTNFDNWGQGTLVTVSSASTKGPSVFPLAPCSRSTS

ESTAALGCLVKDYFPEPVTVSWNSGALTSGVHTFPAVLQSSGLYSLSSVVTVPSSSLGTKTYTCNVDHKP

SNTKVDKRVESKYGPPCPPCPAPEFLGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTVDKSR

WQEGNVFSCSVMHEALHNHYTQKSLSLSLGK

SEQ ID NO: 13: Amino acid sequence of the full light chain of fasinumab
DIQMTQSPSSLSASAGDRVTITCRASQAIRNDLGWYQQKPGKAPKRLIYAAFNLQSGVPSRFSGSGSGT

EFTLTISSLQPEDLASYYCQQYNRYPWTFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSF

NRGEC

-continued

SEQ ID NO: 14: Amino acid sequence of heavy chain of fulranumab
EVQLVESGGGLVQPGGSLRLSCAASGFTLRSYSMNWVRQAPGKGLEWVSYISRSSHTIFYADSVKGRF

TISRDNAKNSLYLQMDSLRDEDTAMYYCARVYSSGWHVSDYFDYWGQGILVTVSSASTKGPSVFPLAPC

SRSTSESTAALGCLVKDYFPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNYKTTPPMLDSDGSFFLYSKLT

VDKSRWQQGNVFSCSVMHEALHNHYTQKSLSLSPGK

SEQ ID NO: 15: Amino acid sequence of light chain of fulranumab
AIQLTQSPSSLSASVGDRVTITCRASQGISSALAWYQQKPGKAPKLLIYDASSLESGVPSRFSGSGSGTD

FTLTISSLQPEDFATYYCQQFNSYPLTFGGGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFN

RGEC

SEQ ID NO: 16: Amino acid sequence of the heavy chain Fab fragment
of tanezumab
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSC

SEQ ID NO: 17: Amino acid sequence of the light chain Fab fragment
of tanezumab
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GEC

SEQ ID NO: 18: Amino acid sequence of the heavy chain Fab fragment
of fasinumab
QVQLVQSGAEVKKPGASVKVSCKVSGFTLTELSIHWVRQAPGKGLEWMGGFDPEDGETIYAQKFQGRV

TMTEDTSTDTAYMELTSLRSEDTAVYYCSTIFGVVTNFDNWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSC

SEQ ID NO: 19: Amino acid sequence of the light chain Fab fragment
of fasinumab
DIQMTQSPSSLSASAGDRVTITCRASQAIRNDLGWYQQKPGKAPKRLIYAAFNLQSGVPSRFSGSGSGT

EFTLTISSLQPEDLASYYCQQYNRYPWTFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSF

NRGEC

SEQ ID NO: 20: Amino acid sequence of the heavy chain Fab fragment
of fulranumab.
EVQLVESGGGLVQPGGSLRLSCAASGFTLRSYSMNWVRQAPGKGLEWVSYISRSSHTIFYADSVKGRF

TISRDNAKNSLYLQMDSLRDEDTAMYYCARVYSSGWHVSDYFDYWGQGILVTVSSASTKGPSVFPLAPS

SKSTSGGTAALGCLVKDYFPEPVTVSWNSGALTSGVHTFPAVLQSSGLYSLSSVVTVPSSSLGTQTYICN

VNHKPSNTKVDKKVEPKSC

SEQ ID NO: 21: Amino acid sequence of the light chain Fab fragment
of fulranumab
AIQLTQSPSSLSASVGDRVTITCRASQGISSALAWYQQKPGKAPKLLIYDASSLESGVPSRFSGSGSGTD

FTLTISSLQPEDFATYYCQQFNSYPLTFGGGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFN

RGEC

SEQ ID NO: 22: Amino acid sequence of scFv of tanezumab
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKGGGGSGGGGSGGGGSQVQLQESGPGLVKPSET

LSLTCTVSGFSLIGYDLNWIRQPPGKGLEWIGIIWGDGTTDYNSAVKSRVTISKDTSKNQFSLKLSSVTAA

DTAVYYCARGGYWYATSYYFDYWGQGTLVTVSS

SEQ ID NO: 23: Amino acid sequence of scFv of fasinumab
DIQMTQSPSSLSASAGDRVTITCRASQAIRNDLGWYQQKPGKAPKRLIYAAFNLQSGVPSRFSGSGSGT

EFTLTISSLQPEDLASYYCQQYNRYPWTFGQGTKVEIKGGGGSGGGGSGGGGSQVQLVQSGAEVKKP

GASVKVSCKVSGFTLTELSIHWVRQAPGKGLEWMGGFDPEDGETIYAQKFQGRVTMTEDTSTDTAYME

LTSLRSEDTAVYYCSTIFGVVTNFDNWGQGTLVTVSS

SEQ ID NO: 24: Amino acid sequence of scFv of fulranumab
AIQLTQSPSSLSASVGDRVTITCRASQGISSALAWYQQKPGKAPKLLIYDASSLESGVPSRFSGSGSGTD

FTLTISSLQPEDFATYYCQQFNSYPLTFGGGTKVEIKGGGGSGGGGSGGGGSEVQLVESGGGLVQPGG

SLRLSCAASGFTLRSYSMNWVRQAPGKGLEWVSYISRSSHTIFYADSVKGRFTISRDNAKNSLYLQMDSL

RDEDTAMYYCARVYSSGWHVSDYFDYWGQGILVTVSS

SEQ ID NO: 25: Amino acid sequence of FGF-18-scFv-tanezumab, fusion
via N-terminus of light domain (with residues 1-169 = FGF-18
moiety; 170-184 = linker; 185-427 = scFv tanezumab as the
anti-NGF inhibitor moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSGGGGSDIQMTQSPSSLSASVGDRVTI

TCRASQSISNNLNWYQQKPGKAPKLLIYYTSRFHSGVPSRFSGSGSGTDFTFTISSLQPEDIATYYCQQE

HTLPYTFGQGTKLEIKGGGGSGGGGSGGGGSQVQLQESGPGLVKPSETLSLTCTVSGFSLIGYDLNWIR

QPPGKGLEWIGIIWGDGTTDYNSAVKSRVTISKDTSKNQFSLKLSSVTAADTAVYYCARGGYWYATSYYF

DYWGQGTLVTVSS

SEQ ID NO: 26: Amino acid sequence of FGF-18-scFv-fasinumab, fusion
via N-terminus of light domain (with residues 1-169 = FGF-18
moiety; 170-184 = linker; 185-425 = scFv fasinumab as the
anti-NGF inhibitor moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSGGGGSDIQMTQSPSSLSASAGDRVTI

TCRASQAIRNDLGWYQQKPGKAPKRLIYAAFNLQSGVPSRFSGSGSGTEFTLTISSLQPEDLASYYCQQY

NRYPWTFGQGTKVEIKGGGGSGGGGSGGGGSQVQLVQSGAEVKKPGASVKVSCKVSGFTLTELSIHW

VRQAPGKGLEWMGGFDPEDGETIYAQKFQGRVTMTEDTSTDTAYMELTSLRSEDTAVYYCSTIFGVVTN

FDNWGQGTLVTVSS

SEQ ID NO: 27: Amino acid sequence of FGF-18-scFv-fulranumab, fusion
via N-terminus of light domain (with residues 1-169 = FGF-18
moiety; 170-184 = linker; 185-429 = scFv fulranumab as the
anti-NGF inhibitor moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSGGGGSAIQLTQSPSSLSASVGDRVTIT

CRASQGISSALAWYQQKPGKAPKLLIYDASSLESGVPSRFSGSGSGTDFTLTISSLQPEDFATYYCQQFN

SYPLTFGGGTKVEIKGGGGSGGGGSGGGGSEVQLVESGGGLVQPGGSLRLSCAASGFTLRSYSMNWV

RQAPGKGLEWVSYISRSSHTIFYADSVKGRFTISRDNAKNSLYLQMDSLRDEDTAMYYCARVYSSGWHV

SDYFDYWGQGILVTVSS

SEQ ID NO: 28: Amino acid sequence of FGF-18-Fab of anti-NGF, fusion
via N-terminus of the light chain (with residues 1-169 = FGF-18
moiety; 170-184 = linker; 185-398 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSGGGGSDIQMTQSPSSLSASVGDRVTI

TCRASQSISNNLNWYQQKPGKAPKLLIYYTSRFHSGVPSRFSGSGSGTDFTFTISSLQPEDIATYYCQQE

HTLPYTFGQGTKLEIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC

SEQ ID NO: 29: Amino acid sequence of FGF18TF-Fab of anti-NGF, fusion
via N-terminus of the light chain (with residues 1-161 = FGF-18
moiety; 162-186 = linker; 187-400 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPGGGGSGGGGSEPKSSDKTHTGGGGSDIQMTQSPSSLSASVGDR

VTITCRASQSISNNLNWYQQKPGKAPKLLIYYTSRFHSGVPSRFSGSGSGTDFTFTISSLQPEDIATYYCQ

QEHTLPYTFGQGTKLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

SEQ ID NO: 30: Amino acid sequence of FGF18QNQS-Fab of anti-NGF, fusion
via N-terminus of the light chain (with residues 1-169 = FGF-18
moiety; 1170-184 = linker; 185-398 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQQNFQSTTVTKEPKSSDKTHTGGGGSDIQMTQSPSSLSASVGDRVTIT

CRASQSISNNLNWYQQKPGKAPKLLIYYTSRFHSGVPSRFSGSGSGTDFTFTISSLQPEDIATYYCQQEH

TLPYTFGQGTKLEIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

SEQ ID NO: 31: Amino acid sequence of FGF18Y191P-Fab of anti-NGF,
fusion via N-terminus of the light chain (with residues 1-169 =
FGF-18 moiety; 170-184 = linker; 185-398 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKPTTVTKEPKSSDKTHTGGGGSDIQMTQSPSSLSASVGDRVTITC

RASQSISNNLNWYQQKPGKAPKLLIYYTSRFHSGVPSRFSGSGSGTDFTFTISSLQPEDIATYYCQQEHT

LPYTFGQGTKLEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC

SEQ ID NO: 32: Amino acid sequence of FGF18_3Ala-Fab of anti-NGF,
fusion via N-terminus of the light chain (with residues 1-169 =
FGF-18 moiety; 170-184 = linker; 185-398 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTGGGGSDIQMTQSPSSLSASVGDRVTITC

RASQSISNNLNWYQQKPGKAPKLLIYYTSRFHSGVPSRFSGSGSGTDFTFTISSLQPEDIATYYCQQEHT

LPYTFGQGTKLEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC

SEQ ID NO: 33: Amino acid sequence of FGF18VS-Fab of anti-NGF,
fusion via N-terminus of the light chain (with residues 1-169 =
FGF-18 moiety; 170-184 = linker; 185-398 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFVSTTVTKEPKSSDKTHTGGGGSDIQMTQSPSSLSASVGDRVTITC

RASQSISNNLNWYQQKPGKAPKLLIYYTSRFHSGVPSRFSGSGSGTDFTFTISSLQPEDIATYYCQQEHT

LPYTFGQGTKLEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC

SEQ ID NO: 34: Amino acid sequence of FGF18-Fab of anti-NGF,
fusion via N-terminus of the heavy chain (with residues 1-169 =
FGF-18 moiety; 170-179 = linker; 180-403 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSQVQLQESGPGLVKPSETLSLTCTVSG

FSLIGYDLNWIRQPPGKGLEWIGIIWGDGTTDYNSAVKSRVTISKDTSKNQFSLKLSSVTAADTAVYYCAR

GGYWYATSYYFDYWGQGTLVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKKVEPKSC

SEQ ID NO: 35: Amino acid sequence of FGF18TF-Fab of anti-NGF,
fusion via N-terminus of the heavy chain (with residues 1-161 =
FGF-18 moiety; 162-186 = linker; 187-410 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPGGGGSGGGGSEPKSSDKTHTGGGGSQVQLQESGPGLVKPSETL

SLTCTVSGFSLIGYDLNWIRQPPGKGLEWIGIIWGDGTTDYNSAVKSRVTISKDTSKNQFSLKLSSVTAAD

TAVYYCARGGYWYATSYYFDYWGQGTLVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDKKVEPKSC

SEQ ID NO: 36: Amino acid sequence of FGF18QNQS-Fab of anti-NGF,
fusion via N-terminus of the heavy chain (with residues 1-169 =
FGF-18 moiety; 170-184 = linker; 185-408 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQQNFQSTTVTKEPKSSDKTHTGGGGSQVQLQESGPGLVKPSETLSLTC

TVSGFSLIGYDLNWIRQPPGKGLEWIGIIWGDGTTDYNSAVKSRVTISKDTSKNQFSLKLSSVTAADTAVY

YCARGGYWYATSYYFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSC

SEQ ID NO: 37: Amino acid sequence of FGF18Y191P-Fab of anti-NGF,
fusion via N-terminus of the heavy chain (with residues 1-169 =
FGF-18 moiety; 170-184 = linker; 185-408 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKPTTVTKEPKSSDKTHTGGGGSQVQLQESGPGLVKPSETLSLTC

TVSGFSLIGYDLNWIRQPPGKGLEWIGIIWGDGTTDYNSAVKSRVTISKDTSKNQFSLKLSSVTAADTAVY

YCARGGYWYATSYYFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSC

SEQ ID NO: 38: Amino acid sequence of FGF18_3Ala-Fab of anti-NGF,
fusion via N-terminus of the heavy chain (with residues 1-169 =
FGF-18 moiety; 170-184 = linker; 185-408 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTGGGGSQVQLQESGPGLVKPSETLSLTC

TVSGFSLIGYDLNWIRQPPGKGLEWIGIIWGDGTTDYNSAVKSRVTISKDTSKNQFSLKLSSVTAADTAVY

YCARGGYWYATSYYFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSC

SEQ ID NO: 39: Amino acid sequence of FGF18VS-Fab of anti-NGF,
fusion via N-terminus of the heavy chain (with residues 1-169 =
FGF-18 moiety; 170-184 = linker; 185-408 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFVSTTVTKEPKSSDKTHTGGGGSQVQLQESGPGLVKPSETLSLTC

TVSGFSLIGYDLNWIRQPPGKGLEWIGIIWGDGTTDYNSAVKSRVTISKDTSKNQFSLKLSSVTAADTAVY

YCARGGYWYATSYYFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSC

SEQ ID NO: 40: Amino acid sequence of Fab of anti-NGF-FGF18_delta8,
fusion via C-terminus of the light chain (with residues 1-214 =
Fab moiety; 215-234 = linker; 235-395 = FGF-18 moiety)
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQKP

SEQ ID NO: 41: Amino acid sequence of Fab of anti-NGF-FGF18QNQS-,
fusion via C-terminus of the light chain (with residues 1-214 =
Fab moiety; 215-234 = linker; 235-403 = FGF-18 moiety)
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQQNFQSTTVTK

SEQ ID NO: 42: Amino acid sequence of Fab of anti-NGF-FGF18Y191P,
fusion via C-terminus of the light chain (with residues 1-214 =
Fab moiety; 215-234 = linker; 235-403 = FGF-18 moiety)
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQKPFKPTTVTK

SEQ ID NO: 43: Amino acid sequence of Fab of anti-NGF-FGF18_3Ala,
fusion via C-terminus of the light chain (with residues 1-214 =
Fab moiety; 215-234 = linker; 235-403 = FGF-18 moiety)
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQAAFAYTTVTK

SEQ ID NO: 44: Amino acid sequence of Fab of anti-NGF-FGF18VS,
fusion via C-terminus of the light chain (with residues 1-214 =
Fab moiety; 215-234 = linker; 235-403 = FGF-18 moiety)
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQKPFVSTTVTK

SEQ ID NO: 45: Amino acid sequence of Fab of anti-NGF-FGF18TF,
fusion via C-terminus of the heavy chain (with residues 1-224 =
Fab moiety; 225-244 = linker; 245-405 = FGF-18 moiety)
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCGGGGSEPKSSDKTHTGGGGSEENVDFRIHVENQTRARDDVSRKQLRLYQLYSRT

SGKHIQVLGRRISARGEDGDKYAQLLVETDTFGSQVRIKGKETEFYLCMNRKGKLVGKPDGTSKECVFIE

KVLENNYTALMSAKYSGWYVGFTKKGRPRKGPKTRENQQDVHFMKRYPKGQPELQKP

SEQ ID NO: 46: Amino acid sequence of Fab of anti-NGF-FGF18QNQS,
fusion via C-terminus of the heavy chain (with residues 1-224 =
Fab moiety; 225-244 = linker; 245-413 = FGF-18 moiety)
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCGGGGSEPKSSDKTHTGGGGSEENVDFRIHVENQTRARDDVSRKQLRLYQLYSRT

SGKHIQVLGRRISARGEDGDKYAQLLVETDTFGSQVRIKGKETEFYLCMNRKGKLVGKPDGTSKECVFIE

KVLENNYTALMSAKYSGWYVGFTKKGRPRKGPKTRENQQDVHFMKRYPKGQPELQQNFQSTTVTK

SEQ ID NO: 47: Amino acid sequence of Fab of anti-NGF-FGF18Y191P,
fusion via C-terminus of the heavy chain (with residues 1-224 =
Fab moiety; 225-244 = linker; 245-413 = FGF-18 moiety)
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCGGGGSEPKSSDKTHTGGGGSEENVDFRIHVENQTRARDDVSRKQLRLYQLYSRT

SGKHIQVLGRRISARGEDGDKYAQLLVETDTFGSQVRIKGKETEFYLCMNRKGKLVGKPDGTSKECVFIE

KVLENNYTALMSAKYSGWYVGFTKKGRPRKGPKTRENQQDVHFMKRYPKGQPELQKPFKPTTVTK

-continued

SEQ ID NO: 48: Amino acid sequence of Fab of anti-NGF-FGF18_3Ala, fusion via C-terminus of the heavy chain (with residues 1-224 = Fab moiety; 225-244 = linker; 245-413 = FGF-18 moiety)
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCGGGGSEPKSSDKTHTGGGGSEENVDFRIHVENQTRARDDVSRKQLRLYQLYSRT

SGKHIQVLGRRISARGEDGDKYAQLLVETDTFGSQVRIKGKETEFYLCMNRKGKLVGKPDGTSKECVFIE

KVLENNYTALMSAKYSGWYVGFTKKGRPRKGPKTRENQQDVHFMKRYPKGQPELQAAFAYTTVTK

SEQ ID NO: 49: Amino acid sequence of Fab of anti-NGF-FGF18VS, fusion via C-terminus of the heavy chain (with residues 1-224 = Fab moiety; 225-244 = linker; 245-413 = FGF-18 moiety)
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCGGGGSEPKSSDKTHTGGGGSEENVDFRIHVENQTRARDDVSRKQLRLYQLYSRT

SGKHIQVLGRRISARGEDGDKYAQLLVETDTFGSQVRIKGKETEFYLCMNRKGKLVGKPDGTSKECVFIE

KVLENNYTALMSAKYSGWYVGFTKKGRPRKGPKTRENQQDVHFMKRYPKGQPELQKPFVSTTVTK

SEQ ID NO: 50: Amino acid sequence of FGF-18-Fab of anti-NGF, fusion via N-terminus of light chain of fasinumab (with residues 1-169 = FGF-18 moiety; 170-179 = linker; 180-393 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSDIQMTQSPSSLSASAGDRVTITCRASQ

AIRNDLGWYQQKPGKAPKRLIYAAFNLQSGVPSRFSGSGSGTEFTLTISSLQPEDLASYYCQQYNRYPW

TFGQGTKVEIKRTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

SEQ ID NO: 51: Amino acid sequence of FGF-18-Fab of anti-NGF, fusion via N-terminus of heavy chain of fasinumab (with residues 1-169 = FGF-18 moiety; 170-179 = linker; 180-401 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSQVQLVQSGAEVKKPGASVKVSCKVS

GFTLTELSIHWVRQAPGKGLEWMGGFDPEDGETIYAQKFQGRVTMTEDTSTDTAYMELTSLRSEDTAVY

YCSTIFGVVTNFDNWGQGTLVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKKVEPKSC

SEQ ID NO: 52: Amino acid sequence of FGF-18-Fab of anti-NGF, fusion via N-terminus of light chain of fulranumab (with residues 1-169 = FGF-18 moiety; 170-179 = linker; 180-393 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSAIQLTQSPSSLSASVGDRVTITCRASQ

GISSALAWYQQKPGKAPKLLIYDASSLESGVPSRFSGSGSGTDFTLTISSLQPEDFATYYCQQFNSYPLTF

GGGTKVEIKRTVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

-continued

SEQ ID NO: 53: Amino acid sequence of FGF-18-Fab of anti-NGF, fusion
via N-terminus of heavy chain of fulranumab (with residues 1-169 =
FGF-18 moiety; 170-179 = linker; 180-405 = Fab moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSEVQLVESGGGLVQPGGSLRLSCAASG

FTLRSYSMNWVRQAPGKGLEWVSYISRSSHTIFYADSVKGRFTISRDNAKNSLYLQMDSLRDEDTAMYY

CARVYSSGWHVSDYFDYWGQGILVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSC

SEQ ID NO: 54: Amino acid sequence of FGF18-SEED, AG chain (with
FGF-18 moiety linked in the N-terminus of the sequence; with residues
1-169 = FGF-18 moiety; 170-184 = linker; 185-414 =
AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGSGGSGSGSEPKSSDKTHTCPPCPAPEAAGGPSVF

LFPPKPKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPFRPEVHLLPPSREEMTKNQVSLTCLARGFYPKDIAVE

WESNGQPENNYKTTPSRQEPSQGTTTFAVTSKLTVDKSRWQQGNVFSCSVMHEALHNHYTQKTISLSP

GK

SEQ ID NO: 55: Amino acid sequence of FGF18-SEED, AG chain (with
FGF-18 moiety linked in the N-terminus of the sequence; with residues
1-169 = FGF-18 moiety; 170-179 = linker; 180-409 =
AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSDKTHTCPPCPAPEAAGGPSVFLFPPK

PKDTLMISRTPEVTCVVVDVSHEDPEVKFNWYVDGVEVHNAKTKPREEQYNSTYRVVSVLTVLHQDWLN

GKEYKCKVSNKALPAPIEKTISKAKGQPFRPEVHLLPPSREEMTKNQVSLTCLARGFYPKDIAVEWESNG

QPENNYKTTPSRQEPSQGTTTFAVTSKLTVDKSRWQQGNVFSCSVMHEALHNHYTQKTISLSPGK

SEQ ID NO: 56: Amino acid sequence of an anti-NGF GA chain
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISKAKGQPRE

PQVYTLPPPSEELALNELVTLTCLVKGFYPSDIAVEWLQGSQELPREKYLTWAPVLDSDGSFFLYSILRVA

AEDWKKGDTFSCSVMHEALHNRFTQKSLDRSPGK

SEQ ID NO: 57: Amino acid sequence of FGF18-SEED, AG chain (with
FGF-18 moiety linked in the N-terminus of the sequence; with residues
1-169 = FGF-18 moiety; 170-179 = linker; 180-409 =
AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSDKTHTCPPCPAPEAAGGPSVFLFPPK

PKDTLMISRTPEVTCVVVDVSHEDPEVKFNWYVDGVEVHNAKTKPREEQYNSTYRVVSVLTVLHQDWLN

GKEYKCKVSNKALPAPIEKTISKAKGQPFRPEVHLLPPSREEMTKNQVSLTCLARGFYPKDIAVEWESNG

QPENNYKTTPSRQEPSQGTTTFAVTSKLTVDKSRWQQGNVFSCSVMHEALHNHYTQKTISLSPGK

-continued

SEQ ID NO: 58: Amino acid sequence of an anti-NGF GA chain
QVQLVQSGAEVKKPGASVKVSCKVSGFTLTELSIHWVRQAPGKGLEWMGGFDPEDGETIYAQKFQGRV

TMTEDTSTDTAYMELTSLRSEDTAVYYCSTIFGVVTNFDNWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISKAKGQPRE

PQVYTLPPPSEELALNELVTLTCLVKGFYPSDIAVEWLQGSQELPREKYLTWAPVLDSDGSFFLYSILRVA

AEDWKKGDTFSCSVMHEALHNRFTQKSLDRSPGK

SEQ ID NO: 59: Amino acid sequence of an FGF18-SEED, AG chain (with
FGF-18 moiety linked in the N-terminus of the sequence; with residues
1-169 = FGF-18 moiety; 170-179 = linker; 180-409 =
AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGGGSGGGGSDKTHTCPPCPAPEAAGGPSVFLFPPK

PKDTLMISRTPEVTCVVVDVSHEDPEVKFNWYVDGVEVHNAKTKPREEQYNSTYRVVSVLTVLHQDWLN

GKEYKCKVSNKALPAPIEKTISKAKGQPFRPEVHLLPPSREEMTKNQVSLTCLARGFYPKDIAVEWESNG

QPENNYKTTPSRQEPSQGTTTFAVTSKLTVDKSRWQQGNVFSCSVMHEALHNHYTQKTISLSPGK

SEQ ID NO: 60: Amino acid sequence of an anti-NGF GA chain
EVQLVESGGGLVQPGGSLRLSCAASGFTLRSYSMNWVRQAPGKGLEWVSYISRSSHTIFYADSVKGRF

TISRDNAKNSLYLQMDSLRDEDTAMYYCARVYSSGWHVSDYFDYWGQGILVTVSSASTKGPSVFPLAPS

SKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISKA

KGQPREPQVYTLPPPSEELALNELVTLTCLVKGFYPSDIAVEWLQGSQELPREKYLTWAPVLDSDGSFFL

YSILRVAAEDWKKGDTFSCSVMHEALHNRFTQKSLDRSPGK

SEQ ID NO: 61: Amino acid sequence of FGF18_3Ala_IgG-light chain,
fusion via the N-terminus of the sequence; with residues 1-169 =
FGF-18 moiety; 170-184 = linker; 185-398 = light chain moiety
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTGGGGSDIQMTQSPSSLSASVGDRVTITC

RASQSISNNLNWYQQKPGKAPKLLIYYTSRFHSGVPSRFSGSGSGTDFTFTISSLQPEDIATYYCQQEHT

LPYTFGQGTKLEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC

SEQ ID NO: 62: Amino acid sequence of FGF18_3Ala_IgG-heavy chain,
fusion via the N-terminus of the sequence; with residues 1-169 =
FGF-18 moiety; 170-184 = linker; 185-635 = AG chain moiety
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTGGGGSQVQLQESGPGLVKPSETLSLTC

TVSGFSLIGYDLNWIRQPPGKGLEWIGIIWGDGTTDYNSAVKSRVTISKDTSKNQFSLKLSSVTAADTAVY

YCARGGYWYATSYYFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSCDKTHTC

PPCPAPEAAGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALGAPIEKTISKAKGQPREPQVYTLPPSRDELTKNQVSL

TCLVKGFYPSDIAVEWESNGQPENNYKTTPPVLDSDGSFFLYSKLTVDKSRWQQGNVFSCSVMHEALH

NHYTQKSLSLSPGK

SEQ ID NO: 63: Amino acid sequence of IgG-light chain-FGF18_3Ala,
fusion via the C-terminus of the sequence; with residues 1-214 =
light chain moiety; 215-234 = linker; 235-403 = FGF-18 moiety.
DIQMTQSPSSLSASVGDRVTITCRASQSISNNLNWYQQKPGKAPKLLIYYTSRFHSGVPSRFSGSGSGTD

FTFTISSLQPEDIATYYCQQEHTLPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNR

GECGGGGSEPKSSDKTHTGGGGSEENVDFRIHVENQTRARDDVSRKQLRLYQLYSRTSGKHIQVLGRR

ISARGEDGDKYAQLLVETDTFGSQVRIKGKETEFYLCMNRKGKLVGKPDGTSKECVFIEKVLENNYTALM

SAKYSGWYVGFTKKGRPRKGPKTRENQQDVHFMKRYPKGQPELQAAFAYTTVTK

SEQ ID NO: 64: Amino acid sequence of IgG-heavy chain-FGF18_3Ala,
fusion via the C-terminus of the sequence; with residues 1-451 =
heavy chain moiety; 452-471 = linker; 472-640 = FGF-18 moiety.
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALGAPIEKTISKAKGQPRE

PQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGKGGGGSEPKSSDKTHTGGGGSEENVDFRIHVENQTR

ARDDVSRKQLRLYQLYSRTSGKHIQVLGRRISARGEDGDKYAQLLVETDTFGSQVRIKGKETEFYLCMNR

KGKLVGKPDGTSKECVFIEKVLENNYTALMSAKYSGWYVGFTKKGRPRKGPKTRENQQDVHFMKRYPK

GQPELQAAFAYTTVTK

SEQ ID NO: 65: Amino acid sequence of an anti-NGF GA chain with
point mutations
QVQLQESGPGLVKPSETLSLTCTVSGFSLIGYDLNWIRQPPGKGLEWIGIIWGDTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALGAPIEKTISKAKGQPRE

PQVYTLPPPSEELALNELVTLTCLVKGFYPSDIAVEWLQGSQELPREKYLTWAPVLDSDGSFFLYSILRVA

AEDWKKGDTFSCSVMHEALHNRFTQKSLDRSPGK

SEQ ID NO: 66: Amino acid sequence of FGF18TF_SEED, AG chain (as
the partial heavy chain of the SEEDbody) (with FGF-18 moiety linked
in the N-terminus of the sequence; with residues 1-162 = FGF-18
moiety; 163-176 = linker; 177-406 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPGGGGSGGGGSEPKSSDKTHTCPPCPAPEAAGGPSVFLFPPKPKD

TLMISRTPEVTCVVVDVSHEDPEVKFNWYVDGVEVHNAKTKPREEQYNSTYRVVSVLTVLHQDWLNGK

EYKCKVSNKALGAPIEKTISKAKGQPFRPEVHLLPPSREEMTKNQVSLTCLARGFYPKDIAVEWESNGQP

ENNYKTTPSRQEPSQGTTTFAVTSKLTVDKSRWQQGNVFSCSVMHEALHNHYTQKTISLSPGK

-continued

SEQ ID NO: 67: Amino acid sequence of FGF18QNQS_SEED, AG chain (as
the partial heavy chain of the SEEDbody) (with FGF-18 moiety linked
in the N-terminus of the sequence; with residues 1-169 = FGF-18
moiety; 170-174 = linker; 175-404 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQQNFQSTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPFRPEVHLLPPSREEMTKNQVSLTCLARGFYPKDIAVEWESNGQPENNY

KTTPSRQEPSQGTTTFAVTSKLTVDKSRWQQGNVFSCSVMHEALHNHYTQKTISLSPGK

SEQ ID NO: 68: Amino acid sequence of FGF18Y191P_SEED, AG chain (as
the partial heavy chain of the SEEDbody) (with FGF-18 moiety linked
in the N-terminus of the sequence; with residues 1-169 = FGF-18
moiety; 170-174 = linker; 175-404 = AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKPTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPFRPEVHLLPPSREEMTKNQVSLTCLARGFYPKDIAVEWESNGQPENNY

KTTPSRQEPSQGTTTFAVTSKLTVDKSRWQQGNVFSCSVMHEALHNHYTQKTISLSPGK

SEQ ID NO: 69: Amino acid sequence of FGF18_3Ala_SEED, AG chain (as
the partial heavy chain of the SEEDbody) (with FGF-18 moiety linked
in the N-terminus of the sequence; with residues 1-169 = FGF-18
moiety; 170-174 = linker; 175-404 = AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPFRPEVHLLPPSREEMTKNQVSLTCLARGFYPKDIAVEWESNGQPENNY

KTTPSRQEPSQGTTTFAVTSKLTVDKSRWQQGNVFSCSVMHEALHNHYTQKTISLSPGK

SEQ ID NO: 70: Amino acid sequence of FGF18VS_SEED, AG chain (as
the partial heavy chain of the SEEDbody) (with FGF-18 moiety linked
in the N-terminus of the sequence; with residues 1-169 = FGF-18
moiety; 170-174 = linker; 175-404 = AG chain moiety).
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFVSTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPFRPEVHLLPPSREEMTKNQVSLTCLARGFYPKDIAVEWESNGQPENNY

KTTPSRQEPSQGTTTFAVTSKLTVDKSRWQQGNVFSCSVMHEALHNHYTQKTISLSPGK

SEQ ID NO: 71: Amino acid sequence of an anti-NGF AG chain (as
the full heavy chain of the SEEDbody)
QVQLQESGPGLVKPSETLSLTCTVSGFSLIGYDLNWIRQPPGKGLEWIGIIWGDGTTDYNSAVKSRVTISK

DTSKNQFSLKLSSVTAADTAVYYCARGGYWYATSYYFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKP

SNTKVDKKVEPKSCDKTHTCPPCPAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALGAPIEKTISKAKGQPFR

PEVHLLPPSREEMTKNQVSLTCLARGFYPKDIAVEWESNGQPENNYKTTPSRQEPSQGTTTFAVTSKLT

VDKSRWQQGNVFSCSVMHEALHNHYTQKTISLSPGK

SEQ ID NO: 72: Amino acid sequence of SEED_FGF18TF, GA chain (as
the partial heavy chain of the SEEDbody) (with FGF-18 moiety linked
in the N-terminus of the sequence; with residues 1-161 = FGF-18
moiety; 162-176 = linker; 177-406 = GA chain moiety).
EENVDFRIHVENQTRARDDVSRKQLRLYQLYSRTGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPGGGGSGGGGSEPKSSDKTHTCPPCPAPEAAGGPSVFLFPPKPKD

TLMISRTPEVTCVVVDVSHEDPEVKFNWYVDGVEVHNAKTKPREEQYNSTYRVVSVLTVLHQDWLNGK

EYKCKVSNKALGAPIEKTISKAKGQPREPQVYTLPPPSEELALNELVTLTCLVKGFYPSDIAVEWLQGSQE

LPREKYLTWAPVLDSDGSFFLYSILRVAAEDWKKGDTFSCSVMHEALHNRFTQKSLDRSPGK

SEQ ID NO: 73: Amino acid sequence of SEED_FGF18QNFS, GA chain (as
the partial heavy chain of the SEEDbody) (with FGF-18 moiety linked
in the N-terminus of the s; with residues 1-169 = FGF-18 moiety;
170-174 = linker; 175-404 = GA chain moiety).
EENVDFRIHVENQTRARDDVSRKQLRLYQLYSRTGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQQNFQSTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPREPQVYTLPPPSEELALNELVTLTCLVKGFYPSDIAVEWLQGSQELPRE

KYLTWAPVLDSDGSFFLYSILRVAAEDWKKGDTFSCSVMHEALHNRFTQKSLDRSPGK

SEQ ID NO: 74: Amino acid sequence of SEED_FGF18Y191P, GA chain,
(with FGF-18 moiety linked in the N-terminus of the sequence) (as
the partial heavy chain of the SEEDbody; with residues 1-169 =
FGF-18 moiety; 170-174 = linker; 175-404 = GA chain moiety)
EENVDFRIHVENQTRARDDVSRKQLRLYQLYSRTGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKPTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPREPQVYTLPPPSEELALNELVTLTCLVKGFYPSDIAVEWLQGSQELPRE

KYLTWAPVLDSDGSFFLYSILRVAAEDWKKGDTFSCSVMHEALHNRFTQKSLDRSPGK

SEQ ID NO: 75: Amino acid sequence of SEED_FGF18_3Ala, GA chain
(with FGF-18 moiety linked in the N-terminus of the sequence). (as
the partial heavy chain of the SEEDbody; with residues 1-169 =
FGF-18 moiety; 170-174 = linker; 175-404 = GA chain moiety)
EENVDFRIHVENQTRARDDVSRKQLRLYQLYSRTGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQAAFAYTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPREPQVYTLPPPSEELALNELVTLTCLVKGFYPSDIAVEWLQGSQELPRE

KYLTWAPVLDSDGSFFLYSILRVAAEDWKKGDTFSCSVMHEALHNRFTQKSLDRSPGK

SEQ ID NO: 76: Amino acid sequence of SEED_FGF18VS, GA chain
(with FGF-18 moiety linked in the N-terminus of the sequence). (as
the partial heavy chain of the SEEDbody; with residues 1-169 =
FGF-18 moiety; 170-174 = linker; 175-404 = GA chain moiety)
EENVDFRIHVENQTRARDDVSRKQLRLYQLYSRTGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFVSTTVTKEPKSSDKTHTCPPCPAPEAAGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALGAPIEKTISKAKGQPREPQVYTLPPPSEELALNELVTLTCLVKGFYPSDIAVEWLQGSQELPRE

KYLTWAPVLDSDGSFFLYSILRVAAEDWKKGDTFSCSVMHEALHNRFTQKSLDRSPGK

SEQ ID NO: 77: Amino acid sequence of FGF18_SEED_GS, AG chain
(with FGF-18 moiety linked in the N-terminus of the sequence). (as
the partial heavy chain of the SEEDbody; with residues 1-169 =
FGF-18 moiety; 170-179 = linker; 180-409 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKGGSGGSGSGSDKTHTCPPCPAPEAAGGPSVFLFPPPK

PKDTLMISRTPEVTCVVVDVSHEDPEVKFNWYVDGVEVHNAKTKPREEQYNSTYRVVSVLTVLHQDWLN

GKEYKCKVSNKALPAPIEKTISKAKGQPFRPEVHLLPPSREEMTKNQVSLTCLARGFYPKDIAVEWESNG

QPENNYKTTPSRQEPSQGTTTFAVTSKLTVDKSRWQQGNVFSCSVMHEALHNHYTQKTISLSPGK

SEQ ID NO: 78: Amino acid sequence of FGF18_SEED_CH2, AG chain
(with FGF-18 moiety linked in the N-terminus of the sequence). (as
the partial heavy chain of the SEEDbody; with residues 1-169 =
FGF-18 moiety; 170-177 = linker; 178-407 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKPAPEAAGGDKTHTCPPCPAPEAAGGPSVFLFPPPKPKD

TLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPFRPEVHLLPPSREEMTKNQVSLTCLARGFYPKDIAVEWESNGQP

ENNYKTTPSRQEPSQGTTTFAVTSKLTVDKSRWQQGNVFSCSVMHEALHNHYTQKTISLSPGK

SEQ ID NO: 79: Amino acid sequence of FGF18_SEED_YOL, AG chain
(with FGF-18 moiety linked in the N-terminus of the sequence). (as
the partial heavy chain of the SEEDbody; with residues 1-169 =
FGF-18 moiety; 170-178 = linker; 179-408 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKEEGEFSEARDKTHTCPPCPAPEAAGGPSVFLFPPPKPK

DTLMISRTPEVTCVVVDVSHEDPEVKFNWYVDGVEVHNAKTKPREEQYNSTYRVVSVLTVLHQDWLNG

KEYKCKVSNKALPAPIEKTISKAKGQPFRPEVHLLPPSREEMTKNQVSLTCLARGFYPKDIAVEWESNGQ

PENNYKTTPSRQEPSQGTTTFAVTSKLTVDKSRWQQGNVFSCSVMHEALHNHYTQKTISLSPGK

SEQ ID NO: 80: Amino acid sequence of FGF18_SEED_Hinge, AG chain
(with FGF-18 moiety linked in the N-terminus of the sequence). (as
the partial heavy chain of the SEEDbody; with residues 1-169 =
FGF-18 moiety; 170-174 = linker; 175-404 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKEPKSSDKTHTCPPCPAPEAAGGPSVFLFPPPKPKDTLMI

SRTPEVTCVVVDVSHEDPEVKFNWYVDGVEVHNAKTKPREEQYNSTYRVVSVLTVLHQDWLNGKEYKC

KVSNKALPAPIEKTISKAKGQPFRPEVHLLPPSREEMTKNQVSLTCLARGFYPKDIAVEWESNGQPENNY

KTTPSRQEPSQGTTTFAVTSKLTVDKSRWQQGNVFSCSVMHEALHNHYTQKTISLSPGK

SEQ ID NO: 81: Amino acid sequence of FGF18_SEED_shin, AG chain
(with FGF-18 moiety linked in the N-terminus of the sequence). (as
the partial heavy chain of the SEEDbody; with residues 1-169 =
FGF-18 moiety; 170-399 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKDKTHTCPPCPAPEAAGGPSVFLFPPPKPKDTLMISRTPE

VTCVVVDVSHEDPEVKFNWYVDGVEVHNAKTKPREEQYNSTYRVVSVLTVLHQDWLNGKEYKCKVSNK

ALPAPIEKTISKAKGQPFRPEVHLLPPSREEMTKNQVSLTCLARGFYPKDIAVEWESNGQPENNYKTTPS

RQEPSQGTTTFAVTSKLTVDKSRWQQGNVFSCSVMHEALHNHYTQKTISLSPGK

SEQ ID NO: 82: Amino acid sequence of FGF18_SEED_3Ala, AG chain
(with FGF-18 moiety linked in the N-terminus of the sequence). (as
the partial heavy chain of the SEEDbody; with residues 1-169 =
FGF-18 moiety; 170-172 = linker; 173-402 = AG chain moiety)
EENVDFRIHVENQTRARDDVSRKQLRLYQLYSRTSGKHIQVLGRRISARGEDGDKYAQLLVETDTFGSQ

VRIKGKETEFYLCMNRKGKLVGKPDGTSKECVFIEKVLENNYTALMSAKYSGWYVGFTKKGRPRKGPKT

RENQQDVHFMKRYPKGQPELQKPFKYTTVTKAAADKTHTCPPCPAPEAAGGPSVFLFPPKPKDTLMISR

TPEVTCVVVDVSHEDPEVKFNWYVDGVEVHNAKTKPREEQYNSTYRVVSVLTVLHQDWLNGKEYKCKV

SNKALPAPIEKTISKAKGQPFRPEVHLLPPSREEMTKNQVSLTCLARGFYPKDIAVEWESNGQPENNYKT

TPSRQEPSQGTTTFAVTSKLTVDKSRWQQGNVFSCSVMHEALHNHYTQKTISLSPGK

SEQ ID NO: 83: Amino acid sequence of FGF18CFGF8 (with residues
1-155 = FGF18 moiety; 156-188 = FGF8 moiety)
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQHTTEQSLRFEFLNYPPFTRSLRGSQRTWAPEPR

SEQ ID NO: 84: Amino acid sequence of FGF18CFGF8T (with residues
1-155 = FGF18 moiety; 156-173 = FGF8T moiety)
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQHTTEQSLRFEFLNYPPFT

SEQ ID NO: 85: Amino acid sequence of FGF18CFGF17T (with residues
1-155 = FGF18 moiety; 156-177 = FGF17T moiety)
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQLPFPNHAEKQKQFEFVGSAPTR

SEQ ID NO: 86: Amino acid sequence of FGF18CFGF9 (with residues
1-147 = FGF18 moiety; 148-168 = FGF9 moiety)
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFLPRPVDPDKVPELYKDILSQS

SEQ ID NO: 87: Amino acid sequence of FGF18Y191F
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQPELQKPFKFTTVTK

SEQ ID NO: 88: Amino acid sequence of IgG-heavy chain-wild type
FGF18, fusion via the C-terminus of the sequence; with residues
1-451 = heavy chain moiety; 452-471 = linker; 472-
651 = FGF-18 moiety.
QVQLQESGPGLVKPSETLSLTCTVSGFSLIGYDLNWIRQPPGKGLEWIGIIWGDGTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGKGGGGSEPKSSD

KTHTGGGGSEENVDFRIHVENQTRARDDVSRKQLRLYQLYSRTSGKHIQVLGRRISARGEDGDKYA

QLLVETDTFGSQVRIKGKETEFYLCMNRKGKLVGKPDGTSKECVFIEKVLENNYTALMSAKYSGWY

VGFTKKGRPRKGPKTRENQQDVHFMKRYPKGQPELQKPFKYTTVTKRSRRIRPTHPA

-continued

SEQ ID NO: 89: Amino acid sequence of IgG-heavy chain-sprifermin, fusion via the C-terminus of the sequence; with residues 1-451 = heavy chain moiety; 452-471 = linker; 472-640 = FGF-18 moiety.
QVQLQESGPGLVKPSETLSLTCTVSGFSLIGYDLNWIRQPPGKGLEWIGIIWGDTTDYNSAVKSRV
TISKDTSKNQFSLKLSSVTAADTAVYYCARGGYWYATSYYFDYWGQGTLVTVSSASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNK
ALGAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKGGGGSEPKSSD
KTHTGGGGSEENVDFRIHVENQTRARDDVSRKQLRLYQLYSRTSGKHIQVLGRRISARGEDGDKYA
QLLVETDTFGSQVRIKGKETEFYLCMNRKGKLVGKPDGTSKECVFIEKVLENNYTALMSAKYSGWY
VGFTKKGRPRKGPKTRENQQDVHFMKRYPKGQPELQKPFKYTTVTK SEQ ID NO: 90: Amino acid sequence of SEED_sprifermin, GA chain (as the partial heavy chain of the SEEDbody) (with FGF-18 moiety linked in the N-terminus of the sequence; with residues 1-169 = FGF-18 moiety; 170-184 = linker; 185-414 = GA chain moiety).
EENVDFRIHVENQTRARDDVSRKQLRLYQLYSRTSGKHIQVLGRRISARGEDGDKYAQLLVETDTF
GSQVRIKGKETEFYLCMNRKGKLVGKPDGTSKECVFIEKVLENNYTALMSAKYSGWYVGFTKKGRP
RKGPKTRENQQDVHFMKRYPKGQPELQKPFKYTTVTKGGSGGSGSGSEPKSSDKTHTCPPCPAP
EAAGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALGAPIEKTISKAKGQPREPQVYTLPPPSEELALNELV
TLTCLVKGFYPSDIAVEWLQGSQELPREKYLTWAPVLDSDGSFFLYSILRVAAEDWKKGDTFSCSV
MHEALHNRFTQKSLDRSPGK SEQ ID NO: 91: Amino acid sequence of SEED_wild-typeFGF18, GA chain (as the partial heavy chain of the SEEDbody) (with FGF-18 moiety linked in the N-terminus of the sequence; with residues 1-180 = FGF-18 moiety; 181-185 = linker; 186-415 = GA chain moiety).
EENVDFRIHVENQTRARDDVSRKQLRLYQLYSRTSGKHIQVLGRRISARGEDGDKYAQLLVETDTF
GSQVRIKGKETEFYLCMNRKGKLVGKPDGTSKECVFIEKVLENNYTALMSAKYSGWYVGFTKKGRP
RKGPKTRENQQDVHFMKRYPKGQPELQKPFKYTTVTKRSRRIRPTHPAEPKSSDKTHTCPPCPAP
EAAGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALGAPIEKTISKAKGQPFRPEVHLLPPSREEMTKNQV
SLTCLARGFYPKDIAVEWESNGQPENNYKTTPSRQEPSQGTTTFAVTSKLTVDKSRWQQGNVFSC
SVMHEALHNHYTQKTISLSPGK SEQ ID NO: 92: Amino acid sequence of SEED_FGF18CFGF8, AG chain (as the partial heavy chain of the SEEDbody) (with FGF-18 moiety linked in the N-terminus of the sequence; with residues 1-188 = FGF-18 moiety; 189-193 = linker; 194-423 = AG chain moiety).
EENVDFRIHVENQTRARDDVSRKQLRLYQLYSRTSGKHIQVLGRRISARGEDGDKYAQLLVETDTF
GSQVRIKGKETEFYLCMNRKGKLVGKPDGTSKECVFIEKVLENNYTALMSAKYSGWYVGFTKKGRP
RKGPKTRENQQDVHFMKRYPKGQHTTEQSLRFEFLNYPPFTRSLRGSQRTWAPEPREPKSSDKT
HTCPPCPAPEAAGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALGAPIEKTISKAKGQPFRPEVHLLPPSR
EEMTKNQVSLTCLARGFYPKDIAVEWESNGQPENNYKTTPSRQEPSQGTTTFAVTSKLTVDKSRW
QQGNVFSCSVMHEALHNHYTQKTISLSPGK -continued SEQ ID NO: 93: Amino acid sequence of SEED_FGF18CFGF8T, AG chain
(as the partial heavy chain of the SEEDbody) (with FGF-18 moiety
linked in the N-terminus of the sequence; with residues 1-173 =
FGF-18 moiety; 174-178 = linker; 179-408 = AG chain moiety).
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQHTTEQSLRFEFLNYPPFTEPKSSDKTHTCPPCPAPEAAGGPS

VFLFPPKPKDTLMISRTPEVTCVVVDVSHEDPEVKFNWYVDGVEVHNAKTKPREEQYNSTYRVVSV

LTVLHQDWLNGKEYKCKVSNKALGAPIEKTISKAKGQPFRPEVHLLPPSREEMTKNQVSLTCLARGF

YPKDIAVEWESNGQPENNYKTTPSRQEPSQGTTTFAVTSKLTVDKSRWQQGNVFSCSVMHEALHN

HYTQKTISLSPGK

SEQ ID NO: 94: Amino acid sequence of SEED_FGF18CFGF17, AG chain
(as the partial heavy chain of the SEEDbody) (with FGF-18 moiety
linked in the N-terminus of the sequence; with residues 1-177 =
FGF-18 moiety; 178-182 = linker; 183-412 = AG chain moiety).
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFMKRYPKGQLPFPNHAEKQKQFEFVGSAPTREPKSSDKTHTCPPCPAPEA

AGGPSVFLFPPKPKDTLMISRTPEVTCVVVDVSHEDPEVKFNWYVDGVEVHNAKTKPREEQYNSTY

RVVSVLTVLHQDWLNGKEYKCKVSNKALGAPIEKTISKAKGQPFRPEVHLLPPSREEMTKNQVSLT

CLARGFYPKDIAVEWESNGQPENNYKTTPSRQEPSQGTTTFAVTSKLTVDKSRWQQGNVFSCSVM

HEALHNHYTQKTISLSPGK

SEQ ID NO: 95: Amino acid sequence of SEED_FGF18CFGF9, AG chain
(as the partial heavy chain of the SEEDbody) (with FGF-18 moiety
linked in the N-terminus of the sequence; with residues 1-168 =
FGF-18 moiety; 169-173 = linker; 174-403 = AG chain moiety).
EENVDFRIHVENQTRARDDVSRKQLRLYQLYSRTSGKHIQVLGRRISARGEDGDKYAQLLVETDTF

GSQVRIKGKETEFYLCMNRKGKLVGKPDGTSKECVFIEKVLENNYTALMSAKYSGWYVGFTKKGRP

RKGPKTRENQQDVHFLPRPVDPDKVPELYKDILSQSEPKSSDKTHTCPPCPAPEAAGGPSVFLFPP

KPKDTLMISRTPEVTCVVVDVSHEDPEVKFNWYVDGVEVHNAKTKPREEQYNSTYRVVSVLTVLHQ

DWLNGKEYKCKVSNKALGAPIEKTISKAKGQPFRPEVHLLPPSREEMTKNQVSLTCLARGFYPKDIA

VEWESNGQPENNYKTTPSRQEPSQGTTTFAVTSKLTVDKSRWQQGNVFSCSVMHEALHNHYTQK

TISLSPGK

SEQ ID NO: 96: Amino acid sequence of a mutated AG chain
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPREPQVYTLPPPSEELALNELVTLTCLVKGFYPSDIAVEWLQGSQELPREKY

LTWAPVLDSDGSFFLYSILRVAAEDWKKGDTFSCSVMHEALHNRFTQKSLDRSPGK

SEQ ID NO: 97: Amino acid sequence of SEED_sprifermin, GA chain
(as the partial heavy chain of the SEEDbody) (with FGF-18 moiety
linked in the C-terminus of the sequence; with residues 1-235 =
GA chain moiety; 236-245 = linker; 246-414 = FGF-18 moiety).
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPREPQ

VYTLPPPSEELALNELVTLTCLVKGFYPSDIAVEWLQGSQELPREKYLTWAPVLDSDGSFFLYSILRV

AAEDWKKGDTFSCSVMHEALHNRFTQKSLDRSPGKEPKSSDKTHTEENVDFRIHVENQTRARDDV

-continued

SRKQLRLYQLYSRTSGKHIQVLGRRISARGEDGDKYAQLLVETDTFGSQVRIKGKETEFYLCMNRK

GKLVGKPDGTSKECVFIEKVLENNYTALMSAKYSGWYVGFTKKGRPRKGPKTRENQQDVHFMKRY

PKGQPELQKPFKYTTVTK

SEQ ID NO: 98: Amino acid sequence of SEED_sprifermin, GA chain
(as the partial heavy chain of the SEEDbody) (with FGF-18 moiety
linked in the C-terminus of the sequence; with residues 1-235 =
GAchain moiety; 236-255 = linker; 256-424 = FGF-18 moiety).
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPREPQ

VYTLPPPSEELALNELVTLTCLVKGFYPSDIAVEWLQGSQELPREKYLTWAPVLDSDGSFFLYSILRV

AAEDWKKGDTFSCSVMHEALHNRFTQKSLDRSPGKGGGGSEPKSSDKTHTGGGGSEENVDFRIH

VENQTRARDDVSRKQLRLYQLYSRTSGKHIQVLGRRISARGEDGDKYAQLLVETDTFGSQVRIKGK

ETEFYLCMNRKGKLVGKPDGTSKECVFIEKVLENNYTALMSAKYSGWYVGFTKKGRPRKGPKTRE

NQQDVHFMKRYPKGQPELQKPFKYTTVTK

SEQ ID NO: 99: Amino acid sequence of SEED_sprifermin, GA chain
(as the partial heavy chain of the SEEDbody) (with FGF-18 moiety
linked in the C-terminus of the sequence; with residues 1-235 =
GA chain moiety; 236-250 = linker; 251-419 = FGF-18 moiety)
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPREPQ

VYTLPPPSEELALNELVTLTCLVKGFYPSDIAVEWLQGSQELPREKYLTWAPVLDSDGSFFLYSILRV

AAEDWKKGDTFSCSVMHEALHNRFTQKSLDRSPGKGGGGSGGGGSGGGGSEENVDFRIHVENQ

TRARDDVSRKQLRLYQLYSRTSGKHIQVLGRRISARGEDGDKYAQLLVETDTFGSQVRIKGKETEFY

LCMNRKGKLVGKPDGTSKECVFIEKVLENNYTALMSAKYSGWYVGFTKKGRPRKGPKTRENQQDV

HFMKRYPKGQPELQKPFKYTTVTK

SEQ ID NO: 100: Amino acid sequence of SEED_wildtype FGF18, GA
chain (as the partial heavy chain of the SEEDbody) (with FGF-18
moiety linked in the C-terminus of the sequence; with residues 1-
235 = GA chain moiety; 236-255 = linker; 256-435 =
FGF-18 moiety)
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPREPQ

VYTLPPPSEELALNELVTLTCLVKGFYPSDIAVEWLQGSQELPREKYLTWAPVLDSDGSFFLYSILRV

AAEDWKKGDTFSCSVMHEALHNRFTQKSLDRSPGKGGGGSEPKSSDKTHTGGGGSEENVDFRIH

VENQTRARDDVSRKQLRLYQLYSRTSGKHIQVLGRRISARGEDGDKYAQLLVETDTFGSQVRIKGK

ETEFYLCMNRKGKLVGKPDGTSKECVFIEKVLENNYTALMSAKYSGWYVGFTKKGRPRKGPKTRE

NQQDVHFMKRYPKGQPELQKPFKYTTVTKRSRRIRPTHPA

SEQ ID NO: 101: Amino acid sequence of SEED_sprifermin, AG chain
(as the partial heavy chain of the SEEDbody) (with FGF-18 moiety
linked in the C-terminus of the sequence; with residues 1-235 =
AG chain moiety; 236-255 = linker; 256-424 = FGF-18 moiety)
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPFRPE

VHLLPPSREEMTKNQVSLTCLARGFYPKDIAVEWESNGQPENNYKTTPSRQEPSQGTTTFAVTSKL

TVDKSRWQQGNVFSCSVMHEALHNHYTQKTISLSPGKGGGGSEPKSSDKTHTGGGGSEENVDFR

IHVENQTRARDDVSRKQLRLYQLYSRTSGKHIQVLGRRISARGEDGDKYAQLLVETDTFGSQVRIKG

KETEFYLCMNRKGKLVGKPDGTSKECVFIEKVLENNYTALMSAKYSGWYVGFTKKGRPRKGPKTR

ENQQDVHFMKRYPKGQPELQKPFKYTTVTK

SEQ ID NO: 102: Amino acid sequence of the CH2—CH3 domains of
a GA chain (i.e. partial GA chain)
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPREPQ

VYTLPPPSEELALNELVTLTCLVKGFYPSDIAVEWLQGSQELPREKYLTWAPVLDSDGSFFLYSILRV

AAEDWKKGDTFSCSVMHEALHNRFTQKSLDRSPGK

SEQ ID NO: 103: Amino acid sequence of SEED_sprifermin, AG chain
(as the full heavy chain of the SEEDbody) (with FGF-18 moiety
linked in the C-terminus of the sequence; with residues 1-454 =
AG chain moiety; 455-474 = linker; 475-643 = FGF-18 moiety)
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPFRPEVHLLPPSREEMTKNQVSLTCLARGFYPKDIAVEWESNGQPENNYKT

TPSRQEPSQGTTTFAVTSKLTVDKSRWQQGNVFSCSVMHEALHNHYTQKTISLSPGKGGGGSEPK

SSDKTHTGGGGSEENVDFRIHVENQTRARDDVSRKQLRLYQLYSRTSGKHIQVLGRRISARGEDG

DKYAQLLVETDTFGSQVRIKGKETEFYLCMNRKGKLVGKPDGTSKECVFIEKVLENNYTALMSAKYS

GWYVGFTKKGRPRKGPKTRENQQDVHFMKRYPKGQPELQKPFKYTTVTK

SEQ ID NO: 104: Amino acid sequence of SEED_FGF18Y191P, AG chain
(as the full heavy chain of the SEEDbody) (with FGF-18 moiety
linked in the C-terminus of the sequence; with residues 1-454 =
AG chain moiety; 455-474 = linker; 475-643 = FGF-18 moiety)
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPFRPEVHLLPPSREEMTKNQVSLTCLARGFYPKDIAVEWESNGQPENNYKT

TPSRQEPSQGTTTFAVTSKLTVDKSRWQQGNVFSCSVMHEALHNHYTQKTISLSPGKGGGGSEPK

SSDKTHTGGGGSEENVDFRIHVENQTRARDDVSRKQLRLYQLYSRTSGKHIQVLGRRISARGEDG

DKYAQLLVETDTFGSQVRIKGKETEFYLCMNRKGKLVGKPDGTSKECVFIEKVLENNYTALMSAKYS

GWYVGFTKKGRPRKGPKTRENQQDVHFMKRYPKGQPELQKPFKPTTVTK

SEQ ID NO: 105: Amino acid sequence of SEED_FGF18Y191F, AG chain
(as the full heavy chain of the SEEDbody) (with FGF-18 moiety
linked in the C-terminus of the sequence; with residues 1-454 =
AG chain moiety; 455-474 = linker; 475-643 = FGF-18 moiety)
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPFRPEVHLLPPSREEMTKNQVSLTCLARGFYPKDIAVEWESNGQPENNYKT

TPSRQEPSQGTTTFAVTSKLTVDKSRWQQGNVFSCSVMHEALHNHYTQKTISLSPGKGGGGSEPK

-continued

SSDKTHTGGGGSEENVDFRIHVENQTRARDDVSRKQLRLYQLYSRTSGKHIQVLGRRISARGEDG

DKYAQLLVETDTFGSQVRIKGKETEFYLCMNRKGKLVGKPDGTSKECVFIEKVLENNYTALMSAKYS

GWYVGFTKKGRPRKGPKTRENQQDVHFMKRYPKGQPELQKPFKFTTVTK

SEQ ID NO: 106: Amino acid sequence of SEED_FGF18VS, AG chain
(as the full heavy chain of the SEEDbody) (with FGF-18 moiety
linked in the C-terminus of the sequence; with residues 1-454 =
AG chain moiety; 455-474 = linker; 475-643 = FGF-18 moiety)
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPFRPEVHLLPPSREEMTKNQVSLTCLARGFYPKDIAVEWESNGQPENNYKT

TPSRQEPSQGTTTFAVTSKLTVDKSRWQQGNVFSCSVMHEALHNHYTQKTISLSPGKGGGGSEPK

SSDKTHTGGGGSEENVDFRIHVENQTRARDDVSRKQLRLYQLYSRTSGKHIQVLGRRISARGEDG

DKYAQLLVETDTFGSQVRIKGKETEFYLCMNRKGKLVGKPDGTSKECVFIEKVLENNYTALMSAKYS

GWYVGFTKKGRPRKGPKTRENQQDVHFMKRYPKGQPELQKPFVSTTVTK

SEQ ID NO: 107: Amino acid sequence of the CH2—CH3 domains of
an AG chain (partial AG chain)
EPKSSDKTHTCPPCPAPEAAGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALGAPIEKTISKAKGQPFRPE

VHLLPPSREEMTKNQVSLTCLARGFYPKDIAVEWESNGQPENNYKTTPSRQEPSQGTTTFAVTSKL

TVDKSRWQQGNVFSCSVMHEALHNHYTQKTISLSPGK

SEQ ID NO: 108—Amino acid sequence of SEED_FGF18VS, GA chain
(as the full heavy chain of the SEEDbody) (with FGF-18 moiety
linked in the C-terminus of the sequence; with residues 1-454 =
GA chain moiety; 455-474 = linker; 475-643 = FGF-18 moiety)
QVQLQESGPGLVKPSETLSLTCTVSGFSLIGYDLNWIRQPPGKGLEWIGIIWGDTTDYNSAVKSRV

TISKDTSKNQFSLKLSSVTAADTAVYYCARGGYWYATSYYFDYWGQGTLVTVSSASTKGPSVFPLA

PSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQDWLNGKEYKCKVSNK

ALGAPIEKTISKAKGQPREPQVYTLPPPSEELALNELVTLTCLVKGFYPSDIAVEWLQGSQELPREKY

LTWAPVLDSDGSFFLYSILRVAAEDWKKGDTFSCSVMHEALHNRFTQKSLDRSPGKGGGGSEPKS

SDKTHTGGGGSEENVDFRIHVENQTRARDDVSRKQLRLYQLYSRTSGKHIQVLGRRISARGEDGD

KYAQLLVETDTFGSQVRIKGKETEFYLCMNRKGKLVGKPDGTSKECVFIEKVLENNYTALMSAKYSG

WYVGFTKKGRPRKGPKTRENQQDVHFMKRYPKGQPELQKPFKYTTVTK

SEQ ID NO: 118: amino acid sequence of a linker
GGGGSEPKSSDKTHTGGGGS

SEQ ID NO: 119 amino acid sequence of a linker
GGGGSGGGGSGGGGS

SEQ ID NO: 120: amino acid sequence of a linker
EPKSSDKTHT

SEQ ID NO: 121: amino acid sequence of human FGF8 precursor
(GenBank Ref.: AAC50785.1)
MGSPRSALSCLLLHLLVLCLQAQVTVQSSPNFTQHVREQSLVTDQLSRRLIRTYQLYSRTSGKHVQ

VLANKRINAMAEDGDPFAKLIVETDTFGSRVRVRGAETGLYICMNKKGKLIAKSNGKGKDCVFTEIVL

ENNYTALQNAKYEGWYMAFTRKGRPRKGSKTRQHQREVHFMKRLPRGHHTTEQSLRFEFLNYPP

FTRSLRGSQRTWAPEPR

SEQ ID NO: 122: amino acid sequence of human FGF9 precursor
(GenBank Ref.: NP_002001.1)
MAPLGEVGNYFGVQDAVPFGNVPVLPVDSPVLLSDHLGQSEAGGLPRGPAVTDLDHLKGILRRRQ

LYCRTGFHLEIFPNGTIQGTRKDHSRFGILEFISIAVGLVSIRGVDSGLYLGMNEKGELYGSEKLTQEC

VFREQFEENWYNTYSSNLYKHVDTGRRYYVALNKDGTPREGTRTKRHQKFTHFLPRPVDPDKVPE

LYKDILSQS

SEQ ID NO: 123: amino acid sequence of human FGF17 (GenBank
Ref.: AAI43790.1)
MGAARLLPNLTLCLQLLILCCQTQYVRDQGAMTDQLSRRQIREYQLYSRTSGKHVQVTGRRISATA

EDGNKFAKLIVETDTFGSRVRIKGAESEKYICMNKRGKLIGKPSGKSKDCVFTEIVLENNYTAFQNAR

HEGWFMAFTRQGRPRQASRSRQNQREAHFlKRLYQGQLPFPNHAEKQKQFEFVGSAPTRRTKRT

RRPQPLT

SEQ ID NO: 124: Amino acid sequence of a light chain with
sprifermin in C-term (with residues 1-214 = Light chain;
215-234 = linker; 235-403 = sprifermin moiety)
DIQMTQSPSSLSASVGDRVTITCRASQSISNNLNWYQQKPGKAPKLLIYYTSRFHSGVPSRFSGSGS

GTDFTFTISSLQPEDIATYYCQQEHTLPYTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGL

SSPVTKSFNRGECGGGGSEPKSSDKTHTGGGGSEENVDFRIHVENQTRARDDVSRKQLRLYQLYS

RTSGKHIQVLGRRISARGEDGDKYAQLLVETDTFGSQVRIKGKETEFYLCMNRKGKLVGKPDGTSK

ECVFIEKVLENNYTALMSAKYSGWYVGFTKKGRPRKGPKTRENQQDVHFMKRYPKGQPELQKPFK

YTTVTK

SEQ ID NO: 125: amino acid sequence of a light chain with
wildtype FGF18 term (with residues 1-214 = Light chain;
215-234 = linker; 235-414 = FGF18 moiety)
DIQMTQSPSSLSASVGDRVTITCRASQSISNNLNWYQQKPGKAPKLLIYYTSRFHSGVPSRFSGSGS

GTDFTFTISSLQPEDIATYYCQQEHTLPYTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGL

SSPVTKSFNRGECGGGGSEPKSSDKTHTGGGGSEENVDFRIHVENQTRARDDVSRKQLRLYQLYS

RTSGKHIQVLGRRISARGEDGDKYAQLLVETDTFGSQVRIKGKETEFYLCMNRKGKLVGKPDGTSK

ECVFIEKVLENNYTALMSAKYSGWYVGFTKKGRPRKGPKTRENQQDVHFMKRYPKGQPELQKPFK

YTTVTKRSRRIRPTHPA

SEQ ID NO: 126: amino acid sequence of light chain with
FGF18 in C-term (with residues 1-214 = Light chain;
215-234 = linker; 235-414 = FGF18 moiety)
DIQMTQSPSSLSASVGDRVTITCRASQSISNNLNWYQQKPGKAPKLLIYYTSRFHSGVPSRFSGSGS

GTDFTFTISSLQPEDIATYYCQQEHTLPYTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGL

SSPVTKSFNRGECGGGGSEPKSSDKTHTGGGGSEENVDFRIHVENQTRARDDVSRKQLRLYQLYS

RTSGKHIQVLGRRISARGEDGDKYAQLLVETDTFGSQVRIKGKETEFYLCMNRKGKLVGKPDGTSK

ECVFIEKVLENNYTALMSAKYSGWYVGFTKKGRPRKGPKTRENQQDVHFMKRYPKGQPELQKPFK

YTTVTK

```
SEQ ID NO: 127: amino acid sequence of a linker
GGSGGSGSGSEPKSS

SEQ ID NO: 128: amino acid sequence of a linker
GGGGSGGGGS

SEQ ID NO: 129: amino acid sequence of a linker
EPKSS

SEQ ID NO: 130: amino acid sequence of a linker
GGGGSGGGGSEPKSSDKTHTGGGGS

SEQ ID NO: 131: amino acid sequence of a linker
EPKSSDKTHT

SEQ ID NO: 135: amino acid sequence of a anti-NGF variant CDR-H1
TVSGFSLIGYDLN

SEQ ID NO: 136: amino acid sequence of a anti-NGF variant CDR-H2, ,
with X₁ = D or E; X₂ = N or H; X₃ = S, P, H, or
Q; X₄ = A or S; X₅ is V or L
IIWGX₁GTTDYX₂X₃X₄X₅KS SEQ ID NO: 137: amino acid sequence of a anti-NGF variant CDR-H3
ARGGYWYATSYYFDY SEQ ID NO: 138: amino acid sequence of a anti-NGF variant CDR-L1,
with X₁ = N or Q; X₂ = N or H
RASQSISX₁X₂LN SEQ ID NO: 139: amino acid sequence of a anti-NGF variant CDR-L2
YYTSRFHS SEQ ID NO: 140: amino acid sequence of a anti-NGF variant CDR-L3
QQEHTLPYT
```

EXAMPLES

Material

The FGF18 moiety used as a control was sprifermin. It corresponds to a polypeptide having an amino acid sequence according to SEQ ID NO:2 with an additional Met residue at the N-terminus (as it is expressed in *E. coli*). The anti-NGF moiety used as a control was tanezumab.

Example 1—the Constructs

The proteins were expressed using transient transfection of ExpiCHO™ cells with ExpiFectamine™ Reagent, at 1-liter scale. The ExpiCHO™ cells were seeded 20±2 h prior to transfection with $3.0\times10^6$ vc/ml in ExpiCHO™ expression medium (vc=viable count). The cell count was between $7.0\times10^6$ vc/ml and $10.0\times10^6$ vc/ml at the day of transfection and the viability was higher than 95%. The culture was diluted to $6\times10^6$ vc/ml in 750 ml. ExpiCHO™ Expression medium was used as transfection medium. 2.4 ml ExpiFectamine™ was diluted within 28 ml OptiPro™ and gently mixed. The DNA molecules encoding the protein(s) of interest (encoding any one of the proteins having an amino acid sequence selected from the group consisting of SEQ ID NOs: 1-82) were added to 30 ml OptiPro™ and gently mixed. ExpiFectamine™ and DNA solution was mixed and the complex immediately added to the cells. No complex formation time was necessary. Cells were incubated at 36.5° C. and 5% $CO_2$. 20 hours post transfection the cultures were supplemented with 4.5 μl enhancer and 180 ml feed. Six days after transfection the cells were harvested and separated from supernatant by centrifugation at 4300×g for 20 minutes at 4° C. The supernatant, comprising the proteins of interest was transferred to downstream processing for purification. Standard process was used for purifying the proteins of interest.

Example 2—Bioactivity of the Fusion Proteins

BaF3/FGFR3 cell assay: BaF3 cells expressing FGFR3 and growing only upon FGFR3 activation. Metabolic activity is measured via ATP (with ATP lite) and is proportional to the cell number. BaF3/FGFR3 cells were cultured and passaged in RPMI 1640 medium with 2 mM L-Glutamine, 1 mM Sodium Pyruvate, Penicillin/Streptomycin 1×, 0.6 mg/mL G-418, 50 nM beta-mercaptoethanol and 50 ng/mL IL3. For the assay, cells were first cultured 24 h in the assay medium (same medium without IL3 but with 1 μg/mL heparin instead) and subsequently inoculated at 20 000 cells/well in a white 96 well plate in 100 μL of the assay medium with increasing concentrations of the test compound. Cells were further cultured 48 h at 37° C. The ATP content (proportional to the cell content) was then evaluated with the ATPlite kit (Perkin Elmer, Cat. No. 6016731) according to the recommendation of the manufacturer. rhFGF18 was tested as a control at 0.001, 0.01, 0.1, 1, 10, 100 and 1 000 ng/mL (corresponding to $5.04\times10^{-5}$ to 50.4 nM). The FGF18_anti-NGF constructs were tested at the same equimolar concentrations. Resulting EC50s were calculated with the PadPrism Software v7.0.

U2OS TrkA-P75 assay: U2OS cells expressing TrkA and p75 (NGF receptors) were used. In presence of NGF the receptors dimerize and emit luminescence. U2OS TrkA-p75 cells (Discoverx, Cat. No. 93-0529C3) were cultured in McCoy medium with geneticin 0.2 mg/ml, hygromycin 0.1 mg/mL and FCS 10%. For the assay, 50 000 cells/well were inoculated in a white 96 well plate in 90 μL of assay medium (MEMα with HEPES 10 mM, Penicillin/Streptomycin 0.5×, FCS 2%) and cultured overnight at 37° C. NGF 600 ng/mL was then mixed 1:1 v/v with increasing concentrations of the test compound (20× of the final desired concentration in the wells) and incubated 1 h at room temperature. 10 μL of the NGF/test compound mixture was then added to the cells for 3 h at room temperature. Receptor activation was measured with the Pathhunter Bioassay detection kit (Discoverx, Cat. No. 93-0933E) according to the recommendation of the manufacturer. Tanezumab was tested as a control at 0.457, 1.37, 4.12, 12.36, 37, 111.1, 333.3, and 1 000 ng/mL (corresponding to 0.003 to 6.86 nM). The FGF18_anti-NGF constructs were tested at the same equimolar concentrations. Resulting IC50s were calculated with the PadPrism Software v7.0.

Results: All tested constructs were active in both the BaF3/FGFR3 and U2OS Trka_p75 cell assays indicating that for all constructs both moieties (FGF18 and anti-NGF) were bioactive (see Table 1).

TABLE 1

$EC_{50}$ and $IC_{50}$ obtained for each of the constructs in the BaF3/FGFR3 assay (to monitor FGFR3 activation) and U2OS TrkA_p75 assay (to monitor NGF inhibition) respectively.

| FGF18_anti-NGF constructs | anti-NGF IC50 (nM) | FGF18 EC50 (nM) | Host cells |
|---|---|---|---|
| Parent molecules (tanezumab and rhFGF18) | 0.3-0.6* | 0.02 | |
| FGF18_scFv tanezumab (LH) | 0.43 | 0.16 | HEK293 |
| FGF18_scFv fasinumab (LH) | 0.62 | 0.06 | HEK293 |
| FGF18_Fab tanezumab (LH) | 0.52 | 0.21 | HEK293 |
| FGF18_Fab fasinumab (LH) | 0.54 | 0.27 | HEK293 |
| FGF18_Fab tanezumab (LH) | 0.86 | 0.08 | expiCHO-S ™ |
| FGF18_Fab fulranumab (LH) | 1.61 | 0.07 | expiCHO-S ™ |
| FGF18_Fab fasinumab (LH) | 1.56 | 0.1 | expiCHO-S ™ |
| FGF18_Fab tanezumab (HL) | 0.84 | 0.05 | expiCHO-S ™ |
| FGF18_Fab fulranumab (HL) | 1.07 | 0.06 | expiCHO-S ™ |
| FGF18_Fab fasinumab (HL) | 1.33 | 0.06 | expiCHO-S ™ |
| FGF18 SEED tanezumab (MBE626) | 0.44 | 0.05 | expiCHO-S ™ |
| FGF18 SEED fasinumab (SEED-A) | 0.29 | 0.14 | expiCHO-S ™ |
| FGF18 SEED fulranumab (SEED-B) | 0.25 | 0.06 | expiCHO-S ™ |
| FGF18 SEED (HO124) | 0.89 | 0.07 | expiCHO-S ™ |
| FGF18 SEED (HO110) | 0.89 | 0.02 | expiCHO-S ™ |
| FGF18 SEED (HO113) | 0.95 | 0.10 | expiCHO-S ™ |
| FGF18 SEED (HO114) | 0.88 | 0.02 | expiCHO-S ™ |
| FGF18 SEED (HOF3) | 0.98 | 0.05 | expiCHO-S ™ |

Example 3—Activity of the Fusion Proteins on Primary Chondrocytes

Isolation of the primary chondrocytes: Porcine chondrocytes were isolated from the cartilage of a femoral head of a pig hip. Cells were first inoculated at 20 000 cells/cm$^2$ and cultivated for one week in DMEMHG with 10% FCS, 50 μg/mL ascorbate-2-phosphate and 0.4 mM L-Proline.

Cell culture for gene expression and cell count: The chondrocytes were inoculated in a 24-well plate at 15 000 cells/well in one mL of the same medium as is or supplemented with different concentrations rhFGF18 or the FGF18_anti-NGF constructs (equimolar to rhFGF18). Cells were cultured for seven days. At the end of the culture, cells were either counted with a ViCell™ Cell analyzer (from Beckman Coulter) or lysed for RNA isolation and gene expression. RNA was isolated with the RNeasy minikit (Qiagen, Cat. No. 74104) according to the recommendation of the manufacturer. mRNA concentration and quality was then analysed by an Agilent Bioanalyser with a Agilent RNA 6000 Nano Chip (Agilent, Cat. No. G2938-80023). The reverse transcription was realized with the SuperScript III First-Strand Synthesis SuperMix. The cDNA was then digested by RNAse H to digest RNA and analysed by qPCR with the SYBRGreen Jumpstart Taq Ready Mix in presence of the reverse and forward primer for type I collagen at 200 nM each (Forward (SEQ ID NO: 133): 5'-AAAGGATCTCCTGGTGAAGC-3' and Reverse (SEQ ID NO: 134): 5'-CCTGAGTGGAAGAGTGGAGA-3'). The reaction was performed in the thermocycler Mx3000P from Agilent technologies.

Cell culture for cell shape analysis: The chondrocytes were inoculated in a 96-well plate at 1 000 cells/well in 200 μL of the same medium as is or supplemented with different concentrations of rhFGF18 (10, 100 and 1 000 ng/mL) or the FGF18_anti-NGF constructs (equimolar to rhFGF18). Cells were cultured for five days. Subsequently, cells were fixed with 4% (w/v) paraformaldehyde in PBS, 15 min., washed in PBS three times and then permeabilized with 0.2% (v/v) Triton X100 in PBS, 5 min. at room temperature. The fixed and permeabilized cells were washed three times with PBS and stained with Hoechst 33342 (1/400, Invitrogen Cat No. H1399) and Phalloidin-Alex 488 (1/40, Invitrogen, Cat. No. A12379) in PBS for 1 h at room temperature. Finally, the cells were washed three times with PBS. Images were acquired with an inverted microscope (Zeiss, Axio Observer) using a filter set for green and blue fluorescence.

Figure 2B:
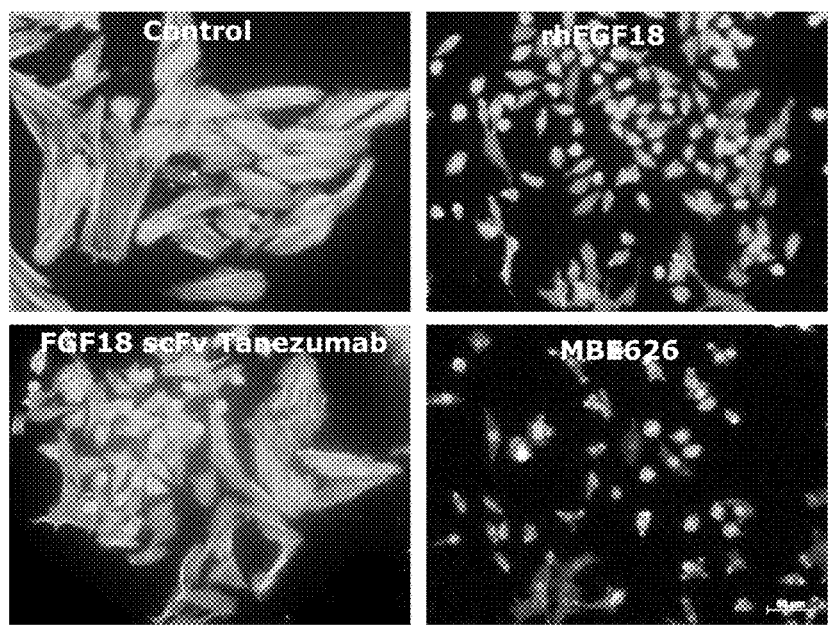

Results for FGF18 scFv Tanezumab: rhFGF18 and FGF18scFv-Tanezumab were tested at 0.015, 0.05, 0.15, 0.5, 1.5, 5, 15 and 50 nM. The effect of the construct FGF18 scFv Tanezumab was less pronounced than the effect of rhFGF18. However, both molecules increased dose-dependently the cell proliferation and decreased type I collagen expression (FIG. 2A). It was also observed that rhFGF18 has an effect on the chondrocyte morphology and favors rounding of the cells and the construct FGF18 scFv Tanezumab had a similar effect with some cells (but not all) displaying a round morphology (FIG. 2B). These results show that the construct FGF18 scFv Tanezumab exert similar effects as rhFGF18.

Results for MBE626: rhFGF18 and MBE626 were tested at 0.504, 5.04 and 50.4 nM. The effect of MBE626 on chondrocyte proliferation was less pronounced than the effect of rhFGF18 but reached 65% of the effect of rhFGF18 at 50.04 nM. Regarding the inhibition of type I collagen expression both molecules performed similarly. In addition, MBE626 induced cell rounding as rhFGF18 did (FIG. 2B). These results show that the construct MBE626 exerts similar effects than rhFGF18.

Example 4—Activity of the Fusion Proteins in a Strong OA-Pain In Vivo Model (MIA Model)

The objective of this study was to determine the dose response (potency) of intraarticular (i.art.) FGF18-scFv (human recombinant FGF18 fused to single chain Fragment of antibody against NGF) on monoiodoacetate (MIA) induced gait disturbance (pain like behavior) in comparison to tanezumab injected i.v.

Figure 3A:
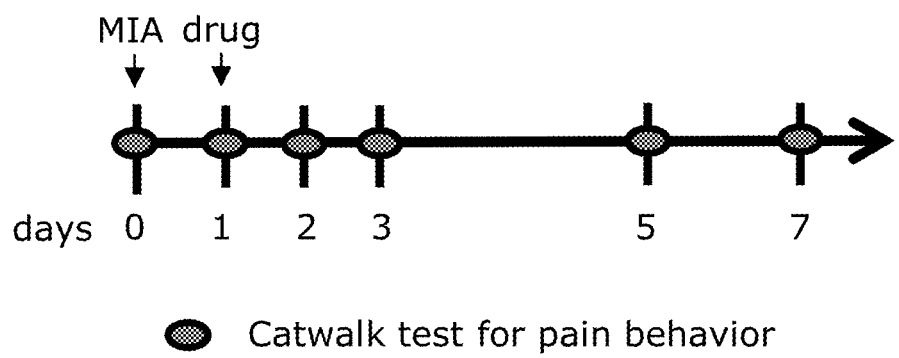
FIGS. 3A-3B.

Experiments: Male Lister Hooded rats from Charles River (250-350 gram) were housed in a connected colony of 48 individuals in 4 storied colony cages. In this cage, rats had the opportunity to jump between levels and walk through a staircase to enable natural physical activities. To induce cartilage degradation with subsequent inflammation, 30 μl of 100 μg/μl MIA (Sigma Aldrich, Art. No. 19148 Lot. LBB0968V) dissolved in 0.9% NaCl was injected i.art. into the right knee joint of isoflurane anesthetized rats. To evaluate the potential effect on pain, longitudinal gait analysis was performed using the Noldus catwalk XT 10.0 system (Noldus, Wageningen, The Netherlands). This system uses an illuminated glass bottom tunnel where paw contact areas on the glass is brightly illuminated and recorded by a video camera from below. Rats are day night inverted and analyzed during the dark, active phase. Walking through the tunnel (acquired area) must be completely voluntary and within a 10-sec time frame. For each animal, three independent runs were acquired. If an animal stops or stands up during video acquisition the data of that run is deleted. If the rat does not perform the catwalk within 5 minutes the next animal will be tested without obtaining any data. The Noldus Catwalk XT 10.0 software is then assigning the paw prints to a certain position (e.g. left forepaw). For a description of gait performance/disturbance the parameter print length is calculated as % of contralateral. The % of contralateral value is averaged for each run to obtain single animal values. To evaluate drug effects, different doses of FGF18-scFv-tanezumab (from 0.03 to 100 µg/joint) or PBS were injected intra articular into the diseased right knee joint at day 1 after MIA injection. Tanezumab was injected i.v. at the same time (at a high dose of 1 mg/kg). The vehicle group received 30 µg/joint PBS intraarticular. Each group consisted of 7 animals. FIG. 3A shows the principle of the study.

Figure 3B:
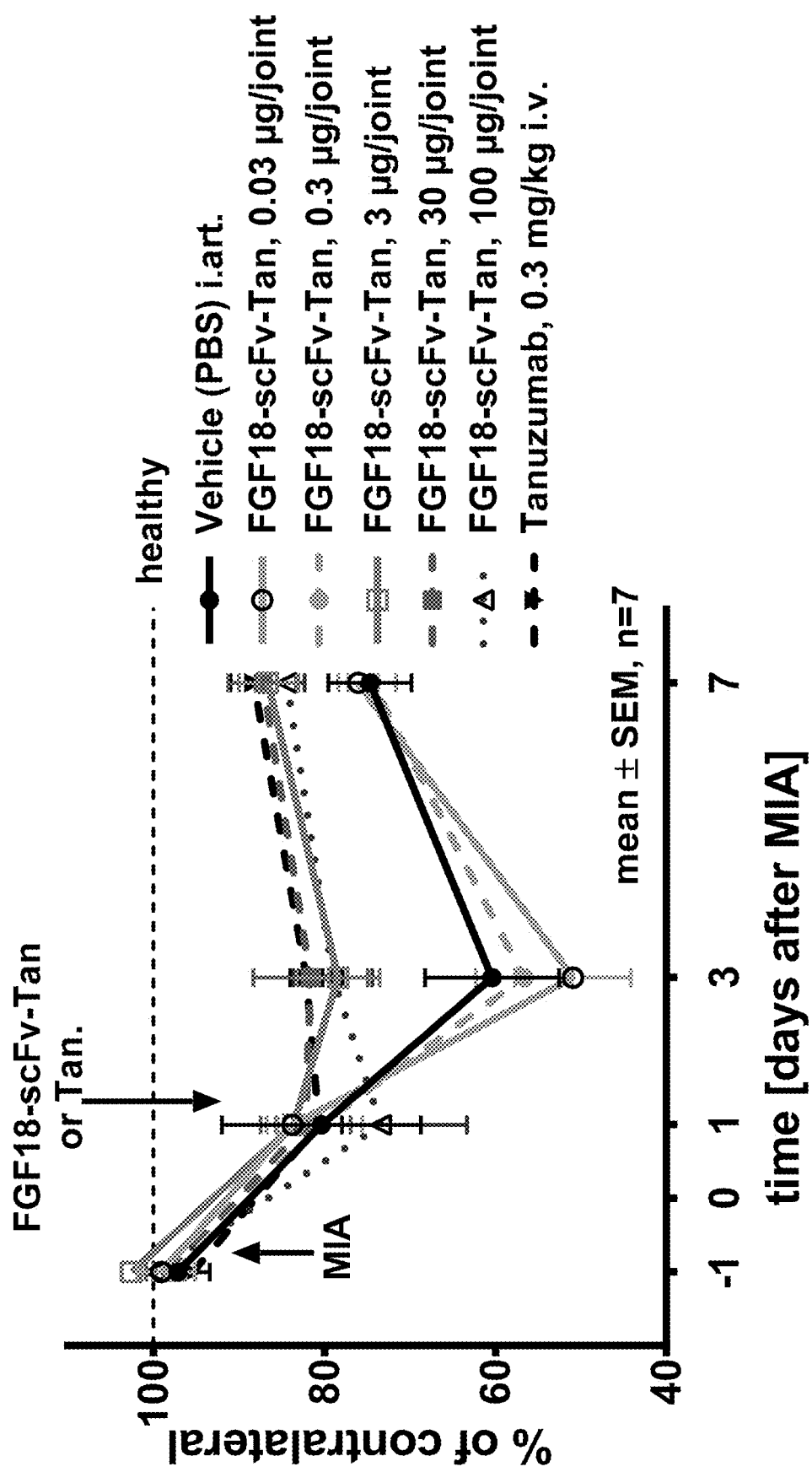

Results: Intra articular injections of FGF18-scFv tanezumab achieved the same efficacy on improving gait disturbance as the clinically proven tanezumab administered intravenous (i.v.) at a high dose (FIG. 3B). The full effect was already achieved with 3 µg/joint FGF18-scFv tanezumab.

Conclusions: I.art. injection of 3 µg/joint FGF-18-scFv and higher doses resulted in the same efficacy as the positive control tanezumab i.v. This result showed that with the new bi functional molecule, in which an anti NGF moiety is fused to FGF18, a meaningful symptomatic benefit can be achieved. Since FGF18, in the rat in vivo, is also active at 1 µg/joint (and higher) the result of this experiment indicates that with the novel bifunctional (>3 µg/joint) molecule an effect on pain can potentially occur at doses at which also a structural benefit from the FGF18 moiety is induced.

Example 5—Duration of the Symptomatic Benefit by the Fusion Protein after One i. Art. Injection in a Chronic OA-Model (ACLT tMx Model)

The objective of this study was to determine the benefit of novel bi-functional molecules, tested at one high dose, on gait disturbance after surgery induced chronic osteoarthritis.

Experiments: Animals, housing conditions and gait analysis were the same than described in example 4. Development of OA was induced by anterior cruciate ligament transection and partial meniscectomy (ACLT+pMx) surgery (i.e. Surgery induced joint instability model to induce chronic osteoarthritis). Rats were anesthetized with isoflurane and shaved around the right knee joint. A longitudinal skin section lateral to the patella on the medial joint was performed with a scalpel. Then the area of the medial quadriceps tendon was cut longitudinally, the patella moved to the front and the joint capsule opened. In knee flexion, the anterior cruciate ligament was disrupted with a small hook. Then, the anterior menisco-tibial tendon was dissected with a scalpel and the medial meniscus on its medial part transected and one half was removed from the joint. Finally, the joint capsule, associated muscles and connective tissue was sutured in layers. Osteoarthritis developed from movements with impaired joint mechanics. This was accelerated by a high level of spontaneous activity in the colony cage. To test drug effects, 30 µg/joint (30 µl of 1 µg/µl in PBS) of FGF18-SEED (MBE626) or FGF18-scFv-tanezumab were injected intra articular into the diseased right knee joint at day 16 after ACLT pMx. The vehicle group received 30 µg/joint PBS intraarticular. As positive reference, tanezumab was injected i.v. at the same time. Each group of animals comprised 9 to 10 animals. FIG. 4A shows the principle of the study.

Results: Both MBE626 and FGF18-scFv-tanezumab caused after its i. art. injection on day 16 after ACLT tMx-an immediate benefit on gait disturbance. Said benefit was stable ≥3 weeks for FGF18-Seed and 1 week for FGF18-scFv-tanezumab (FIGS. 4A-4B). It is noted that the effect of tanezumab i.v. on pain cannot be directly compared to the effect of vehicle i.art. as it is well known that i.art. injection itself induces pain and this does not apply for the i.v. group.

Conclusion: With one i. art. Injection of MBE626 or FGF18-scFv-tanezumab a significant improvement of pain like symptoms could be achieved when ACLT pMx induced chronic osteoarthritis has been established. The benefit was immediate (after 4 h) and lasted for a minimum of 3 weeks. In this period, the symptomatic benefit was comparable to the one after the high dose i.v. tanezumab, indicating that the bifunctional proteins applied via the i.art. route can produce a meaningful and durable benefit on pain symptoms. Since with FGF18 alone, a structural benefit can be achieved with the monthly regimen, the symptomatic benefit lasting 3 weeks can potentially cover % of the treatment period.

Example 6—Dose Dependent Symptomatic and Structural Benefit by the Fusion Protein MBE626 after Three i. Art. Injection with Monthly Interval in a Chronic OA-Model (ACLT pMx Model)

The objective of this study was to determine the benefit of novel bi-functional molecules after chronic repetitive application on structure and symptoms in the same experiment.

Experiments: Animals, housing conditions surgery and gait analysis were the same than described in example 4. Cartilage structure was investigated by histology with toluidine blue and safran staining. The anabolic effect was investigated by a score of the medial tibial compartment which considers the architecture of the surface, matrix staining, tidemark, basal integration, bone abnormalities and chondro-osteophytes. To test drug effects, 2.7 µg/joint, 7 µg/joint, 27 µg/joint or 90 µg/joint of MBE626 were injected intra articular into the diseased right knee joint at day 15, day 43 and day 71 after ACLT pMx (all n=18). The vehicle group received 30 µg/joint PBS intraarticular (n=18). To define the disease window, healthy animals received vehicle PBS (n=14). As positive reference for pain treatment, tanezumab (0.3 mg/kg) was injected i.v. at the same time points (n=10). FIG. 5A shows the principle of the study.

Figure 5B:
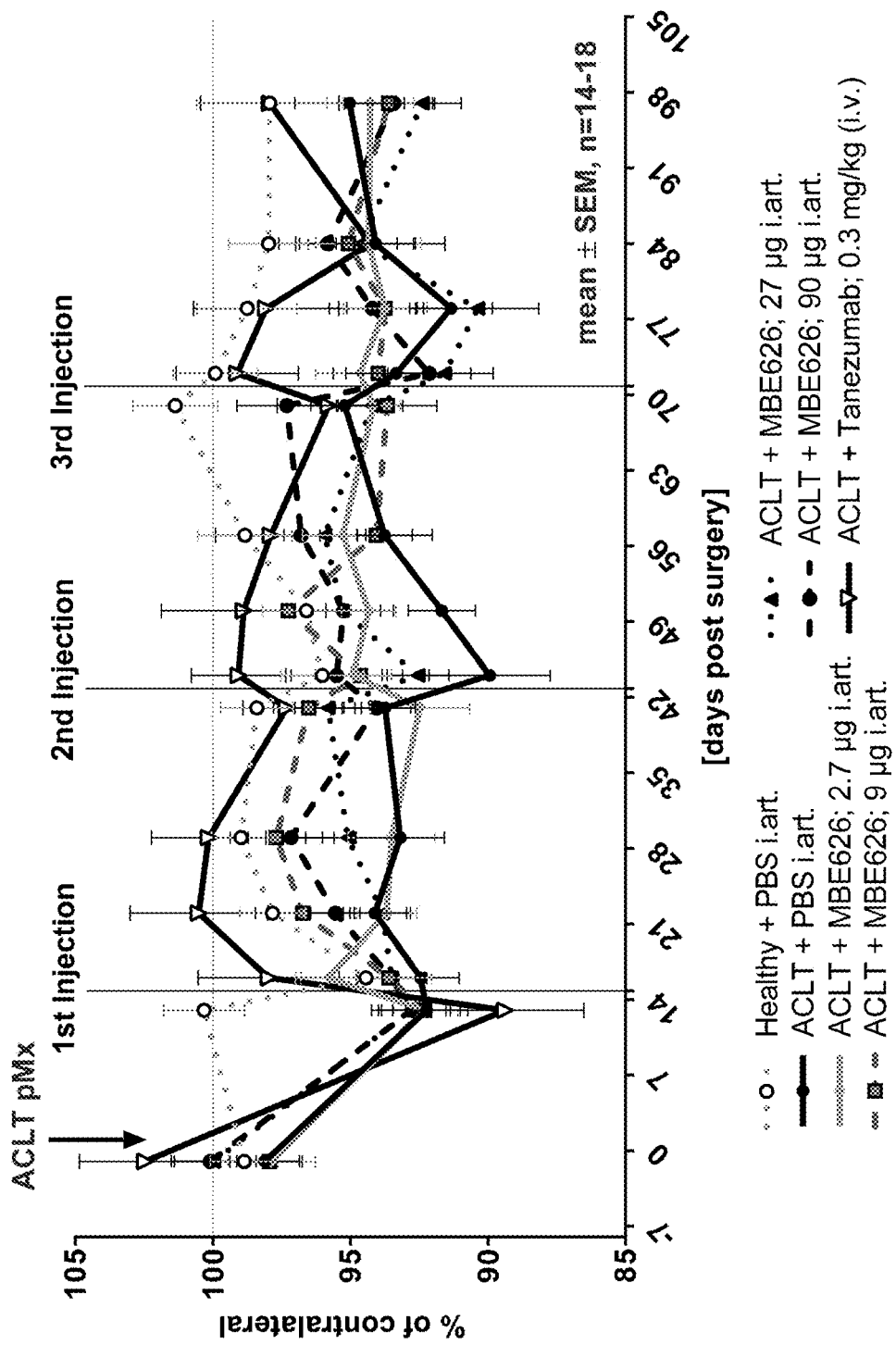
Figure 6:
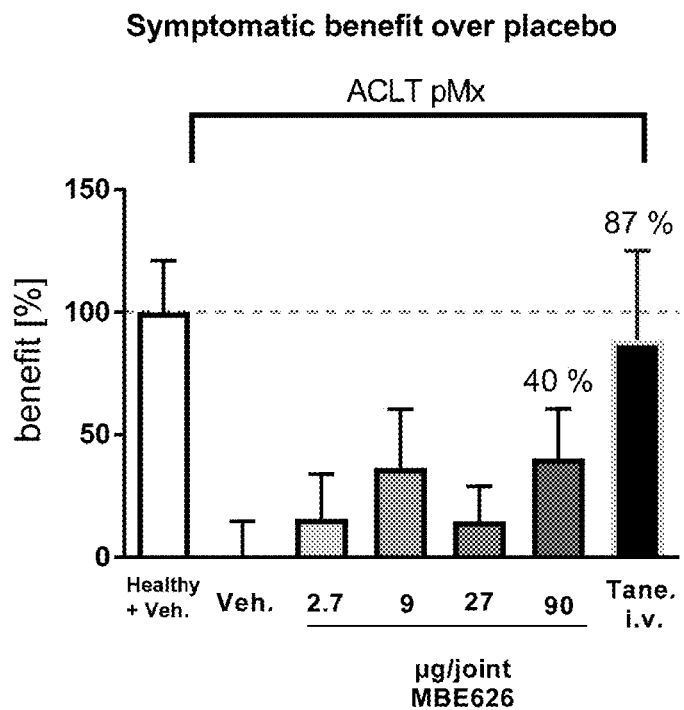
FIG. 6: % benefit over placebo: Area under the curve has been determined from day 13 until 98 (end). Next, the mean of the AUC for the healthy+vehicle group has been set to 100% benefit and the mean of the ACLT pMx+vehicle group has been set to 0% benefit. Based on this normalization, the % benefit over vehicle (placebo) has been calculated for each animal and the mean±SEM is shown (n=10-18 animals/group).
Figure 7:
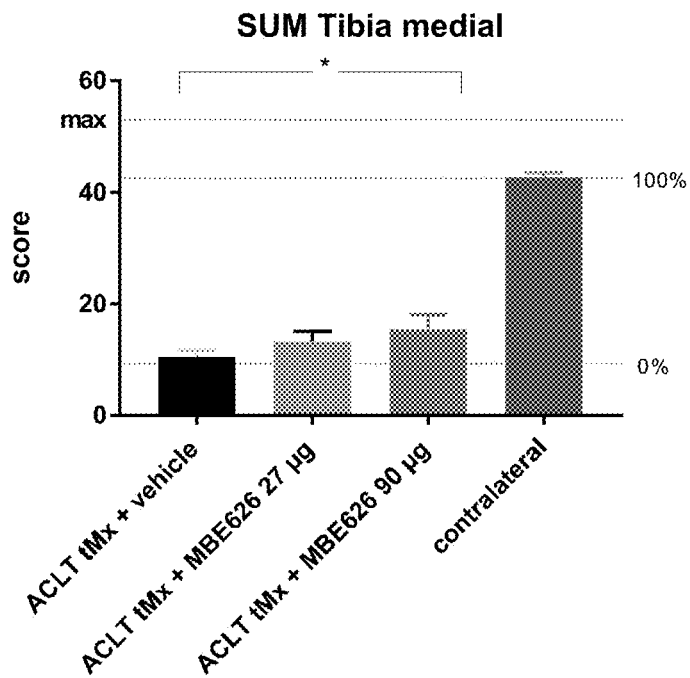
FIG. 7: Cartilage structure determined by histology scoring. Shown is the mean±SEM of 18 animals/group.

Results: MBE626 caused with all tested doses an immediate and long-lasting benefit on gait disturbance (FIG. 5B). After the first injection, this effect was dose dependent which the exception that 27 µg/joint was somewhat less effective at several time points. The strongest benefit was seen with the highest dose (90 µg/joint) reaching 40% benefit over placebo (FIG. 6). In comparison, the positive reference tanezumab (i.v.) showed 87% benefit over placebo. At the endpoint (day 98), histology investigation revealed a trend for an increase in the pro-anabolic score with higher doses of MBE626 (FIG. 7).

Conclusion: The results suggests that chronic treatment with the novel bifunctional protein MBE626 causes a long-term benefit in both, cartilage structure and pain symptoms in parallel.

REFERENCES

1. Lotz, 2010, Arthritis research therapy, 12:211
2. Sanga et al., 2013, Pain, 154:1910-1919
3. Tiseo et al., 2014, Pain, 155:1245-1252.
4. Brown M T, Murphy F T, Radin D M, Davignon I, Smith M D, West C R.
5. J Pain. 2012 August; 13(8):790-8.
6. Ellsworth et al., 2002, Osteoarthritis and Cartilage, 10: 308-320
7. Shimoaka et al., 2002, JBC 277(9):7493-7500
8. WO2008023063
9. Hague et al., 2007, Histol. Histopathol., 22:97-105
10. WO2004032849
11. WO9816644
12. Kabat et al. 1991; J. Immunol 147:1709-1719
13. Chothia and Lesk 1987; J Mol Biol 196: pp. 901-917.
14. Ridgway et al., 1996, Protein Engineering, 9(7):617-621
15. Davis et al. 2010; Protein Eng Des Sel 23: pp. 195-202.
16. U.S. Pat. No. 8,871,912
17. Custers et al., 2007, Osteoarthritis and Cartilage, 15:1241-1248
18. The Merck manual, 17th edition, 1999
19. ICRS publication:
   see Worldwide Website:
   cartilage.org/_files/contentmanagement/ICRS_evaluation.pdf, page 13
20. Zhou et al., 2016, Osteoarthritis and Cartilage, 24:2181-2192

---

The invention claimed is:

1. A fusion protein comprising an FGF-18 moiety fused to an anti-NGF moiety and optionally comprising a linker between the two moieties, wherein said fusion protein is a SEEDbody comprising SEQ ID NO: 55, SEQ ID NO: 56 and SEQ ID NO: 11.

2. A pharmaceutical composition comprising a fusion protein according to claim 1 and at least one excipient.

3. A method of treating a cartilage disorder comprising the administration of a fusion protein according to claim 1, or a pharmaceutical composition thereof, to a subject having a cartilage disorder.

4. The method according to claim 3, wherein the cartilage disorder is osteoarthritis.

5. The method according to claim 3, wherein the cartilage disorder is cartilage injury.

* * * * *

UNITED STATES PATENT AND TRADEMARK OFFICE
CERTIFICATE OF CORRECTION

| | |
|---|---|
| PATENT NO. | : 11,572,395 B2 |
| APPLICATION NO. | : 16/648677 |
| DATED | : February 7, 2023 |
| INVENTOR(S) | : Anne Gigout et al. |

It is certified that error appears in the above-identified patent and that said Letters Patent is hereby corrected as shown below:

On the Title Page

Item (54) "FUSION PROTEIN COMPRISING AN FGF-18 MOIETY" should read --FUSION PROTEIN COMPRISING FGF-18 AND AN ANTI-NGF ANTIBODY--.

In the Specification

Column 1,
Lines 1-2, "FUSION PROTEIN COMPRISING AN FGF-18 MOIETY" should read --FUSION PROTEIN COMPRISING FGF-18 AND AN ANTI-NGF ANTIBODY--.

Column 23,
Line 29, "moiety; 1170-184" should read --moiety; 170-184--.

Column 64,
Line 27, "% of the" should read --¾ of the--.

Signed and Sealed this
Fifth Day of September, 2023

Katherine Kelly Vidal
*Director of the United States Patent and Trademark Office*